US009950039B2

(12) United States Patent
Souhami et al.

(10) Patent No.: US 9,950,039 B2
(45) Date of Patent: Apr. 24, 2018

(54) INSULIN GLARGINE/LIXISENATIDE FIXED RATIO FORMULATION

(71) Applicant: Sanofi-Aventis Deutschland GmbH, Frankfurt (DE)

(72) Inventors: Elisabeth Souhami, Paris (FR); Louise Silvestre, Paris (FR)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/965,586

(22) Filed: Dec. 10, 2015

(65) Prior Publication Data

US 2016/0199452 A1 Jul. 14, 2016

(30) Foreign Application Priority Data

Dec. 12, 2014 (EP) .................................... 14197685
Nov. 10, 2015 (EP) .................................... 15193940

(51) Int. Cl.
 *A61K 38/26* (2006.01)
 *A61K 38/28* (2006.01)
 *A61P 3/10* (2006.01)

(52) U.S. Cl.
 CPC .............. *A61K 38/26* (2013.01); *A61K 38/28* (2013.01)

(58) Field of Classification Search
 None
 See application file for complete search history.

(56) References Cited

U.S. PATENT DOCUMENTS

| | | | |
|---|---|---|---|
| 3,758,683 A | 9/1973 | Jackson | |
| 3,868,358 A | 2/1975 | Jackson | |
| 4,153,689 A | 5/1979 | Hirai et al. | |
| 4,258,134 A | 3/1981 | Yoshida et al. | |
| 4,367,737 A | 2/1983 | Kozam et al. | |
| 4,608,364 A | 8/1986 | Grau | |
| 4,614,730 A | 9/1986 | Hansen et al. | |
| 4,644,057 A | 2/1987 | Bicker et al. | |
| 4,689,042 A | 8/1987 | Sarnoff et al. | |
| 4,701,440 A | 10/1987 | Grau | |
| 4,731,405 A | 3/1988 | Kirsch et al. | |
| 4,783,441 A | 11/1988 | Thurow | |
| 4,839,341 A | 6/1989 | Massey et al. | |
| 4,863,902 A | 9/1989 | Amagase et al. | |
| 4,885,164 A | 12/1989 | Thurow | |
| 4,923,162 A | 5/1990 | Fleming et al. | |
| 4,959,351 A | 9/1990 | Grau | |
| 4,960,702 A | 10/1990 | Rice et al. | |
| 4,994,439 A | 2/1991 | Longenecker et al. | |
| 5,008,241 A | 4/1991 | Markussen et al. | |
| 5,034,415 A | 7/1991 | Rubin | |
| 5,070,186 A | 12/1991 | Joergensen | |
| 5,101,013 A | 3/1992 | Dorschug et al. | |
| 5,177,058 A | 1/1993 | Dorschug | |
| 5,187,177 A | 2/1993 | Garzaran | |
| 5,227,293 A | 7/1993 | Stengelin et al. | |
| 5,253,785 A | 10/1993 | Haber et al. | |
| 5,272,135 A | 12/1993 | Takruri | |
| 5,358,708 A | 10/1994 | Patel | |
| 5,358,857 A | 10/1994 | Stengelin et al. | |
| 5,370,629 A | 12/1994 | Michel et al. | |
| 5,397,771 A | 3/1995 | Bechgaard et al. | |
| 5,407,609 A | 4/1995 | Tice et al. | |
| 5,424,286 A | 6/1995 | Eng | |
| 5,428,006 A | 6/1995 | Bechgaard et al. | |
| 5,473,049 A | 12/1995 | Obermeier et al. | |
| 5,474,978 A | 12/1995 | Bakaysa et al. | |
| 5,478,323 A | 12/1995 | Westwood et al. | |
| 5,496,924 A | 3/1996 | Habermann et al. | |
| 5,506,203 A | 4/1996 | Backstrom et al. | |
| 5,509,905 A | 4/1996 | Michel | |
| 5,514,646 A | 5/1996 | Chance et al. | |
| 5,524,286 A | 6/1996 | Chiesa et al. | |
| 5,534,488 A | 7/1996 | Hoffmann | |
| 5,545,618 A | 8/1996 | Buckley et al. | |
| 5,547,929 A | 8/1996 | Anderson, Jr. et al. | |
| 5,559,094 A | 9/1996 | Brems et al. | |
| 5,595,756 A | 1/1997 | Bally et al. | |
| 5,597,796 A | 1/1997 | Brange | |
| 5,614,219 A | 3/1997 | Wunderlich et al. | |
| 5,614,492 A | 3/1997 | Habener | |
| 5,631,224 A | 5/1997 | Efendic et al. | |
| 5,654,008 A | 8/1997 | Herbert et al. | |
| 5,656,722 A | 8/1997 | Dorschug | |
| 5,663,291 A | 9/1997 | Obermeier et al. | |

(Continued)

FOREIGN PATENT DOCUMENTS

AU 593274 B2 2/1990
AU 612324 B2 7/1991

(Continued)

OTHER PUBLICATIONS

Abraira et al., "Glycaemic separation and risk factor control in the Veterans Affairs Diabetes Trial: an interim report" Diabetes Obes Metab 11(2)150-56 (2009; Epub Jul. 29, 2008).
Aguilar, "Heart failure and diabetes: Time to pay attention" American Heart Journal, 162(5):795-97 (Nov. 2011).
American Diabetes Association, "Type 2 Diabetes in Children and Adolescents," Diabetes Care, Mar. 2000, vol. 23 (3), pp. 381-389.
American Diabetes Association, "Standards of Medical Care in Diabetes—2011," Diabetes Care, Jan. 2011, vol. 34 (Suppl 1), pp. S11-S61.
Ampudia-Blasco et al., "Basal Plus Basal-Bolus approach in type 2 diabetes" Diabetes Technol Ther. 13 Suppl1: S75-83 (Jun. 2011).
Aquiliante, "Sulfonylurea Pharmacogenomics in Type 2 Diabetes: The Influence of Drug Target and Diabetes Risk Polymorphisms," Expert Review of Cardiovascular Therapy, Mar. 2010, vol. 8 (3), pp. 359-372.

(Continued)

*Primary Examiner* — Julie Ha
*Assistant Examiner* — Kristina M Hellman
(74) *Attorney, Agent, or Firm* — McDonnell Boehnen Hulbert & Berghoff LLP

(57) ABSTRACT

The present invention refers to a pharmaceutical composition comprising (a) lixisenatide or/and a pharmaceutically acceptable salt thereof, and (b) insulin glargine or/and a pharmaceutically acceptable salt thereof, wherein the compound (b) and compound (a) are present in a fixed ratio.

7 Claims, 29 Drawing Sheets

(56) References Cited

U.S. PATENT DOCUMENTS

| | | |
|---|---|---|
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,879,584 A | 3/1999 | Bianchetti et al. |
| 5,948,751 A | 9/1999 | Kimer et al. |
| 5,952,297 A | 9/1999 | De et al. |
| 5,985,309 A | 11/1999 | Edwards et al. |
| 5,986,048 A | 11/1999 | Rubroeder et al. |
| 6,006,753 A | 12/1999 | Efendic |
| 6,034,054 A | 3/2000 | Defelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Dorschug |
| 6,110,703 A | 8/2000 | Egel-Mitani et al. |
| 6,174,856 B1 | 1/2001 | Langballe et al. |
| 6,191,102 B1 | 2/2001 | Dimarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | Desimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,417,164 B1 | 7/2002 | Kolterman et al. |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van et al. |
| 6,767,887 B1 | 7/2004 | Hoffmann et al. |
| 6,818,738 B2 | 11/2004 | Havelund |
| 6,852,694 B2 | 2/2005 | Van et al. |
| 6,875,589 B1 | 4/2005 | Doerschug et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | Defelippis et al. |
| 7,115,563 B2 | 10/2006 | Younis et al. |
| 7,119,086 B2 | 10/2006 | Di et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | Defelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuehn et al. |
| 8,633,156 B2 | 1/2014 | Habermann et al. |
| 8,735,349 B2 | 5/2014 | Silvestre et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | Defelippis et al. |
| 2003/0170691 A1 | 9/2003 | Gimeno et al. |
| 2004/0037893 A1 | 2/2004 | Hansen et al. |
| 2004/0048783 A1 | 3/2004 | Brunner-Schwarz et al. |
| 2004/0092590 A1 | 5/2004 | Arterburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | DeFelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |

(56) References Cited

U.S. PATENT DOCUMENTS

| | | |
|---|---|---|
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Rlabermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0116179 A1 | 5/2013 | Hess et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |
| 2014/0371141 A1 | 12/2014 | Souhami et al. |

FOREIGN PATENT DOCUMENTS

| | | |
|---|---|---|
| CA | 1173388 A | 8/1984 |
| CA | 1258427 A | 8/1989 |
| CA | 1336329 C | 7/1995 |
| CA | 1341203 C | 3/2001 |
| CA | 2662084 A1 | 3/2008 |
| CN | 1276731 A | 12/2000 |
| CN | 1413582 A | 4/2003 |
| CN | 101366692 A | 2/2009 |
| CN | 101444618 A | 6/2009 |
| CN | 101454019 A | 6/2009 |
| CN | 101670096 A | 3/2010 |
| DE | 19637230 A1 | 3/1998 |
| DE | 10 2008 003 566 | 7/2009 |
| DE | 10 2008 003 568 | 7/2009 |
| DE | 102008053048 A1 | 4/2010 |
| EP | 0018609 B1 | 9/1983 |
| EP | 0046979 B1 | 9/1983 |
| EP | 0132769 A1 | 2/1985 |
| EP | 0140084 A1 | 5/1985 |
| EP | 0166529 A1 | 1/1986 |
| EP | 0200383 A2 | 11/1986 |
| EP | 0211299 A2 | 2/1987 |
| EP | 0 214 826 | 3/1987 |
| EP | 0224885 A1 | 6/1987 |
| EP | 0227938 A2 | 7/1987 |
| EP | 0229956 A1 | 7/1987 |
| EP | 0229998 A2 | 7/1987 |
| EP | 0254516 A2 | 1/1988 |
| EP | 0305760 A2 | 3/1989 |
| EP | 0 368 187 | 5/1990 |
| EP | 0 375 437 | 6/1990 |
| EP | 0 383 472 | 8/1990 |
| EP | 0194864 B1 | 6/1992 |
| EP | 0 419 504 | 1/1994 |
| EP | 0600372 A1 | 6/1994 |
| EP | 0668282 A1 | 8/1995 |
| EP | 0668292 A2 | 8/1995 |
| EP | 0 678 522 | 10/1995 |
| EP | 0837072 A2 | 4/1998 |
| EP | 0845265 A1 | 6/1998 |
| EP | 0 885 961 | 12/1998 |
| EP | 1 076 066 | 2/2001 |
| EP | 1172114 A2 | 1/2002 |
| EP | 1196444 A1 | 4/2002 |
| EP | 1222207 A1 | 7/2002 |
| EP | 1 523 993 | 4/2005 |
| EP | 1364029 B1 | 12/2005 |
| EP | 1 906 991 | 4/2008 |
| EP | 2112161 A2 | 10/2009 |
| EP | 2 187 950 | 5/2010 |
| EP | 2324853 A1 | 5/2011 |
| EP | 2329848 A1 | 6/2011 |
| EP | 2389945 A1 | 11/2011 |
| EP | 0921812 B2 | 12/2011 |
| EP | 2387989 B1 | 7/2014 |
| FR | 2456522 A1 | 12/1980 |
| GB | 835638 A | 5/1960 |
| GB | 840870 A | 7/1960 |
| GB | 1527605 A | 10/1978 |
| GB | 1554157 A | 10/1979 |
| JP | S61212598 A | 9/1986 |
| JP | S6399096 A | 4/1988 |
| JP | H02218696 A | 8/1990 |
| JP | 2-264798 | 10/1990 |
| JP | H03504240 A | 9/1991 |
| JP | H06506444 A | 7/1994 |
| JP | 2001521004 A | 11/2001 |
| JP | 2002516880 A | 6/2002 |
| JP | 2003505347 A | 2/2003 |
| JP | 2006-515267 | 5/2006 |
| JP | 2006137678 A | 6/2006 |
| JP | 2007204498 A | 8/2007 |
| JP | 2009091363 A | 4/2009 |
| JP | 2012-505852 | 3/2012 |
| JP | 2012-255040 | 12/2012 |
| RU | 2386631 C2 | 4/2010 |
| TW | 157005 B | 5/1991 |
| TW | 562806 B | 11/2003 |
| WO | WO-8300288 A1 | 2/1983 |
| WO | WO-8806599 A1 | 9/1988 |
| WO | WO-8910937 A1 | 11/1989 |
| WO | WO-9007522 A1 | 7/1990 |
| WO | WO-9011299 A1 | 10/1990 |
| WO | WO-9103550 A1 | 3/1991 |
| WO | WO-9116929 A1 | 11/1991 |
| WO | WO 92/00321 | 1/1992 |
| WO | WO-9212999 A1 | 8/1992 |
| WO | WO-9318786 A1 | 9/1993 |
| WO | WO-9414461 A1 | 7/1994 |
| WO | WO-9500550 A1 | 1/1995 |
| WO | WO-9524183 A1 | 9/1995 |
| WO | WO-9604307 A1 | 2/1996 |
| WO | WO-9607399 A1 | 3/1996 |
| WO | WO-9611705 A1 | 4/1996 |
| WO | WO 96/32414 | 10/1996 |
| WO | WO-9634882 A1 | 11/1996 |
| WO | WO-9641606 A2 | 12/1996 |
| WO | WO-9701331 A2 | 1/1997 |
| WO | WO-9748413 A1 | 12/1997 |
| WO | WO 98/05351 | 2/1998 |
| WO | WO 98/08871 | 3/1998 |
| WO | WO-9808531 A1 | 3/1998 |
| WO | WO-9808873 A1 | 3/1998 |
| WO | WO-9819698 A1 | 5/1998 |
| WO | WO 98/30231 | 7/1998 |
| WO | WO-9835033 A1 | 8/1998 |
| WO | WO-9839022 A1 | 9/1998 |
| WO | WO-9842749 A1 | 10/1998 |
| WO | WO-9856406 A1 | 12/1998 |
| WO | WO-9856418 A1 | 12/1998 |
| WO | WO 99/07404 | 2/1999 |
| WO | WO 99/25727 | 5/1999 |

(56) References Cited

FOREIGN PATENT DOCUMENTS

| | | |
|---|---|---|
| WO | WO 99/25728 | 5/1999 |
| WO | WO-9921573 A1 | 5/1999 |
| WO | WO-9921578 A1 | 5/1999 |
| WO | WO-9924071 A1 | 5/1999 |
| WO | WO-9940788 A1 | 8/1999 |
| WO | WO 99/43708 | 9/1999 |
| WO | WO-9946283 A1 | 9/1999 |
| WO | WO-9962558 A1 | 12/1999 |
| WO | WO-0023098 A1 | 4/2000 |
| WO | WO-0023099 A1 | 4/2000 |
| WO | WO-0029013 A1 | 5/2000 |
| WO | WO-0041546 A2 | 7/2000 |
| WO | WO-0066629 A1 | 11/2000 |
| WO | WO-0074736 A1 | 12/2000 |
| WO | WO 01/02039 | 1/2001 |
| WO | WO 01/04156 | 1/2001 |
| WO | WO-0100223 A2 | 1/2001 |
| WO | WO-0112155 A1 | 2/2001 |
| WO | WO-0121154 A2 | 3/2001 |
| WO | WO 01/24814 | 4/2001 |
| WO | WO-0125278 A1 | 4/2001 |
| WO | WO-0128555 A1 | 4/2001 |
| WO | WO-0132157 A2 | 5/2001 |
| WO | WO-0137808 A1 | 5/2001 |
| WO | WO-0143762 A2 | 6/2001 |
| WO | WO-0151071 A2 | 7/2001 |
| WO | WO-0152937 A1 | 7/2001 |
| WO | WO-0193837 A2 | 12/2001 |
| WO | WO-0200243 A2 | 1/2002 |
| WO | WO-0224214 A2 | 3/2002 |
| WO | WO-02064115 A1 | 8/2002 |
| WO | WO-02065985 A2 | 8/2002 |
| WO | WO-02066628 A2 | 8/2002 |
| WO | WO-02068660 A1 | 9/2002 |
| WO | WO-02070722 A1 | 9/2002 |
| WO | WO-02076495 A1 | 10/2002 |
| WO | WO-02079250 A1 | 10/2002 |
| WO | WO-03002021 A2 | 1/2003 |
| WO | WO 03/020201 | 3/2003 |
| WO | WO-03035028 A1 | 5/2003 |
| WO | WO-03035051 A2 | 5/2003 |
| WO | WO-03044210 A2 | 5/2003 |
| WO | WO-03053339 A2 | 7/2003 |
| WO | WO-03066084 A1 | 8/2003 |
| WO | WO-03094951 A1 | 11/2003 |
| WO | WO-03094956 A1 | 11/2003 |
| WO | WO-03101395 A2 | 12/2003 |
| WO | WO-03105888 A1 | 12/2003 |
| WO | WO 2004/005342 | 1/2004 |
| WO | WO 2004/035623 | 4/2004 |
| WO | WO-2004045592 A2 | 6/2004 |
| WO | WO-2004050115 A2 | 6/2004 |
| WO | WO-2004064862 A1 | 8/2004 |
| WO | WO-2004078196 A2 | 9/2004 |
| WO | WO-2004078197 A1 | 9/2004 |
| WO | WO-2004078198 A1 | 9/2004 |
| WO | WO-2004080480 A1 | 9/2004 |
| WO | WO-2004096854 A2 | 11/2004 |
| WO | WO-2004105781 A2 | 12/2004 |
| WO | WO-2004107979 A1 | 12/2004 |
| WO | WO 2005/023291 | 3/2005 |
| WO | WO-2005021022 A2 | 3/2005 |
| WO | WO-2005028516 A2 | 3/2005 |
| WO | WO 2005/046716 | 5/2005 |
| WO | WO-2005048950 A2 | 6/2005 |
| WO | WO-2005112949 A1 | 12/2005 |
| WO | WO-2005117948 A1 | 12/2005 |
| WO | WO 2006/000567 | 1/2006 |
| WO | WO-2006015879 A1 | 2/2006 |
| WO | WO 2006/029634 | 3/2006 |
| WO | WO 2006/051103 | 5/2006 |
| WO | WO-2006051110 A2 | 5/2006 |
| WO | WO-2006058620 A2 | 6/2006 |
| WO | WO-2006110551 A2 | 10/2006 |
| WO | WO 2007/006307 | 1/2007 |
| WO | WO-2007001150 A2 | 1/2007 |
| WO | WO-2007024700 A2 | 3/2007 |
| WO | WO-2007028394 A2 | 3/2007 |
| WO | WO-2007031187 A1 | 3/2007 |
| WO | WO-2007035665 A1 | 3/2007 |
| WO | WO-2007036299 A2 | 4/2007 |
| WO | WO-2007037607 A1 | 4/2007 |
| WO | WO-2007044867 A2 | 4/2007 |
| WO | WO-2007050656 A2 | 5/2007 |
| WO | WO-2007075534 A2 | 7/2007 |
| WO | WO-2007081792 A2 | 7/2007 |
| WO | WO-2007081824 A2 | 7/2007 |
| WO | WO-2007082381 A1 | 7/2007 |
| WO | WO-2007095288 A2 | 8/2007 |
| WO | WO-2007104786 A1 | 9/2007 |
| WO | WO-2007109221 A2 | 9/2007 |
| WO | WO-2007113205 A1 | 10/2007 |
| WO | WO-2007120899 A2 | 10/2007 |
| WO | WO-2008006496 A1 | 1/2008 |
| WO | WO-2008013938 A2 | 1/2008 |
| WO | WO 2008/021560 | 2/2008 |
| WO | WO-2008023050 A1 | 2/2008 |
| WO | WO-2008028914 A1 | 3/2008 |
| WO | WO-2008034881 A1 | 3/2008 |
| WO | WO-2008124522 A2 | 10/2008 |
| WO | WO-2008133908 A2 | 11/2008 |
| WO | WO-2008145323 A1 | 12/2008 |
| WO | WO-2009004627 A2 | 1/2009 |
| WO | WO-2009030498 A2 | 3/2009 |
| WO | WO-2009030499 A1 | 3/2009 |
| WO | WO 2009/039963 | 4/2009 |
| WO | WO-2009048959 A1 | 4/2009 |
| WO | WO 2009/063072 | 5/2009 |
| WO | WO-2009056569 A1 | 5/2009 |
| WO | WO 2009/087081 | 7/2009 |
| WO | WO 2009/087082 | 7/2009 |
| WO | WO-2009089181 A1 | 7/2009 |
| WO | WO-2009098318 A1 | 8/2009 |
| WO | WO-2009102467 A2 | 8/2009 |
| WO | WO 2009/143014 | 11/2009 |
| WO | WO-2009134380 A2 | 11/2009 |
| WO | WO-2010030670 A2 | 3/2010 |
| WO | WO-2010043566 A2 | 4/2010 |
| WO | WO-2010044867 A1 | 4/2010 |
| WO | WO-2010089304 A1 | 8/2010 |
| WO | WO-2010092163 A2 | 8/2010 |
| WO | WO 2010/138671 | 12/2010 |
| WO | WO-2011012719 A1 | 2/2011 |
| WO | WO-2011017554 A2 | 2/2011 |
| WO | WO-2011029892 A2 | 3/2011 |
| WO | WO-2011058082 A1 | 5/2011 |
| WO | WO-2011058083 A1 | 5/2011 |
| WO | WO-2011089203 A1 | 7/2011 |
| WO | WO-2011103575 A1 | 8/2011 |
| WO | WO-2011122921 A2 | 10/2011 |
| WO | WO-2011128374 A1 | 10/2011 |
| WO | WO-2011144673 A2 | 11/2011 |
| WO | WO-2011144674 A2 | 11/2011 |
| WO | WO-2011147980 A1 | 12/2011 |
| WO | WO-2011157402 A1 | 12/2011 |
| WO | WO-2011160066 A1 | 12/2011 |
| WO | WO-2012012352 A2 | 1/2012 |
| WO | WO-2012028172 A1 | 3/2012 |
| WO | WO-2012055967 A2 | 5/2012 |
| WO | WO-2012065996 A1 | 5/2012 |
| WO | WO-2012066086 A1 | 5/2012 |
| WO | WO-2012080320 A1 | 6/2012 |
| WO | WO-2012104342 A1 | 8/2012 |
| WO | WO-2012125569 A2 | 9/2012 |
| WO | WO-2012156296 A1 | 11/2012 |
| WO | WO-2012156299 A1 | 11/2012 |
| WO | WO-2012177929 A2 | 12/2012 |
| WO | WO-2013060850 A1 | 5/2013 |
| WO | WO-2014017849 A1 | 1/2014 |
| WO | WO-2014118355 A1 | 8/2014 |

(56) References Cited

FOREIGN PATENT DOCUMENTS

| WO | WO 2014/202483 | 12/2014 |
|---|---|---|
| WO | WO 2015/059302 | 4/2015 |

OTHER PUBLICATIONS

Atkinson et al., "validation of a general measure of treatment satisfaction, the Treatment Satisfaction Questionnaire for Medication (TSQM), using a national panel study of chronic disease" Health Qual Life Outcomes, 2:12, pp. 1-13 Feb. 2004).
Beckman et al., "Diabetes and atherosclerosis: epidemiology, pathophysiology, and management" JAMA 287 (19):2570-81 (May 2002).
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Brazier et al., "Testing the validity of the Euroqol and comparing it with the SF-36 health survey questionnaire," Qual Life Res 2(3):169-80 (Jun. 1993).
Byetta® Product information, EMA pp. 1-2, accessed Jun. 10, 2016.
Byetta® Summary of product characteristics, Annex I, pp. 1-71, (2011).
Canadian Cardiovascular Society Grading of Angina Pectoris, From http://www.sscts.org/pages/Classificationanginaccs.aspx. Accessed May 27, 2016, one page.
Canadian Diabetes Association, Clinical Practice Guidelines Expert Committee, Canadian Diabetes Association 2008, Clinical Practice Guidelines for the Prevention and Management of Diabetes in Canada, Canadian Journal of Diabetes, 2008, pp. S162-S167.
Cannon et al., "Intensive versus Moderate Lipid Lowering with Statins after Acute Coronary Syndromes." New England Journal Medicine, Apr. 2004; Epub 2004 Mar. 8, 2004, vol. 350 (15), pp. 1495-1504.
Centers for Disease Control and Prevention, National Diabetes Fact Sheet: General Information and National Estimates on Diabetes in the United States, 2003, Revolution Education Atlanta, GA: U.S. Department of Health and Human Services, Centers for Disease Control and Prevention, 2004, pp. 1-8.
Classification of Functional Capacity and Objective Assessment, My.AmericanHeart, 1994—last accessed Oct. 23, 2015, pp. 1-2.
Clinical Trials Archive for Trial No. NCT00688701 updated Sep. 30, 2012. Accessed at: https://clinicaltrials.gov/ archive/ NCT00688701/2012.09.30/changes Accessed on Jun. 2, 2016, pp. 1-5 submitted.
Clinical Trials History for Trial No. NCT00688701 last updated Mar. 25, 2014. Accessed at https://clinicaltrials.gov/archive/ NCT00688701 Accessed on Jun. 2, 2016, pp. 1-2 submitted.
D'Alessio et al., "The role of dysregulated glucagon secretion in type 2 diabetes" Diabetes, Obesity and Metabolism, 13(Supppl. 1):126-132 (Oct. 2011).
Das, et al., "The British Cardiac Society Working Group Definition of Myocardial Infarction: Implications for Practice," Heart, 2005, vol. 92 (1), pp. 21-26, (Jan. 2006; Epub Apr. 14, 2005).
De Lemos et al., "Early intensive vs. a delayed conservative simvastatin strategy in patients with acute coronary Syndromes: phase Z of the A to Z trial." JAMA 292(11):1307-16 (Sep. 2004; Epub Aug. 30, 2004).
Definition of "Combination", Concise Oxford English Dictionary, edited by A. Stevenson and M. Waite, Oxford University press, 12th Edition, Aug. 2011, 4 pages submitted, see p. 285.
Definition of Phase, Clinical Trials.gov NIH, accessed, Mar. 2016, one page.
Del Prato & Tiengo, The importance of first-phase insulin secretion: implications for the therapy of type 2 diabetes mellitus. Diabetes Metab Res Rev. 17(3):164-74 (May-Jun. 2001).
Del Prato et al., "Global Partnership for Effective Diabetes Management Tailoring treatment to the individual in type 2 diabetes practical guidance from the Global partnership for effective diabetes management" Int J Clin Pract 64 (3):295-304 (Feb. 2010).
DeWitt & Hirsch, "Outpatient insulin therapy in type 1 and type 2 diabetes mellitus: scientific review." JAMA 289(17):2254-64 (May 2003).
Diabetes Control and Complications Trial/ Epidemiology of Diabetes Interventions and Complications Research Group, "Intensive Diabetes Treatment and Cardiovascular Disease in Patients with Type 1 Diabetes," New England Journal Medicine, Dec. 2005, vol. 353 (25), pp. 2643-2259.
Diabetes Control and Complications Trial, "Intensive diabetes therapy and carotid intima—media thickness in type 1 diabetes," New England Journal Medicine Jun. 2003, vol. 348 (23), pp. 2294-2303.
Dinneen & Gerstein, "The association of microalbuminuria and mortality in non-insulin dependent diabetes mellitus. A systematic overview of the literature." Arch Intern Med 157(13):1413-8 (Jul. 1997.
Dolan, "Modeling valuations for EuroQol health states." Med Care 35(11):1095-1108 (Nov. 1997).
Druet et al., "Characterization of Insulin Secretion and Resistance in Type 2 Diabetes of Adolescents," The Journal of Clinical Endocrinology & Metabolism, Feb. 2006, vol. 91 (2), pp. 401-404 (Epub Nov. 15, 2005).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
EMA—European Medicines Agency, "Note for guidance on non-clinical safety studies for the conduct of human clinical Trials and marketing authorization for pharmaceuticals," Jul. 2008, pp. 1-22.
Encyclopedia of Drugs, "METFORMIN" Moscow, Drug Register of 2001, p. 549, English translation provided pp. 1-2.
English translation of the TIPO Search Report for ROC Patent Application No. 101131466; dated Mar. 2, 2016, one page.
European Medicines Agency, Committee for Medicinal Products for Human Use (CHMP), "Assessment Report—Lyxumia", Nov. 28, 2012, pp. 1-81.
European Public Assessment Report (EPAR) Optisulin, EPAR Summary for the Public. Feb. 2009, pp. 1-3.
EuroQol Group, "EuroQol—a new facility for the measurement of health-related quality of life." Health policy (Amsterdam, Netherlands) 16(3):199-208 (Dec. 1990).
Extended European Search Report for European Application No. 15159064.3, dated Oct. 19, 2015, pp. 1-4.
FDA—Food and Drug Administration, CFR—Code of Federal Regulations Title 21, Chapter 1, Subchapter D, Part 312.21, "Phases of an investigation," Apr. 1, 2015, pp. 1-2.
FDA, Food and Drug Administration. Guidance for Industry—Diabetes Mellitus: Developing Drugs and Therapeutic Biologics for Treatment and Prevention. pp. 1-34 (Feb. 2008).
Final Rejection issued in U.S. Appl. No. 12/617,805; dated May 25, 2016, pp. 1-9.
Final Rejection issued in U.S. Appl. No. 13/633,496; dated Aug. 26, 2015, pp. 1-16.
Final Rejection issued in U.S. Appl. No. 13/633,563; dated Apr. 8, 2016, pp. 1-12.
Final Rejection issued in U.S. Appl. No. 13/509,507; dated May 13, 2016, pp. 1-11.
Final Rejection issued in U.S. Appl. No. 14/303,895; dated Apr. 27, 2015, pp. 1-10.
Final Rejection issued in U.S. Appl. No. 13/382,772; dated Feb. 24, 2016, pp. 1- 36.
Forman et al., "Higher Levels of Albuminuria within the Normal Range Predict Incident Hypertension." Journal of American Social Nephrology, Oct. 2008, vol. 19 (10), pp. 1983-1988.
Game, "Novel hypoglycaemic agents: Considerations in patients with chronic kidney disease" Nephron Clin Pract.126(1):14-18 (Jan. 11, 2014).
Gerstein et al., "Albuminuria and risk of cardiovascular events, death, and heart failure in diabetic and nondiabetic Individuals." JAMA 286(4):421-6 (Jul. 2001 ).

(56) References Cited

OTHER PUBLICATIONS

Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Gromada et al., "Alpha-Cells of the Endocrine Pancreas: 35 Years of Research but the Enigma Remains" Endocrine Reviews 28(1):84-116 (Jan. 2007).
Harkavyi & Whitton, "Glucagon-like peptide 1 receptor stimulation as a means of neuroprotection" British Journal of Pharmacology 159(3):495-501 (2010; Epub Jan. 29, 2010).
Hasslacher et al., "Diabetic kidney disease" Expand Clin Endocrinol Diabetes 122(7):391-94 (Jul. 2014).
Hinnen "Therapeutic Options for the Management of Postprandial Glucose in Patients With Type 2 Diabetes on Basal Insulin," Clinical Diabetes, 2015, vol. 33 (4), pp. 175-180.
Holman et al., "Three-year efficacy of complex insulin regimens in type 2 diabetes." N Engl J Med. 361 (18):1736-47 (Oct. 2009; Epub Oct. 22, 2009).
Hubschle et al., "Anti-atherosclerotic activity of lixisenatide in ApoE knockout mice" Abstract 809, Diabetologia, 55 (Supplement 1 ):5334 (Oct. 2012).
IDF Clinical Guidelines Task Force, Global Guideline for Type 2 Diabetes, Brussels: International Diabetes Federation, Aug. 2005, pp. 1-82.
IDF, International Diabetes Federation Guideline Development Group, "Guideline for management of postmeal glucose in diabetes," Diabetes Research Clinical Practice, 2012, pp. 1-13.
International Search Report by the ISA for International Application No. PCT/EP2016/055267; dated Jun. 7, 2016, pp. 1-7.
International Search Report by the ISA for International Application No. PCT/EP2016/055267; dated May 20, 2016, pp. 1-7.
International Search Report by the ISA for International Application No. PCT/EP2016/055954; dated Sep. 9, 2016, pp. 1-12.
Inzucchi et al., "Management of hyperglycaemia in type 2 diabetes: a patient-centered approach. Position statement of the American Diabetes Association (ADA) and the European Association for the Study of Diabetes (EASD)." Diabetologia. 55(6):1577-96 (Jun. 2012; Epub Apr. 20, 2012).
Johnson et al., "Diabetes, Insulin Resistance, and Metabolic Syndrome in Horses," Journal of Diabetes Science and Technology, May 2012, vol. 6 (3), pp. 534-540.
Jones et al., "Effect of Metformin in Pediatric Patients with Type 2 Diabetes: A Randomized Controlled Trial," Diabetes Care, Jan. 2002, vol. 25 (1), pp. 89-94.
Juniper et al., "Determining a minimal important change in a disease-specific quality of life questionnaire." J Clin Epidemiol47(1):81-87 (Jan. 1994).
Katz et al., "The clinical burden of type 2 diabetes in patients with acute coronary syndromes: Prognosis and implications for short- and long-term management" Diabetes and Vascular Disease Research, 11 (6):395-409 (Nov. 2014).
Kelly et al., "Systematic Review: Glucose Control and Cardiovascular Disease in Type 2 Diabetes." Annals Internal Medicine, 2009, vol. 151 (6), pp. 394-403, Sep. 2009; Epub 2009 Jul. 20.
Kendall et al., "Clinical Application of Incretin-Based Therapy: Therapeutic Potential, Patient Selection and Clinical Use." European Journal of Internal Medicine, Jul. 2009, vol. 20 (Suppl 2), pp. S329-S339.
Khaw et al., "Glycated Haemoglobin, Diabetes, and Mortality in Men in Norfolk Cohort of European Prospective Investigation of Cancer and Nutrition (EPIC Norfolk)." BMJ, Jan. 2001, vol. 322 (7277), pp. 15-18.
Kim et al., "Retinopathy in Monkeys with Spontaneous Type 2 Diabetes" Investigative Opth & Visual Science, Dec. 2004, vol. 45 (12), pp. 4543-4553.
King et al., Global burden of diabetes, 1995-2025. Prevalence, numerical estimates and projections. Diabetes Care 21(9):1414-31 (Sep. 1998).
Kolotkin et al., "Assessing impact of weight on quality of life." Obes Res. 3(1 ):49-56 (Jan. 1995).
Kolotkin et al., "Development of a brief measure to assess quality of life in obesity." Obes Res. 9(2):102-11 (Feb. 2001).
Kondrat'ev VA Methodical Guidelines, May 7, 2010, p. 5 (in Russian only), found on Mar. 24, 2016, found from Internet: StudFields.ru>preview/4510743).
Korytkowski, "When oral agents fail: practical barriers to starting insulin." Int J Obes Relat Metab Disord. 26 Suppl 3 :S18-24 (Sep. 2002).
Lovshin & Drucker, "Incretin-based therapy for type 2 diabetes mellitus." Nat. Rev. Endocrinol. 5(5):262-69 (May 2009).
Madsbad, "Impact of Postprandial Glucose Control on Diabetes-Related Complications: How is the Evidence Evolving?" Journal of Diabetes and Its Complications, 2016, vol. 30, pp. 374-385, Available online Oct. 9, 2015.
McFarlane, "Insulin therapy and type 2 diabetes: management of weight gain," J Clin Hypertens (Greenwich). 11 (10):601-7 (Oct. 2009).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Meadows et al, "The diabetes health profile (DHP): a new instrument for assessing the psychosocial profile of insulin requiring patients: development and psychometric evaluation," Qual. Life Res. 5(2):242-54 (Apr. 1996).
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Meier et al., "Effect of lixisenatide vs liraglutide on glycaemic control, gastric emptying and safety parameters in optimised insuline glargine type 2 diabetes mellitus +/− metformin" Abstract and Poster 926, 5oth EASD Annual Meeting, Vienna, Austria Sep. 15-19, 2014, pp. 1-3.
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Merck Index, "Metformin", The Merck Index, 15th Edition (2013), RSC Publishing, 4 pages submitted, see entry 6009, p. 1102.
Miyazaki et al., "Improved Glycemic Control and Enhanced Insulin Sensitivity in Type 2 Diabetic Subjects Treated with Pioglitazone", Diabetes Care, Apr. 2001, vol. 24(4), pp. 710-719.
Monnier & Colette, "Addition of rapid-acting insulin to basal insulin therapy in type 2 diabetes: indications and modalities." Diabetes Metab 32(1):7-13 (Feb. 2006).
Monnier et al., "Postprandial and Basal Glucose in Type 2 Diabetes: Assessment and Respective Impacts" Diabetes Technology & Therapeutics, 2011, vol. 13 (Suppl 1), pp. S25-S32.
Nathan et al., "Medical Management of Hyperglycemia in Type 2 Diabetes: A Consensus Algorithm for the Initiation and Adjustment of Therapy" Diabetes Care, 32(1):193-203 (Jul. 2009).
Nathan et al., "Modern-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).
NCT00713830, ClinicalTrials.gov "GLP-1 Agonist in Patients with Type 2 Diabetes for Glycemic Control and Safety Evaluation, on Top of Sulfonylurea", 2016, pp. 1-3, accessed Mar. 16, 2016, (Updated Jul. 13, 2008).
NCT00866658 ClinicalTrials.gov, "GLP-1 Agonist AVE0010 in Patients with Type 2 Diabetes for Glycemic Control Safety Evaluation, on Top of Basil Insulin+/− Sulfonylurea," 2016, pp. 1-3, accessed Mar. 16, (Updated Jan. 2010).
NCT00976937, ClinicalTrials.gov, "24-week Study Comparing Lixisenatide (AVE001 0) to Sitagliptin as add-on to Metformin in Obese Type 2 Diabetic Patients Younger Than 50," last updated Mar. 10, 2014, Retrieved Aug. 31, 2016, pp. 1-5.

(56) References Cited

OTHER PUBLICATIONS

NCT01169779, Clinical Trials.gov, "Efficacy and Safety of Lixisenatide in Patients with Type 2 Diabetes Mellitus Insufficiently Controlled by Metformin," 2016, pp. 1-3, accessed Mar. 16, 2016, (updated Mar. 28, 2011).
NICE, National Institute for Health and Care Excellence, "Evidence Summary: New Medicine, ESNM26: Type 2 Diabetes: lixisenatide; Key Points from the Evidence," Sep. 24, 2013, pp. 1-26.
NIH, National Institute of Diabetes and Digestive and Kidney Disease, "Hypoglycimia," Mar. 16, 2016, pp. 1-8.
Nihonn-Iyakuhin-shu Iryoyaku "Pioglitazone hydrochloride, Insulin sensitizing hypoglycemic agent" 2009 Edition, Jiho Inc. p. 1901 (2009). English summary submitted.
Nilsson et al., "Effects of GI vs Content of Cereal Fibre of the Evening Meal on Glucose Tolerance at a Subsequent Standardized Breakfast," European Journal of Clinical Nutrition, Jun. 2008, vol. 62 (6), pp. 712-720 (Epub May 23, 2007).
Non-Final Rejection in U.S. Appl. No. 13/633,496; dated Apr. 21, 2016, pp. 1-12.
Non-Final Rejection issued in U.S. Appl. No. 13/467,707; dated Jun. 30, 2016, pp. 1-9.
Nowels et al., "Validation of the EQ-50 quality of life instrument in patients after myocardial infarction." Qual Life Res 14(1):95-105 (Feb. 2005).
Olansky, "Do Incretin-Based Therapies Cause Acute Pancreatitis?," Journal of Diabetes Science and Technology, Jan. 2010, vol. 4 (1), pp. 228-229.
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Park et al., "Long-Term Treatment of Glucagon-Like Peptide-1 Analog Exendin-4 Ameliorates Diabetic Nephropathy through Improving Metabolic Anomalies in db/db Mice." Journal American Society Nephrology, 2007, vol. 18 (4), pp. 1227-1238 (Apr. 2007; Epub Mar. 14, 2007).
Partial International Search Report by the ISA for International Application No. PCT/EP2016/055954; dated Jun. 21, 2016, pp. 1-6.
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (2011).
Petersen & Christensen et al., Clinical potential of lixisenatide once daily treatment for type 2 diabetes mellitus Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Pinhas-Hamiel et al., "Clinical Presentation and Treatment of Type 2 Diabetes in Children," Pediatric Diabetes, Dec. 2007, vol. 8 (Suppl. 9), pp. 16-27.
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Ratner et al., "Efficacy and safety of lixisenatide once-daily versus placebo in patients with type 2 diabetes mellitus insufficiently controlled on sulfonylurea +/- metformin (GetGoal-S)" Presentation Abstract for Presentation No. 785. 47th EASD Annual Meeting, Lisbon, Sep. 12-16, 2011, pp. 1-3.
Ray et al., "Effect of intensive control of glucose on cardiovascular outcomes and death in patients with diabetes mellitus: a meta-analysis of randomized controlled trials." Lancet 373(9677):1765-72 (May 2009).
Register of medicaments (RM), 2003, issue 10, p. 517.
Remington: The Science and Practice of Pharmacy, Twentieth Edition, Lippincott Williams & Wilkins, USA, "Oral Hypoglycemic and Hyperglycemic Drugs" pp. 1373 and 1375; (2000).

"Remington: The Science and Practice of Pharmacy", Twentieth Edition, Lippincott Williams & Wilkins, USA, "Pancreatic Disorders" pp. 1081-1082 and "Metformin Hydrochloride" p. 1375, (2000,5 pages).
Rosenstock et al., Advancing Basal Insulin Glargine with Prandial Lixisenatide QD vs. Insulin Glulisine QD or TID in T2DM: The GetGoaiDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones & Khan, Insulin-associated weight gain in diabetes: causes, effects and coping strategies. Diabetes Obes Metab. 9(6):799-812 (Nov. 2007).
Sanofi Press Release entitled "Sanofi Announces Top-Line Results for Cardiovascular Outcomes Study of Lyxumia® (lixisenatide)." dated Mar. 19, 2015, Paris, France, pp. 1-2.
Sanofi-Aventis Press Release, "A Promising R&D Portfolio, Well Positioned to Deliver Future Growth," Sep. 17, 2007, pp. 1-11.
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).
Schwartz et al., "New Equations to Estimate GFR in Children with CKD," Journal of the American Society of Nephrology, Mar. 2009, vol. 20 (3), pp. 629-637 (Epub Jan. 21, 2009).
Seino et al., "Lixisenatide significantly improves glycemic control in Asian patients with T2DM insufficiently controlled on basal insulin± SU." Diabetes, Abstract book for 71st Scientific Session. p. A76; Abstract 278-0R (2011).
Shaw et al., "US valuation of the EQ-5D health states: development and testing of the D1 valuation model." Med Care 43(3):203-20 (Mar. 2005).
Sillars et al., "Sulphonylurea-metformin combination therapy, cardiovascular disease and allcause mortality: the Fremantle Diabetes Study." Diabetes Obes Metab. 12(9):757-65 (Sep. 2010).
Spertus et al., "Monitoring the quality of life in patients with coronary heart disease." Am J Cardiol. 74(12):1240-44 (Dec. 1994).
Spertus J.A., et al., "Development and Evaluation of the Seattle Anginal Questionnaire: a New Functional Status Measure for Coronary Artery Disease." Journal American College of Cardiology, Feb. 1995, vol. 25 (2), pp. 333-341.
Spertus et al., "Health Status Predicts Long-Term Outcome in Outpatients with Coronary Disease." Circulation, Jul. 2002, vol. 106 (1), pp. 43-49.
Srinivasan et al., "Animal Models in Type 2 Diabetes Research: An Overview." Indian Journal Medical Research, Mar. 2007, vol. 125, pp. 451-472.
Standardized Definitions for Cardiovascular Outcomes Trials: Draft Recommendations. Division of Metabolism and Endocrinology Products. Center for Drug Evaluation and Research (CDER). pp. 1-34, Mar. 24, 2010.
Tanner et al., "Standards from Birth to Maturity for Height, Weight, Height Velocity, and Weight Velocity: British Children, Part II," Archives of Disease in Childhood, 1966, vol. 41 (220), pp. 613-635.
The Advance Collaborative Group, "Intensive Blood Glucose Control and Vascular Outcomes in Patients with Type 2 Diabetes." New England Journal of Medicine, Jun. 2008, vol. 358 (24), pp. 2560-2572.
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
Tirosh et al., "Normal Fasting Plasma Glucose Levels and Type 2 Diabetes in Young Men" New England Journal of Medicine, 353(14):1454-62 (Oct. 2005).
UK Prospective Diabetes Study (UKPDS) Group, "Tight Blood Pressure Control and Risk of Macrovascular and Microvascular Complications in Type 2 Diabetes (UKPDS 38)," BMJ, Sep. 1998, vol. 317, pp. 703-713.

(56) References Cited

OTHER PUBLICATIONS

Weir "Glucagon-like peptide-1 (7-37) actions on endocrine pancreas." Diabetes 38(3):338-42 (Mar. 1989).
WHO, World Health Organization Media Center. Diabetes Fact Sheet. Available from: http://www.who.int/mediacentre/factsheets/fs312/en/index.html. Accessed Jun. 13, 2016, pp. 1-6.
WHO, World Health Organization Media Center. Obesity and overweight, Fact Sheet No. 311. Updated Jan. 2015, pp. 1-5.
Wikipedia® Entry for "Body Mass Index" Retrieved from the Internet: https://en.wikipedia.org/wiki/Body mass_index, 2016, pp. 1-14, retrieved Feb. 26, 2016.
Wikipedia® Entry for "Metformin" Retrieved from the Internet: https://en.wikipedia.org/wiki/Metformin 2016, pp. 1-21, retrieved Apr. 11, 2016.
Wikipedia® Entry for "Pioglitazone" Retrieved from the Internet: https://en.wikipedia.org/wiki/Pioglitazone 2016, pp. 1-3, retrieved Apr. 11, 2016.
Wikipedia® Entry for "Lixisenatide" Retrieved from the Internet: https://en.wikipedia.org/wiki/Lixisenatidehttps://en.wikipedia.org/wiki/Lixisenatide, pp. 1-2, updated Dec. 2015.
Wild et al., "Global prevalence of diabetes: estimates for the year 2000 and projections for 2030." Diabetes Care 27 (5):1047-53 (May 2004).
Williams et al., "Macrovascular disease in Diabetes." In handbook of Diabetes. 2nd ed. Williams G, Pickup JC, Eds. Oxford, UK, Blackwell Science pp. 151-158 (1999).
Wivioti et al., "Greater Clinical Benefit of More Intensive Oral Anti platelet Therapy With Prasugrel in Patients With Diabetes Mellitus in the Trial to Assess Improvement in Therapeutic Outcomes by Optimizing Platelet Inhibition With Prasugrei-Thrombolysis in Myocardial Infarction 38," Circulation, 2008, vol. 118 (16), pp. 1626-1636, Oct. 2008; Epub Aug. 31, 2008.
Wohlfart et al., "Cardioprotective effects of lixisenatide in rat myocardial ischemia- reperfusion injury studies" Journal of Translational Medicine, 11(1):84, 12 pages (Mar. 2013).
World Health Organisation Report on "Definition and Diagnosis of Diabetes Mellitus and Intermediate Hyperglycemia: Report of a WHO/IDF Consultation," 2006, pp. 1-50.
World Health Organization, "Definition, Diagnosis and Classification of Diabetes Mellitus and its Complications, Part 1: Diagnosis and Classification of Diabetes Mellitus," WHO/NCD/NCS/99.2, Geneva, 1999, pp. 1-66.
Wright et al., U.K. Prospective Diabetes Study Group. "Sulfonylurea inadequacy: efficacy of addition of insulin over years in patients with type 2 diabetes in the UK. Prospective Diabetes Study (UKPDS 57)." Diabetes Care 25 (2):330-36 (Feb. 2002).
Yusuf et al., "Effects of Clopidogrel in Addition to Aspirin in Patients with Acute Coronary Syndromes without ST-Segment Elevation." New England Journal Medical, Aug. 2001, vol. 345 (7), pp. 494-502.
Zimmet et al., "Global and societal implications of the diabetes epidemic." Nature 414(6865):782-87 (Dec. 2001).
Zoungas et al., "Combined Effects of Routine Blood Pressure Lowering and Intensive Glucose Control on Macrovascular and Microvascular Outcomes in Patients With Type 2 Diabetes. New results from the ADVANCE trial." Diabetes Care, 2009, vol. 32(11), pp. 2068-2074, Nov. 2009; Epub Aug. 3, 2009.
American Diabetes Association, "Diagnosis and Classification of Diabetes Mellitus", Diabetes Care, 37 (Supplement 1):S81-S90 (Jan. 2014).
American Diabetes Association Annual Scientific Sessions, "New Diabetes Compound AVE0010 Showed Clear Dose Response Results With Once-A-Day Injection in Phase IIbStudy", published Jun. 9, 2008, two pages.
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
Giacometti et al., "In vitro activity of the histatin derivative P-113 against multidrug-resistant pathogens responsible for pneumonia in immunocompromised patients." 49(3):1249-52 (Mar. 2005).
Glucophage XR, Product Information, Bristol-Meyers Squibb Company (Jan. 2009).
Lantus® Drug Description, downloaded Nov. 12, 2015, one page.
Miller et al., "Type 2 diabetes in the child and adolescent", In: Lifshitz F (ed) Pediatric Endocrinology: 5th edition, vol. 1, New York, Marcel Dekker, pp. 169-188 (2007).
Raman & Heptulla, "New potential adjuncts to treatment of children with type 1 diabetes mellitus" Pediatric Research, 65(4):370-74 (Apr. 2009).
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.
Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, pp:1-12 (2015). retrieved from the internet: http://en.sanofi.com/img/content/study/PKD11475_summary.pdf (issued Jan. 13, 2015; retrieved on Jun. 16, 2015).
Sanofi Presentation, "Natixis Conference on Diabetes" Pierre Chancel, pp. 1-23, Nov. 8, 2011.
Shehadeh et al., "Can GLP-1 preparations be used in children and adolescents with diabetes mellitus?" Pediatric Endocrinology Reviews, 11(3):324-27 (Mar. 2014).
Tanner & Davies, "Clinical longitudinal standards for height and height velocity for North American children." J Pediatr. 107(3):317-29 (Sep. 1985).
Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.
Wolever et al., "Second-meal effect: low-glycemic-index foods eaten at dinner improve subsequent breakfast glycemic response." Am J Clin Nutr 48(4):1041-47 (Oct. 1988).
Zeitler et al., "ISPAD Clinical Practice Consensus Guidelines 2014. Type 2 diabetes in the child and adolescent." Pediatr Diabetes 15(Suppl 20):26-46 (Sep. 2014).
Zimmet et al., "The metabolic syndrome in children and adolescents." Lancet 369(9579):2059-61 (Jun. 2007).
Final Rejection ssued in U.S. Appl. No. 13/123,835; dated Nov. 18, 2015, pp. 1-16.
Final Rejection issued in U.S. Appl. No. 13/382,442; dated Sep. 21, 2016, pp. 1-32.
Non-Final Rejection issued in U.S. Appl. No. 13/509,542; dated Nov. 23, 2016, pp. 1-34.
Final Rejection in U.S. Appl. No. 13/633,496; dated Oct. 13, 2016, pp. 1-10.
International Search Report by the ISA for International Application No. PCT/EP2009/000018; dated Jun. 30, 2009, pp. 1-8.
International Search Report by the ISA for International Application No. PCT/EP2016/050804; dated Mar. 4, 2016, pp. 1-4.
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
U.S. Appl. No. 14/995,910, filed Jan. 14, 2016, Bergmann et al.
U.S. Appl. No. 15/073,364, filed Mar. 17, 2016, Belder et al.
U.S. Appl. No. 15/068,286, filed Mar. 11, 2016, Roy et al.
U.S. Appl. No. 13/382,772, filed May 29, 2012, Schoette.
U.S. Appl. No. 13/382,442, filed Feb. 21, 2012, Schoette.
U.S. Appl. No. 13/509,507, filed Jul. 30, 2014, Brunner-Schwarz et al.
U.S. Appl. No. 13/509,542, filed Aug. 2, 2012, Hagendorf et al.
U.S. Appl. No. 14/172,151, filed Feb. 4, 2014, Bley et al.
U.S. Appl. No. 12/617,805, filed Nov. 13, 2009, Silvestre et al.
U.S. Appl. No. 12/617,811, filed Nov. 13, 2009, Silvestre et al.
U.S. Appl. No. 14/220,562, filed Mar. 20, 2014, Becker et al.

(56) References Cited

OTHER PUBLICATIONS

U.S. Appl. No. 13/700,631, filed Nov. 11, 2012, Becker et al.
U.S. Appl. No. 13/819,114, filed Apr. 29, 2013, Boka et al.
U.S. Appl. No. 13/363,956, filed Feb. 1, 2012, Silvestre et al.
U.S. Appl. No. 13/432,811, filed Mar. 28, 2012, Boka et al.
U.S. Appl. No. 13/469,633, filed May 11, 2012, Ruus et al.
U.S. Appl. No. 13/467,707, filed May 9, 2012, Niemoller et al.
U.S. Appl. No. 13/468,422, filed May 10, 2012, Silvestre et al.
U.S. Appl. No. 13/467,757, filed May 9, 2012, Silvestre et al.
U.S. Appl. No. 13/595,590, filed Aug. 27, 2012, Niemoller et al.
U.S. Appl. No. 13/602,913, filed Sep. 4, 2012, Hess et al.
U.S. Appl. No. 13/633,563, filed Oct. 2, 2012, Stechl et al.
U.S. Appl. No. 13/633,496, filed Oct. 2, 2012, Stechl et al.
U.S. Appl. No. 13/661,476, filed Oct. 26, 2012, Silvestre et al.
U.S. Appl. No. 14/303,895, filed Jun. 13, 2014, Souhami et al.
U.S. Appl. No. 13/123,835, filed Sep. 30, 2011, Werner et al.
18th World Health Congress (Helsinki). WMA Declaration of Helsinki—Ethical Principles for Medical Research Involving Human Subjects; WMA; Jun. 1964, pp. 1-8.
Abbas T., et al., "Impairment of Synaptic Plasticity and Memory formation in GLP-1 Receptor Ko Mice: Interaction Between Type 2 Diabetes and Alzheimer's Disease," Behavioural Brain Research, 2009, vol. 205 (1), pp. 265-271.
Action to Control Cardiovascular Risk in Diabetes Study Group, "Effects of Intensive Glucose Lowering in Type 2 Diabetes," The New England Journal of Medicine, 2008, vol. 358 (24), pp. 2545-2559.
Actrapid® prescribing information, Apr. 2011, pp. 1-4.
Actrapid® summary of product characteristics, Apr. 2011, pp. 1-11.
Aderinwale O.G., et al., "Current Therapies and New Strategies for the Management of Alzheimer's Disease," American Journal of Alzheimer's Disease and Other Dementias, 2010, vol. 25 (5), pp. 414-424.
Agholme L., et al., "An in Vitro Model for Neuroscience: Differentiation of SH-SY5Y Cells into Cells with Morphological and Biochemical Characteristics of Mature Neurons," Journal of Alzheimer's Disease, 2010, vol. 20, pp. 1069-1082.
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Ahualli J., "The Double Duct Sign," Radiology, 2007, vol. 244 (1), pp. 314-315.
Akbar D.H., "Sub-Optimal Postprandial Blood Glucose Level in Diabetics Attending the Outpatient Clinic of a University Hospital," Saudi Med Journal, 2003, vol. 24 (10), pp. 1109-1112.
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
Aoki K., et al., "Hydrolysis of Nonionic Surfactants," Annual Report Takeda Research Laboratory, 1968, vol. 27, pp. 172-176.
Apidra® prescribing information, Apr. 2012, pp. 1-6.
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Arnolds S., et al., "Basal Insulin Glargine Vs Prandial Insulin Lispro in Type 2 Diabetes," Lancet, 2008, vol. 378 (9636), pp. 370-371.
Arnolds S., et al., "Further Improvement in Postprandial Glucose Control with Addition of Exenatide or Sitagliptin to Combination therapy with Insulin Glargine and Metformin—A Proof-of-Concept Study," Diabetes Care, 2010, vol. 33 (7), pp. 1509-1515.
Auerbach R., et al., "Angiogenesis Assays: Problems and Pitfalls," Cancer Metastasis Reviews, 2000, vol. 19 (1-2), pp. 167-172.
Bakaysa D.L., et al., "Physicochemical Basis for the Rapid Time-Action of Lysb28 Prob29-Insulin: Dissociation of a Protein-Ligand Complex," Protein science, 1996, vol. 5 (12), pp. 2521-2531.

Banks W.A., et al., "Brain Uptake of the Glucagon-Like Peptide-1 Antagonist Exendin(9-39) After intranasal Administration," The Journal of Pharmacology and Experimental Therapeutics, 2004, vol. 309 (2), pp. 469-475.
Barnett A., "Dosing of Insulin Glargine in the Treatment of Type 2 Diabetes," Clinical Therapeutics, 2007, vol. 29 (6), pp. 987-999.
Barnett A.H., et al., "Tolerability and Efficacy of Exenatide and Titrated Insulin Glargine in Adult Patients with Type 2 Diabetes Previously Uncontrolled with Metformin or a Sulfonylurea: A Multinational, Randomized, Open-Label, Two-Period, Crossover Noninferiority Trial," Clinical Therapeutics, 2007, vol. 29 (11), pp. 2333-2348.
Barnett A.H., "Insulin Glargine in the Treatment of Type 1 and Type 2 Diabetes," Vascular Health and Risk Management, 2006, vol. 2 (1), pp. 59-67.
Barnett A.H., "Lixisenatide: Evidence for its Potential Use in the Treatment of Type 2 Diabetes," Core Evidence, 2011, vol. 6, pp. 67-79.
Barnett R.O., et al., "Insulin Analogues," Lancet, 1997, vol. 349 (9044), pp. 47-51.
Behar J., et al., "Functional Gallbladder and Sphincter of Oddi Disorders," Gastroenterology, 2006, vol. 130 (5), pp. 1498-1509.
Beintema J.J., et al., "Molecular Evolution of Rodent Insulins," Molecular Biology and Evolution, 1987, vol. 4 (1), pp. 10-18.
Berger M., "Towards More Physiological Insulin Therapy in the 1990s a Comment," Diabetes Research and Clinical Practice, 1989, vol. 6 (4), pp. S25-S31.
Berlie H., et al., "Glucagon-Like Peptide-1 Receptor Agonists as Add-On therapy to Basal Insulin in Patients with Type 2 Diabetes: A Systematic Review," Diabetes, Metabolic Syndrome and Obesity: Targets and Therapy, 2012, vol. 5, pp. 165-174.
Berlinsulin® H prescribing information, Apr. 2012, pp. 1-4.
Berlinsulin® H summary of product characteristics, Apr. 2012, pp. 1-11.
Bertram L., et al., "The Genetics of Alzheimer Disease: Back to the Future," Neuron, 2010, vol. 68 (2), pp. 270-281.
Best, Mathmatics and Statistics pp. 1-39, 1988.
Bethel M.A., et al., "Basal Insulin Therapy in Type 2 Diabetes," The Journal of the American Board of the Family Practice, 2005, vol. 18 (3), pp. 199-204.
Bhatt N.P., et al., "Chemical Pathways of Peptide Degradation. I. Deamidation of Adrenocorticotropic Hormone," Pharmaceutical Research, 1990, vol. 7 (6), pp. 593-599.
Blanchard V., et al., "Time Sequence of Maturation of Dystrophic Neurites Associated with Abeta Deposits in APP/PS1 Transgenic Mice," Experimental Neurology, 2003, vol. 184, pp. 247-263.
Bland J.M., et al., "Measurement Error," British Medical Journal, 1996, vol. 312 (7047), pp. 1654.
Bolen S., et al., "Systematic Review: Comparative Effectiveness and Safety of oral Medications for Type 2 Diabetes Mellitus," Annals of Internal Medicine, 2007, vol. 147 (6), pp. 386-399.
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli G.B., et al., "Efficacy and Safety of Lixisenatide once Daily Vs Placebo in People with Type 2 Diabetes Insufficiently Controlled on Metformin (Getgoal-F1)," Diabetic Medicine, 2014, vol. 31 ( 2), pp. 176-184.
Bolli G.B., "The Pharmacokinetic Basis of Insulin Therapy in Diabetes Mellitus," Diabetes Research and Clinical Practice, 1989, vol. 6 (4), pp. S3-S15.
Boutajangout A., et al., "Characterisation of Cytoskeletal Abnormalities in Mice Transgenic for Wild-Type Human Tau and Familial Alzheimer's Disease Mutants of APP and Presenilin-1," Neurobiology of Disease, 2004, vol. 15 (1), pp. 47-60.
Boutajangout A., et al., "Increased Tau Phosphorylation But Absence of formation of Neurofibrillary Tangles in Mice Double Transgenic for Human Tau and Alzheimer Mutant (M146L) Presenilin-1," Neuroscience Letters, 2002, vol. 318 (1), pp. 29-33.
Brange "Galenics of Insulin" 1987, p. 35-36.

(56) References Cited

OTHER PUBLICATIONS

Brange J., et al., "Chemical Stability of Insulin 3. Influence of Excipients, formulation, and Ph," Acta Pharmaceutica Nordica, 1992, vol. 4 (3), pp. 149-158.
Brange J., et al., "Design of Insulin Analogues for Meal-Related therapy," Journal of Diabetes and Its Complications, 1993, vol. 7 (2), pp. 106-112.
Brange J., et al., "Insulin Structure and Stability," Pharmaceutical Biotechnology, 1993, vol. 5, pp. 315-350.
Brange J., et al., "Monomeric Insulins and their Experimental and Clinical Implications," Diabetes Care, 1990, vol. 13 (9), pp. 923-954.
Brange J., et al., "Neutral Insulin Solutions Physically Stabilized by Addition of Zn2+," Diabetic Medicine, 1986, vol. 3, pp. 532-536.
Brange J., et al., "Toward Understanding Insulin Fibrillation," Journal of Pharmaceutical Sciences, 1997, vol. 86 (5), pp. 517-525.
Brod M., et al., "Adherence Patterns in Patients with Type 2 Diabetes on Basal Insulin Analogues: Missed, Mistimed and Reduced Doses," Current Medical Research and Opinion, 2012, vol. 28 (12), pp. 1933-1946.
Brod M., et al., "Examining Correlates of Treatment Satisfaction for injectable Insulin in Type 2 Diabetes: Lessons Learned from a Clinical Trial Comparing Biphasic and Basal Analogues," Health Quality of Life Outcomes, 2007, vol. 5, pp. 1-10.
Broderick J., et al., "Guidelines for the Management of Spontaneous intracerebral Hemorrhage in Adults," Circulation, 2007, vol. 116 (16), pp. e391-e413.
Brown J.B., et al., "Slow Response to Loss of Glycemic Control in Type 2 Diabetes Mellitus," American Journal of Managed Care, 2003, vol. 9 (3), pp. 213-217.
"Buffer" Oxford Dictionary of Biochemistry and Molecular Biology, Oxford University Press, 2001, p. 83.
Burgermeister W., et al., "The Isolation of Insuin from the Pancreas," Insulin, 1975, vol. Part 2, pp. 715-727.
Burke G.T., et al., "Nature of the B10 Amino Acid Residue Requirements for High Biological Activity of Insulin," International Journal of Peptide and Protein Research, 1984, vol. 23 (4), pp. 394-401.
Buse J.B., et al., "Use of Twice-Daily Exenatide in Basal Insulin-Treated Patients with Type 2 Diabetes: A Randomized, Controlled Trial," Annals of Internal Medicine, 2011, vol. 154 (2), pp. 103-112.
Byetta—Summary of Product Characteristics, updated Jan. 27, 2015, last accessed Apr. 18, 2015, pp. 1-12.
Byrne M.M., et al., "Inhibitory Effects of Hyperglycaemia on Fed Jejunal Motility: Potential Role of Hyperinsulinaemia," European Journal of Clinical Investigation, 1998, vol. 28 (1), pp. 72-78.
Cadario B., "SITAGLIPTIN," Drug Information Perspectives, 2010, vol. 30 (4), pp. 1-6.
Campas C., et al., "Ave-0010 GLP-1 Receptor Agonist Treatment of Diabetes," Drugs of the Future, 2008, vol. 33 (10), pp. 838-840.
Campbell R.K., et al., "Insulin Glargine," Clinical Therapeutics, 2001, vol. 23 (12), pp. 1938- 1957.
Casas C., et al., "Massive CA1/2 Neuronal Loss with Intraneuronal and N-Terminal Truncated Abeta42 Accumulation in a Novel Alzheimer Transgenic Model," American Journal of Pathology, 2004, vol. 165 (4), pp. 1289-1300.
Chancel, "Natixis Conference on Diabetes." Sanofi, Paris, pp. 1-23 (Nov. 8, 2011).
Charles M.A., et al., "Prevention of Type 2 Diabetes: Role of Metformin," Drugs, 1999, vol. 58 (Suppl 1), pp. 71-73.
Chatterjee S., et al., "Insulin Glargine and its Place in the Treatment of Types 1 and 2 Diabetes Mellitus," Expert Opinion on Pharmacotherapy, 2006, vol. 7 (10), pp. 1357-1371.
Chen Y.E., et al., "Tissue-Specific Expression of Unique mRNAs That Encode Proglucagon-Derived Peptides or Exendin 4 in the Lizard," The Journal of Biological Chemistry, 1997, vol. 272 (7), pp. 4108-4115.
Cheung Y.T., et al., "Effects of All-Trans-Retinoic Acid on Human SH-SY5Y Neuroblastoma as in Vitro Model in Neurotoxicity Research," Neurotoxicology, 2009, vol. 30 (1), pp. 127-135.

Childs B.P., et al., "Defining and Reporting Hypoglycemia in Diabetes: A Report from the American Diabetes Association Workgroup on Hypoglycemia," Diabetes Care, 2005, vol. 28 (5), pp. 1245-1249.
Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Christensen M., et al., "Lixisenatide, A Novel GLP-1 Receptor Agonist for the Treatment of Type 2 Diabetes Mellitus," IDrugs: The Investigational Drugs Journal, 2009, vol. 12 (8), pp. 503-513.
Christensen M., et al., "Lixisenatide for Type 2 Diabetes Mellitus," Expert Opinion on Investigational Drugs, 2011, vol. 20 (4), pp. 549-557.
Cochran E., et al., "The Use of U-500 in Patients with Extreme Insulin Resistance," Diabetes Care, 2005, vol. 28 (5), pp. 1240-1244.
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino E., et al., "Therapy with Insulin Glargine (Lantus) in toddlers, Children and Adolescents with Type 1 Diabetes," Diabetes Research and Clinical Practice, 2005, vol. 70 (1), pp. 1-7.
FDA Frequently Asked Questions about Combination Products;accessed from www.fda.gov/CombinationProducts/AboutCombinationProducts/usm101496.1/htm, 2009 downloaded Jul. 13, 2012, pp. 1-18.
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Crapo P.A., et al., "Postprandial Plasma-Glucose and—Insulin Responses to Different Complex Carbohydrates," Diabetes, 1977, vol. 26 (12), pp. 1178-1183.
Croom K.F., et al., "Liraglutide a Review of its Use in Type 2 Diabetes Mellitus," Drugs, 2009, vol. 69 (14), pp. 1985-2004.
Cryer P.E., "Hypoglycemia Is the Limiting Factor in the Management of Diabetes," Diabetes/Metabolism Research and Reviews, 1999, vol. 15 (1), pp. 42-46.
Cvetkovic R.S., et al., "Exenatide a Review of its Use in Patients with Type 2 Diabetes Mellitus (As an Adjunct to Metformin and/or a Sulfonylurea)," Drugs, 2007, vol. 67 (6), pp. 935-954.
Czech C., et al., "Proteolytical Processing of Mutated Human Amyloid Precursor Protein in Transgenic Mice," Brain Research Molecular Brain Research, 1997, vol. 47 (1-2), pp. 108-116.
D'Alessio D., "GLP-1 Receptor Agonists: Strategies for PPG Control," Medical Nursing Education, 2011, vol. 3, pp. 1-26.
D'Alessio D.A., et al., "Glucagon-Like Peptide 1 Enhances Glucose tolerance both by Stimulation of Insulin Release and by increasing Insulin-Independent Glucose Disposal," Journal of Clinical Investigation, 1994, vol. 93 (5), pp. 2263-2266.
Database, Adiscti, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
De Arriba S.G., et al., "Carbonyl Stress and Nmda Receptor Activation Contribute to Methylglyoxal Neurotoxicity," Free Radical Biology and Medicine, 2006, vol. 40 (5), pp. 779-790.
De La Pena A., et al., "Pharmacokinetics and Pharmacodynamics of High-Dose Human U-500 Insulin Versus Human Regular U-100 Insulin in Healthy Obese Subjects," Diabetes Care, 2011, vol. 34 (12), pp. 2496-2501.
De Rosa R., et al., "Intranasal Administration of Nerve Growth Factor (Ngf) Rescues Recognition Memory Deficits in Ad11 Anti-

(56) References Cited

OTHER PUBLICATIONS

Ngf Transgenic Mice," Proceedings of the National Academy of Sciences of the United States of America, 2005, vol. 102 (10), pp. 3811-3816.
Deacon C.F., et al., "Dipeptidyl Peptidase IV inhibition Potentiates the Insulinotropic Effect of Glucagon-Like Peptide 1 in the Anesthetized Pig," Diabetes, 1998, vol. 47 (5), pp. 764-769.
Deacon C.F., et al., "Dipeptidyl Peptidase IV Resistant Analogues of Glucagon-Like Peptide-1 Which have Extended Metabolic Stability and Improved Biological Activity," Diabetologia, 1998, vol. 41 (3), pp. 271-278.
Definition of indication, Merriam-Webster online, accessed Oct. 22, 2015, 2 pages.
Definition of palliative, http://medicaldictionary.thefreedictionary.com/, accessed on Nov. 6, 2014, pp. 1-2.
Definition of sphincter of pancreatic duct in the Medical Dictionary, http://medicaldictionary.thefreedictionary.com/, accessed on May 22, 2014, pp. 1-2.
Defronzo R.A., et al., "Effects of Exenatide (Exendin-4) on Glycemic Control and Weight Over 30 Weeks in Metformin-Treated Patients with Type 2 Diabetes," Diabetes care, 2005, vol. 28 (5), pp. 1092-1100.
Defronzo R.A., "Pathogenesis of Type 2 Diabetes: Implications for Metformin," Drugs, 1999, vol. 58 (Suppl 1), pp. 29-30.
Defronzo R.A., "Pharmacologic therapy for Type 2 Diabetes Mellitus," Annals of Internal Medicine, 1999, vol. 131 (4), pp. 281-303.
Delatour B., et al., "Alzheimer Pathology Disorganizes Cortico-Cortical Circuitry: Direct Evidence from a Transgenic Animal Model," Neurobiology of Disease, 2004, vol. 16 (1), pp. 41-47.
Devries J.H., et al., "Sequential intensification of Metformin Treatment in Type 2 Diabetes with Liraglutide Followed by Randomized Addition of Basal Insulin Prompted by AlC Targets," Diabetes Care, 2012, vol. 35 (7), pp. 1446-1454.
Dewitt D.E., "Case Study: Treating New on-Set Catabolic Type 2 Diabetes with Glargine and Lispro," Clinical Diabetes, 2006, vol. 24 (4), pp. 180-181.
Diabetes Prevention Program Research Group, "Reduction in the incidence of Type 2 Diabetes with Lifestyle intervention or Metformin," The New England Journal of Medicine, 2002, vol. 346 (6), pp. 393-403.
Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dixon G.H., et al., "Regeneration of Insulin Activity from the Separated and inactive A and B Chains," Nature, 1960, vol. 188 (4752), pp. 721-724.
Donelli G., et al., "Plastic Biliary Stent Occlusion: Factors Involved and Possible Preventive Approaches," Clinical Medicine & Research, 2007, vol. 5 (1), pp. 53-60.
Dormandy J.A., et al., "Secondary Prevention of Macrovascular Events in Patients with Type 2 Diabetes in the Proactive Study (Prospective Pioglitazone Clinical Trial in Macrovascular Events): A Randomised Controlled Trial," Lancet, 2005, vol. 366 (9493), pp. 1279-1289.
Doyle M.E. et al., "Mechanisms of Action of Glucagon-Like Peptide 1 in the Pancreas," Pharmacology & Therapeutics, 2007, vol. 113 (3), pp. 546-593.
Drucker D.J. et al., "The incretin System: Glucagon-Like Peptide-1 Receptor Agonists and Dipeptidyl Peptidase-4 inhibitors in Type 2 Diabetes," Lancet, 2006, vol. 368 (9548), pp. 1696-1705.
Drucker D.J., "Glucagon-Like Peptides," Diabetes, 1998, vol. 47 (2), pp. 159-169.
Drucker D.J., "Mini Review: the Glucagon-Like Peptides," Endocrinology, 2001, vol. 142 (2), pp. 521-527.
Drucker D.J., "The Biology of Incretin Hormones," Cell Metabolism, 2006, vol. 3 (3), pp. 153-165.
DrugBank, "Insulin glargine," available online at http://www.drugbank.ca/drugs/DB00047, 16 pages (accessed online Sep. 25, 2014).
Drury P.L., et al., "Diabetic Nephropathy," British Medical Bulletin, 1989, vol. 45 (1), pp. 127-147.
Dubois B., et al., "Revising the Definition of Alzheimer's Disease: A New Lexicon," Lancet Neurology, 2010, vol. 9 (11), pp. 1118-1127.
Dunn C.J., et al., "Insulin Glargine: An Updated Review of its Use in the Management of Diabetes Mellitus," Drugs, 2003, vol. 63 (16), pp. 1743-1778.
During M.J., et al., "Glucagon-Like Peptide-1 Receptor is involved in Learning and Neuroprotection," Nature Medicine, 2003, vol. 9 (9), pp. 1173-1179.
Eckert A., et al., "Alzheimer's Disease-Like Alterations in Peripheral Cells from Presenilin-1 Transgenic Mice," Neurobiology of Disease, 2001, vol. 8 (2), pp. 331-342.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6017; Clinical Trial Eudra CT No. 2007-005884-92, accessed Apr. 24, 2015, one page.
EFC6018; Clinical trial EudraCT 2007-005887-29, "GETGOAL—MONO" accessed Jul. 27, 2014; pp. 1-16.
EMA—Science Medicines Health "TOUJEO" EPAR Summary for the Public, first published Nov. 5, 2009, pp. 1-3.
EMA Press Release, "European Medicines Agency recommends suspension of Avandia, Avandamet and Avaglim" pp. 1-2 (Sep. 23, 2010).
English translation of Search Report for Chinese Patent Application No. 201280053404.6; dated Feb. 10, 2015, pp. 1-3.
English translation of Search Report for Chinese Patent Application No. 20140220537.9; dated Feb. 13, 2015, pp. 1-2.
European Medicines Agency—Science Medicines Health, "Guideline on clinical investigation of medicinal products in the treatment of diabetes mellitus" Committee for Medicinal Products for Human Use, Jan. 20, 2010, pp. 1-19.
Ex Parte Herrmann, Appeal No. 2009-001777 U.S. Appl. No. 10/616,457 (B. Pai. Nov. 13, 2009).
Executive Summary, "Standards of Medical Care in Diabetes—2009" Diabetes Care,32(Suppl. 1):S6-S12 (Jan. 2009).
Extended European Search Report for Euorpean Application No. 98 11 0889.7; dated Oct. 14, 1998, pp. 1-4.
Extended European Search Report for European Application No. 09 17 5876.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 6, 2011, pp. 1-12.
Extended European Search Report for European Application No. 11 16 0270.2; dated Sep. 19, 2011, pp. 1-8.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 305 126; dated Apr. 11, 2013, pp. 1-7.
Extended European Search Report for European Application No. 13 305 432.0; dated Sep. 13, 2013, pp. 1-5.
Extended European Search Report for European Application No. 14 16 6877.2; dated Aug. 18, 2014, pp. 1-6.
Extended European Search Report for European Application No. 14 19 7154.9: dated Apr. 8, 2015, pp. 1-7.
Fabunmi R., et al., "Patient Characteristics, Drug Adherence Patterns, and Hypoglycemia Costs for Patients with Type 2 Diabetes

(56) References Cited

OTHER PUBLICATIONS

Mellitus Newly initiated on Exenatide or Insulin Glargine," Current Medical Research and Opinion, 2009, vol. 25 (3), pp. 777-786.
Faivre E., et al., "Effects of Gip Analogues in Neuronal Signalling, Cell Proliferation and Learning and Memory," Regulatory Peptides, 2010, vol. 164 (1), pp. 40-41.
FDA Guidance for Industry, US Department of Health and Human Services, Food and Drug Administration, Center for Drug Evaluation and Research (COER), pp. 1-11, Feb. 2014.
FDA label of Apidra®, May 2014, pp. 1-35.
FDA label of Humalog®, Mar. 2013, pp. 1-27.
FDA label of Lantus®, Oct. 2013, pp. 1-44.
Feinglos M.N., et al., "Effects of Liraglutide (Nn2211), A Long-Acting GLP-1 Analogue, on Glycaemic Control and Bodyweight in Subjects with Type 2 Diabetes," Diabetic Medicine, 2005, vol. 22 (8), pp. 1016-1023.
Fieller E.C., "Symposium on Interval Estimation; Some Problems with Interval Estimation," Journal of the Royal Statistical Society, 1954, vol. 16 (2), pp. 175-185.
Final Office Action from U.S. Appl. No. 12/617,805; dated Feb. 11, 2013, pp. 1-13.
Final Office Action from U.S. Appl. No. 12/617,805; dated Jan. 12, 2012, pp. 1-14.
Final Office Action from U.S. Appl. No. 12/617,805; dated Jan. 13, 2015, pp. 1-11.
Final Office Action issued in U.S. Appl. No. 13/602,913; dated Apr. 2, 2015, pp. 1-7.
Final Office Action issued in U.S. Appl. No. 13/602,913; dated Jun. 20, 2014, pp. 1-27.
Final Office Action issued in U.S. Appl. No. 13/602,913; dated Sep. 13, 2013, pp. 1-11.
Final Rejection in U.S. Appl. No. 13/633,496; dated Nov. 18, 2014, pp. 1-11.
Final Rejection in U.S. Appl. No. 13/633,496; dated Nov. 4, 2013, pp. 1-7.
Final Rejection in U.S. Appl. No. 13/633,563; dated Apr. 22, 2015, pp. 1-12.
Final Rejection in U.S. Appl. No. 13/633,563; dated Dec. 16, 2013, pp. 1-58.
Final Rejection issued in U.S. Appl. No. 14/172,151; dated Jul. 20, 2015, pp. 1-18.
Final Rejection issued in U.S. Appl. No. 12/617,811; dated Jan. 4, 2013, pp. 1-6.
Final Rejection issued in U.S. Appl. No. 12/617,811; dated Jul. 31, 2015, pp. 1-15.
Final Rejection issued in U.S. Appl. No. 13/110,568; dated Feb. 21, 2013, pp. 1-20.
Final Rejection issued in U.S. Appl. No. 13/310,118; dated Aug. 2, 2012, pp. 1-20.
Final Rejection issued in U.S. Appl. No. 13/363,956; dated May 20, 2014, pp. 1-16.
Final Rejection issued in U.S. Appl. No. 13/382,442; dated Jul. 17, 2013, pp. 1-30.
Final Rejection issued in U.S. Appl. No. 13/382,442; dated Jun. 13, 2014, pp. 1-29.
Final Rejection issued in U.S. Appl. No. 13/382,772; dated Jun. 3, 2014, pp. 1-34.
Final Rejection issued in U.S. Appl. No. 13/382,772; dated Feb. 10, 2015, pp. 1-36.
Final Rejection issued in U.S. Appl. No. 13/467,707; dated Feb. 25, 2014, pp. 1-18.
Final Rejection issued in U.S. Appl. No. 13/467,707; dated Jan. 7, 2015, pp. 1-8.
Final Rejection issued in U.S. Appl. No. 13/468,422; dated Jan. 6, 2014, pp. 1-21.
Final Rejection issued in U.S. Appl. No. 13/468,422; dated Jan. 23, 2015, pp. 1-27.
Final Rejection issued in U.S. Appl. No. 13/469,633; dated Dec. 4, 2013, pp. 1-17.
Final Rejection issued in U.S. Appl. No. 13/469,633; dated Jan. 23, 2015, pp. 1-12.
Final Rejection issued in U.S. Appl. No. 13/509,507; dated Jul. 23, 2015, pp. 1-11.
Final Rejection issued in U.S. Appl. No. 13/509,542; dated Nov. 21, 2013, pp. 1-34.
Final Rejection issued in U.S. Appl. No. 13/509,542, dated Jan. 28, 2015, pp. 1-26.
Final Rejection issued in U.S. Appl. No. 13/595,590; dated Apr. 2, 2014, pp. 1-7.
Final Rejection issued in U.S. Appl. No. 13/595,590; dated Dec. 19, 2014, pp. 1-14.
Final Rejection issued in U.S. Appl. No. 13/661,476, dated Oct. 2, 2014, pp. 1-33.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Final Rejection issued in U.S. Appl. No. 13/700,631; dated Apr. 13, 2015, pp. 1-19.
Final Rejection issued in U.S. Appl. No. 13/700,631; dated Jun. 18, 2014, pp. 1-25.
Final Rejection issued in U.S. Appl. No. 13/819,114; dated Mar. 2, 2015, pp. 1-10.
Final-Rejection issued in U.S. Appl. No. 13/432,811; dated Dec. 12, 2014, pp. 1-8.
Final-Rejection issued in U.S. Appl. No. 13/432,811; dated Mar. 31, 2015, pp. 1-9.
Final-Rejection issued in U.S. Appl. No. 13/432,811; dated Sep. 6, 2014, pp. 1-8.
Fonseca V.A., et al., "Efficacy and Safety of the once-Daily GLP-1 Receptor Agonist Lixisenatide in Monotherapy: A Randomized, Double-Blind, Placebo-Controlled Trial in Patients with Type 2 Diabetes (Getgoal-Mono)," Diabetes Care, 2012, vol. 35 (6), pp. 1225-1231.
Fox J.D., et al., "Single Amino Acid Substitutions on the Surface of *Escherichia coli* Maltose-Binding Protein can have a Profound Impact on the Solubility of Fusion Proteins," Protein Science, 2001, vol. 10 (3), pp. 622-630.
Fransson J., et al., "Oxidation of Human Insulin-Like Growth Factor I in formulation Studies: Kinetics of Methionine Oxidation in Aqueous Solution and in Solid State," Pharmaceutical Research, 1996, vol. 13 (8), pp. 1252-1257.
Galloway J.A., et al., "New forms of Insulin," Diabetes, 1972, vol. 21 (2 Suppl), pp. 637-648.
Gallwitz B., "Liraglutide. GLP-1 Receptor Agonist Treatment of Type 2 Diabetes Treatment of Obesity," Drugs of the Future, 2008, vol. 33 (1), pp. 13-20.
Gandhi S., et al., "Molecular Pathogenesis of Parkinson's Disease," Human Molecular Genetics, 2005, vol. 14 (18), pp. 2749-2755.
Garber A., et al., "Liraglutide Versus Glimepiride Monotherapy for Type 2 Diabetes (Lead-3 Mono): A Randomised, 52-Week, Phase III, Double-Blind, Parallel-Treatment Trial," The Lancet, 2009, vol. 373 (9662), pp. 473-481.
Garg R., et al., "U-500 Insulin: Why, When and How to Use in Clinical Practice," Diabetes/Metabolism Research and Reviews, 2007, vol. 23 (4), pp. 265-268.
Garriques L.N., et al., "The Effect of Mutations on the Structure of Insulin Fibrils Studied by Fourier Transform infrared (FTIR) Spectroscopy and Electron Microscopy," Journal of Pharmaceutical Sciences, 2002, vol. 91 (12), pp. 2473-2480.
Gault V.A., et al., "GLP-1 Agonists Facilitate Hippocampal Ltp and Reverse the Impairment of LTP induced by Beta-Amyloid," European Journal of Pharmacology, 2008, vol. 587 (1-3), pp. 112-117.
Gavin J.R., "Report of the Expert Committee on the Diagnosis and Classification of Diabetes Mellitus," Diabetes Care, 1997, vol. 20 (7), pp. 1183-1197.
Geiger R., "The Chemistry of Insulin," Chemiker Zeitung, 1976, vol. 100 (3), pp. 54-56.
Gengler S., et al., "Val(8)GLP-1 Rescues Synaptic Plasticity and Reduces Dense Core Plaques in APP/PS1 Mice," Neurobiology of Aging, 2012, vol. 33 (2), pp. 265-276.

(56) References Cited

OTHER PUBLICATIONS

Gerich et al., "Monotherapy with GLP-1 receptor agonist, Lixisenatide, significantly improves glycaemic control in type 2 diabetic patients," Diabetologia 53(Supplement 1)p. S330, Abstract 830, Presented at 46th Annual Meeting of EASD, Stockholm, Sweden, p. 1 (Sep. 2010).
Giugliano D., et al., "Treatment Regimens with Insulin Analogues and Haemoglobin A1C Target <7% in Type 2 Diabetes: A Systematic Review," Diabetes Research and Clinical Practice, 2010, vol. 92 (1), pp. 1-10.
Goke R., et al., "Distribution of GLP-1 Binding Sites in the Rat Brain: Evidence That Exendin-4 is a Ligand of Brain GLP-1 Binding Sites," European Journal of Neuroscience, 1995, vol. 7 (11), pp. 2294-2300.
Goldstein D.E., et al., "Tests of Glycemia in Diabetes," Diabetes Care, 1995, vol. 18 (6), pp. 896-909.
Gough K., et al., "Assessment of Dose Proportionality: Report from the Statisticians in the Pharmaceutical Industry/ Pharmacokinetics UK Joint Working Party," Drug Information Journal, 1995, vol. 29, pp. 1039-1048.
Goykhman S., et al., "Insulin Glargine: A Review 8 Years After its introduction," Expert Opinion on Pharmacotherapy, 2009, vol. 10 (4), pp. 705-718.
Greig N.H., et al., "Once Daily Injection of Exendin-4 to Diabetic Mice Achieves Long-Term Beneficial Effects on Blood Glucose Concentrations," Diabetologia, 1999, vol. 42 (1), pp. 45-50.
European Medicines Agency, "Toujeo (previously Optisulin) insulin glargine," <http://www.ema.europa.eu/ema/index.jsp?curl=pages/medicines/human/medicines/000309/human_med_000955.jsp&mid=WCOb01ac058001d124>, last updated Jan. 25, 2016, visited Feb. 3, 2016, pp. 1-6—screenshot of "About" tab of webpage and printouts of "About" tab of webpage with listed items collapsed and expanded.
NHSC—National Horizon Scanning Center, "AVE0010 (ZP10) for type 2 diabetes mellitus" University of Birmingham, England; pp. 1-6 (Dec. 2008).
Gura T., "Systems for Identifying New Drugs are often Faulty," Science, 1997, vol. 278 (5340), pp. 1041-1042.
Gutniak M., et al., "Antidiabetogenic Effect of Glucagon-Like Peptide-1 (7-36) Amide in Normal Subjects and Patients with Diabetes Mellitus," The New England Journal of Medicine, 1992, vol. 326 (20), pp. 1316-1322.
Gygi S.P., et al, "Quantitative Analysis of Complex Protein Mixtures Using Isotope-Coded Affinity Tags," Nature Biotechnology, 1999, vol. 17 (10), pp. 994-999.
Hamilton A., et al., "Novel GLP-1 Mimetics Developed to Treat Type 2 Diabetes Promote Progenitor Cell Proliferation in the Brain," Journal of Neuroscience Research, 2011, vol. 89 (4), pp. 481-489.
Hamilton A., et al., "Receptors for the incretin Glucagon-Like Peptide-1 are Expressed on Neurons in the Central Nervous System," NeuroReport, 2009, vol. 20 (13), pp. 1161-1166.
Hanas R., et al., "2010 Consensus Statement on the Worldwide Standardization of the Hemoglobin A1C Measurement," Diabetes Care, 2010, vol. 33 (8), pp. 1903-1904.
Hanefeld M., et al., "The Postprandial State and the Risk of Atherosclerosis," Diabetic Medicine, 1997, vol. 14 (Suppl 3), pp. S6-S11.
Hanefeld M., "Normnahe Postprandiale Hyperglykamie-Eine Essenzielle Komponente Guter Diabeteskontrolle Und Pravention Kardiovaskularer Erkrankungen (Near-Normal Postprandial Hyperglycemia—An Essential Component of Good Diabetes Control and Prevention of Cardiovascular Diseases)," Paul Langerhans Lecture Diabetologie and Stoffwechsel, 2007, vol. 2, pp. 362-369.
Hanna et al., "Canadian Diabetes Association Clinical Practice Guidelines Expert Committee Pharmacologic Management of Type 2 Diabetes," Canadian Journal of Diabetes, 2003, vol. 27 (Supp 2), pp. S37-S42.
Harkavyi A., et al., "Glucagon-Like Peptide I Receptor Stimulation Reverses Key Deficits in Distinct Rodent Models of Parkinson's Disease," Journal of Neuroinflammation, 2008, vol. 5 (19), pp. 1-9.
Harris S.B., et al., "Clinical inertia in Patients with T2Dm Requiring Insulin in Family Practice," Canadian Family Physician, 2010, vol. 56 (12), pp. e418-e424.
Hartmann H., et al., "Biological Activity of Des-(B26-B30)-Insulinamide and Related Analogues in Rat Hepatocyte Cultures," Diabetologia, 1989, vol. 32 (7), pp. 416-420.
Hellstrom M., et al., "T1388 GTP-010 as a Therapetuic tool in IBS Pain Relief: Prospective, Randomized, Palebo-Controlled Study of a GLP-1 Analog," Gastroenterology, 2008, vol. 134 (4), pp. A-544.
Higgins G.C., et al., "Oxidative Stress: Emerging Mitochondrial and Cellular themes and Variations in Neuronal Injury," Journal of Alzheimer's Disease, 2010, vol. 20, pp. S453-S473.
Himeno T., et al., "Beneficial Effects of Exendin-4 on Experimental Polyneuropathy in Diabetic Mice," Diabetes, 2011, vol. 60 (9), pp. 2397-2406.
Hinds K., et al., "Synthesis and Characterization of Poly(Ethylene Glycol)-Insulin Conjugates," Bioconjugate Chemistry, 2000, vol. 11 (2), pp. 195-201.
HOE 901/2004 Study Investigators Group, "Safety and Efficacy of Insulin Glargine (Hoe 901) Versus NPH Insulin in Combination with oral Treatment in Type 2 Diabetic Patients," Diabetic Medicine, 2003, vol. 20, pp. 545-551.
Holman R.R., et al., "10-Year Follow-Up of intensive Glucose Control in Type 2 Diabetes," The New England Journal of Medicine, 2008, vol. 359 (15), pp. 1577-1589.
Holscher C., "Development of Beta-Amyloid-induced Neurodegeneration in Alzheimer's Disease and Novel Neuroprotective Strategies," Reviews in the Neurosciences, 2005, vol. 16 (3), pp. 181-212.
Holscher C., et al., "New Roles for Insulin-Like Hormones in Neuronal Signalling and Protection: New Hopes for Novel Treatments of Alzheimer's Disease?," Neurobiology of Aging, 2008, vol. 31 (9), pp. 1495-1502.
Holscher C., "Incretin Analogues that have been Developed to Treat Type 2 Diabetes Hold Promise as a Novel Treatment Strategy for Alzheimer's Disease," Recent Patents on Cns Drug Discovery, 2010, vol. 5 (2), pp. 109-117.
Holscher C., "Possible Causes of Alzheimer's Disease: Amyloid Fragments, Free Radical, and Calcium Homeostasis," Neurobiology of Disease, 1998, vol. 5 (3), pp. 129-141.
Holscher C., "The Role of GLP-1 in Neuronal Activity and Neurodegeneration," Vitamins and Hormones, 2010, vol. 84, pp. 331-354.
Holst J.J., et al., "Combining GLP-1 Receptor Agonists with Insulin: therapeutic Rationales and Clinical Findings," Diabetes, Obesity and Metabolism, 2013, vol. 15 (1), pp. 3-14.
Home P.D., et al., "Insulin Treatment: A Decade of Change," British Medical Bulletin, 1989, vol. 45 (1), pp. 92-110.
http://diabetes.emedtv.com/lantus/generic-lantus.html; one page, last accessed Dec. 23, 2015.
Humalog® prescribing information, Apr. 2012, pp. 1-6.
Hunter K., et al., "Drugs Developed to Treat Diabetes, Liraglutide and Lixisenatide, Cross the Blood Brain Barrier and Enhance Neurogenesis," BMC Neuroscience, 2012, vol. 13, pp. 1-6.
Inpharma, Product News. "AVE0010 set to deliver in type 2 diabetes mellitus," Database Adisnews, retrieved from STN, Jun. 2008, pp. 1-3.
"Insulin Aspart Injection." Formulated Preparations: Specific Monographs. British Pharmacopoeia 3. pp. 1-3 (2012).
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.

(56) References Cited

OTHER PUBLICATIONS

International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-16.
International Search Report by the ISA for International Application No. PCT/EP2012/055660; dated May 10, 2012, pp. 1-6.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/069485; dated Dec. 11, 2012, pp. 1-5.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4.
Inzucchi S.E., et al., "Management of Hyperglycemia in Type 2 Diabetes: A Patient-Centered Approach," Diabetes Care, 2012, vol. 35, pp. 1364-1379.
Isacson R., et al., "The Glucagon-Like Peptide 1 Receptor Agonist Exendin-4 improves Reference Memory Performance and Decreases Immobility in the forced Swim Test," European Journal of Pharmacology, 2009, vol. 650 (1), pp. 249-255.
ISPAD, International Diabetes Federation; "Global/IDF/ISPAD Guideline for Diabetes in Childhood and Adolescence," pp. 1-132 (2011).
Jackson R.L., et al., "Neutral Regular Insulin," Diabetes, 1972, vol. 21 (4), pp. 235-245.
Jain R.K., "Barriers to Drug Delivery in Solid Tumors," Scientific American, 1994, vol. 271 (1), pp. 58-65.
Jang J.H., et al., "Neuroprotective Effects of *Triticum aestivum* L. Against B-Amyloid-induced Cell Death and Memory Impairments," Phytotherapy Research, 2010, vol. 24 (1), pp. 76-84.
Jekel P.A., et al., "Use of Endoproteinase Lys-C from Lysobacter Enzymogenes in Protein Sequence Analysis," Analytical Biochemistry, 1983, vol. 134 (2), pp. 347-354.
Jendle J., et al., "Insulin and Glp-1 Analog Combinations in Type 2 Diabetes Mellitus: a Critical Review," Expert Opinion on Investigational Drugs, 2012, vol. 21 (10), pp. 1463-1474.
Jimenez S., et al., "Inflammatory Response in the Hippocampus of PS1M146L/App751SL Mouse Model of Alzheimer'S Disease: Age-Dependent Switch in the Microglial Phenotype from Alternative to Classic," The Journal of Neuroscience, 2008, vol. 28 (45), pp. 11650-11661.
Johnson et al., "When is a unit of insulin not a unit of insulin? Detemir dosing in type 2 diabetes" Poster, one page, 2008. http://professional.diabetes.org/ContenUPosters/2008/p8-LB.pdf.

Jorgensen K.H., et al., "Five Fold Increase of Insulin Concentration Delays the Absorption of Subcutaneously Injected Human Insulin Suspensions in Pigs," Diabetes Research and Clinical Practice, 2000, vol. 50, pp. 161-167.
Kaarsholm N.C., et al., "Engineering Stability of the Insulin Monomer Fold with Application to Structure-Activity Relationships," Biochemistry, 1993, vol. 32 (40), pp. 10773-10778.
Kadima W., "Role of Metal Ions in the T-to R-Allosteric Transition in the Insulin Hexamer," Biochemistry, 1999, vol. 38 (41), pp. 13443-13452.
Kaduszkiewicz H., et al., "Cholinesterase inhibitors for Patients with Alzheimer's Disease: Systematic Review of Randomised Clinical Trials," British Medical Journal (Clinical Research ed.), 2005, vol. 331 (7512), pp. 321-327.
Kaech S., et al., "Culturing Hippocampal Neurons," Nature Protocols, 2006, vol. 1 (5), pp. 2406-2415.
Kahn S.E., et al., "Glycemic Durability of Rosiglitazone, Metformin, or Glyburide Monotherapy," The New England Journal of Medicine, 2006, vol. 355 (23), pp. 2427-2443.
Kakhki V.R.D., et al., "Normal Values of Gallbladder Ejection Fraction Using 99m Tc-Sestamibi Scintigraphy after a Fatty Meal formula," Journal of Gastrointestinal and Liver Diseases, 2007, vol. 16 (2), pp. 157-161.
Kamisawa T., et al., "Pancreatographic investigation of Pancreatic Duct System and Pancreaticobiliary Malformation," Journal of Anatomy, 2008, vol. 212 (2), pp. 125-134.
Kanazawa M., et al., "Criteria and Classification of Obesity in Japan and Asia-Oceania," Asia Pacific Journal of Clinical Nutrition, 2002, vol. 11 (Suppl 7), pp. S732-S737.
Kang S., et al., "Subcutaneous Insulin Absorption Explained by Insulin's Physicochemical Properties Evidence from Absorption Studies of Soluble Human Insulin and Insulin Analogues in Humans," Diabetes Care, 1991, vol. 14 (11), pp. 942-948.
Kao C.H., et al., "the Evaluation of Gallbladder Function by Quantitative Radionuclide Cholescintigraphy in Patients with Noninsulin-Dependent Diabetes Mellitus," Nuclear Medicine Communications, 1993, vol. 14 (10), pp. 868-872.
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kastin A.J., et al., "Entry of Exedin-4 into Brain is Rapid but may be Limited at High Doses International Journal of Obesity and Related Metabolic Disorders," Journal of the International Association for the Study of Obesity, 2003, vol. 27 (3), pp. 313-318.
Kastin A.J., et al., "Interactions of Glucagon-Like Peptide-1 (GLP-1) with the Blood-Brain Barrier," Journal of Molecular Neuroscience, 2001, vol. 18 (1-2), pp. 7-14.
Kemmler W., et al., "Studies on the Conversion of ProInsulin to Insulin," The Journal of Biological Chemistry, 1971, vol. 246 (22), pp. 6786-6791.
Kendall D.M., et al., "Effects of Exenatide (Exendin-4) on Glycemic Control Over 30 Weeks in Patients with Type 2 Diabetes Treated with Metformin and a Sulfonylurea," Diabetes care, 2005, vol. 28 (5), pp. 1083-1091.
Kielgast U., et al., "Treatment of Type 1 Diabetic Patients with Glucagon-Like Peptide-1 (GLP-1) and GLP-1R Agonists," Current Diabetes Reviews, 2009, vol. 5 (4), pp. 266-275.
Kim S., et al., "Exendin-4 Protects Dopaminergic Neurons by Inhibition of Microglial Activation and Matrix Metalloproteinase-3 Expression in an Animal Model of Parkinson's Disease," Journal of Endocrinology, 2009, vol. 202 (3), pp. 431-439.
Knee T.S., et al., "A Novel Use of U-500 Insulin for Continuous Subcutaneous Insulin infusion in Patients with Insulin Resistance: a Case Series," Endocrine Practice, 2003, vol. 9 (3), pp. 181-186.
Knudsen L.B., et al., "Potent Derivatives of Glucagon-Like Peptide-1 with Pharmacokinetic Properties Suitable for once Daily Administration," Journal of Medicinal Chemistry, 2000, vol. 43 (9), pp. 1664-1669.
Kohn W.D., et al., "Pi-Shifted Insulin Analogs with Extended in Vivo Time Action and Favorable Receptor Selectivity," Peptides, 2007, vol. 28 (4), pp. 935-948.

(56) References Cited

OTHER PUBLICATIONS

Kohner E.M., "Diabetic Retinopathy," British Medical Bulletin, 1989, vol. 45 (1), pp. 148-173.
Kolterman O.G., et al., "Synthetic Exendin-4 (Exenatide) Significantly Reduces Postprandial and Fasting Plasma Glucose in Subjects with Type 2 Diabetes," The Journal of Clinical Endocrinology & Metabolism, 2003, vol. 88 (7), pp. 3082-3089.
Korczyn A.D., et al, "Emerging therapies in the Pharmacological Treatment of Parkinson's Disease," Drugs, 2002, vol. 62 (5), pp. 775-786.
Krishnamurthy G.T., et al., "Constancy and Variability of Gallbladder Ejection Fraction: Impact on Diagnosis and therapy," Journal of Nuclear Medicine, 2004, vol. 45 (11), pp. 1872-1877.
Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).
Langston J.W., et al., "Chronic Parkinsonism in Humans due to a Product of Meperedine-Analog Synthesis," Science, 1983, vol. 219 (4587), pp. 979-980.
Langui D., et al., "Subcellular Topography of Neuronal Aβ Peptide in APPxPS1 Transgenic Mice," The American Journal of Pathology, 2004, vol. 165 (5), pp. 1465-1477.
Lantus® ANNEX I—Summary of product characteristics. Date of first authorisation: Jun. 9, 2000, pp. 1-164.
Lantus® prescribing information, May 2012, pp. 1-6.
Lantus® Product Information—European Medicines Agency, first published Aug. 5, 2009, pp. 1-2.
Larsen B.D., et al., "Sequence-Assisted Peptide Synthesis (SAPS)," Journal of Peptide Research, 1998, vol. 52 (6), pp. 470-476.
Larsen P.J., et al., "Combination of the Insulin Sensitizer, Pioglitazone, and the Long-Acting GLP-1 Human Analog, Liraglutide, Exerts Potent Synergistic Glucose-Lowering Efficacy in Severely Diabetic ZDF Rats," Diabetes, Obesity and Metabolism, 2008, vol. 10, pp. 301-311.
Laursen K., et al., "Enhanced Monitoring of Biopharmaceutical Product Purity Using Liquid Chromatography-Mass Spectrometry," Journal of Chromatography a, 2011, vol. 1218 (28), pp. 4340-4348.
Lee C.H., et al., "Ischemia-Induced Changes in Glucagon-Like Peptide-1 Receptor and Neuroprotective Effect of its Agonist, Exendin-4, in Experimental Transient Cerebral Ischemia," Journal of Neuroscience Research, 2011, vol. 89 (7), pp. 1103-1113.
Leib R.D., et al., "Direct Quantitation of Peptide Mixtures without Standards Using Clusters formed by Electrospray Ionization Mass Spectrometry," Analytical Chemistry, 2009, vol. 81 (10), pp. 3965-3972.
Lens J., "The Terminal Carboxyl Groups of Insulin," Biochimica et Biophysica Acta, 1949, vol. 3, pp. 367-370.
Levemir® prescribing information, Dec. 2011, pp. 1-6.
Levene P.A., et al., "Calculation of Isoelectric Point," The Journal of Biological Chemistry, 1923, vol. 55, pp. 801-813.
Levin P., et al., "Combination therapy with Insulin Glargine and Exenatide: Real-World Outcomes in Patients with Type 2 Diabetes," Current Medical Research and Opinion, 2012, vol. 28 (3), pp. 439-446.
Levine R.L., et al., "Oxidation of Methionine in Proteins: Roles in Antioxidant Defense and Cellular Regulation," IUBMB life, 2000, vol. 50 (4-5), pp. 301-307.
Leyer S., et al., "The Role of the C-Terminus of the Insulin B-Chain in Modulating Structural and Functional Properties of the Hormone," International Journal of Peptide and Protein Research, 1995, vol. 46 (5), pp. 397-407.
Li H., et al., "Chronic Treatment of Exendin-4 Affects Cell Proliferation and Neuroblast Differentiation in the Adult Mouse Hippocampal Dentate Gyrus," Neuroscience letters, 2010, vol. 19, pp. 1205-1219.
Li L., et al., "Common Pathological Processes in Alzheimer Disease and Type 2 Diabetes: A Review," Brain Research Reviews, 2007, vol. 56, pp. 384-402.
Li Y., et al., "Enhancing the GLP-1 Receptor Signaling Pathway Leads to Proliferation and Neuroprotection in Human Neuroblastoma Cells," Journal of Neurochemistry, 2010, vol. 113 (6), pp. 1621-1631.
Li Y., et al., "GLP-1 Receptor Stimulation Preserves Primary Cortical and Dopaminergic Neurons in Cellular and Rodent Models of Stroke and Parkinsonism," Proceedings of the National Academy of Sciences of the United States of America, 2009, vol. 106 (4), pp. 1285-1290.
Li Y., et al., "GLP-1 Receptor Stimulation Reduces Amyloid-Beta Peptide Accumulation and Cytotoxicity in Cellular and Animal Models of Alzheimer's Disease," Journal of Alzheimer's Disease, 2010, vol. 19 (4), pp. 1205-1219.
Lill N., "Production of Fast-Acting Insulins and Delayed-Release Insulins—How can this Problem be Solved by Technology? Insulin formulations," Pharmazie in Unserer Zeit, 2001, vol. 30 (1), pp. 56-61.
Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.
Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposited, pp. 1-3.
Insulinpraparat Wikipedia, http://de.wikipedia.org/wiki/Insulinpr%C3%A4parat, pp. 1-15 (Feb. 5, 2013).
Insuman® Comb25 prescribing information, Feb. 2011, pp. 1-4.
Insuman® Infusat prescribing information, Feb. 2011, pp. 1-4.
Lotharius J., et al., "Effect of Mutant Alpha-Synuclein on Dopamine Homeostasis in a New Human Mesencephalic Cell Line," The Journal of Biological Chemistry, 2002, vol. 277 (41), pp. 38884-38894.
Lotharius J., et al., "Progressive Degeneration of Human Mesencephalic Neuron-Derived Cells Triggered by Dopamine-Dependent Oxidative Stress is Dependent on the Mixed-Lineage Kinase Pathway," Journal of Neuroscience, 2005, vol. 25 (27), pp. 6329-6342.
Lougheed W.D., et al., "Physical Stability of Insulin Formulations," Diabetes, 1983, vol. 32 (5), pp. 424-432.
Lyxumia 10 micrograms solution for injection, Summary of Product Characteristics, updated Oct. 31, 2014, pp. 1-12.
Lyxumia® ANNEX I—Summary of product characteristics. Date of first authorisation: Feb. 1, 2013, pp. 1-92.
Lyxumia, Chemical Subgroup A10BX, Community Register of Medicinal Products for Human Use, Eurpean Commission Public Health, p. 1-2 (May 2, 2013).
Lyxumia® Product Information—European Medicines Agency, first published Mar. 14, 2013, pp. 1-2.
Mancuso M., et al., "Clinical Features and Pathogenesis of Alzheimer's Disease: involvement of Mitochondria and Mitochondrial DNA," Advances in Experimental Medicine and Biology, 2010, vol. 685, pp. 34-44.
Marbury T.C., et al., "A Pilot Study to Examine the Feasibility of Insulin Glargine in Subjects with Impaired Fasting Glucose, Impaired Glucose tolerance or New-onset Type 2 Diabetes," Experimental and Clinical Endocrinology & Diabetes, 2008, vol. 116 (5), pp. 282-288.
Margolis R.L., et al., "Diagnosis of Huntington Disease," Clinical Chemistry, 2003, vol. 49 (10), pp. 1726-1732.
Markussen J., et al., "Soluble, Prolonged-Acting Insulin Derivatives. I. Degree of Protraction and Crystallizability of Insulins Substituted in the Termini of the B-Chain," Protein Engineering, 1987, vol. 1 (3), pp. 205-213.
Markussen J., et al., "Soluble, Prolonged-Acting Insulin Derivatives II Degree of Protraction and Crystallizability of Insulins Substituted in Positions A17, B8, B13, B27 and B30," Protein Engineering, 1987, vol. 1 (3), pp. 215-223.
Markussen J., et al., "Soluble, Prolonged-Acting Insulin Derivatives. III. Degree of Protraction, Crystallizability and Chemical Stability of Insulins Substituted in Positions A21, B13, B23, B27 and B30," Protein Engineering, 1988, vol. 2 (2), pp. 157-166.

(56) References Cited

OTHER PUBLICATIONS

Martin B., et al., "Exendin-4 Improves Glycemic Control, Ameliorates Brain and Pancreatic Pathologies, and Extends Survival in a Mouse Model of Huntington's Disease," Diabetes, 2009, vol. 58 (2), pp. 318-328.
Martin L.J., et al., "Neurodegeneration in Excitotoxicity, Global Cerebral Ischemia, and Target Deprivation: A Perspective on the Contributions of Apoptosis and Necrosis," Brain Research Bulletin, 1998, vol. 46 (4), pp. 281-309.
Mattson M.P., "Calcium and Neurodegeneration," Aging Cell, 2007, vol. 6 (3), pp. 337-350.
McClean P.L., et al., "Glucagon-Like Peptide-1 Analogues Enhance Synaptic Plasticity in the Brain: A Link between Diabetes and Alzheimer's Disease," European Journal of Pharmacology, 2010, vol. 630 (1-3), pp. 158-162.
McClean P.L., et al., "The Diabetes Drug Liraglutide Prevents Degenerative Processes in a Mouse Model of Alzheimer's Disease," The Journal of Neuroscience, 2011, vol. 31 (17), pp. 6587-6594.
Mecklenburg R.S., et al., "Complications of Insulin Pump therapy: The Effect of Insulin Preparation," Diabetes Care, 1985, vol. 8 (4), pp. 367-370.
Medline Plus, "Obesity" available at http://www.nlm.nih.gov/medlineplus/obesity.html, Retrieved Aug. 22, 2013, one page.
Meier J.J., "GLP-1 Receptor Agonists for individualized Treatment of Type 2 Diabetes Mellitus," Nature Reviews. Endocrinology, 2012, vol. 8 (12), pp. 728-742.
Merrifield B., "Solid Phase Synthesis," Science, 1986, vol. 232 (4748), pp. 341-347.
Mikhail N.E., "Is Liraglutide a Useful Addition to Diabetes therapy?," Endocrine Practice, 2010, vol. 16 (6), pp. 1028-1037.
Monnier L., et al., "The Loss of Postprandial Glycemic Control Precedes Stepwise Deterioration of Fasting with Worsening Diabetes," Diabetes Care, 2007, vol. 30 (2), pp. 263-269.
Moreno-Gonzalez I., et al., "Extracellular Amyloid-B and Cytotoxic Glial Activation Induce Significant Entorhinal Neuron Loss in Young PS1M146L/APP751SL Mice," Journal of Alzheimer's Disease, 2009, vol. 18, pp. 755-776.
Moretto T.J., et al., "Efficacy and tolerability of Exenatide Monotherapy Over 24 Weeks in Antidiabetic Drug-Naive Patients with Type 2 Diabetes: A Randomized, Double-Blind, Placebo-Controlled, Parallel-Group Study," Clinical Therapeutics, 2008, vol. 30 (8), pp. 1448-1460.
Muller G., et al., "Insulin Signaling in the Yeast *Saccharomyces cerevisiae*. 1. Stimulation of Glucose Metabolism and Snf 1 Kinase by Human Insulin," Biochemistry, 1998, vol. 37 (24), pp. 8683-8695.
Muzaffar M., et al., "The Mechanism of Enhanced Insulin Amyloid Fibril formation by Naciis Better Explained by a Conformational Change Model," PLoS One, 2011, vol. 6 (11), pp. 1-11.
Nakagawa A., et al., "Receptor Gene Expression of Glucagon-Like Peptide-1, but not Glucose-Dependent Insulinotropic Polypeptide, in Rat Nodose Ganglion Cells," Autonomic Neuroscience, 2004, vol. 110, pp. 36-43.
Nathan D.M., et al., "Management of Hyperglycaemia in Type 2 Diabetes Mellitus: A Consensus Algorithm for the initiation and Adjustment of therapy. Update Regarding the Thiazolidinediones," Diabetologia, 2008, vol. 51 (1), pp. 8-11.
Nathan M.D., et al., "Insulinotropic Action of Glucagon Like Peptide-1-(7-37) in Diabetic and Nondiabetic Subjects," Diabetes Care, 1992, vol. 15 (2), pp. 270-276.
Nauck M.A., et al., "Comparative Evaluation of Incretin-Based Antidiabetic Medications and Alternative therapies to be Added to Melformin in the Case of Monotherapy Failure," Journal of Diabetes Investigation, 2010, vol. 1 (1-2), pp. 24-36.
Nauck M.A., et al., "Effects of Subcutaneous Glucagon-Like Peptide 1 (GLP-1 [7-36 Amide]) in Patients with NIDDM," Diabetologia, 1996, vol. 39 (12), pp. 1546-1553.
Nauck M.A., et al., "Glucagon-Like Peptide 1 and its Potential in the Treatment of Non-Insulin-Dependent Diabetes Mellitus," Hormone and Metabolic Research, 1997, vol. 29 (9), pp. 411-416.

NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00688701 Clinical Trials.gov "GLP-1 Receptor Agonist Lixisenatide in Patients with Type 2 Diabetes for Glycemic Control and Safety Evaluation in Monotherapy (GETGOAL-MONO)" accessed Jul. 27, 2014; pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
Nauck et al., " Glucagon-like peptide 1 (GLP-1) as a new therapeutic approach for type 2-diabetes," Exp Clin Endocrinol. Diabetes 105(4):187-95 (1997).
NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011).
Final Rejection issued in U.S. Appl. No. 13/382,442; dated Aug. 11, 2015, pp. 1-35.
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GETGOAL-P)" pp. 1-8 (Jun. 27, 2011).
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
NCT01174810, ClinicalTrials.gov "Exendin-4 as a Treatment for Parkinson's Disease—Pilot Study" accessed Aug. 8, 2011, pp. 1-5.
NCT01195454, NIH Clinical Trials, "Euglycemic clamp dose-response study comparing insulin glargine U300 with Lantus U100" last updated Dec. 13, 2010, pp. 1-4.
NCT01255163, ClinicalTrials.gov "A Clinical Trial of Exendin-4 for the Treatment of Alzheimer's Disease" accessed Aug. 8, 2011, pp. 1-7.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
Needleman S.B., et al., "A General Method Applicable to the Search for Similarities in the Amino Acid Sequence of Two Proteins," Journal of Molecular Biology, 1970, vol. 48 (3), pp. 443-453.
Neidle, "18.2 Failure Modes in the Discovery Process" Cancer Drug Design and Discovery, Elsevier/Academic Press, pp. 427-431 (2008).
Nettleton E.J., et al., "Characterization of the Oligomeric States of Insulin in Self-Assembly and Amyloid Fibril formation by Mass Spectrometry," Biophysical Journal, 2000, vol. 79 (2), pp. 1053-1065.
Nicklas et al., "Inhibition of Nadh-Linked Oxidation in Brain Mitochondria by 1-Methyl-4-Phenyl-Pyridine, A Metabolite of the Neurotoxin, 1-Methyl-4-Phenyl-1,2,5,6-Tetrahydropyridine," Life Sciences, 1985, vol. 36, pp. 2503-2508.
Nielsen L.L., et al., "Pharmacology of Exenatide (Synthetic Exendin-4): A Potential therapeutic for Improved Glycemic Control of Type 2 Diabetes," Regulatory Peptides, 2004, vol. 117 (2), pp. 77-88.
Noble S.L., et al., "Insulin Lispro: A Fast-Acting Insulin Analog," American Family Physician, 1998, vol. 57 (2), pp. 279-286.

(56) References Cited

OTHER PUBLICATIONS

Non-Final Office Action from U.S. Appl. No. 12/617,805; dated Jul. 24, 2014, pp. 1-12.
Non-Final Office Action from U.S. Appl. No. 12/617,805; dated May 2, 2012, pp. 1-11.
Non-Final Office Action from U.S. Appl. No. 12/617,805; dated May 10 2011, pp. 1-12.
Non-Final Office Action from U.S. Appl. No. 12/617,805; dated Sep. 15, 2015, pp. 1-12.
Non-Final Office Action issued in U.S. Appl. No. 13/602,913; dated Dec. 2, 2014, pp. 1-12.
Non-Final Office Action issued in U.S. Appl. No. 13/602,913; dated Jan. 13, 2014, pp. 1-53.
Non-Final Office Action issued in U.S. Appl. No. 13/602,913; dated May 17, 2013, pp. 1-7.
Non-Final Rejection in U.S. Appl. No. 13/633,496; dated Apr. 29, 2013, pp. 1-53.
Non-Final Rejection in U.S. Appl. No. 13/633,496; dated Apr. 6, 2015, pp. 1-14.
Non-Final Rejection in U.S. Appl. No. 13/633,496; dated May 22, 2014, pp. 1-11.
Non-Final Rejection in U.S. Appl. No. 13/633,563; dated Dec. 1, 2014, pp. 1-9.
Non-Final Rejection in U.S. Appl. No. 13/633,563; dated Jul. 1, 2013, pp. 1-56.
Non-Final Rejection in U.S. Appl. No. 13/633,563; dated Jun. 4, 2014, pp. 1-11.
Non-Final Rejection in U.S. Appl. No. 13/633,563; dated Oct. 6, 2015, pp. 1-12.
Non-Final Rejection issued in U.S. Appl. No. 14/172,151; dated Mar. 24, 2015, pp. 1-16.
Non-Final Rejection issued in U.S. Appl. No. 12/617,811; dated Apr. 27, 2011, pp. 1-10.
Non-Final Rejection issued in U.S. Appl. No. 12/617,811; dated Jan. 14, 2015, pp. 1-15.
Non-Final Rejection issued in U.S. Appl. No. 12/617,811; dated Jun. 21, 2012, pp. 1-7.
Non-Final Rejection issued in U.S. Appl. No. 12/617,811; dated Oct. 27, 2011, pp. 1-13.
Non-Final Rejection issued in U.S. Appl. No. 13/110,568; dated Mar. 19, 2012, pp. 1-18.
Non-Final Rejection issued in U.S. Appl. No. 13/310,118, dated Mar. 19, 2012, pp. 1-19.
Non-Final Rejection issued in U.S. Appl. No. 13/310,118, dated Mar. 29, 2013, pp. 1-21.
Non-Final Rejection issued in U.S. Appl. No. 13/310,118, dated Mar. 25, 2015, pp. 1-15.
Non-Final Rejection issued in U.S. Appl. No. 13/363,956; dated Apr. 10, 2013, pp. 1-15.
Non-Final Rejection issued in U.S. Appl. No. 13/363,956; dated Feb. 11, 2015, pp. 1-18.
Non-Final Rejection issued in U.S. Appl. No. 13/363,956; dated May 29, 2015, pp. 1-17.
Non-Final Rejection issued in U.S. Appl. No. 13/363,956; dated Nov. 20, 2013, pp. 1-10.
Non-Final Rejection issued in U.S. Appl. No. 13/382,442; dated Nov. 7, 2012, pp. 1-26.
Non-Final Rejection issued in U.S. Appl. No. 13/382,442; dated Dec. 19, 2013, pp. 1-29.
Non-Final Rejection issued in U.S. Appl. No. 13/382,442; dated Feb. 5, 2015, pp. 1-31.
Non-Final Rejection issued in U.S. Appl. No. 13/382,772; dated Nov. 21, 2013, pp. 1-42.
Non-Final Rejection issued in U.S. Appl. No. 13/382,772; dated Sep. 29, 2014, pp. 1-33.
Non-Final Rejection issued in U.S. Appl. No. 13/382,772; dated Sep. 14, 2015, pp. 1-42.
Non-Final Rejection issued in U.S. Appl. No. 13/467,707; dated Jul. 15, 2013, pp. 1-20.
Non-Final Rejection issued in U.S. Appl. No. 13/467,707; dated Jul. 25, 2014, pp. 1-22.
Non-Final Rejection issued in U.S. Appl. No. 13/467,707; dated Sep. 16, 2015, pp. 1-13.
Non-Final Rejection issued in U.S. Appl. No. 13/468,422; dated Nov. 4, 2015; pp. 1-27.
Non-Final Rejection issued in U.S. Appl. No. 13/469,633; dated Aug. 19, 2013, pp. 1-25.
Non-Final Rejection issued in U.S. Appl. No. 13/469,633; dated Aug. 22, 2014, pp. 1-23.
Non-Final Rejection issued in U.S. Appl. No. 13/469,633; dated Mar. 27, 2013, pp. 1-39.
Non-Final Rejection issued in U.S. Appl. No. 13/509,507; dated Aug. 6, 2013, pp. 1-11.
Non-Final Rejection issued in U.S. Appl. No. 13/509,507; dated Sep. 19, 2014, pp. 1-9.
Non-Final Rejection issued in U.S. Appl. No. 13/509,507; dated Feb. 19, 2015, pp. 1-10.
Non-Final Rejection issued in U.S. Appl. No. 13/509,507; dated Dec. 8, 2015, pp. 1-14.
Non-Final Rejection issued in U.S. Appl. No. 13/509,542; dated May 23, 2013, pp. 1-21.
Non-Final Rejection issued in U.S. Appl. No. 13/509,542; dated Apr. 2, 2014, pp. 1-20.
Non-Final Rejection issued in U.S. Appl. No. 13/509,542; dated Aug. 11, 2015, pp. 1-30.
Non-Final Rejection issued in U.S. Appl. No. 13/595,590; dated Jun. 5, 2015, pp. 1-9.
Non-Final Rejection issued in U.S. Appl. No. 13/595,590; dated Oct. 16, 2013, pp. 1-7.
Non-Final Rejection issued in U.S. Appl. No. 13/595,590; dated Sep. 5, 2014, pp. 1-10.
Non-Final Rejection issued in U.S. Appl. No. 13/661,476; dated Jun. 4, 2015, pp. 1-31.
Non-Final Rejection issued in U.S. Appl. No. 13/661,476, dated Dec. 4, 2013, pp. 1-11.
Non-Final Rejection issued in U.S. Appl. No. 13/661,476, dated Mar. 6, 2014, pp. 1-28.
Non-Final Rejection issued in U.S. Appl. No. 13/661,476, dated Sep. 16, 2013, pp. 1-19.
Non-Final Rejection issued in U.S. Appl. No. 13/692,640; dated May 6, 2014, pp. 1-10.
Non-Final Rejection issued in U.S. Appl. No. 13/692,640; dated Oct. 31, 2013, pp. 1-10.
Non-Final Rejection issued in U.S. Appl. No. 13/700,631; dated Apr. 22, 2013, pp. 1-27.
Non-Final Rejection issued in U.S. Appl. No. 13/700,631; dated Dec. 17, 2015, pp. 1-18.
Non-Final Rejection issued in U.S. Appl. No. 13/700,631; dated Nov. 18, 2014, pp. 1-22.
Non-Final Rejection issued in U.S. Appl. No. 13/700,631; dated Nov. 29, 2013, pp. 1-23.
Non-Final Rejection issued in U.S. Appl. No. 13/819,114; dated Dec. 2, 2015, pp. 1-14.
Non-Final Rejection issued in U.S. Appl. No. 13/819,114; dated Jul. 31, 2014, pp. 1- 9.
Non-Final Rejection issued in U.S. Appl. No. 14/220,562; dated Apr. 8, 2015, pp. 1-18.
Non-Final Rejection issued in U.S. Appl. No. 14/303,895; dated May 21, 2015, pp. 1-11.
Non-Final Rejection issued in U.S. Appl. No. 14/303,895; dated Sep. 9, 2015, pp. 1-12.
Non-Final Rejection issued in U.S. Appl. No. 13/467,757; dated Apr. 17, 2013, pp. 1-9.
Non-Final Rejection issued in U.S. Appl. No. 13/468,422; dated Jun. 4, 2014, pp. 1-24.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Non-Final Rejection issued in U.S. Appl. No. 13/382,772; dated Apr. 10, 2013, pp. 1-48.

(56) References Cited

OTHER PUBLICATIONS

Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.
Non-Final-Rejection issued in U.S. Appl.No. 13/432,811; dated Sep. 9, 2015, pp. 1-11.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov C., "Glucagon-Like Peptide-1, A New Hormone of the Entero-insular Axis," Diabetologia, 1992, vol. 35 (8), pp. 701-711.
Ott P., et al., "Diabetes in Germany(Dig) Study a Prospective 4-Year-Follow-Up Study on the Quality of Treatment for Type 2 Diabetes in Daily Practice," Deutsche Medizinische Wochenschrift, 2009, vol. 134 (7), pp. 291-297.
Park C.W., et al., "PPARalpha Agonist Fenofibrate Improves Diabetic Nephropathy in Db/Db Mice," Kidney International, 2006, vol. 69 (9), pp. 1511-1517.
Parkin "Guideline for Management of Postmeal Glucose" International Diabetes Federation, pp. 1-32 (Oct. 2007).
Patel & Advance Collaborative Group, "Effects of a Fixed Combination of Perindopril and indapamide on Macrovascular and Microvascular Outcomes in Patients with Type 2 Diabetes Mellitus (the Advance Trial): A Randomised Controlled Trial," Lancet, 2007, vol. 370 (9590), pp. 829-840.
Patel K., et al., "Chemical Pathways of Peptide Degradation. II. Kinetics of Deamidation of an Asparaginyl Residue in a Model Hexapeptide," Pharmaceutical Research, 1990, vol. 7 (8), pp. 703-711.
Pederson R.A., et al., "Improved Glucose tolerance in Zucker Fatty Rats by oral Administration of the Dipeptidyl Peptidase IV inhibitor Isoleucine Thiazolidide," Diabetes, 1998, vol. 47 (8), pp. 1253-1258.
Perfetti R., "Combining Basal Insulin Analogs with Glucagon-Like Peptide-1 Mimetics," Diabetes Technology & Therapeutics, 2011, vol. 13 (9), pp. 873-881.
Perry T., et al., "A Novel Neurotrophic Property of Glucagon-Like Peptide 1: A Promoter of Nerve Growth Factor-Mediated Differentiation in PC12 Cells," The Journal of Pharmacology and Experimental Therapeutics, 2002, vol. 300 (3), pp. 958-966.
Perry T., et al., "Evidence of GLP-1-Mediated Neuroprotection in an Animal Model of Pyridoxine-induced Peripheral Sensory Neuropathy," Experimental Neurology, 2007, vol. 203 (2), pp. 293-301.
Perry T., et al., "Protection and Reversal of Excitotoxic Neuronal Damage by Glucagon-Like Peptide-1 and Exendin-4," The Journal of Pharmacology and Experimental Therapeutics, 2002, vol. 302 (3), pp. 881-888.
Perry T., et al., "The Glucagon-Like Peptides: A Double-Edged therapeutic Sword?," Trends in Pharmacological Sciences, 2003, vol. 24 (7), pp. 377-383.
Perry T.A., et al., "A New Alzheimer's Disease interventive Strategy: GLP-1," Current Drug Targets, 2004, vol. 5 (6), pp. 565-571.
Pillion D.J., et al., "Dodecylmaltoside-Mediated Nasal and Ocular Absorption of Lyspro-Insulin: Independence of Surfactant from Multimer Dissociation," Pharmaceutical Research, 1998, vol. 15(10), pp. 1637-1639.
Pinget et al., "Efficacy and Safety of Lixisenatide Once Daily Versus Placebo in Patients With Type 2 Diabetes Insufficiently Controlled on Pioglitazone (GetGoal-P)" Diabetes, 61(Supp 1): A258, Poster 1010-P (Jun. 2012).
Pohl M., et al., "Molecular Cloning of the Heloderman and Exendin-4 cDNAs in the Lizard," The Journal of Biological Chemistry, 1998, vol. 273 (16), pp. 9778-9784.
Porter D.W., et al., "Four Weeks Administration of Liraglutide Improves Memory and Learning as Well as Glycaemic Control in Mice with High Fat Dietary-induced Obesity and Insulin Resistance," Diabetes, Obesity and Metabolism, 2010, vol. 12 (10), pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini N., "Methods of Measuring Gallbladder Motor Functions—the Need for Standardization: Scintigraphy," Digestive and Liver Disease, 2003, vol. 35 (Suppl 3), pp. S62-S66.
"Preferable." Merriam-Webster.com. Merriam-Webster, n.d. Web. Sep. 7, 2015. http://www.merriamwebster.com/dictionary/preferable).
Pugeat M., et al., "Insulin Resistance, Polycystic Ovary Syndrome and Metformin," Drugs, 1999, vol. 58 (Suppl 1), pp. 41-46.
Quianzon C.L., et al., "Lixisentide-Once Daily Glucagon-Like Peptide-1 Receptor Agonist in the Management of Type 2 Diabetes," US Endocrinology, 2011, vol. 7 (2), pp. 104-109.
Raccah D., et al., "When Basal Insulin therapy in Type 2 Diabetes Mellitus is not Enough—What Next?," Diabetes/Metabolism Research and Reviews, 2007, vol. 23 (4), pp. 257-264.
Raju R.P., et al., "Optimum Palliation of inoperable Hilar Cholangiocarcinoma: Comparative Assessment of the Efficacy of Plastic and Self-Expanding Metal Stents," Digestive Diseases and Sciences, 2011, vol. 56, pp. 1557-1564.
Ramos B., et al., "Early Neuropathology of Somatostatin/NPY Gabaergic Cells in the Hippocampus of a Ps1xAPP Transgenic Model of Alzheimer's Disease," Neurobiology of Aging, 2006, vol. 27 (11), pp. 1658-1672.
Rao A.D., et al., "Is the Combination of Sulfonylureas and Metformin Associated with an increased Risk of Cardiovascular Disease or all-Cause Mortality? A Meta-Analysis of Observational Studies," Diabetes Care, 2008, vol. 31 (8), pp. 1672-1678.
Raufman "Bioactive peptides from lizard venoms," Regul Pept 61(1):1-18 (1996).
Ratner R.E., et al., "Dose-Dependent Effects of the Once-Daily GLP-1 Receptor Agonist Lixisenatide in Patients with Type 2 Diabetes Inadequately Controlled with Metformin: A Randomized Double-Blind, Placebo-Controlled Trial," Diabetic Medicine, 2010, vol. 27 (9), pp. 1024-1032.
Ratner R.E., et al., "Post-Meal Pharmacodynamics Profile of Ave0010, A Once-Daily GLP-1 Receptor Agonist, in Patiens with Type 2 Diabetes Inadequately Controlled on Metformin," Diabetologia, 2009, vol. 52 (Suppl 1), pp. S60. Abstract 131.
Ratner R.E., et al., "A Dose-Finding Study of the New GLP-1 Agonist AVE0010 in Type 2 Diabetes Insufficiently Controlled with Metformin," Diabetes, 68th Annual Meeting of the American Diabetes Association, San Francisco, Jun. 6-10, 2008, vol. 57 (Suppl 1), p. A129. Poster.
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle M., et al., "Contributions of Basal and Postprandial Hyperglycemia over a Wide Range of A 1 C Levels before and after Treatment Intensification in Type 2 Diabetes," Diabetes Care, 2011, vol. 34, pp. 2508-2514.
Riddle M.C., et al., "Adding Once-Daily Lixisenatide for Type 2 Diabetes Inadequately Controlled by Established Basal Insulin: A 24-Week, Randomized, Placebo-Controlled Comparison (Getgoal-L)," Diabetes Care, 2013, vol. 36 (9), pp. 2489-2496.
Riddle M.C., et al., "Adding once-Daily Lixisenatide for Type 2 Diabetes inadequately Controlled with Newly initiated and Continuously Titrated Basal Insulin Glargine," Diabetes Care, 2013, pp. 2497-2503.
Ritzel U., et al., "A Synthetic Glucagon-Like Peptide-1 Analog with Improved Plasma Stability," The Journal of Endocrinology, 1998, vol. 159 (1), pp. 93-102.
Rohrmann C.A., "Differential Diagnosis of Pancreatic and Biliary Duct Diseases," Diseases of the Abdomen and Pelvis Syllabus, 1999, pp. 170-174.

(56) References Cited

OTHER PUBLICATIONS

Zealand Pharma Company Announcement "Zealand Pharma, Additional positive results from Global Phase III program with-3-lixisenatide for type 2 diabetes", Apr. 12, 2011, pp. 1-3, URL, http://files.shareholder.com/downloads/ABEA-58QR0J/0x0x458202/3ccd84a6-5f99-451a-ada0-0a8282da3dad/ZEAL_News_2011_4_12Company_Releases.pdf.
Rosenstock J., et al., "Dose Range Effects of the New Once Daily GLP-1 Receptor Agonist Ave0010 Added to Metformin in Type 2 Diabetes," Diabetologia, 2008, vol. 51 (Suppl 1), pp. S66. Abstract 145.
Rosenstock J., et al., "Post-Meal Effects of Ave0010, A Once-Daily GLP-1 Receptor Agonist, in Type 2 Diabetes Inadequately Controlled on Metformin," Diabetes, 2009, vol. 58 (Suppl 1), pp. A151-A152. Abstract 564P.
Rosenstock J., et al., "Efficacy and Safety of Lixisenatide Once Daily vs Exenatiide Twice Daily in Type 2 DM Inadequately Controlled on Metformin (GetGoal-X)," 71st Scientific Sessions, Nov. 2011. Poster.
Rubino A., et al., "Delayed initiation of Subcutaneous Insulin therapy after Failure of oral Glucose-Lowering Agents in Patients with Type 2 Diabetes: A Population-Based Analysis in the UK," Diabetic Medicine, 2007, vol. 24 (12), pp. 1412-1418.
Sampson H.A., et al., "Second Symposium on the Definition and Management of Anaphylaxis: Summary Report—Second National institute of Allergy and infectious Disease/Food Allergy and Anaphylaxis Network Symposium," The Journal of Allergy and Clinical Immunology, 2006, vol. 117 (2), pp. 391-397.
Sanger F., et al., "The Amide Groups of Insulin," The Biochemical Journal, 1955, vol. 59 (3), pp. 509-518.
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi's Lantus Draft Prescribing Information/Package Insert: "NDA 21-081 DRAFT package insert" (Sponsor revision #5) Date of submission: Apr. 20, 2000; see http://www.drugbank.ca/system/fds_labels/DB00047.pdf 1265922812; pp. 1-14.
Sanofi Press Release entitled "FDA Accepts Sanofi's New Drug Application for Basal Insulin Toujeo®," dated Jul. 8, 2014, pp. 1-2.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release, "Once Daily Lixisenatide (Ave 0010) Given as Monotherapy Successfully Meets Phase III Study Endpoints in Diabetes" Paris, France (Apr. 15, 2010) pp. 1-2.
Sanofi-aventis Press Release (Peron and Schaeffer), "Sanofi-aventis Announces Positive Top-line Lixisenatide Phase III Results" Paris, France (Feb. 2, 2011) pp. 1-2.
Sanofi Press Release entitled "Sanofi Receives FDA Approval of Once-Daily Basal Insulin Toujeo®," dated Feb. 26, 2015, pp. 1-4.
Schapira A.H., "Causes of Neuronal Death in Parkinson's Disease," Advances in Neurology, 2001, vol. 86, pp. 155-162.
Schellenberger V., et al., "Attempts for Quantifying the S' Subsite Specificity of Serine Proteases, Selected Papers Presented at the 2nd International Meeting on the Molecular and Cellular Regulation of Enzyme Activity, Advances in the Biosciences, Peptides and Proteases," Recent Advances, 1987, vol. 65, pp. 159-166.
Schellenberger V., et al., "Protease-Catalyzed Kinetically Controlled Peptide Synthesis," Angewante Chemie, 1991, vol. 30 (11), pp. 1437-1449.
Schindowski K., et al., "Impact of Aging: Sporadic, and Genetic Risk Factors on Vulnerability to Apoptosis in Alzheimer's Disease," Neuromolecular Medicine, 2003, vol. 4 (3), pp. 161-178.
Schmitz C., et al., "Hippocampal Neuron Loss Exceeds Amyloid Plaque Load in a Transgenic Mouse Model of Alzheimer's Disease," The American Journal of Pathology, 2004, vol. 164 (4), pp. 1495-1502.
Schwartz G.P., et al., "A Superactive Insulin: [B10-Aspartic Acid]Insulin(Human)," Proceedings of the National Academy of Sciences of the United States of America, 1987, vol. 84 (18), pp. 6408-6411.
Search Report of the Indecopi for Patent Application in Peru No. 000643-2012/DIN, dated Jul. 23, 2015, pp. 1-2.
Search Report of the Intellectual Property Corporation of Malaysia for Malaysian Patent Application No. PI 2011006204; dated Sep. 15, 2015, pp. 1-3.
Secnik Boye K., et al., "Patient-Reported Outcomes in a Trial of Exenatide and Insulin Glargine for the Treatment of Type 2 Diabetes," Health and Quality of Life Outcomes, 2006, vol. 4 (80), pp. 1-8.
Seino Y., et al., "Report of the Committee on the Classification and Diagnostic Criteria of Diabetes Mellitus," Journal of the Japan Diabetes Society, 2010, vol. 53, pp. 450-467 (In Japanese) English summary also provided.
Seino Y., et al., "Randomized, Double-Blind, Placebo-Controlled Trial of the Once-Daily GLP-1 Receptor Agonist Lixisenatide in Asian Patients with Type 2 Diabetes Insufficiently Controlled on Basal Insulin with or without a Sulfonylurea (Getgoal-L-Asia)," Diabetes, Obesity and Metabolism, 2012, vol. 14 (10), pp. 910-917.
Sharplin P., et al., "Improved Glycaemic Control by Switching from Insulin NPH to Insulin Glargine: A Retrospective Observational Study," Cardiovascular Diabetology, 2009, vol. 8 (3), pp. 1-8.
Sherer T.B., et al., "Subcutaneous Rotenone Exposure Causes Highly Selective Dopaminergic Degeneration and A-Synuclein Aggregation," Experimental Neurology, 2003, vol. 179, pp. 9-16.
Sluzky V., et al., "Kinetics of Insulin Aggregation in Aqueous Solutions Upon Agitation in the Presence of Hydrophobic Surfaces," Proceedings of the National Academy of Sciences of the United States of America, 1991, vol. 88 (21), pp. 9377-9381.
Smolka M.B., et al., "Optimization of the Isotope-Coded Affinity Tag-Labeling Procedure for Quantitative Proteome Analysis," Analytical Biochemistry, 2001, vol. 297 (1), pp. 25-31.
Sporn M.B., et al., "Chemoprevention of Cancer," Carcinogenesis, 2000, vol. 21 (3), pp. 535-530.
St. John Providence Health Center, "Preventing Obesity" http://www.stjohnprovidence.org/HealthInfolib/swarticle.aspx?type=85&id= P07863, Retrieved Aug. 22, 2013, pp. 1-2.
Starkova N.T., "Clinical Endocrinology," Guide for physicians, Medicine, 1991, pp. 192-262.
Stolk R.P., et al., "Insulin and Cognitive Function in an Elderly Population the Rotterdam Study," Diabetes Care, 1997, vol. 20 (5), pp. 792-795.
Summary of Product Characteristics Lyxumia 10 micrograms solution for injection, pp. 1-93, published Mar., 14, 2013.
Sundby F., "Separation and Characterization of Acid-induced Insulin Transformation Products by Paper Electrophoresis in 7 M Urea," The Journal of Biological Chemistry, 1962, vol. 237 (11), pp. 3406-3411.

(56) References Cited

OTHER PUBLICATIONS

Tanner C.M., et al., "Rotenone, Paraquat, and Parkinson's Disease," Environmental Health Perspectives, 2011, vol. 119 (6), pp. 866-872.
Tempero M.A., "How I Treat Pancreatic Ductal Adenocarcinoma," Current Clinical Issues, Journal of Oncology Practice, 2008, vol. 4 (1), pp. 46-47.
Teramoto S., et al., "Exendin-4, a Glucagon-Like Peptide-1 Receptor Agonist, provides Neuroprotection in Mice Transient Focal Cerebral lschemia," Journal of Cerebral Blood Flow and Metabolism, 2011, vol. 31 ( 8), pp. 1696-1705.
Tessari P., et al., "Insulin in Methionine and Homocysteine Kinetics in Healthy Humans: Plasma Vs intracellular Models," American Journal of Physiology. Endocrinology and Metabolism, 2005, vol. 288 (6), pp. E1270-E1276.
Tetich M., et al., "Neuroprotective Effects of (24R)-1,24-Dihydroxycholecalciferol in Human Neuroblastoma SH-SY5Y Cell Line," The Journal of Steroid Biochemistry and Molecular Biology, 2004, vol. 89-90 (1-5), pp. 365-370.
Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.
Thong K.Y., et al., "Safety, Efficacy and tolerability of Exenatide in Combination with Insulin in the Association of British Clinical Diabetologists Nationwide Exenatide Audit," Diabetes, Obesity and Metabolism, 2011, vol. 13 (8), pp. 703-710.
Thurow H., et al., "Stabilisation of Dissolved Proteins against Denaturation at Hydrophobic Interfaces," Diabetologia, 1984, vol. 27 (2), pp. 212-218.
Toth M.L., et al., "Neurite Sprouting and Synapse Deterioration in the Aging Caenorhabditis Elegans Nervous System," The Journal of Neuroscience, 2012, vol. 32 (26), pp. 8778-8790.
Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 750, 753 and 754 of Igaku No Ayumi, "Incretin Receptors," 2010, May, vol. 233; No. 9: 750-754, pp. 1-4.
Turner R.C., et al., "Glycemic Control with Diet, Sulfonylurea, Metformin, or Insulin in Patients with Type 2 Diabetes Mellitus: Progressive Requirement for Multiple therapies (UKPDS 49)," JAMA, 1999, vol. 281 (21), pp. 2005-2012.
Tyler-Cross R., et al., "Effects of Amino Acid Sequence, Buffers, and Ionic Strength on the Rate and Mechanism of Deamidation of Asparagine Residues in Small Peptides," The Journal of Biological Chemistry, 1991, vol. 266 (33), pp. 22549-22556.
UK Prospective Diabetes Study (UKPDS) Group, "Effect of intensive Blood-Glucose Control with Metformin on Complications in Overweight Patients with Type 2 Diabetes (UKPDS 34)," Lancet, 1998, vol. 352 (9131), pp. 854-865.
UK Prospective Diabetes Study (UKPDS) Group, "Intensive Blood-Glucose Control with Sulphonylureas or Insulin Compared with Conventional Treatment and Risk of Complications in Patients with Type 2 Diabetes (UKPDS 33)," The Lancet, 1998, vol. 352, pp. 837-853.
"Suspension" Stedman's Medical Dictionary, 20th Edition, p. 1450 (Williams & Wilkins Co., Baltimore 1961).
"Suspension" Taber's Cyclopedic Medical Dictionary, 19th Edition, p. 2097 (F.A. Davis Co., Philadelphia 2001).
Valle J., et al., "Cisplatin Plus Gemcitabine Versus Gemcitabine for Biliary Tract Cancer," The New England Journal of Medicine, 2010, vol. 362 (14), pp. 1273-1281.

Van Delden, "Pancreas-Carcinoma, CT Assessment of Resectability," Radiology Department of the Academical Medical Centre, Apr. 2006, pp. 1-12.
Varadarajan S., et al., "Review: Alzheimer's Amyloid Beta-Peptide-Associated Free Radical Oxidative Stress and Neurotoxicity," Journal of Structural Biology, 2000, vol. 130 (2-3), pp. 184-208.
Venezia V., et al., "Apoptotic Cell Death and Amyloid Precursor Protein Signaling in Neuroblastoma SH-SY5Y Cells," Annals of the New York Academy of Sciences, 2004, vol. 1030, pp. 339-347.
Victoza® ANNEX I—Summary of product characteristics. First published 2009, pp. 1-32.
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Volund A., et al., "In Vitro and in Vivo Potency of Insulin Analogues Designed for Clinical Use," Diabetic Medicine, 1991, vol. 8 (9), pp. 839-847.
Vora J., et al., "Incretin-Based therapy in Combination with Basal Insulin: A Promising Tactic for the Treatment of Type 2 Diabetes," Diabetes & Metabolism, 2013, vol. 39 (1), pp. 6-15.
Wafa W.S., et al., "Use of U-500 Regular Insulin in Type 2 Diabetes," Diabetes Care, 2006, vol. 29 (9), pp. 2175-2176.
Wajchenberg B.L., "Clinical Approaches to Preserve Beta-Cell Function in Diabetes," Advances in Experimental Medicine and Biology, 2010, vol. 654, pp. 515-535.
Wan Z., et al., "Enhancing the Activity of Insulin at the Receptor Interface: Crystal Structure and Photo-Cross-Linking of A8 Analogues," Biochemistry, 2004, vol. 43 (51), pp. 16119-16133.
Wang L., et al., "Real-World Outcomes of US Employees with Type 2 Diabetes Mellitus Treated with Insulin Glargine or Neutral Protamine Hagedorn Insulin: A Comparative Retrospective Database Study," BMJ Open, 2013, vol. 3 (4), pp. e002348 1-9.
Ward J.D., "Diabetic Neuropathy," British Medical Bulletin, 1989, vol. 45 (1), pp. 111-126.
Watson G.S., et al., "Insulin increases CSF Abeta42 Levels in Normal Older Adults," Neurology, 2003, vol. 60 (12), pp. 1899-1903.
Weiss M.A., et al., "Activities of Monomeric Insulin Analogs at Position A8 are Uncorrelated with their thermodynamic Stabilities," The Journal of Biological Chemistry, 2001, vol. 276 (43), pp. 40018-40024.
Werner et al., "Abstract, Insulin Glargine U-100 Has a Favourable Time-Action Profile Compared to U-40 or NPH Insulin in Healthy, Normoglycaemic Dogs", Poster 37th Annual Meeting of Endocrine Society of India, Tirupati, A.P., India, ESICON, 2007, p. 2.
Werner U., et al., "Pharmacological Profile of Lixisenatide: A New GLP-1 Receptor Agonist for the Treatment of Type 2 Diabetes," Regulatory Peptides, 2010, vol. 164 (2-3), pp. 58-64.
White I.R., et al., "Randomized Clinical Trials with Added Rescue Medication: Some Approaches to their Analysis and interpretation," Statistics in medicine, 2001, vol. 20 (20), pp. 2995-3008.
Whittingham J.L., et al., "Insulin at pH 2: Structural Analysis of the Conditions Promoting Insulin Fibre formation," Journal of Molecular Biology, 2002, vol. 318 (2), pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
Widjaja A., et al., "UKPDS 20: Plasma Leptin, Obesity, and Plasma Insulin in Type 2 Diabetic Subjects," The Journal of Clinical Endocrinology and Metabolism, 1997, vol. 82 (2), pp. 654-657.
Wiernsperger N.F., et al., "The Antihyperglycaemic Effect of Metformin: Therapeutic and Cellular Mechanisms," Drugs, 1999, vol. 58 (Suppl 1), pp. 31-39.
Wirths O., et al., "Intraneuronal Abeta Accumulation Precedes Plaque formation in beta-Amyloid Precursor Protein and Presenilin-1 Double-Transgenic Mice," Neuroscience Letters, 2001, vol. 306 (1-2), pp. 116-120.
Wirths O., et al., "Intraneuronal APP/A Beta Trafficking and Plaque formation in Beta-Amyloid Precursor Protein and Presenilin-1 Transgenic Mice," Brain Pathology, 2002, vol. 12 (3), pp. 275-286.

(56) References Cited

OTHER PUBLICATIONS

Wirths O., et al., "Reelin in Plaques of Beta-Amyloid Precursor Protein and Presenilin-1 Double-Transgenic Mice," Neuroscience Letters, 2001, vol. 316 (3), pp. 145-148.
Wollen K.A., "Alzheimer's Disease: the Pros and Cons of Pharmaceutical, Nutritional, Botanical, and Stimulatory therapies, with a Discussion of Treatment Strategies from the Perspective of Patients and Practitioners," Alternative Medicine Review, 2010, vol. 15 (3), pp. 223-244.
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
Written Opinion of the ISA for International Application No. PCT/EP2011/058079, dated Mar. 22, 2012, pp. 1-8.
Xie H., et al., "Characterization of Protein Impurities and Site-Specific Modifications Using Peptide Mapping with Liquid Chromatography and Data Independent Acquisition Mass Spectrometry," Analytical Chemistry, 2009, vol. 81 (14), pp. 5699-5708.
Yki-Jarvinen H., et al., "Insulin Glargine or Nph Combined with Metformin in Type 2 Diabetes: The Lanmet Study," Diabetologia, 2006, vol. 49 (3), pp. 442-451.
Yki-Jarvinen H., "Thiazolidinediones," The New England Journal of Medicine, 2004, vol. 351 (11), pp. 1106-1118.
Yoon N.M., et al., "Exenatide Added to Insulin therapy: A Retrospective Review of Clinical Practice Over Two Years in an Academic Endocrinology Outpatient Setting," Clinical Therapeutics, 2009, vol. 31 (7), pp. 1511-1523.
Yu Z.P., et al., "Effect of Zinc Sulphate and Zinc Methionine on Growth, Plasma Growth Hormone Concentration, Growth Hormone Receptor and Insulin-Like Growth Factor-I Gene Expression in Mice," Clinical and Experimental Pharmacology & Physiology, 2005, vol. 32 (4), pp. 273-278.
Zealand Pharma Press Release entitled "Sanofi-Aventis finalize phase IIa clinical study with GLP-1 agonist for type 2 diabetes licensed from Zealand Pharma" dated Mar. 3, 2005, one page.
Ziemer D.C., et al., "Clinical Inertia Contributes to Poor Diabetes Control in a Primary Care Setting," The Diabetes Educator, 2005, vol. 31 (4), pp. 564-571.
Ziessman H.A., et al., "Sincalide-Stimulated Cholescintigraphy: A Multicenter Investigation to Determine Optimal Infusion Methodology and Gallbladder Ejection Fraction Normal Values," Journal of Nuclear Medicine, 2010, vol. 51 (2), pp. 277-281.
Zimmet P., et al., "Clinical Efficacy of Metformin Against Insulin Resistance Parameters: Sinking the Iceberg," Review Article, Drugs, 1999, vol. 58 (Suppl 1), pp. 21-28.
Zinman B., et al., "Efficacy and Safety of the Human Glucagon-Like Peptide-1 Analog Liraglutide in Combination with Metformin and Thiazolidinedione in Patients with Type 2 Diabetes (LEAD-4 Met+TZD)," Diabetes Care, 2009, vol. 32 (7), pp. 1224-1230.
Zinman B., "The Physiologic Replacement of Insulin an Elusive Goal," The New England Journal of Medicine, 1989, vol. 321 (6), pp. 363-370.
Chi et al., "Excipients and their Effects on the Quality of Biologics" pp. 1-9, (May 2012).
Non-Final Rejection issued in U.S. Appl. No. 13/382,442; dated Mar. 31, 2016, pp. 1-29.
English translation of the TIPO Search Report for ROC Patent Application No. 104116749, dated Feb. 22, 2016, one page.
Ahmad & Swann, and Bloomgren "Exenatide and rare adverse events." N Engl J Med 358(18):1969-72 (May 2008).
Albert-Ludwigs University Freiburg, Institute fur Medizinische Biometrie und Statistik "Non-Inferiority Trials" dated Mar. 29, 2017, one page.
Denker et al., "Exenatide (Exendin-4)-Induced Pancreatitis: A case report" Diabetes Care 29(2):471 (Feb. 2006).
American Diabetes Association, "Standards of Medical Care in Diabetes 2008." Diabetes Care 31(Supplement 1):S12-S54.
American Diabetes Association, "Standards of Medical Care in Diabetes." Diabetes Care 28(Supplement 1): S4-S36 (Jan. 2005).

Bastyr et al., "Therapy focused on lowering postprandial glucose, not fasting glucose, may be superior for lowering HbA1c. IOEZ Study Group." Diabetes Care 23(9):1236-41 (Sep. 2000).
Bell et al., "Sequence of the Human Insulin Gene, "Journal of Nature, 1980, vol. 284 (5751), pp. 26-32.
Bennett, "Impact of the new WHO classification and diagnostic criteria." Diabetes Obes Metab 1(Supplement 2):S1-S6 (1999).
Buse et al., "Effects of exenatide (Exendin-4) on glycemic control over 30 weeks in sulfonylurea-treated patients with type 2 diabetes." Diabetes Care 27(11):2628-35 (Nov. 2004).
BYETTA® European Public Assessment Report (EPAR), pp. 1-36 (Feb. 16, 2012).
BYETTA® Labeling Revision, pp. 1-24 (Jan. 11, 2008).
BYETTA® Prescribing Information, pp. 1-34 (Revised Oct. 2009).
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Non-Final Office Action issued in U.S. Appl. No. 15/275,867; dated Jun. 1, 2017; pp. 1-11.
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
de la Loge et al., "Cross-cultural development and validation of a patient self-administered questionnaire to assess quality of life in upper gastrointestinal disorders: The PAGI-QOL." Quality of Life Research 13(10):1751-62 (Dec. 2004).
De Venciana et al., "Postprandial versus preprandial blood glucose monitoring in women with gestational diabetes mellitus requiring insulin therapy." N Engl J Med 333(19):1237-41 (Nov. 1995).
Definition of "induce" Dictionary.com; last accessed Sep. 29, 2016, pp. 1-6.
Definition of "prevent" Dictionary.com; last accessed Sep. 29, 2016, pp. 1-6.
Degn et al., "Effect of Intravenous Infusion of Exenatide (Synthetic Exendin-4) on Glucose-Dependent Insulin Secretion and Counterregulation During Hypoglycemia." Diabetes 53(9):2397-2403 (Sep. 2004).
Donahue et al., "Postchallenge glucose concentration and coronary heart disease in men of Japanese ancestry. Honolulu Heart Program." Diabetes 36(6):689-92 (Jun. 1987).
Eckert et al., "Assessing the progression of Parkinson's disease: A metabolic network approach," Lancet Neurol. 6 (10):926-32 (Oct. 2007).
European Diabetes Policy Group, "A desktop guide to Type 2 diabetes mellitus." Diabetic Medicine 16 (9):716-730 (1999).
European Medicines Agency, "Guideline on clinical investigation of medicinal products in the treatment of hypertension" (EMA/238/1995 Rev 3) pp. 1-18 (Nov. 18, 2010).
Faichney, "Metformin in Type 1 diabetes: Is This a Good or Bad Idea?" Diabetes Care 26(5):1655 (May 2003).
Non-Final Rejection in U.S. Appl. No. 13/633,496; dated May 25, 2017, pp. 1-10.
Final Rejection issued in U.S. Appl. No. 14/172,151; dated Jan. 4, 2016, pp. 1-20.
Forlenza et al., "Diagnosis and biomarkers of predementia in Alzheimer's disease," BMC Medicine 8:89 pp. 1-14 (Dec. 2010).
Ganz et al., "The association of body mass index with the risk of type 2 diabetes: a case-control study nested in an electronic health records system in the United States." Diabetology & Metabolic Syndrome, 6:50, pp. 1-8 (Apr. 2014).
GenBank: AAA52578.1 "GM-CSF [*Homo sapiens*]" dated Nov. 8, 1994; accessed Jan. 18, 2017, one page.
GenBank: AAA59149.1 "Interleukin 4 [*Homo sapiens*]" dated Jan. 6, 1995; accessed Jan. 18, 2017, one page.
GenBank: AAP20099.1 "Interferon Alpha 2B [Homo sapiens]" dated Apr. 30, 2003; accessed Jan. 18, 2017, one page.
Gerich, "Insulin glargine: long-acting basal insulin analog for improved metabolic control." Curr Med Res Opin. 20(1):31-37 (Jan. 2004).

(56) References Cited

OTHER PUBLICATIONS

Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Halimi, "DPP-4 inhibitors and GLP-1 analogues: for whom? Which place for incretins in the management of type 2 diabetic patients?", Diabetes & Metabolism 34(Supplement 2):S91-S95 (Feb. 2008).
Heine & Dekker, "Beyond postprandial hyperglycemia: metabolic factors associated with cardiovascular disease." Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).
Hollander & Kushner, "Type 2 Diabetes Comorbidities and Treatment Challenges: Rationale for DPP4-Inhibitors" Postgraduate Medicine, 122(3):71-80 (May 2010).
Janka et al., "Comparison of basal insulin added to oral agents versus twice-daily premixed insulin as initial insulin therapy for type 2 diabetes." Diabetes Care 28(2):254-59 (Feb. 2005).
Januvia—EPAR Summary for the Public, pp. 1-3 (Aug. 2012).
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Lepore et al., "Pharmacokinetics and pharmacodynamics of subcutaneous injection of long-acting human insulin analog glargine, NPH insulin, and ultralente human insulin and continuous subcutaneous infusion of insulin lispro." Diabetes 49(12):2142-48 (Dec. 2000).
Mac Conell et al., "Exenatide resulted in significantly greater improvements in postprandial glycaemic control compared to sitagliptin," Diabetologia 51(Supplement 1) p. S348, Abstract 872, one page (2008).
Mainous et al., "Impact of the population at risk of diabetes on projections of diabetes burden in the United States: an epidemic on the way." Diabetologia 50(5):934-40 (May 2007; Epub Nov. 21, 2006).
Matthews et al., "Homeostasis model assessment: insulin resistance and beta-cell function from fasting plasma glucose and insulin concentrations in man." Diabetologia 28(7):412-419 (Jul. 1985).
Mokdad et al., "Prevalence of Obesity, Diabetes, and Obesity-Related Health Risk Factors." JAMA, 289(1):76-79 (Jan. 2003).
Monnier et al., "Contribution of fasting and postprandial plasma glucose increments to the overall diurnal hyperglycemia of type 2 diabetic patients: variations with increasing levels of HbA1c." Diabetes Care 26(3):881-85 (Mar. 2003).
Mudaliar & Edelman, "Insulin therapy in type 2 diabetes." Endocrinol Metab Clin North Am. 30(4):935-82 (Dec. 2001).
Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-75 (Jan. 2008).
Nathan et al., "Translating the A1c Assay Into Estimated Average Glucose values." Diabetes Care 31 (8):1473-78 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).

Non-Final Rejection issued in U.S. Appl. No. 14/172,151; dated Jan. 19, 2017, pp. 1-20.
Non-Final Rejection issued in U.S. Appl. No. 13/467,707; dated Nov. 7, 2016, pp. 1-17.
Non-Final Rejection issued in U.S. Appl. No. 13/509,507; dated Sep. 21, 2016, pp. 1-7.
Non-Final Rejection issued in U.S. Appl. No. 13/633,563; dated Oct. 5, 2016, pp. 1-12.
Non-Final Rejection issued in U.S. Appl. No. 14/303,895; dated Mar. 24, 2017, pp. 1-17.
Non-Final Rejection issued in U.S. Appl. No. 15/068,286; dated Apr. 11, 2017, pp. 1-12.
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Osterbye et al., "Sulfatide promotes the folding of proinsulin, preserves insulin crystals, and mediates its monomerization." Glycobiology 11(6):473-79 (Jun. 2001).
Pinget M., et al., "Efficacy and safety of lixisenatide once daily versus placebo in type 2 diabetes insufficiently controlled on pioglitazone (GetGoal-P)," Diabetes, Obesity and Metabolism, 2013, vol. 15 (11), pp. 1000-1007.
Riddle, "Combined Therapy With Insulin Plus Oral Agents: Is There Any Advantage?" Diabetes Care 31(Supplement2):S125-S130 (Feb. 2008).
Riddle et al., "The treat-to-target trial: randomized addition of glargine or human NPH insulin to oral therapy of type 2 diabetes patients." Diabetes Care 26(11):3080-86 (Nov. 2003).
Riddle, "Timely initiation of basal insulin." Am J Med 116(Suppl 3A):3S-9S (Feb. 2004).
Russell-Jones, "Current developments in the treatment of diabetes: the incretin therapies" Br J Diabetes Vase Dis. 10:21-30 (Feb. 2010).
Sacks et al., "Guidelines and Recommendations for Laboratory Analysis in the Diagnosis and Management of Diabetes Mellitus." Clinical Chemistry 48(3):436-72 (Mar. 2002).
Sloop et al., "Glucagon as a target for the treatment of Type 2 diabetes." Expert Opin Ther Targets. 9(3):593-600 (Jun. 2005).
Spasov & Chepurnova, "Scientific Approaches to Combination Therapy for Type 2 Diabetes Mellitus," Bulletin of Volgograd State Medical University, 1(37):8-10 (2011). See English Abstract.
Stumvoll et al., "Type 2 diabetes: Principles of pathogenesis and therapy." Lancet 365(9467):1333-46 (Apr. 2005).
UK Prospective Diabetes Study (UKPDS) Group 28: A randomized trial of efficacy of early addition of metformin in sulfonylurea-treated type 2 diabetes. Diabetes Care, 21(1):87-92 (Jan. 1998).
van Gaal & De Leeuw, "Rationale and options for combination treatment of type 2 diabetes." Diabletologia 46 (Supplement 1):M44-M50 (Mar. 2003).
van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).
Vilsboll et al., "Liraglutide, a Long-Acting Human Glucagon-Like Peptide-1 Analog, Given as Monotherapy Significantly Improves Glycemic Control and Lowers Body Weight Without Risk of Hypoglycemia in Patients With Type 2 Diabetes, " Journal of Diabetes Care, 2007, vol. 30 (6), pp. 1608-1610.
Wahlin-Boll et al., "Impaired effect of sulfonylurea following increased dosage." Eur J Clin Pharmacol 22(1):21-25 (1982).
Werner, "Preclinical pharmacology of the new GLP-1 receptor agonist AVE0010", Ann. Endocrinol. (Paris), 69 (2):164-65 (Apr. 2008).
Wikipedia® entry for "Stratified sampling" Retrieved on Mar. 28, 2017, pp. 1-4.
Williams & Pickup, "Macrovascular disease in Diabetes." In handbook of Diabetes. 2nd ed. Williams G, Pickup JC, Eds. Oxford, UK, Blackwell Science Chapter 21; pp. 151-158 (1999).
Yki-Jarvinen, "Combination Therapies with insulin in type 2 diabetes." Diabetes Care 24(4):758-67 (Apr. 2001).
Yki-Jarvinen et al., "Comparison of Bedtime insulin regimes in patients with type 2 diabetes mellitus." Annals of Internal Medicine 130(5):389-96 (Mar. 1999).

(56) References Cited

OTHER PUBLICATIONS

Zinman et al., "The Effect of Adding Exenatide to a Thiazolidinedione in Suboptimally Controlled Type 2 Diabetes" Annals of Internal Medicine, 146(7):477-85 (Apr. 2007).
Non-Final Rejection issued in U.S. Appl. No. 14/965,586; dated Mar. 22, 2017, pp. 1-17.
Non-Final Office Action issued in U.S. Appl. No. 15/340,969; dated Jul. 24, 2017, pp. 1-6.
Non-Final Rejection issued in U.S. Appl. No. 15/197,378; dated Jun. 15, 2017, pp. 1-13.
Ahren, "GLP-1 for type 2 diabetes", Experimental Cell Research, 317(9):1239-45 (Jan. 2011).
American Diabetes Association, "Standards of Medical Care in Diabetes—2017" Diabetes Care 40(Supplement 1):S1-S142 (Jan. 2017).
Bergenstal et al., "Type 2 Diabetes: Assessing the Relative Risks and Benefits of Glucose-lowering Medications" The American Journal of Medicine 123(4):e9-e18 (Apr. 2010).
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
BYETTA® Summary of Product Characteristics, updated Jul. 22, 2016, last accessed Jul. 31, 2017, pp. 1-13.
Definition of "reduce" Dictionary.com; last accessed Aug. 13, 2017, pp. 1-4.
Godoy-Matos, "The role of glucagon on type 2 diabetes at a glance," Diabetology & Metabolic Syndrome 6:91, pp. 1-5 (Aug. 2014).
Home et al., "Management of type 2 diabetes: updated NICE guidance" BMJ 336:1306-1308 (Jun. 2008).
Ismail-Beigi et al., "Individulaizing Glycemic Targets in Type 2 Diabetes Mellitus: Implications of Recent Clinical Trials" Annals of Internal Medicine 154(8):554-559 (Apr. 2011).
Lee et al., "Goals of Glycemic Control in Frail Older Patients with Diabetes" JAMA 305(13):1350-51 (Apr. 2011).
Nathan et al., "Medical Management of Hyperglycemia in Type 2 Diabetes: A Consensus Algorithm for the Initiation and Adjustment of Therapy" Diabetologia 52:17-30 (2009: Epub Oct. 22, 2008).
NCT00866658 ClinicalTrials.gov, "GLP-1 agonist AVE0010 in patients with type 2 diabetes for glycemic control and safety evaluation, on top of basal insulin +/− sulfonylurea" p. 1-3, accessed Mar. 16, 2016 (updated Aug. 3, 2010).
NICE, National Institute for Health and Care Excellence, "Type 2 diabetes in adults: management" pp. 1-45 (Dec. 2, 2015).
Rodbard et al., "Statement by an American Association of Clinical Endocrinologists/American College of Endocrinology Consensus Panel on Type 2 Diabetes Mellitus: An Algorithm for Glycemic Control" Endocrine Practice 15(6):540-59 (Sep./Oct. 2009).
Sanofi-aventis Press Release, Once Daily Lixisenatide in Combination with Basal Insulin Demonstrates Significant Improvement in Glucose Cantor Paris, France (Sep. 30, 2010) pp. 1-3.
Sutter Medical Foundation, "Type 2 Diabetes Adult Outpatient Insulin Guidelines" Feb. 2011, pp. 1-6.
U.S. Appl. No. 15/340,969, filed Nov. 1, 2016, Werner et al.
U.S. Appl. No. 15/595,929, filed May 15, 2017, Brunner-Schwarz et al.
U.S. Appl. No. 15/275,867, filed Sep. 26, 2016, Silvestro et al.
U.S. Appl. No. 15/237,285, filed Aug. 15, 2016, Boka et al.
U.S. Appl. No. 15/144,270, filed May 2, 2016, Silvestre et al.
U.S. Appl. No. 15/197,378, filed Jun. 29, 2016, Niemoller et al.
U.S. Appl. No. 15/146,255, filed May 4, 2016, Hess et al.
U.S. Appl. No. 15/657,683, filed Jul. 24, 2017, Souhami et al.
U.S. Appl. No. 15/646,760, filed Jul. 11, 2017, Roy et al.
U.S. Appl. No. 15/411,557, filed Jan. 20, 2017, Boka et al.
Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55 (1993).
Heinrich et al., "Pre-proglucagon messenger ribonucleic acid: nucleotide and encoded amino acid sequences of the rat pancreatic complementary deoxyribonucleic acid," Endocrinol. 115(6):2176-81 (1984).
Holst, "Glucagon-like Peptide-1, A Gastrointestinal Hormone with a Pharmaceutical Potential," Current Medicinal Chemistry 6:1005-17 (1999).
Lopez-Delgado et al., "Effects of Glucagon-Like Peptide I on the Kinetics of Glycogen Synthase a in Hepatocytes from Normal and Diabetic Rats," Endocrinology 139(6):2811-2817 (1998).
English Translation of TIPO Search Report for ROC Patent Application No. 101130936, dated Dec. 1, 2015, one page.
Pi-Sunyer et al., "The effects of pharmacologic agents for type 2 diabetes mellitus on body weight". Postgrad Med. 120(2):5-17 (Jul. 2008).
Schubert-Zsilavecz et al., "Better blood sugar control in diabetics. Insulin glargin—a long acting insulin analogue," Pharmazie in Unserer Zeit 30(2):125-30 (2001). With English translation.
Tews et al., Abstract of Oral Presentation "Enhanced Protection Against Cytokine- and Fatty Acid-induced Apoptosis in Ins-1 Beta-Cells by Combined Treatment with Insulin Glargine and the Novel GLP-1 Receptor Agonist AVE0010" Diabetes, 56(Suppl. 1):A72-A73 (2007).
Tews et al., "Enhanced protection against cytokine- and fatty acid-induced apoptosis in pancreatic beta cells by combined treatment with glucagon-like peptide-1 receptor agonists and insulin analogues." Horm Metab Res. 40 (3):172-80 (Mar. 2008).
The Diabetes Control and Complications Trial Research Group, "The Effect of Intensive Treatment of Diabetes on the Development and Progression of Long-Term Complications in Insulin-Dependent Diabetes Mellitus", The New England Journal of Medicine, 329:977-86 (Sep. 1993).
Uttenthel et al., "Molecular forms of flucagon-like peptide-1 in human pancreas and glucagonomas," J. Clin. Endocrinol. Metabol. 61(3):472-79 (1985).
Weyer et al., "Long-term changes in insulin action and insulin secretion associated with gain, loss, regain and maintenance of body weight", Diabetologia, (43)1:36-46 (Jan. 2000).
WHO Rational Use of Medicines,http://www.who.int/medicines/areas/rational_use/en/downloaded Dec. 18, 2014 10:02:48 AM (2012).
Non-Final Office Action issued in U.S. Appl. No. 13/123,835; dated May 28, 2015, pp. 1-11.
Non-Final Office Action issued in U.S. Appl. No. 13/123,835; dated Dec. 22, 2014, pp. 1-13.
Final Office Action issued in U.S. Appl. No. 13/123,835; dated Feb. 12, 2013, pp. 1-13.
Non-Final Office Action issued in U.S. Appl. No. 13/123,835; dated Jul. 19, 2012, pp. 1-14.
Final Rejection issued in U.S. Appl. No. 13/509,542, dated Feb. 10, 2016, pp. 1-40.
Final-Rejection issued in U.S. Appl. No. 13/432,811; dated Feb. 10, 2016, pp. 1-9.
Final Rejection issued in U.S. Appl. No. 13/467,707; dated Feb. 12, 2016, pp. 1-12.
International Search Report by the ISA for International Application No. PCT/EP2009/063195; dated May 6, 2010.
International Search Report by the ISA for International Application No. PCT/EP2015/079285; dated Mar. 9, 2016, pp. 1-7.
Search Report of the Intellectual Property Office of Singapore for Patent Application No. 102015008711, dated Nov. 2, 2015, pp. 1-3.

Plot of mean 7-point SMPG at baseline and Week 30 – mITT population

*If SAE is received on a Friday or 1 day prior to any Holiday the SAE report must be sent to S-A GPE the same day

FIGURE 23

| Page: | Trial ID: | Visit: | Subj. No: | Date:(dd/mon/yyyy) |
|---|---|---|---|---|

Treatment Related Impact Measure – Diabetes (TRIM-D)

The following questions are concerned with the MEDICATION that you take for your diabetes. If you take more than one medication for your diabetes, or take medication for other conditions, please consider only your MEDICATION when answering these questions.

Please circle the response that most closely represents how you have felt about your MEDICATION over the PAST TWO WEEKS. Please mark only one number for each question. Remember there are no right or wrong answers to these questions.

| 1. How satisfied or dissatisfied have you been with: | *Not at all satisfied* | *A little satisfied* | *Somewhat satisfied* | *Very satisfied* | *Extremely satisfied* |
|---|---|---|---|---|---|
| a. The ease and convenience of your medication | 1 | 2 | 3 | 4 | 5 |
| 2. How convenient or inconvenient is it for you to: | *Not at all convenient* | *A little convenient* | *Somewhat convenient* | *Very convenient* | *Extremely convenient* |
| a. Carry your medication and supplies around with you | 1 | 2 | 3 | 4 | 5 |
| b. Store your medication | 1 | 2 | 3 | 4 | 5 |
| c. Take your medication at the right time | 1 | 2 | 3 | 4 | 5 |
| d. Prepare your medication for use | 1 | 2 | 3 | 4 | 5 |
| e. Monitor your blood sugar as often as necessary | 1 | 2 | 3 | 4 | 5 |
| 3. How often does taking your MEDICATION interfere or not interfere with your: | *Never/ Almost never interferes* | *Rarely interferes* | *Sometimes interferes* | *Often interferes* | *Almost always/ Always interferes* |
| a. Meal time planning | 1 | 2 | 3 | 4 | 5 |
| b. Social activities | 1 | 2 | 3 | 4 | 5 |

FIGURE 24

| Page: | Trial ID: | Visit: | Subj. No: | Date (dd/mon/yyyy) |
|---|---|---|---|---|
| | | | _ _ _ _ _ _ | _ _ I _ _ _ I _ _ _ _ |

| 4. How satisfied or dissatisfied are you with your MEDICATION'S ability to: | *Not at all satisfied* | *A little satisfied* | *Somewhat satisfied* | *Very satisfied* | *Extremely satisfied* |
|---|---|---|---|---|---|
| a. Help you control your diabetes | 1 | 2 | 3 | 4 | 5 |
| b. Help you avoid high blood sugar (hyperglycemia) | 1 | 2 | 3 | 4 | 5 |
| c. Help you avoid low blood sugar (hypoglycemia) | 1 | 2 | 3 | 4 | 5 |
| d. Help you manage your weight | 1 | 2 | 3 | 4 | 5 |
| e. Help you prevent feeling tired or a lack of energy | 1 | 2 | 3 | 4 | 5 |

| 5. Because of your MEDICATION, how OFTEN: | *Never/ Almost never* | *Rarely* | *Sometimes* | *Often* | *Almost always/ Always* |
|---|---|---|---|---|---|
| a. Do you have to limit your daily activities | 1 | 2 | 3 | 4 | 5 |
| b. Do you accomplish less than you would like to | 1 | 2 | 3 | 4 | 5 |
| c. Do you feel tension in your relationships with friends or family | 1 | 2 | 3 | 4 | 5 |

| 6. Thinking about your MEDICATION, how often do you: | *Never/ Almost never* | *Rarely* | *Sometimes* | *Often* | *Almost always/ Always* |
|---|---|---|---|---|---|
| a. Miss a dose | 1 | 2 | 3 | 4 | 5 |
| b. Delay or postpone taking your medication | 1 | 2 | 3 | 4 | 5 |
| c. Take your medication at a different time than prescribed | 1 | 2 | 3 | 4 | 5 |
| d. Feel embarrassed or awkward when taking your medication | 1 | 2 | 3 | 4 | 5 |
| e. Worry that you forgot to take or missed your last dose of medication | 1 | 2 | 3 | 4 | 5 |

FIGURE 25

| Page: | Trial ID: | Visit: | Subj. No: | Date:(dd/mon/yyyy) |
|---|---|---|---|---|

| 7. When I take diabetes MEDICATION I feel: | Never/ Almost never | Rarely | Sometimes | Often | Almost always/ Always |
|---|---|---|---|---|---|
| a. Depressed | 1 | 2 | 3 | 4 | 5 |
| b. Worried that the medication is not helping to slow down or prevent complications from my diabetes | 1 | 2 | 3 | 4 | 5 |
| c. Nervous or anxious | 1 | 2 | 3 | 4 | 5 |
| d. Worried about my blood sugar control | 1 | 2 | 3 | 4 | 5 |
| e. Unhealthy | 1 | 2 | 3 | 4 | 5 |
| f. Angry | 1 | 2 | 3 | 4 | 5 |
| g. Worried about side effects from my medication | 1 | 2 | 3 | 4 | 5 |

Thank You!

FIGURE 26

By placing a tick in one box in each group below, please indicate which statements best describe your own health state today.

Mobility
I have no problems in walking about ☐
I have some problems in walking about ☐
I am confined to bed ☐

Self-Care
I have no problems with self-care ☐
I have some problems washing or dressing myself ☐
I am unable to wash or dress myself ☐

Usual Activities (*e.g. work, study, housework, family or leisure activities*)
I have no problems with performing my usual activities ☐
I have some problems with performing my usual activities ☐
I am unable to perform my usual activities ☐

Pain/Discomfort
I have no pain or discomfort ☐
I have moderate pain or discomfort ☐
I have extreme pain or discomfort ☐

Anxiety/Depression
I am not anxious or depressed ☐
I am moderately anxious or depressed ☐
I am extremely anxious or depressed ☐

FIGURE 28

Impact of Weight on Quality of Life

Please answer the following statements by circling the number that best applies to you in the past week. Be as honest as possible. There are no right or wrong answers.

| Physical Function | ALWAYS TRUE | USUALLY TRUE | SOMETIMES TRUE | RARELY TRUE | NEVER TRUE |
|---|---|---|---|---|---|
| 1. Because of my weight I have trouble picking up objects. | 5 | 4 | 3 | 2 | 1 |
| 2. Because of my weight I have trouble tying my shoelaces. | 5 | 4 | 3 | 2 | 1 |
| 3. Because of my weight I have difficulty getting up from chairs. | 5 | 4 | 3 | 2 | 1 |
| 4. Because of my weight I have trouble using stairs. | 5 | 4 | 3 | 2 | 1 |
| 5. Because of my weight I have difficulty putting on or taking off my clothes. | 5 | 4 | 3 | 2 | 1 |
| 6. Because of my weight I have trouble with mobility (getting around). | 5 | 4 | 3 | 2 | 1 |
| 7. Because of my weight I have trouble crossing my legs. | 5 | 4 | 3 | 2 | 1 |
| 8. I feel short of breath with only mild exertion (e.g. climbing a single flight of stairs). | 5 | 4 | 3 | 2 | 1 |
| 9. I am troubled by painful or stiff joints. | 5 | 4 | 3 | 2 | 1 |
| 10. My ankles and lower legs are swollen at the end of the day. | 5 | 4 | 3 | 2 | 1 |
| 11. I am worried about my health. | 5 | 4 | 3 | 2 | 1 |
| Self-esteem | ALWAYS TRUE | USUALLY TRUE | SOMETIMES TRUE | RARELY TRUE | NEVER TRUE |
| 1. Because of my weight I am self-conscious. | 5 | 4 | 3 | 2 | 1 |
| 2. Because of my weight my self-esteem is not what it could be. | 5 | 4 | 3 | 2 | 1 |
| 3. Because of my weight I feel unsure of myself. | 5 | 4 | 3 | 2 | 1 |
| 4. Because of my weight I don't like myself. | 5 | 4 | 3 | 2 | 1 |
| 5. Because of my weight I am afraid of being rejected. | 5 | 4 | 3 | 2 | 1 |
| 6. Because of my weight I avoid looking in mirrors or seeing myself in photographs. | 5 | 4 | 3 | 2 | 1 |
| 7. Because of my weight I am embarrassed to be seen in public places. | 5 | 4 | 3 | 2 | 1 |

Copyright 2000. Duke University. All Rights Reserved
Direct all correspondence to Ronette L. Kolotkin, Ph.D., Obesity and Quality of Life Consulting,
5004 Norwood Avenue, Durham, NC 27707 USA; email: rkolotkin@yahoo.com; fax: 959-493-9925
IWQOL-Lite-English for UK

FIGURE 29

| Sexual Life | | ALWAYS TRUE | USUALLY TRUE | SOMETIMES TRUE | RARELY TRUE | NEVER TRUE |
|---|---|---|---|---|---|---|
| 1. | Because of my weight I do not enjoy sexual activity. | 5 | 4 | 3 | 2 | 1 |
| 2. | Because of my weight I have little or no sexual desire. | 5 | 4 | 3 | 2 | 1 |
| 3. | Because of my weight I have difficulty with sexual performance. | 5 | 4 | 3 | 2 | 1 |
| 4. | Because of my weight I avoid sexual encounters whenever possible. | 5 | 4 | 3 | 2 | 1 |

| Public Distress | | ALWAYS TRUE | USUALLY TRUE | SOMETIMES TRUE | RARELY TRUE | NEVER TRUE |
|---|---|---|---|---|---|---|
| 1. | Because of my weight I experience ridicule, teasing, or unwanted attention. | 5 | 4 | 3 | 2 | 1 |
| 2. | Because of my weight I worry about fitting into seats in public places (e.g. theatres, cinemas, restaurants, cars, or aeroplanes). | 5 | 4 | 3 | 2 | 1 |
| 3. | Because of my weight I worry about fitting through aisles or turnstiles. | 5 | 4 | 3 | 2 | 1 |
| 4. | Because of my weight I worry about finding chairs that are strong enough to hold my weight. | 5 | 4 | 3 | 2 | 1 |
| 5. | Because of my weight I experience discrimination by others. | 5 | 4 | 3 | 2 | 1 |
| Work | (Note: For those not in paid employment, answer with respect to your daily activities.) | ALWAYS TRUE | USUALLY TRUE | SOMETIMES TRUE | RARELY TRUE | NEVER TRUE |
| 1. | Because of my weight I have trouble getting things done or carrying out my responsibilities. | 5 | 4 | 3 | 2 | 1 |
| 2. | Because of my weight I am less productive than I could be. | 5 | 4 | 3 | 2 | 1 |
| 3. | Because of my weight I don't receive appropriate pay rises, promotions or recognition at work. | 5 | 4 | 3 | 2 | 1 |
| 4. | Because of my weight I am afraid to go for job interviews. | 5 | 4 | 3 | 2 | 1 |

INSULIN GLARGINE/LIXISENATIDE FIXED RATIO FORMULATION

This application claims the benefit of European Application No. 14 197 685.2, filed Dec. 12, 2014, and of European Application No. 15 193 940.2, filed Nov. 10, 2015, the disclosures of both of which are herein incorporated by reference in their entirety.

Subject of the present invention is a pharmaceutical composition comprising (a) lixisenatide or/and a pharmaceutically acceptable salt thereof, and (b) insulin glargine or/and a pharmaceutically acceptable salt thereof, wherein the compound (b) and compound (a) are present in a ratio of about 2.6 to about 3.4 U of compound (b) per µg of compound (a).

In a healthy person the release of insulin by the pancreas is strictly coupled to the concentration of blood glucose. An increased level of blood glucose, as appears after meals, is rapidly counterbalanced by a respective increase in insulin secretion. In fasting condition the plasma insulin level drops to a basal value which is sufficient to ensure the continuous supply of glucose to insulin-sensitive organs and tissues and to keep the hepatic glucose production at a low level at night.

In contrast to diabetes type 1, there is not generally a lack of insulin in diabetes type 2 but in many cases, particularly in progressive cases, the treatment with insulin is regarded as the most suitable therapy, if required in combination with orally administered anti-diabetic drugs.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro and macro-vascular damages that possibly manifest themselves in retinopathies, nephropathies or neuropathies and lead to blindness, renal failure and the loss of extremities and are accompanied by an increased risk of cardiovascular diseases. It can thus be concluded that an improved therapy of diabetes primarily has to aim keeping blood glucose in the physiological range as closely as possible.

A particular risk exists for overweight patients suffering from diabetes type 2, e.g. patients with a body mass index (BMI)≥30 kg/m$^2$. In these patients the risks of diabetes overlap with the risks of overweight, leading e.g. to an increase of cardiovascular diseases compared with diabetes type 2 patients being of a normal weight. Thus, it is particularly necessary to treat diabetes in these patients while reducing the overweight.

Metformin is a biguanide hypoglycemic agent used in the treatment of non-insulin-dependent diabetes mellitus (diabetes mellitus type 2) not responding to dietary modification. Metformin improves glycemic control by improving insulin sensitivity and decreasing intestinal absorption of glucose. Metformin is usually administered orally. However, control diabetes mellitus type 2 in obese patients by metformin may be insufficient. Thus, in these patients, additional measures for controlling diabetes mellitus type 2 may be required.

The compound desPro$^{36}$Exendin-4(1-39)-Lys$_6$-NH$_2$ (AVEOO10, lixisenatide) is a derivative of Exendin-4. Lixisenatide is disclosed as SEQ ID NO:93 in WO 01/04156:

```
SEQ ID NO: 1: Lixisenatide (44 amino acids)
H-G-E-G-T-F-T-S-D-L-S-K-Q-M-E-E-E-A-V-R-L-F-I-E-W-
L-K-N-G-G-P-S-S-G-A-P-P-S-K-K-K-K-K-K-NH2

SEQ ID NO: 2: Exendin-4 (39 amino acids)
H-G-E-G-T-F-T-S-D-L-S-K-Q-M-E-E-E-A-V-R-L-F-I-E-W-
L-K-N-G-G-P-S-S-G-A-P-P-P-S-NH2
```

Exendins are a group of peptides which can lower blood glucose concentration. The Exendin analogue lixisenatide is characterised by C-terminal truncation of the native Exendin-4 sequence. Lixisenatide comprises six C-terminal lysine residues not present in Exendin-4.

In the context of the present invention, lixisenatide includes pharmaceutically acceptable salts thereof. The person skilled in the art knows pharmaceutically acceptable salts of lixisenatide. A preferred pharmaceutically acceptable salt of lixisenatide employed in the present invention is acetate.

Insulin glargine is 31$^B$-32$^B$-Di-Arg human insulin, an analogue of human insulin, with further substitution of asparagine in position A21 by glycine. Insulin glargine is also termed Gly(A21)-Arg(B31)-Arg(B32)-human insulin. In the present invention, insulin glargine includes pharmaceutically acceptable salts thereof.

Insulin glargine is disclosed in U.S. Pat. No. 5,656,722.

Lantus® is an insulin product containing insulin glargine providing 24 hours basal insulin supply after single dose subcutaneous injection.

A dose of 100 U insulin glargine requires injection of 1 mL Lantus® U100, each mL Lantus® U100 contains 100 U insulin glargine. 100 U insulin glargine correspond to 3.6378 mg insulin glargine.

WO 2011/147980 discloses an on-site mixture comprising a fixed concentration of insulin glargine and a variable concentration of lixisenatide. This document also discloses an exemplary on-site mixed preparation containing 100 U/mL insulin glargine and 66.67 µg/mL (or 800/300*25 µg/mL) lixisenatide, 60.6 µg/mL (or 800/330*25 µg/mL) lixisenatide, 55.56 µg/mL (or 800/360*25 µg/mL) lixisenatide, 51.28 µg/mL lixisenatide (or 800/390*25 µg/mL lixisenatide), 47.62 µg/mL (or 800/420*25 µg/mL) lixisenatide, 44.44 µg/mL (or 800/450*25 µg/mL) lixisenatide, 41.67 µg/mL (or 800/480*25 µg/mL) lixisenatide, 39.22 µg/mL (or 800/510*25 µg/mL) lixisenatide, 37.04 µg/mL (or 800/540*25 µg/mL) lixisenatide, 35.09 µg/mL (or 800/570*25 µg/mL) lixisenatide, or 33.33 µg/mL (or 800/600*25 µg/mL) lixisenatide.

Example 1 describes a randomized, 30-week, active-controlled, open label, 2 treatment-arm, parallel-group, multicenter study comparing the efficacy and safety of the insulin glargine/lixisenatide fixed ratio combination to insulin glargine with or without metformin in patients with T2DM. In this study, (I) a pharmaceutical composition comprising 100 U/ml insulin glargine and 50 µg/mL lixisenatide, and (II) a pharmaceutical composition comprising 100 U/ml insulin glargine and 33 µg/mL lixisenatide is used. Furthermore, a combination of (I) and (II) is used.

Example 2 describes a randomized, 3-treatment arm clinical study comparing the efficacy and safety of insulin glargine/lixisenatide fixed ratio combination to insulin glargine alone and to lixisenatide alone on top of metformin in patients with type 2 diabetes mellitus.

Example 2 demonstrates statistical superiority of the fixed ratio combination compared to insulin glargine on HbA1c change as well as statistical superiority of the fixed ratio combination over lixisenatide (Table 9 of Example 2).

Example 2 demonstrates that significantly more patients treated with the fixed ratio combination reached an HbA1c<7% and HbA1c≤6.5% compared to those receiving insulin glargine or lixisenatide (Table 10 of Example 2).

Example 2 demonstrates that treatment with the fixed ratio formulation significantly improved postprandial glycemic control. The 2-hour glucose excursion was significantly improved compared with treatment with insulin glargine (Table 11 of Example 2). An improvement by the fixed dose ratio formulation was also observed for the 2-hour postprandial plasma glucose (PPG) compared with lixisenatide and insulin glargine (Table 12).

Body weight decreased in the fixed ratio combination and lixisenatide groups and increased in the insulin glargine group. A statistically significant difference in the body weight change was found between the fixed ratio combination group and the insulin glargine group (Table 13).

The reductions in fasting plasma glucose (FPG) were similar in the fixed ratio combination and the insulin glargine group, and it was significantly lower in the lixisenatide group (Table 14).

Patients treated with fixed ratio combination had a statistically significant greater decrease in average 7-point SMPG profile compared to patients treated with insulin glargine and patients treated with lixisenatide respectively (Table 15).

In the clinical trial described in Example 2, a higher proportion of patients reached the composite endpoint of HbA1c<7.0% with no body weight gain in the fixed ratio combination group compared to the insulin glargine group and the lixisenatide group (Table 16). More patients reached the triple composite endpoint of HbA1c<7.0% with no body weight gain and with no documented (plasma glucose concentration ≤70 mg/dL [3.9 mmol/L]) symptomatic hypoglycemia during the study in the fixed dose ration composition group compared to the insulin glargine group and the lixisenatide group, respectively (Table 17).

In summary, the fixed ratio combination added to metformin for patients not well controlled with metformin with or without a second oral antidiabetic drug (OAD) significantly improved HbA1c and reduced 2-hour glucose excursions and 2-hour PPG, average 7-point SMPG and body weight in comparison to insulin glargine. The combination also significantly improved HbA1c, FPG, and average 7-point SMPG in comparison with lixisenatide.

The advantages of starting with the fixed ratio combination compared to starting with each component alone in patients not well controlled on an oral antidiabetic drug is therefore evidenced based on the advantages demonstrated for HbA1c and body weight vs insulin glargine, and for HbA1c, FPG and gastrointestinal tolerability in comparison to lixisenatide.

Example 3 describes a randomized, 2-treatment arm clinical study comparing the efficacy and safety of insulin glargine/lixisenatide fixed ratio combination to insulin glargine with or without metformin in patients with type 2 diabetes mellitus.

The fixed ratio combination with or without metformin for patients not adequately controlled with basal insulin with or without oral antidiabetic drugs significantly improved HbA1c (Table 8 of Example 3), allowed more patients to reach HbA1c treatment target (Table 9), reduced 2-hour glucose excursions (Table 10) and 2-hour PPG (Table 11), average 7-point SMPG (Table 13) and body weight (Table 12) in comparison to insulin glargine.

A first aspect of the present invention is a pharmaceutical composition comprising
Lixisenatide (desPro$^{36}$Exendin-4(1-39)-Lys$_6$-NH$_2$) or/and a pharmaceutically acceptable salt thereof, and
insulin glargine or/and a pharmaceutically acceptable salt thereof,
wherein the compound (b) and compound (a) are present in a ratio of about 2.6 to about 3.4 U of compound (b) per µg of compound (a).

Compound (b) and compound (a) can also be present in a ratio of about 2.8 to about 3.2 U of compound (b) per µg of compound (a). Compound (b) and compound (a) can also be present in a ratio of about 2.9 to about 3.1 U of compound (b) per µg of compound (a). Compound (b) and compound (a) can also be present in a ratio of about 3 U of compound (b) per µg of compound (a).

The concentration ratio of compound (b) to compound (a) in the pharmaceutical composition as described herein is a fixed ratio.

In the present invention, compound (a) and compound (b) are provided in a single composition in a pre-determined fixed ratio. Also within the scope of the present invention are two separate compositions, the first composition comprising compound (a) and the second composition comprising compound (b), to be administered to a patient in need thereof as defined herein, in a fixed ratio as defined herein.

In the composition of the present invention, the concentration of compound (a) is preferably not a concentration selected from 66.67 µg/mL 60.6 µg/mL, 55.56 µg/mL, 51.28 µg/mL, 47.62 µg/mL, 44.44 µg/mL, 41.67 µg/mL, 39.22 µg/mL, 37.04 µg/mL, and 35.09 µg/mL.

In the composition of the present invention, the concentration of compound (a) is preferably not a concentration selected from 800/300*25 µg/mL, 800/330*25 µg/mL, 800/360*25 µg/mL, 800/390*25 µg/mL, 800/420*25 µg/mL, 800/450*25 µg/mL, 800/480*25 µg/mL, 800/510*25 µg/mL, 800/540*25 µg/mL and 800/570*25 µg/mL.

In the composition of the present invention, the concentration of compound (a) can be in the range of 25-40 µg/ml. The concentration ratio of compound (b) to compound (a) can be in the range of 2.6 to 3.4 U/µg, 2.8 to 3.2 U/µg, 2.9 to 3.1 U/µg or about 3 U/µg.

In the composition of the present invention, the concentration of compound (b) can be in the range of 65-136 U/ml, 70-128 U/ml, 72.5-124 U/ml or 75-120 U/ml.

In the composition of the present invention, the concentration of compound (a) can be in the range of 25-40 µg/ml, and the concentration of compound (b) can be in the range of 65-136 U/mL, 70-128 U/mL, 72.5-124 U/mL or 75-120 U/mL.

In the composition of the present invention, the concentration of compound (a) can be in the range of 25-38 µg/ml. The concentration ratio of compound (b) to compound (a) can be in the range of 2.6 to 3.4 U/µg, 2.8 to 3.2 U/µg, 2.9 to 3.1 U/µg or about 3 U/µg.

In the composition of the present invention, the concentration of compound (b) can be in the range of 65-129.2 U/ml, 70-121.6 U/ml, 72.5-117.8 U/ml or 75-114 U/ml.

In the composition of the present invention, the concentration of compound (a) can be in the range of 25-38 µg/ml, and the concentration of compound (b) can be in the range of 65-129.2 U/ml, 70-121.6 U/ml, 72.5-117.8 U/ml or 75-114 U/ml.

In the composition of the present invention, the concentration of compound (a) can be in the range of 30-35 µg/ml.

The concentration ratio of compound (b) to compound (a) can be in the range of 2.6 to 3.4 U/μg, 2.8 to 3.2 U/μg, 2.9 to 3.1 U/μg or about 3 U/μg.

In the composition of the present invention, the concentration of compound (b) can be in the range of 78-119 U/mL, 84-112 U/mL, 87-108.5 U/mL, or 90-105 U/mL.

In the composition of the present invention, the concentration of compound (a) can be in the range of 30-35 μg/mL, and the concentration of compound (b) can be in the range of 78-119 U/mL, 84-112 U/mL, 87-108.5 U/mL, or 90-105 U/mL.

In the pharmaceutical composition, the concentration of compound (a) can also be about 33 μg/mL or about 33.3 μg/mL. The concentration ratio of compound (b) to compound (a) can be in the range of 2.6 to 3.4 U/μg, 2.8 to 3.2 U/μg, 2.9 to 3.1 U/μg, or about 3 U/μg. The concentration of compound (b) can be in the range of 85.8-112.2 U/mL, 92.4-105.6 U/mL, 95.7-102.3 U/mL, or can be about 100 U/mL.

In particular, the concentration ratio of compound (b) to compound (a) is about 3 U/μg. More particularly, in the composition having a concentration ratio of compound (b) to compound (a) of about 3 U/μg, the concentration of compound (a) is about 33 μg/mL or about 33.3 μg/mL, and the concentration of compound (b) is about 100 U/mL.

If the pharmaceutical composition as described herein comprises compound (a) in a concentration range of 25 to 40 μg/mL, the concentration of compound (a) is preferably not a concentration selected from 39.22 μg/mL, 37.04 μg/mL and 35.09 μg/mL. In the concentration range of 25 to 40 μg/mL, the concentration of compound (a) preferably is not a concentration selected from 800/510*25 μg/mL, 800/540*25 μg/mL, 800/570*25 μg/mL.

If the pharmaceutical composition as described herein comprises compound (a) in a concentration range of 25 to 38 μg/mL, the concentration of compound (a) is preferably not a concentration selected from 37.04 μg/mL and 35.09 μg/mL. In the concentration range of 25 to 38 μg/mL, the concentration of compound (a) preferably is not a concentration selected from 800/540*25 μg/mL, 800/570*25 μg/mL.

Yet another aspect of the present invention is a combination comprising (I) a pharmaceutical composition comprising
  Lixisenatide (desPro$^{36}$Exendin-4(1-39)-Lys$_6$-NH$_2$) or/and a pharmaceutically acceptable salt thereof, and
  insulin glargine or/and a pharmaceutically acceptable salt thereof,
wherein the compound (b) and compound (a) are present in a ratio of about 1.6 to about 2.4 U of compound (b) per μg of compound (a), and (II) a pharmaceutical composition comprising
  Lixisenatide (desPro$^{36}$Exendin-4(1-39)-Lys$_6$-NH$_2$) or/and a pharmaceutically acceptable salt thereof, and
  insulin glargine or/and a pharmaceutically acceptable salt thereof, wherein the compound (b) and compound (a) are present in a ratio of about 2.6 to about 3.4 U of compound (b) per μg of compound (a).

In the combination, composition (II) can be a composition covered by the ratio of about 2.6 to about 3.4 U of compound (b) per μg of compound (a) as described herein.

The combination of the present invention can be used in the treatment of any disease or condition described herein.

In composition (I), compound (b) and compound (a) can also be present in a ratio of about 1.8 to about 2.2 U of compound (b) per μg of compound (a). Compound (b) and compound (a) can also be present in a ratio of about 1.9 to about 2.1 U of compound (b) per μg of compound (a). Compound (b) and compound (a) can also be present in a ratio of about 2 U of compound (b) per μg of compound (a).

In composition (I), the concentration ratio of compound (b) to compound (a) is a fixed ratio.

In composition (I), the concentration of compound (a) can be in the range of 40-60 μg/ml. The concentration ratio of compound (b) to compound (a) can be in the range of 1.6 to 2.4 U/μg, 1.8 to 2.2 U/μg, 1.9 to 2.1 U/μg or about 2 U/μg.

In composition (I), the concentration of compound (b) can be in the range of 64-144 U/ml, 72-132 U/ml, 76-126 U/ml or 80-120 U/ml.

In composition (I), the concentration of compound (a) can be in the range of 40-60 μg/ml, and the concentration of compound (b) can be in the range of 64-144 U/ml, 72-132 U/ml, 76-126 U/ml or 80-120 U/ml.

In composition (I), the concentration of compound (a) can be in the range of 45-55 μg/ml.

The concentration ratio of compound (b) to compound (a) can be in the range of 1.6 to 2.4 U/μg, 1.8 to 2.2 U/μg, 1.9 to 2.1 U/μg or about 2 U/μg.

In composition (I), the concentration of compound (b) can be in the range of 72-132 U/ml, 81-121 U/ml, 85.5-115.5 U/ml, or 90-110 U/ml.

In composition (I), the concentration of compound (a) can be in the range of 45-55 μg/ml, and the concentration of compound (b) can be in the range of 72-132 U/ml, 81-121 U/ml, 85.5-115.5 U/ml, or 90-110 U/ml.

In composition (I), the concentration of compound (a) can also be about 50 μg/mL. The concentration ratio of compound (b) to compound (a) can be in the range of 1.6 to 2.4 U/μg, 1.8 to 2.2 U/μg, 1.9 to 2.1 U/μg or about 2 U/μg. The concentration of compound (b) can be in the range of 80-120 U/ml, 90-110 U/ml, 95-105 U/ml, or can be about 100 U/ml.

In particular, in composition (I), the concentration of compound (a) is about 50 μg/ml, and the concentration of compound (b) is about 100 U/ml.

If the pharmaceutical composition (I) comprises compound (a) in a concentration range of 40 to 60 μg/ml, the concentration of compound (a) preferably is not a concentration selected from 55.56 μg/mL, 51.28 μg/mL, 47.62 μg/mL, 44.44 μg/mL, and 41.67 μg/mL. In the concentration range of 40 to 60 μg/ml, the concentration of compound (a) preferably is not a concentration selected from 800/360*25 μg/mL, 800/390*25 μg/mL, 800/420*25 μg/mL, 800/450*25 μg/mL, and 800/480*25 μg/mL.

If the pharmaceutical composition (I) comprises compound (a) in a concentration range of 45 to 55 μg/ml, the concentration of compound (a) preferably is not a concentration selected from 51.28 μg/mL and 47.62 μg/mL. In the concentration range of 45 to 55 μg/ml, the concentration of compound (a) preferably is not a concentration selected from 800/390*25 μg/mL and 800/420*25 μg/mL.

The pharmaceutical composition as described herein preferably is not an on-site mixed composition or formulation. The on-site mixed composition or formulation is prepared "on-site", for example shortly (e.g. less than 10 min, less than 20 min or less than 30 min) before administration or/and in the presence of the patient to be treated. In this context, an on-site mixed composition or formulation can be a composition or formulation prepared from at least two separate compositions, each comprising at least one of lixisenatide and insulin glargine. In particular, an on-site mixed formulation or composition is a composition prepared from two separate compositions, the first composition comprising lixisenatide and insulin glargine, and the second composition comprising insulin glargine. More particular, in this context, the on-site mixed formulation or composition is prepared from a first composition containing 800 μg/mL lixisenatide and 100 U/mL insulin glargine, and a second composition containing 100 U/ml insulin glargine. In this context, the on-site mixed composition or formulation can comprise a fixed volume of the first composition and a variable volume of the second composition.

In particular, a pharmaceutical composition (I) comprising 2 U insulin glargine per μg lixisenatide, as described herein or (II) 3 U insulin glargine per μg lixisenatide is not an on-site mixed composition.

The composition or combination of the present invention can be used for the treatment of diabetes mellitus type 1 or/and 2 patients, or/and for the treatment of conditions associated with diabetes type diabetes mellitus type 1 or/and 2.

In particular the composition or combination of the present invention can be used for the treatment of diabetes mellitus type 2 patients, or/and for the treatment of conditions associated with diabetes type diabetes mellitus type 2. Such conditions include a decrease of glucose tolerance, an increased postprandial plasma glucose concentration, an increase in fasting plasma glucose concentration, or/and an increased $HbA_{1c}$ value, compared for example with persons not suffering from diabetes type 2 or with a normoglycemic condition.

The composition or combination of the present invention can be used in glycemic control in diabetes type 2 patients. In the present invention, "improvement of glycemic control" or "glycemic control" in particular refers to improvement of glucose tolerance, improvement of postprandial plasma glucose concentration, improvement of fasting plasma glucose concentration, or/and improvement of the $HbA_{1c}$ value.

In particular, improvement of glucose tolerance includes improvement of the postprandial plasma glucose concentration, improvement of the postprandial plasma glucose excursion or/and improvement of fasting plasma glucose concentration. More particular, improvement of glucose tolerance includes improvement of the postprandial plasma glucose concentration.

In particular, improvement of postprandial plasma glucose concentration is reduction of the postprandial plasma glucose concentration. Reduction means in particular that the plasma glucose concentration reaches normoglycemic values or at least approaches these values.

In particular, improvement of postprandial plasma glucose excursion is reduction of the postprandial plasma glucose excursion. Reduction means in particular that the plasma glucose excursion reaches normoglycemic values or at least approaches these values.

In particular, improvement of fasting plasma glucose concentration is reduction of the fasting plasma glucose concentration. Reduction means in particular that the plasma glucose concentration reaches normoglycemic values or at least approaches these values.

In particular, improvement of the $HbA_{1c}$ value is reduction of the $HbA_{1c}$ value. Reduction of the $HbA_{1c}$ value in particular means that the $HbA_{1c}$ value is reduced below 6.5% or 7%, for example after treatment for at least one month, at least two months, at least three months, at least four months, at least five months, at least six months or at least one year.

The pharmaceutical composition or combination as described herein may be administered in combination with metformin or/and a pharmaceutically acceptable salt thereof, in particular as add-on to the treatment with metformin or/and a pharmaceutically acceptable salt thereof. Metformin is the international nonproprietary name of 1,1-dimethylbiguanide (CAS Number 657-24-9). In the present invention, the term "metformin" includes any pharmaceutically acceptable salt thereof.

In the present invention, metformin may be administered orally. The skilled person knows formulations of metformin suitable for treatment of diabetes type 2 by oral administration. Metformin may be administered to a patient in need thereof, in an amount sufficient to induce a therapeutic effect. Metformin may be administered in a dose of at least 1.0 g/day or at least 1.5 g/day. For oral administration, metformin may be formulated in a solid dosage form, such as a tablet or pill. Metformin may be formulated with suitable pharmaceutically acceptable carriers, adjuvants, or/and auxiliary substances.

In the present invention, the terms "add-on", "add-on treatment", "add-on therapy" and "on top of" relate to treatment of diabetes mellitus type 2 with the metformin and the composition of the present invention, as described herein. The composition of the present invention and metformin may be administered by different administration routes. Metformin may be administered orally, and the composition of the present invention may be administered parenterally.

The patient to be treated by the composition of the present invention may be a patient suffering from diabetes type 2.

The patient to be treated by the composition of the present invention suffering from diabetes type 2 may be a patient suffering from diabetes type 2, wherein diabetes type 2 is not adequately controlled by treatment with metformin alone, for example by treatment with metformin for at least 2 or at least 3 months, for example with a dose of at least 1.0 g/day or at least 1.5 g/day of metformin. In particular, the diabetes type 2 is not adequately controlled by treatment with metformin alone at the onset of treatment with the composition or combination of the present invention.

The patient to be treated by the composition of the present invention suffering from diabetes type 2 may be a patient suffering from diabetes type 2, wherein diabetes type 2 is not adequately controlled by treatment with insulin glargine alone, for example by treatment with insulin glargine for at least 2 or at least 3 months. In particular, the diabetes type 2 is not adequately controlled by treatment with insulin glargine alone at the onset of treatment with the composition or combination of the present invention.

The patient to be treated by the composition of the present invention suffering from diabetes type 2 may be a patient suffering from diabetes type 2, wherein diabetes type 2 is not adequately controlled by treatment with lixisenatide alone, for example by treatment with lixisenatide for at least 2 or at least 3 months. In particular, the diabetes type 2 is not adequately controlled by treatment with lixisenatide alone at the onset of treatment with the composition or combination of the present invention.

The patient to be treated by the composition of the present invention suffering from diabetes type 2 may be a patient suffering from diabetes type 2, wherein diabetes type 2 is not adequately controlled by treatment with at least one oral antidiabetic drug and insulin glargine alone, such as metformin and insulin glargine alone, or with at least one oral antidiabetic drug and lixisenatide alone, such as metformin and lixisenatide alone, for example by treatment for at least 2 or at least 3 months. In particular, the diabetes type 2 is not adequately controlled by treatment with at least one oral antidiabetic drug and insulin glargine alone, such as metformin and insulin glargine alone, or with at least one oral antidiabetic drug and lixisenatide alone, such as metformin and lixisenatide alone at the onset of treatment with the composition or combination of the present invention. The oral antidiabetic drug may be selected from the group consisting of metformin, sulfonylureas, DPP-4 inhibitors, SGLT-2 inhibitors (sodium glucose co-transporter 2 inhibitors) and glinides, and combinations thereof. Preferred combinations comprise two of these oral antidiabetics, for example metformin plus sulfonylurea, metformin plus DPP-4 inhibitor, metformin plus glinide, metformin plus SGLT-2 inhibitor, sulfonylurea plus DPP-4 inhibitor. The oral antidiabetic drug may be a single oral antidiabetic drug, such as metformin only, sulfonylurea only, DPP-4 inhibitor (dipeptidyl-peptidase 4 inhibitor) only, SGLT-2 inhibitor only, or a glinide only.

In the present invention, a patient the diabetes type 2 of which is not adequately controlled if at least one physiological parameter describing blood glucose concentration (i.e. the HbA1c value, the postprandial plasma glucose concentration, the postprandial plasma glucose excursion, or/and the fasting plasma glucose concentration) exceeds normoglycemic values, as described herein. In particular, a patient the diabetes type 2 of which is not adequately controlled may have
(i) a HbA1c value in the range of 7% to 10% or even larger,
(ii) a postprandial glucose excursion, in particular a 2-hour postprandial glucose excursion, of at least 2 mmol/L, or even larger,
(iii) a postprandial plasma glucose concentration, in particular a 2-hour postprandial glucose concentration, of at least 10 mmol/L, or even larger, or/and
(iv) a fasting plasma glucose of at least 7.0 mmol/L or at least 8.0 mmol/L, or even larger.

Before onset of the treatment of the present invention, the patient to be treated may have received at least one oral antidiabetic drug (OAD), such as metformin, sulfonylurea, DPP-4 inhibitor, SGLT-2 inhibitor (sodium glucose co-transporter 2 inhibitor) or/and a glinide, optionally combined with lixisenatide or insulin glargine. Before onset of the treatment of the present invention, the patient to be treated may have received a combination of at least two of these oral antidiabetics, for example metformin plus sulfonylurea, metformin plus DPP-4 inhibitor, metformin plus glinide, metformin plus SGLT-2 inhibitor, sulfonylurea plus DPP-4 inhibitor, optionally combined with lixisenatide or insulin glargine. Before onset of the treatment of the present invention, the patient to be treated may also have received a single oral antidiabetic drug (OAD), such as metformin only, sulfonylurea only, DPP-4 inhibitor (dipeptidyl-peptidase 4 inhibitor) only, SGLT-2 inhibitor only, or glinide only, optionally combined with lixisenatide or insulin glargine. At the onset of the treatment according to the present invention, the treatment with an oral antidiabetic drug, especially an oral antidiabetic drug which is not metformin, may be discontinued.

The patient to be treated by the composition of the present invention suffering from diabetes type 2 may be an obese patient. In the present invention, an obese patient may have a body mass index of at least 30 kg/m$^2$, at least 31 kg/m$^2$, at least 32 kg/m$^2$ or at least 33 kg/m$^2$. Preferred is a body mass index of at least 30 kg/m$^2$ or at least 31 kg/m$^2$.

The patient to be treated by the composition of the present invention suffering from diabetes type 2 may have a normal body weight. In the present invention, a patient having normal body weight may have a body mass index in the range of 17 kg/m$^2$ to 25 kg/m$^2$, 17 kg/m$^2$ to <30 kg/m$^2$ or <30 kg/m$^2$.

The patient to be treated by the composition of the present invention may be an adult patient. The patient may have an age of at least 18 years of may have an age in the range of 18 to 80 years, of 18 to 50 years, or 40 to 80 years, or 50 to 60 years, or 50 to 64 years, or 65 to 74 years, or at least 75 years. The patient may be at least 50 years old. The patient may be younger than 50 years.

The patient to be treated by the composition of the present invention may be a patient who does not receive an antidiabetic treatment, for instance by insulin or/and related compounds, metformin or GLP-1 agonists such as lixisenatide, in particular at the onset of the treatment of the present invention. In particular, the patient to be treated does not receive a GLP-1 receptor agonist (such as lixisenatide) or/and an insulin.

The patient to be treated by the composition of the present invention may suffer from diabetes mellitus type 2 for at least 1 year or at least 2 years. In particular, in the diabetes type 2 patient, diabetes mellitus type 2 has been diagnosed at least 1 year or at least 2 years before onset of therapy by the composition or combination of the present invention.

The diabetes type 2 patient may have a HbA$_{1c}$ value of at least about 9%, at least 8.5%, at least 8%, at least about 7.5%, or at least 7.0%, or the patient may have a HbA$_{1c}$ value of about 7% to about 10%, in particular (I) when the patient is treated with (a) metformin, a sulfonylurea, a DPP-4 inhibitor, an SGLT-2 inhibitor or/and a glinide, or a combination thereof, optionally with lixisenatide or insulin glargine, (b) metformin, (c) metformin and lixisenatide, (d) insulin glargin, or (e) metformin and insulin glargine alone, or (II) without an antidiabetic treatment. In particular, these HbA1c values are reached at the onset of the treatment with the composition or combination of the present invention, or before such treatment, for example within one month before such treatment. The combination of oral antidiabetics may be a combination of at least two oral antidiabetics, for example metformin plus sulfonylurea, metformin plus DPP-4 inhibitor, metformin plus glinide, metformin plus SGLT-2 inhibitor, sulfonylurea plus DPP-4 inhibitor, optionally combined with lixisenatide or insulin glargine. Preferred is a HbA$_{1c}$ value of at least about 8% or at least about 8.5%.

In yet another aspect of the present invention, the composition or combination as described herein can be used for improving the HbA$_{1c}$ value in a patient suffering from diabetes type 2, as described herein.

In yet another aspect of the present invention, the composition or combination as described herein can be used for improving glucose tolerance in a patient suffering from diabetes type 2, as described herein.

In yet another aspect of the present invention, the composition or combination as described herein can be used for improving postprandial plasma glucose concentration in a patient suffering from diabetes type 2, as described herein.

In yet another aspect of the present invention, the composition or combination as described herein can be used for improving postprandial plasma glucose excursion, in particular the 2-hour postprandial glucose excursion, in a patient suffering from diabetes type 2, as described herein.

In yet another aspect of the present invention, the composition or combination as described herein can be used for improving fasting plasma glucose concentration in a patient suffering from diabetes type 2, as described herein.

In yet another aspect of the present invention, the composition or combination as described herein can be used for improving average 7-point SMPG profile. Self-monitored plasma glucose (SMPG)", as used herein, is in particular the "7-point Self Monitored Plasma Glucose". "7-point Self Monitored Plasma Glucose" in particular refers to the measurement of plasma glucose seven times a day and calculation of the average plasma glucose concentration therefrom. The "7-point Self Monitored Plasma Glucose" value is in particular an average plasma glucose concentration including fasting and postprandial conditions. In particular, measurements of plasma glucose concentration are performed pre-breakfast, post-breakfast (e.g. 2-hour post-breakfast), pre-lunch, post-lunch (e.g. 2-hour post-lunch), pre-dinner, post-dinner (e.g. 2-hour post-dinner) and at bed-time. The treatment by the combination of the present invention, as described herein, can improve the self-monitored plasma glucose.

In yet another aspect of the present invention, the composition or combination as described herein can be used for improving body weight in a patient suffering from diabetes type 2, as described herein.

In the present invention, normoglycemic values are blood glucose concentrations of in particular 60-140 mg/dl (corresponding to 3.3 bis 7.8 mM). This range refers in particular to blood glucose concentrations under fasting conditions or/and postprandial conditions.

The diabetes type 2 patient may have a postprandial plasma glucose, in particular a 2-hour postprandial plasma glucose concentration of at least 10 mmol/L, at least 12 mmol/L, at least 13 mmol/L, at least 14 mmol/L, at least 14.5 mmol/L, at least 15 mmol/L, at least 16 mmol/L, or at least 17 mmol/L, in particular (I) when the patient is treated with (a) metformin, a sulfonylurea, a DPP-4 inhibitor, an SGLT-2 inhibitor or/and a glinide, or a combination thereof, optionally with lixisenatide or insulin glargine, (b) metformin, (c) metformin and lixisenatide, (d) insulin glargin, or (e) metformin and insulin glargine alone, or (II) without an antidiabetic treatment. In particular, these plasma glucose concentrations are reached at the onset of the treatment with the composition or combination of the present invention, or before such treatment, for example within one month before such treatment. These plasma glucose concentrations exceed normoglycemic concentrations. The combination of oral antidiabetics may be a combination of at least two oral antidiabetics, for example metformin plus sulfonylurea, metformin plus DPP-4 inhibitor, metformin plus glinide, metformin plus SGLT-2 inhibitor, sulfonylurea plus DPP-4 inhibitor, optionally combined with lixisenatide or insulin glargine. Preferred is a postprandial plasma glucose, in particular a 2-hour postprandial plasma glucose concentration, of at least 14 mmol/L, at least 14.5 mmol/L or at least 15 mmol/L.

The diabetes type 2 patient may have a glucose excursion (in particular a 2-hour postprandial glucose excursion) of at least 2 mmol/L, at least 3 mmol/L, at least 4 mmol/L, at least 5 mmol/L, at least 5.5 mmol/L, at least 6 mmol/L, at least 6.5 mmol/L, or at least 7 mmol/L, in particular (I) when the patient is treated with (a) metformin, a sulfonylurea, a DPP-4 inhibitor, an SGLT-2 inhibitor or/and a glinide, or a combination thereof, optionally with lixisenatide or insulin glargine, (b) metformin, (c) metformin and lixisenatide, (d) insulin glargin, or (e) metformin and insulin glargine alone, or (II) without an antidiabetic treatment. In particular, these plasma glucose excursions are reached at the onset of the treatment with the composition or combination of the present invention, or before such treatment, for example within one month before such treatment. These plasma glucose excursions exceed normoglycemic conditions. The combination of oral antidiabetics may be a combination of at least two oral antidiabetics, for example metformin plus sulfonylurea, metformin plus DPP-4 inhibitor, metformin plus glinide, metformin plus SGLT-2 inhibitor, sulfonylurea plus DPP-4 inhibitor, optionally combined with lixisenatide or insulin glargine. Preferred is a glucose excursion of at least 5 mmol/L or at least 7 mmol/L.

In the present invention, the glucose excursion is in particular the difference of the 2-hour postprandial plasma glucose concentration and the plasma glucose concentration 30 minutes prior to a meal test (2-hour postprandial glucose excursion). In the present invention, the glucose excursion may also be calculated as the difference of the 30-min or 1-hour postprandial plasma glucose concentration and the plasma glucose concentration 30 minutes prior to a meal test (30-min or 1-hour postprandial glucose excursion). It is preferred that the glucose excursion is a 2-hour postprandial glucose excursion.

"Postprandial" is a term that is well known to a person skilled in the art of diabetology. The term "postprandial" describes in particular the phase after a meal or/and exposure to glucose under experimental conditions. In a healthy person this phase is characterised by an increase and subsequent decrease in blood glucose concentration. The term "postprandial" or "postprandial phase" typically ends up to 2 h after the ingestion of a meal or/and exposure to glucose. In the present invention, the term "postprandial plasma glucose" is in particular a 30-min, 1-hour or 2-hour postprandial plasma glucose, i.e. a postprandial plasma glucose determined 30 min, 1 hour or 2 hours after the ingestion of a meal or/and exposure to glucose. In particular, the postprandial plasma glucose concentration is a 2-hour postprandial plasma glucose concentration.

The diabetes type 2 patient as disclosed herein may have a fasting plasma glucose concentration of at least 7 mmol/L, at least 8 mmol/L, at least 9 mmol/L, at least 9.5 mmol/L, at least 10 mmol/L, or at least 11 mmol/L, in particular (I) when the patient is treated with (a) metformin, a sulfonylurea, a DPP-4 inhibitor, an SGLT-2 inhibitor or/and a glinide, or a combination thereof, optionally with lixisenatide or insulin glargine, (b) metformin, (b) metformin and lixisenatide, (c) insulin glargin, or (d) metformin and insulin glargine alone, or (II) without an antidiabetic treatment. In particular, these plasma glucose concentrations are reached at the onset of the treatment with the composition or combination of the present invention, or before such treatment, for example within one month before such treatment. These fasting plasma glucose concentrations exceed normoglycemic concentrations. The combination of oral antidiabetics may be a combination of at least two oral antidiabetics, for example metformin plus sulfonylurea, metformin plus DPP-4 inhibitor, metformin plus glinide, metformin plus SGLT-2 inhibitor, sulfonylurea plus DPP-4 inhibitor, optionally combined with lixisenatide or insulin glargine. Preferred is a fasting plasma glucose concentration of at least 7 mmol/L, at least 9 mmol/L or at least 9.5 mmol/L.

The diabetes type 2 patient as disclosed herein may have a self-monitored plasma glucose concentration of at least 8 mmol/L, at least 9 mmol/L, at least 10 mmol/L, or at least 11 mmol/L, in particular when the patient is treated with (a) metformin, a sulfonylurea, a DPP-4 inhibitor, an SGLT-2 inhibitor or/and a glinide, or a combination thereof, optionally with lixisenatide or insulin glargine, (b) metformin, (c) metformin and lixisenatide, (d) insulin glargin, or (e) metformin and insulin glargine alone, or (II) without an antidiabetic treatment. In particular, these plasma glucose concentrations are reached at the onset of the treatment with the composition or combination of the present invention, or before such treatment, for example within one month before such treatment. These plasma glucose concentrations exceed normoglycemic concentrations. The combination of oral antidiabetics may be a combination of at least two oral antidiabetics, for example metformin plus sulfonylurea, metformin plus DPP-4 inhibitor, metformin plus glinide, metformin plus SGLT-2 inhibitor, sulfonylurea plus DPP-4 inhibitor, optionally combined with lixisenatide or insulin glargine.

Preferred is a self-monitored plasma glucose concentration of at least 9 mmol/L or at least 10 mmol/L.

In the present invention, the composition as described herein may be administered to a patient in need thereof, in an amount sufficient to induce a therapeutic effect.

In the present invention, the composition as described herein may comprise at least one of suitable pharmaceutically acceptable carriers, adjuvants, or/and auxiliary substances.

The composition as described herein may be administered parenterally, e.g. by injection (such as by intramuscular or by subcutaneous injection). Suitable injection devices, for instance the so-called "pens" comprising a cartridge comprising the active ingredient, and an injection needle, are known.

The pharmaceutical composition as described herein can be provided within a container, for example an ampoule, a vial or a "pen", as described herein, to be used by the patient. For example, the pharmaceutical composition being a liquid formulation can be provided within a vial. From such vial, the patient can draw up the required dose into a syringe (in particular a single-use syringe). In particular, the combination of the present invention can be provided in a pen.

The dosage of the composition as described herein may be determined by one of the active agents of the composition to be administered, i.e. by the amount of insulin glargine or by the amount of lixisenatide. It is contemplated that in this case, the second active agent of the composition is administered in an amount defined by the fixed-dose ratio of the composition.

The dose of the composition as described herein may be determined by the amount of lixisenatide to be administered.

In the present invention, the composition or combination as described herein may be administered in an amount in the range of 10 to 15 μg lixisenatide per dose or 15 to 20 μg lixisenatide per dose.

In the present invention, the composition or combination as described herein may be administered in a daily dose in the range of 10 to 20 μg lixisenatide, in the range of 10 to 15 μg lixisenatide, or in the range of 15 to 20 μg lixisenatide.

The composition as described herein may be administered by one injection per day.

The pharmaceutical composition as described herein may be administered in a dose of 0.05 to 0.5 μg/kg body weight lixisenatide.

The dose of the composition of the present invention may also be determined by the amount of insulin glargine required. For example, the insulin glargine dose to be injected may be 40 U or less, or in a range from 10 to 40 U insulin glargine or 20 U to 40 U insulin glargine. The insulin glargine dose to be injected may also be 60 U or less, or in a range from 10 U to 60 U insulin glargine or 30 U to 60 U insulin glargine. The daily insulin glargine dose to be injected may be 40 U or less, or in a range from 10 to 40 U insulin glargine or 20 U to 40 U insulin glargine. The daily insulin glargine dose to be injected also may be 60 U or less, or in a range from 10 U to 60 U insulin glargine or 30 U to 60 U insulin glargine.

The composition of the present invention may be administered in a dose of 0.25 to 1.5 U/kg body weight insulin glargine.

In the present invention, the composition as described herein may be a liquid composition. The skilled person knows liquid compositions of lixisenatide suitable for parenteral administration. The skilled person also knows liquid compositions of insulin glargine suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition of the present invention may comprise a suitable preservative. A suitable preservative may be selected from phenol, m-cresol, benzyl alcohol and p-hydroxybenzoic acid ester. A preferred preservative is m-cresol.

The liquid composition of the present invention may comprise a tonicity agent. A suitable tonicity agent may be selected from glycerol, lactose, sorbitol, mannitol, glucose, NaCl, calcium or magnesium containing compounds such as $CaCl_2$. The concentration of glycerol, lactose, sorbitol, mannitol and glucose may be in the range of 100-250 mM. The concentration of NaCl may be up to 150 mM. A preferred tonicity agent is glycerol.

The liquid composition of the present invention may comprise methionine from 0.5 μg/mL to 20 μg/mL, preferably from 1 μg/ml to 5 μg/ml. Preferably, the liquid composition comprises L-methionine.

Yet another aspect of the present invention refers to a method of treatment of a medical indication, disease or condition, as described herein. For example, the method may comprise the administration of the composition as described herein. The method may be a method of treatment of diabetes type 2 patients, or/and of treatment of conditions associated with diabetes type 2, as described herein. The patient may be a patient as defined herein.

A further aspect of the present invention is a method for improvement of glycemic control in diabetes type 2 patients, said method comprising administering the composition of the present invention to a patient in need thereof. In the method of the present invention, the patient may be the patient defined herein.

Yet another aspect of the present invention refers to the use of the composition as described herein for the manufacture of a composition for the treatment of a medical indication, disease or condition, as described herein. For example, the composition of the present invention can be used for the manufacture of a composition for the treatment of diabetes type 2 patients, or/and for the treatment of conditions associated with diabetes type 2. In particular, the composition of the present invention can be used for the manufacture of a composition for the improvement of glycemic control, improvement of glucose tolerance, improvement of postprandial plasma glucose concentration, improvement of postprandial plasma glucose excursion, improvement of fasting plasma glucose concentration, or/and improvement of the $HbA_{1c}$ value. The patient may be a patient as defined herein.

Yet another aspect of the present invention relates to the use of a combination as described herein for the preparation of medicament for the treatment of a medical indication, disease or condition, as described herein, in particular of diabetes mellitus type 1 or/and 2.

Yet another aspect of the present invention relates to the combination as described herein for use in the treatment of a medical indication, disease or condition, as described herein, in particular for use in the treatment of diabetes mellitus type 1 or/and 2.

Yet another aspect of the present invention is a method of treatment of diabetes mellitus type 1 or/and 2, comprising administering (I) a pharmaceutical composition comprising
    Lixisenatide (desPro$^{36}$Exendin-4(1-39)-Lys$_6$-NH$_2$) or/and a pharmaceutically acceptable salt thereof, and
    insulin glargine or/and a pharmaceutically acceptable salt thereof,
    wherein the compound (b) and compound (a) are present in a ratio of about 1.6 to about 2.4 U of compound (b) per µg of compound (a), or/and (II) a pharmaceutical composition comprising
    Lixisenatide (desPro$^{36}$Exendin-4(1-39)-Lys$_6$-NH$_2$) or/and a pharmaceutically acceptable salt thereof, and
    insulin glargine or/and a pharmaceutically acceptable salt thereof,
    wherein the compound (b) and compound (a) are present in a ratio of about 2.6 to about 3.4 U of compound (b) per µg of compound (a).

In this method, the specific compositions as described herein, being covered by composition (I) or/and (II), can be used.

The patient to be treated by this method may be any patient as described herein.

In particular, in the method of the present invention, composition (I) or composition (II) is administered.

In this method, the pharmaceutical composition of (I) can be administered if the diabetes mellitus type 1 or/and 2 patient requires a dose of insulin glargine of less than or equal to 40 U, and the pharmaceutical composition of (II) can be administered if the diabetes mellitus type 1 or/and 2 patient requires a dose of insulin glargine of more than 40 U.

In this method, the pharmaceutical composition of (I) can be administered if the diabetes mellitus type 1 or/and 2 patient requires a dose of insulin glargine in the range of 10 to 40 U, and the pharmaceutical composition of (II) can be administered if the diabetes mellitus type 1 or/and 2 patient requires a dose of insulin glargine in the range of more than 40 U up to 60 U.

By this method, over-dosing of lixisenatide or/and insulin glargine can be avoided. In particular, over-dosing of lixisenatide can be avoided. If composition (I) is administered, the lixisenatide dose can be in the range of about 15.4 to about 25 µg, or about 16.7 to about 25 µg, or a range as described herein, when a dose of 40 U of insulin glargine is administered. If composition (II) is administered, the lixisenatide dose can be in the range of about 17.6 to about 23.1 µg, or a range as described herein, when a dose of 60 U of insulin glargine is administered.

In this method, the pharmaceutical composition of (I) can be administered if the diabetes mellitus type 1 or/and 2 patient requires a dose of insulin glargine of less than or equal to 30 U, and the pharmaceutical composition of (II) can be administered if the diabetes mellitus type 1 or/and 2 patient requires a dose of insulin glargine of more than 30 U.

In this method, the pharmaceutical composition of (I) can be administered if the diabetes mellitus type 1 or/and 2 patient requires a dose of insulin glargine in the range of 10 to 30 U, and the pharmaceutical composition of (II) can be administered if the diabetes mellitus type 1 or/and 2 patient requires a dose of insulin glargine in the range of more than 30 U up to 60 U.

In this method, the insulin glargine dose is in particular a daily dose of insulin glargine.

In this method, the lixisenatide dose is in particular a daily dose of lixisenatide.

In this method, the pharmaceutical composition of (I) can be administered if the diabetes mellitus type 1 or/and 2 patient requires a daily dose of insulin glargine of less than or equal to 40 U, and the pharmaceutical composition of (II) can be administered if the diabetes mellitus type 1 or/and 2 patient requires a daily dose of insulin glargine of more than 40 U.

In this method, the pharmaceutical composition of (I) can be administered if the diabetes mellitus type 1 or/and 2 patient requires a daily dose of insulin glargine in the range of 10 to 40 U, and the pharmaceutical composition of (II) can be administered if the diabetes mellitus type 1 or/and 2 patient requires a daily dose of insulin glargine in the range of more than 40 U up to 60 U.

In this method, the pharmaceutical composition of (I) can be administered if the diabetes mellitus type 1 or/and 2 patient requires a daily dose of insulin glargine of less than or equal to 30 U, and the pharmaceutical composition of (II) can be administered if the diabetes mellitus type 1 or/and 2 patient requires a daily dose of insulin glargine of more than 30 U.

In this method, the pharmaceutical composition of (I) can be administered if the diabetes mellitus type 1 or/and 2 patient requires a daily dose of insulin glargine in the range of 10 to 30 U, and the pharmaceutical composition of (II) can be administered if the diabetes mellitus type 1 or/and 2 patient requires a daily dose of insulin glargine in the range of more than 30 U up to 60 U.

In this method, the patient to be treated can be a patient as defined herein.

The invention is further illustrated by the following figures and examples.

BRIEF DESCRIPTION OF THE DRAWINGS

FIG. 23 shows questions 1-3 of the Treatment-Related Impact Measure for Diabetes (TRIM-D) questionnaire.

FIG. 24 shows questions 4-6 of the Treatment-Related Impact Measure for Diabetes (TRIM-D) questionnaire.

FIG. 25 shows question 7 of the Treatment-Related Impact Measure for Diabetes (TRIM-D) questionnaire.

FIG. 26 shows page 1 of the EuroQoL Five Dimension (EQ-5D) questionnaire.

FIG. 28 shows page 1 of the Impact of Weight on Quality of Life-Lite (IWQOL-Lite) questionnaire.

FIG. 29 shows page 2 of the Impact of Weight on Quality of Life-Lite (IWQOL-Lite) questionnaire.

EXAMPLE 1

Figure 1:
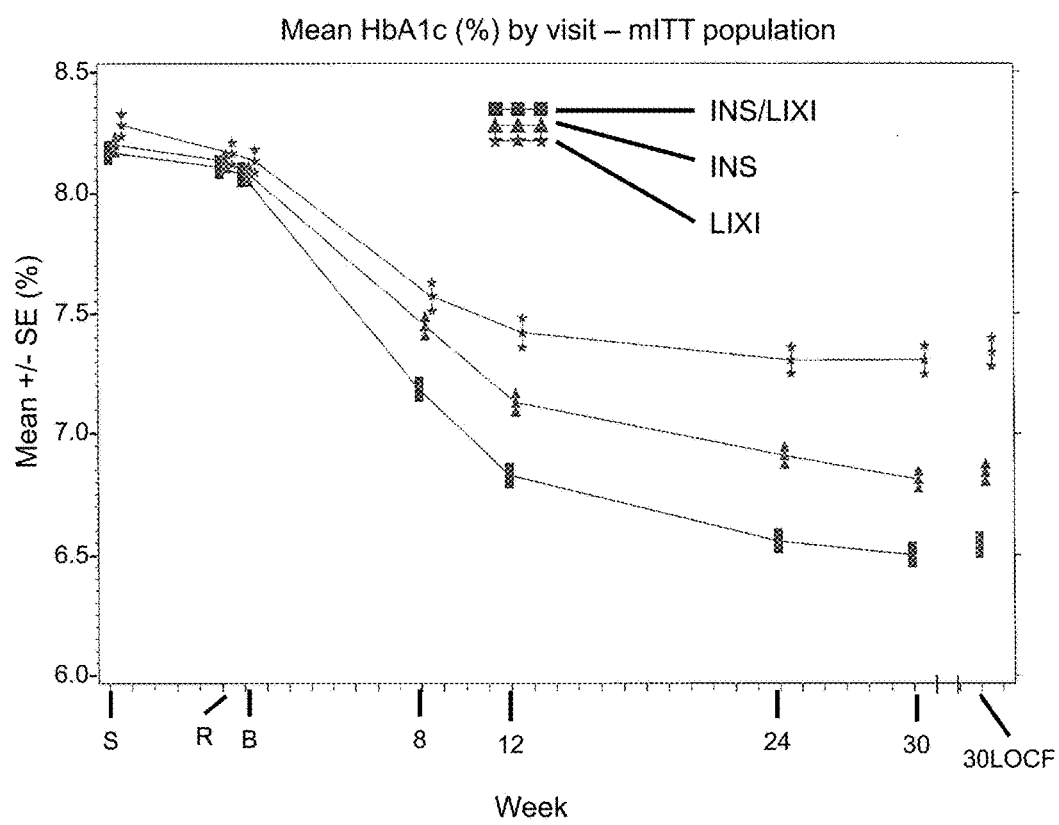
FIG. 1—Mean HbA1c (%) by visit—mITT population. S=Screening (Week −6), R=Run-in (Week −1), B=Baseline, LOCF=Last observation carried forward. INS/LIXI=fixed ratio combination, INS=Insulin Glargine, LIXI=Lixisenatide. Note: The plot included all scheduled measurements obtained during the study, including those obtained after IMP discontinuation or introduction of rescue medication.

A randomized, 30-week, active-controlled, open label, 2 treatment-arm, parallel-group, multicenter study comparing the efficacy and safety of the insulin glargine/lixisenatide fixed ratio combination to insulin glargine with or without metformin in patients with Type 2 Diabetes Mellitus.

Clinical Trial Summary

| Compound: HOE901 (insulin glargine)/AVE0010 (lixisenatide) combination | |
|---|---|
| TITLE | A randomized, 30-week, active-controlled, open label, 2 treatment-arm, parallel-group, multicenter study comparing the efficacy and safety of the insulin glargine/lixisenatide fixed ratio combination to insulin glargine with or without metformin in patients with T2DM |
| INVESTIGATOR/TRIAL LOCATION | Multinational |
| PHASE OF DEVELOPMENT | Phase III |
| STUDY | Primary Objective |

-continued

| Compound: HOE901 (insulin glargine)/AVE0010 (lixisenatide) combination |  |
|---|---|
| OBJECTIVE(S) | To demonstrate over 30 weeks the superiority on $HbA_{1c}$ reduction of the insulin glargine/lixisenatide fixed ratio combination versus insulin glargine in type 2 diabetic patients with or without metformin.<br>Secondary Objective(s)<br>To assess over 30 weeks the effects of the insulin glargine/lixisenatide fixed ratio combination versus insulin glargine on:<br>    Percentage of patients reaching $HbA_{1c}$ targets;<br>    Glycemic control in relation to a meal as evaluated by glucose excursion and 2-hour Post-prandial Plasma Glucose (PPG) during a standardized meal test;<br>    Body weight;<br>    7-point Self-Monitored Plasma Glucose (SMPG) profile;<br>    Percentage of patients reaching $HbA_{1c}$ targets with no body weight gain and/or documented symptomatic hypoglycemia;<br>    Insulin glargine dose;<br>    Fasting Plasma Glucose (FPG)<br>To assess the safety and tolerability in each treatment group.<br>To assess the development of anti-insulin antibodies and anti-lixisenatide antibodies (fixed ratio combination treatment group for the latter).<br>To assess the total and active plasma concentration of lixisenatide before and following injection (fixed ratio combination treatment group).<br>To assess the treatment effects of each treatment group on Patient Reported Outcomes (PROs) measured by the following questionnaires:<br>    Treatment related impact measure-diabetes (TRIM-D)<br>    EudoQol-5D (EQ-5D)<br>    Impact of Weight on Quality of Life-Lite (IWQoL-Lite)<br>To assess patient's overall response to treatment for each treatment group using patient-and physician-rated global treatment effectiveness evaluation scales |
| STUDY DESIGN | Open-label, 1:1 randomized, active-controlled, 2-arm, 30-week treatment duration, parallel-group multinational and multicenter study comparing the insulin glargine/lixisenatide fixed ratio combination to insulin glargine.<br>The randomization will be stratified by value of $HbA_{1c}$ at visit 5 (week-1) (<8%, ≥8%) and metformin use at screening (Y, N).<br>The study will comprise 3 periods:<br>    An up-to 8-week screening period, which includes<br>        An up to 2-week screening phase: Run-in visit can be performed less than 2 weeks after screening visit if the laboratory data are available.<br>        A 6-week run-in phase: Switching to (if appropriate) and/or dose optimization of insulin glargine, continuing metformin (if appropriate) and stopping sulfonylurea(SU), glinide, sodium-glucose co-transporter 2 inhibitor (SGLT-2i) or dipeptidyl-peptidase-4 inhibitor (DPP-4i) if previously taken at V2.<br>    A 30-week open-label randomized treatment period<br>        At the end of the screening period, patients whose $HbA_{1c}$ is ≥ 7% and ≤ 10%, whose mean fasting SMPG calculated from the self-measurements for the 7 days prior to randomization visit is ≤ 140 mg/dL (7.8 mmol/L) and whose insulin glargine daily dose is ≥ 20 u or ≤ 50 U, will enter a 30-week, open-label randomized treatment period comparing lixisenatide/insulin glargine fixed ratio combination to insulin glargine (± metformin for both treatments).<br>    A 3-day post-treatment safety follow-up period for all the patients after permanent IMP discontinuation (except for patients who prematurely discontinue the study treatment; those patients should continue in the study up to the scheduled date of study completion). |
| STUDY POPULATION Main Selection Criteria | Inclusion Criteria:<br>Patients with type 2 diabetes mellitus diagnose at least 1 year before the screening visit.<br>Patients who have been treated with basal insulin for at least 6 months before the screening visit.<br>Patients who have been treated for at least 3 months prior to the screening visit, with a stable basal insulin regimen (i.e. type of insulin and time/frequency of the injection). |

| Compound: HOE901 (insulin glargine)/AVE0010 (lixisenatide) combination |
| --- |

| | |
|---|---|
| | The total daily basal insulin dose should be stable (± 20%) and between 15 and 40 U/day for at least 2 months prior to the screening visit.<br>Patients wo have been treated with basal insulin alone or in combination with a stable dose for at least 3 months before the screening visit of 1 to 2 OADs that can be: metformin (≥ 1500 mg/day or maximal tolerated dose), a sulfonylurea, a glinide, a dipeptidyl-peptidase-4 inhibitor or a SGLT-2 inhibitor.<br>Patients with FPG ≤ 180 mg/dL (10.0 mmol/L) at screening visit.<br>Signed written informed consent.<br>Exclusion Criteria:<br>  Age under legal age of adulthood at screening visit.<br>  HbA1c at screening visit < 7.5% and > 10%.<br>  Pregnancy of lactation, women of childbearing potential with no effective contraceptive method.<br>  Use of other oral or injectable glucose-lowering agents than stated in the inclusion criteria in a period of 3 months prior to screening.<br>  Previous use of insulin regimen other than basal insulin (e.g. prandial or pre-mixed insulin) more than 3 months ago.<br>  Note: Short term treatment due to intercurrent illness including gestational diabetes is allowed at the discretion of the investigator<br>  Discontinuation of a previous treatment with GLP-1 RAs due to safety/tolerability issue or lack of efficacy.<br>  Laboratory findings at the screening visit, including:<br>  Amylase and/or lipase > 3 times the upper limit of the normal laboratory range (ULN);<br>  ALT or AST > 3ULN;<br>  Calcitonin ≥ 20 pg/ml (5.9 pmol/L);<br>  Positive pregnancy test.<br>  Any contraindication to metformin use, according to local labeling. (e.g. renal impairment defined as creatinine > 1.4 mg/dL in women, > 1.5 mg/dL in men, or creatinine clearance < 60 mL/min, etc.) if the patient is taking metformin.<br>  Patient who has a renal function impairment with creatinine clearance < 30 mL/min (using the Cockroft and Gault formula) or end-stage renal disease for patients not treated with metformin.<br>  Contraindication to use of insulin glargine, or lixisenatide.<br>  History of hypersensitivity to insulin glargine, lixisenatide or to any of the excipients.<br>  History of allergic reaction to any GLP-1 RA or insulin glargine or to metacresol.<br>  Personal or immediate family history of medullary thyroid cancer (MTC) or genetic condition that predisposes to MTC (e.g. multiple endocrine neoplasia syndromes).<br>  History of pancreatitis (unless pancreatitis was related to gallstones and cholecystectomy was already performed), chronic pancreatitis, pancreatitis during a previous treatment with incretin therapies, pancreatectomy, stomach/gastric surgery.<br>Exclusion criteria for randomization at the end of the screening period:<br>  HbA$_{1c}$ < 7% or > 10% at visit 5 (week-1).<br>  Mean fasting SMPG calculated from the self-measurements for 7 days the week before randomization visit (V6) is > 140 mg/dL (7.8 mmol/L).<br>  Average insulin glargine daily dose < 20 U or > 50 U calculated for the last 3 days the week before visit 6.<br>  Amylase and/or lipase > 3ULN at visit 5 (week-1). |
| Total expected number of patients | Approximately 700 randomized patents (350 per arm). |
| STUDY TREATMENTS(s) | |
| Investigational medicinal product(s): Formulation | Tested drug:<br>Insulin glargineilixisenatide fixed ratio combination<br>Insulin glargine/lixisenatide fixed ratio combination is supplied as a sterile aqueous solution in a pre-filled disposable SoloStar ® pen-injector (100 U/mL insulin glargine with 33 or 50 μg/mL lixisenatide depending on the pen) |

| | |
|---|---|
| | Compound: HOE901 (insulin glargine)/AVE0010 (lixisenatide) combination |
| | Pen-injector devices:<br>The combination product will be self-administered with a pre-filled disposable SoloStar ® pen-injector.<br>The dose of the combination will be titrated depending on the insulin glargine needs of the patient. Only the insulin glargine dose appears in the pen dosing window. The dose (µg) of lixisenatide does not appear in the dose window although lixisenatide is pre-mixed in the cartage. The lixisenatide dose is increased or decreased concomitantly with any insulin glargine dose change and also depends on the insulin glargine/lixisenatide fixed ratio of the combination product.<br>Two pens with different insulin glargine/lixisenatide fixed ratios will<br>be used to allow insulin glargine titration from 10 to 60 U while limiting lixisenatide dose to a maximum of 20 µg/day:<br>  Pen A (yellow label, yellow dose button): pre-filled disposable SoloStar ® pen-injector containing 3 ml of sterile solution of 100 U/mL insulin glargine and 50 µg/mL lixisenatide in ratio of 2:1 (2 units of insulin glargine per 1 µg lixisenatide). This pen allows administration of daily combination doses between 10 U/5 µg and 40 U/20 µg.<br>  Pen B (red label, red dose button): pre-filed disposable SoloStar ® pen-injector containing 3 ml of sterile solution of 100 U/mL insulin glargine and 33 µg/mL lixisenatide in ratio of 3:1 (3 units of insulin glargine per 1 µg lixisenatide). This pen allows administration of daily combination doses between 30 U/10 µg and 60 U/20 µg. It is intended mainly to be used for patients requiring insulin glargine daily doses between 40 and 60 U. However, it may also be used for insulin glargine daily doses between 30 and 40 U either at initiation of treatment (See below) or during the treatment phase to allow dose decrease e.g. in case of hypoglycemia without necessitating a return to pen A.<br>Patients who started treatment with Pen A and require a daily dose of insulin glargine above 40 U will be switched to Pen B.<br>Control drug:<br>Insulin glargine (Lantus)<br>Insulin glargine is supplied as a sterile aqueous solution, in a pre-filled disposable SoloStar ® pen-injector (100 U/mL insulin glargine).<br>Pen-injector device:<br>The pre-filled disposable SoloStar ® pen-injector is specifically labeled for the use in the study and contains in total 300 units/3 ml of insulin glargine.<br>Disposable pre-filled pen-injectors Lantus ® SoloStar ® are provided to all patients at V2 and to patients randomized in the insulin glargine arm at V6 (week 0, Day 1) and thereafter for the IMP injection. |
| Route(s) of administration | Subcutaneous injector for both IMPs |
| Dose regimen | During run-in phase:<br>Starting dose of insulin glargine<br>From the star of run-in (visit 2), the only basal insulin allowed is insulin glargine. Patients receiving any basal insulin other than insulin glargine before screening will switch to once daily insulin glargine at the start of visit 2.<br>The initial dose of insulin glargine will be the dose of previous basal insulin if they were receiving 1 daily injection or the total daily dose of precious insulin minus 20% if they were receiving more than 1 daily injection. Patients receiving insulin glargine prior to the study will start run-in at their pre-study dose level. Insulin glargine can be injected at any time of the day but at the same time every day. The time of the once daily injection is at the discretion of the patient and investigator and will be fixed at the time of Visit 2 and should remain approximately the same throughout the study (during run-in phase for all patients and also during the randomized treatment period for patients randomized to the insulin glargine treatment group).<br>Adjustment of insulin glargine dose<br>During run-in phase, doses will be adjusted based on daily measured fasting SMPG with the goal of improving fasting glycemic control and allowing patients to meet the randomization criteria (HbA1c at visit 5 ≥ 7% and ≤ 10%; mean fasting SMPG ≤ 140 mg/dL [7.8 mmol/L] measured for 7 days the week before visit 6).<br>The titration procedure to reach these criteria while avoiding hypoglycemia is left at the discretion of the investigator. Small decreases of dose are permitted in case of hypoglycemia, at the |

| Compound: HOE901 (insulin glargine)/AVE0010 (lixisenatide) combination |
|---| discretion of the investigator.

During open-label randomized treatment period:
Insulin glargine/lixisenatide fixed ratio combination group
Patients who received insulin glargine (Lantus) in the morning during the run-in phase:
Patients having the day before Visit 6 (D-1) a daily insulin glargine dose of
- < 30 U will start the combination treatment with pen A at a dose of 20 U of insulin glargine/10 µg of lixisenatide
- ≥30 U will start the combination treatment with pen B at a dose of 30 U of insulin glargine/10 µg of lixisenatide.

First injection will be done on site morning of the randomization.
Patients who received insulin glargine at another time of the day than morning during the run-in phase
Patients will have to switch to an administration within one hour prior to breakfast. A procedure for transitioning time administration is offered below, alternated changeover regimens may be employed if desired:
- The morning of the baseline visit (D1) after randomization: injection while patient is on site, of an insulin glargine dose equal to ½-⅔ (to be decided by the investigator) of the dose injected the day prior to randomization (D-1)
- The next morning (D2), patients having the day before Visit 6 (D-1) a daily insulin glargine dose of
  - < 30 U will start the combination treatment with pen A at a dose of 20 U of insulin glargine/10 µg of lixisenatide
  - ≥30 U will start the combination treatment with pen B at a dose of 30 U of insulin glargine/10 µg of lixisenatide.

For all patients this first dose (either 20 U/10 µg or 30 U/10 µg) will
be maintained stable for 2 weeks. For two additional weeks, dose increase, if necessary, will be limited to a maximum increase of +2 U and not more often than once a week.
After the first 4 weeks, the doses will be titrated once a week according to the algorithm described in table below to achieve glycemic targets (Fasting SMPG in the range of 80 to 100 mg/dL [4.4 to 5.6 mmol/L]) without hypoglycemia. Thereafter, until the end
of the study, the dose will be adjusted as necessary to maintain these fasting SMPG targets.

Dose adjustment algorithm

| Median of fasting SMPG values from preceding 3 days | Insulin glargine dose adjustments (U/day) |
|---|---|
| >140 mg/dL (> 7.8 mmol/L) | +4 |
| >100 and ≤ 140 mg/dL (> 5.6 and ≥ 7.8 mmol/L) | + 2 |
| Glycemic target: 80 and 100 mg/dL (4.4 and 5.6 mmol/L), inclusive | No change |
| ≥60 and < 80 mg/dL (≥ 3.3 and < 4.4 mmol/L) | −2 |
| <60 mg/dL (< 3.3 mmol/L) or occurrence of 2 (or more) symptomatic hypoglycemic episodes or one severe hypoglycemic episode (requiring assistance) documented in the preceding week. | −2 to −4 or at the discretion of the investigator or medically qualified designee |

Insulin glargine (Lantus ®) group
Patients who are randomized to insulin glargine group will administer the day of randomization the same daily dose of insulin glargine as the day prior to randomization visit, and then continue the insulin dose titration as necessary during the open-label randomized treatment period.
Time injection time should remain the same as the one determined at visit 2 and used during the run-in phase.
Dose will be adjusted weekly following the same algorithm described above for the fixed ratio combination.
In both treatment groups
Dose changes are based on a median of fasting SMPG values from last 3 days measured by the patient using glucometers and accessories supplied by the sponsor for this study. Doses may be reduced or modified at any time for hypoglycemia and according

| Compound: HOE901 (insulin glargine)/AVE0010 (lixisenatide) combination | |
|---|---|
| | to the best clinical judgment of investigator.<br>The total daily insulin glargine dose will be capped at 60 U. In case<br>a dose > 60 U of insulin glargine is needed to maintain HbA1c<br>below predefined thresholds value, the dose should be kept at<br>60 U and a recue therapy should be introduced (See Section on<br>Rescue Therapy below). All assessments planned at the end of<br>treatment visit are to be performed before initiating recue therapy. |
| Noninvestigational medicinal product(s)/ (if applicable) Formulation | Background treatment metformin (commercial metformin tablet) and rescue therapy will be considered as NIMP(s) |
| Route(s) of administration | Oral administration for metformin |
| Dose regimen | Background therapy metformin (if appropriate) should be<br>administered according to local product labeling.<br>If patients are on metformin, if should be at a stable dose of at<br>least 1500 mg/day or maximal tolerated dose for at least 3 months<br>prior to screening. This should be continued and the dose should<br>remain stable throughout the study unless there is a specific<br>safety issue related to this treatment.<br>Sulfonylureas, glinides, SGLT-2 inhibitors and DPP-4 inhibitors, if<br>previously taken, will be stopped at the start of run-in (Visit 2). |
| Rescue Therapy | Routine fasting SMPG and central laboratory alerts on FPG and<br>HbA1c are required to ensure that glycemic parameter results<br>remain under predefined thresholds values.<br>In the event that FPG/HbA1c exceed the threshold values (see<br>Section 7.4), if no reason can be found for insufficient glucose<br>control, or if appropriate actions fail or if a dose > 60 U as<br>necessary to decrease FPG/HbA1c to be under the threshold<br>values, a short/rapid-acting insulin may be added as recue<br>therapy starting with a single daily administration that should be<br>given at another meal than breakfast in the fixed ratio combination<br>group, and at any meal for the insulin glargine group. No other<br>OAD or basal insulin should be used as recue mediation in any of<br>the treatment arms.<br>All assessments planned at the end of treatment visit are to be<br>performed before initiating recue therapy. After these<br>assessments are completed and recue therapy initiated, the<br>patient will remain in the study and continue to administer the<br>study treatment (including background therapy) The planned visits<br>and assessments (except the standardized meal test) should be<br>performed until the last scheduled visit. |
| ENDPOINT(S) | Primary endpoint<br>    Change in HbA1c from baseline to week 30.<br>Secondary Endpoints(s)<br>Efficacy:<br>    Percentage of patients reaching HbA1c < 7% or ≤ 6.5 at<br>    week 30<br>    Change in 2-hour PPG and in blood glucose excursion<br>    during standardized meal test from baseline to week 30;<br>    Change in body weight from baseline to week 30;<br>    Change in 7-point SMPG profiles from baseline to week 30<br>    (each time point and average daily value);<br>    Percentage of patients reaching HbA1c < 7% with no body<br>    weight gain at week 30;<br>    Change in daily dose of insulin glargine from baseline to<br>    week 30;<br>    Change in FPG from baseline to week 30;<br>    Percentage of patients reaching HbA1c < 7% at week 30<br>    with no documented [PG ≤ 70 mg/dL (3.9 mmol/L)]<br>    symptomatic hypoglycemia during the 30-week<br>    randomized treatment period;<br>    Percentage of patients reaching HbA1c < 7% with no body<br>    weight fain at week 30 and with no documented<br>    [PG ≤ 70 mg/dL (3.9 mmol/L)] symptomatic hypoglycemia<br>    during the 30-week randomized treatment period;<br>    Change in 30-minute and 1-hour PPG and blood-glucose<br>    excursion during standardized meal test from baseline to<br>    week 30;<br>    Percentage of patients requiring a recue therapy during<br>    30-week open-label treatment period.<br>Safety:<br>    Symptomatic hypoglycemia (documented, probably,<br>    severe symptomatic hypoglycemia);<br>    Adverse events, serious adverse events and AESI, safety<br>    laboratory values, vital signs, and Electrocardiogram<br>    (ECG); |

| | |
|---|---|
| | Compound: HOE901 (insulin glargine)/AVE0010 (lixisenatide) combination |
| | Immunogenicity (antibody variables): Anti-lixisenatide antibodies and/or anti-insulin antibodies (depending on the treatment group) will be measured at Day 1 of the treatment phase and at Week 30.<br>Other Endpoints(s)<br>Pharmacokinetics parameters<br>  Total and active plasma concentrations of lixisenatide will be assessed in the time frame from 1 to 4 hours post-injection at Day 1 of the treatment phase and prior to injection as well as in the time frame from 1 to 4 hours post-injection at Week 30 (for patients in the insulin glargine/lixisenatide fixed ratio combination).<br>Patient Reported Outcomes (PROs)<br>  Changes in patient reported outcomes (PRO) scores will be assessed from baseline to week 30 for Treatment related impact measure-diabetes (TRIM-D), EuroQol-5D (EQ-5D), and impact of Weight on Quality of Life-Lite (IWOoL-Lite) questionnaires;<br>  Patient- and physician-rated global treatment effectiveness evaluation scale will also be evaluated at the end of the study. |
| ASSESSMENT SCHEDULE | Visit schedule:<br>The schedule of study-related procedures/assessments is detailed in Study Flowchart (Section 1.2).<br>Early termination:<br>Patients who prematurely and permanently discontinue IMP administration for any reason should have as soon as possible a visit with assessments normally planned for the last dosing day with the IMP, ie, "final on-treatment assessment", including PK and antibody samples, mean test and PRO assessments, if possible.<br>Note: Patients who prematurely discontinued the IMP should continue in the study up to the schedule state of study completion. They should be followed up according to the study procedures as specified in the protocol (Except 3-day safety post-treatment follow-up, PK and antibody assessments, meal test and PRO assessments). |
| STATISTICAL CONSIDERATIONS | Sample size determination<br>A sample size of 350 patients per arm will provide more than 95% power to detect a difference of 0.4% in the HbA1c change from baseline to week 30 between the insulin glargine/lixisenatide fixed ratio combination and insulin glargine. This calculation assumes a common standard deviation of 1.1% at the 5% significance level (2-sided).<br>Analysis Population:<br>The primary efficacy population will be the modified Intent-To-Treat (mITT) population, which includes all randomized patients who received at least one dose of investigational medicinal product, and have both a baseline assessment and at least one post-baseline assessment of any primary or secondary efficacy endpoints, irrespective of compliance with the study protocol and procedures. Patients will be analyzed in efficacy analyses by the treatment regimen allocated by the IVRS/IWRS according to the randomization schedule at randomization visit (as randomized). The safety analysis will be conducted on the safety population, defined as all randomized patients exposed to at least one dose of investigational medicinal product, regardless of the amount of treatment administered. Patients will be analyzed according to the treatment regimen actually received.<br>Primary efficacy endpoint analysis<br>Analyses of the primary efficacy endpoint (change from baseline to week 30 in HbA1c) will be performed using the mITT population, using HbA1c values obtained from the scheduled visits during the on-treatment period. The on-treatment period for HbA1c is defined as the time from the first dose of investigational medicinal product to 14 days after the last dose or up to the introduction of rescue therapy, whichever is the earliest. The |

| Compound: HOE901 (insulin glargine)/AVE0010 (lixisenatide) combination | |
|---|---|
| | statistical test will be two-sided at the alpha level of 0.05. The primary analysis method for the primary efficacy endpoint will be a mixed-effect model with repeated measures (MMRM) under the missing at random framework. The MMRM model will include the treatment groups, randomization strata, visit, treatment-by-visit interaction, and country as fixed-effect factors, and the baseline HbA1c-by-visit interaction as covariate. The baseline value is defined as the last available value prior to the first dose administration of investigational medicinal product. The adjusted mean change in HbA1c from baseline to Week 30 for each treatment group will be estimated in the framework of this model, as well as the between-group difference and the 95% CI for the adjusted mean.<br>The MMRM model will be run using SAS ® (Version 9.2 or higher) MIXED procedure (PROC MIXED) with an unstructured correlation matrix to model the within-patient errors. Parameters will be estimated using the restricted maximum likelihood method with the Newton-Raphson algorithm. Denominator degree of freedom will be estimated using the Kenward-Roger approximation by fitting values from post-randomization scheduled visits in the on-treatment period. This model will use only scheduled HbA1c measurements obtained during the on-treatment period.<br>For the primary efficacy endpoint, sensitivity analyses will be performed as necessary to explore different methods for handling missing data.<br>Secondary efficacy endpoint analysis<br>The continuous secondary efficacy endpoints will be analyzed using a similar MMRM method. Differences between treatment groups and confidence intervals will be estimated within the framework of MMRM. Categorical efficacy endpoints will be analyzed by Cochran-Mantel-Haenszel method stratified by the randomization strata.<br>Safety analysis<br>Safety analyses for the 30-week treatment period will be descriptive, based on the safety population (randomized and exposed). Treatment-emergent adverse events (TEAEs) are defined as adverse events (AEs) that developed or worsened or became serious during the period from the administration of first dose of the study treatments up to 3 days after the last administration.<br>Pharmacokinetics parameters<br>Lixisenatide plasma concentrations (total and active) of patients in the insulin glargine/lixisenatide fixed ratio combination group will be listed and summarized by visit and time window and by anti-lixisenatide antibody status in the PK population, using descriptive statistics by N, geometric mean, coefficient of variation, median, minimum and maximum.<br>Patient Reported Outcomes<br>Descriptive statistics (mean, median, standard deviation and range) for absolute values and for changes from baseline (TRIM-D, EQ-5D and IWQOI-Lite) will be presented by treatment arm per visit for the global score, sub-scores as well as for each item of the three PROs questionnaires.<br>Descriptive statistics (mean, median, standard deviation and range) for patient- and physician- rated global evaluation scales will also be presented by treatment arm at the end of the study. |
| DURATION OF STUDY PERIOD (per patient) | Maximum duration of approximately 39 weeks: an up to 8-week screening period (with an up to 2-week screening phase and a 6-week run-in phase), a 30-week randomized treatment period and 3 days post-treatment safety follow up period. |

1 FLOW CHARTS

1.1 Graphical Study Design

Figure 15:
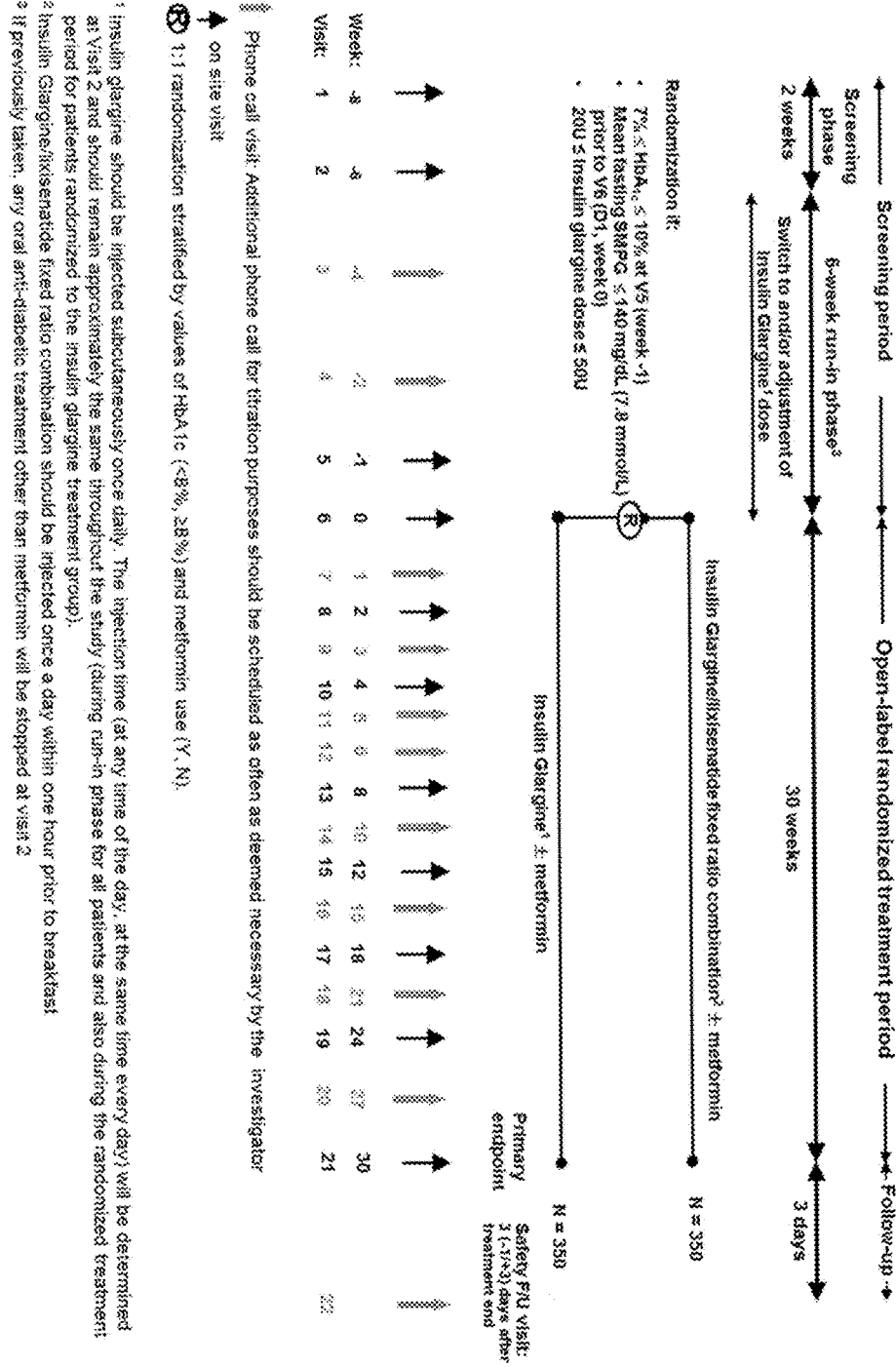
FIG. 15 shows the graphical study design of Example 1.

See FIG. 15

1.2 STUDY FLOW CHART

| | Study period | | | Post-treatment |
|---|---|---|---|---|
| | Screening period[a] | | | follow-up visit |
| | Screening phase | Run-in phase | Open-label randomization treatment period[a] VISIT: Time window: V3-5: ±3 days/V 7-15: ±3 days/V 16-21: ±5 days/V 22: −1/+3 day | |
| | 1 | 2  3☎  4☎ | 5  6  7☎  8  9☎  10  11☎  12☎  13  14☎  15  16☎  17  18☎  19  20  21[b] | 22 V21 + 3 days ☎ |
| | | | WEEK | |
| | −8 | −6  −4  −2 | −1  0  1  2  3  4  5  6  8  10  12  15  18  21  24  27 | 30 |
| Informed Consent | x | | | |
| Inclusion/Exclusion Criteria | x | x | x | |
| Medical, surgical, diabetes, cardiovascular & allergy history, alcohol & smoking habits, demography, prior medications | x | | | |
| Physical Examination | x | | x | x |
| Height | x | | | |
| Body weight | x | | x  x  x  x  x  x | x |
| Vital Signs | x | x | x  x  x  x  x  x  x  x | x |
| 12-lead ECG | x | | | x |
| Diet and Lifestyle counseling | | x | x | |
| IVRS/IWRS contact | x | x | x  x  x  x  x  x | x |
| Randomization | | | x | |
| Concomitant medication recording AE/SAE/Hypoglycemia | | | Continuously assessed and recorded all along the study | |
| Glucometer dispensation & training (including training on glucose measurements)[c] | | x | | |
| Diary dispensation/collection (reviewed at each on-site visit) | | x | x  x  x  x  x  x  x  x | |
| Training to self-injection with Lantus ® Solostar ®[c] | | x | | |
| Insulin glargine (Lantus ® Solostar ®) dispensation | | x | x  x  x  x  x  x | |
| Training to injection using disposable fixed ratio combination pens (Pen A and Pen B)[c] | | | x | |
| Fixed ratio combination pen dispensed | | | x  x  x  x  x  x | |
| Daily fasting SMPG | | x  x  x | x  x  x  x  x  x  x  x  x  x  x  x  x  x | x |
| 7-point SMPG profiles (on 2 different days in the week prior to the visit) | | | x  x | x |
| Insulin glargine dose adjustment | | x  x  x | x  x  x  x  x  x  x  x  x  x  x  x  x  x  x  x | |
| Fixed ratio combination dose adjustment | | | x  x  x  x  x  x  x  x  x  x  x  x  x  x | |
| Record of IMPs doses (on the last 3 days each week until week 12 and then the last 3 days in the week before each visit)[d] | | x  x | x  x  x  x  x  x  x  x  x  x  x  x  x  x  x  x | |
| Count returned pens | | | x  x  x  x  x  x  x  x | x |
| Compliance check | | x  x | x  x  x  x  x  x  x  x  x  x  x  x  x  x  x | x |
| PROs questionnaires (TRIM-D, EQ-5D, IWQoL-Lite) | | | x  x | x |
| Patient-rated Global treatment effectiveness Scale | | | | x |

-continued

1.2 STUDY FLOW CHART

Study period: Screening period / Open-label randomization treatment period / Post-treatment follow-up visit Screening phase / Run-in phase / Open-label randomization treatment period[a] / follow-up visit VISIT: Time window: V3-5: ±3 days/V 7-15: ±3 days/V 16-21: ±5 days/V 22: −1/+3 day Visits: 1, 2, 3, 4, 5, 6, 7, 8, 9, 10, 11, 12, 13, 14, 15, 16, 17, 18, 19, 20, 21[b], 22 (V21 + 3 days)

WEEK: −8, −6, −4, −2, −1, 0, 1, 2, 3, 4, 5, 6, 8, 10, 12, 15, 18, 21, 24, 27, 30

| Assessment | V1 | V2 | V3 | V4 | V5 | V6 | V7 | V8 | V9 | V10 | V11 | V12 | V13 | V14 | V15 | V16 | V17 | V18 | V19 | V20 | V21 | V22 |
|---|---|---|---|---|---|---|---|---|---|---|---|---|---|---|---|---|---|---|---|---|---|---|
| Physician-rated Global treatment effectiveness evaluation Scale | | | | | | | | | | | | | | | | | | | | | x | |
| Central Laboratory testings | | | | | | | | | | | | | | | | | | | | | | |
| HbA1c (central laboratory) | x | | | | x | x | | | | | | | | x | x | | | x | | | x | |
| Fasting Plasma Glucose (central laboratory) | x | | | | x | x | | | | | | x | | x | x | | | x | | | x | |
| 2-h standardized meal test | | | | | x | | | | | | | | | | | | | | | | x | |
| Total-; LDL-; HDL-Cholesterol, triglycerides | | | | | | x | | | | | | | | | | | | | | | x | |
| Urinalysis[e] & Hepatitis B surface antigen and hepatitis C antibody | x | | | | | | | | | | | | | | | | | | | | | |
| Albumin/creatinine ratio (1st morning urines) | | | x | | | | | | | | | | | | | | | | | | x | |
| Women only: FSH, Estradiol (if necessary to define menopausal status) | x | | | | | | | | | | | | | | | | | | | | | |
| Women only: serum pregnancy test (if child-bearing potential) | x | | | | x | | | | | | | | | x | | | | | | | x | |
| Safety laboratory[f]: hematology, serum chemistry | x | | | | | x | | | | | | | | x | | | | | | | x | |
| Amylase, Lipase | x | | | | x | x | x | | x | | | | | x | | | | x | | | x | |
| Serum Calcitonin | x | | | | | x | | | | | | | | x | | | | | | | x | |
| Anti-lixisenatide antibodies and/or anti-insulin antibodies (depending on the treatment group)[h] | | | | | | x | | | | | | | | | | | | | | | x[g] | |
| Lixisenatide total and active plasma concentration (fixed ratio combination treatment group) | | | | | x | | | | | | | | | | | | | | | | x | |
| Optional pharmacogenetic sampling[i] | | | | | | x | | | | | | | | | | | | | | | | |

[a]Additional phone calls for titration purposes should be scheduled as often as deemed necessary by the Investigator; Run-in visit (V2) can be performed less than 2 weeks after screening visit (V1) if the laboratory data are available.
[b]In case of rescue therapy, all assessments (including 2-hour standardized meal test but except for PK and antibody assessments) planned in V21 should be performed before starting rescue medication, patients then continue the IMP treatment, and all visit and assessments (including PK and antibody assessments but except for meal test, and PRO assessments) should be performed as scheduled. In case of premature IMP discontinuation, all assessments (including 2-hour standardized meal test only if the patient received the UMP the day of the meal test) planned in V21 should be performed before premature IMP discontinuation, patients should continue in the study up to the scheduled date of study completion, and all assessments (except the 3-day safety post-treatment follow-up, meal test, PK and antibody assessments, and PRO assessments) should be performed as schedule.
[c]Repeated as often as necessary.
[d]Missed IMP injection should be recorded in the e-CRF.
[e]Screening urinalysis: (pH, glucose, ketones, leucocytes, blood, protein).
[f]Safety Laboratory: hematology = WBC, RBC, Hemoglobin, Hematocrit, platelets, differential blood count (Neutrophils, lymphocytes, monocytes, eosinophils, basophils). Serum chemistry = total bilirubin, G-GT, AST, ALT, ALP, creatinine, uric acid, sodium, potassium, phosphorus, calcium.
[g]One additional sample will be taken at Week 30 for potential additional measurements of immunogenicity.
[h]Samples for antibody assessment to be taken prior to injection.
[i]Samples could also be collected at any later visit

2 LIST OF ABBREVIATIONS

ADA American Diabetes Association
AE Adverse event
AESI Adverse Event of Special Interest
ALP Alkaline phosphatase
ALT Alanine aminotransferase
ANCOVA Analysis of covariance
ARAC Allergic reaction assessment committee
AST Aspartate aminotransferase
BID Bis in die=twice daily
BMI Body mass index
bpm Beat per minute
CAC Cardiovascular events Adjudication Committee
CRF Case report form
CSR Clinical study report CI Confidence Interval
CMH Cochran-Mantel-Haenszel
CMPC Committee for Proprietary Medicinal Products
CT Computerized tomography
D Day
DBP Diastolic blood pressure
dL Deciliter
DNA Deoxyribonucleic acid
DMC Data Monitoring Committee
DRF Discrepancy resolution form
eg Exempli gratia=for example
EASD European association for the study of diabetes
ECG Electrocardiogram
e-CRF Electronic case report form
EQ-5D EuroQol five dimension
EDTA Ethylene diamine tetra-acetic acid
ELISA Enzyme linked immuno-sorbent assay
FPG Fasting plasma glucose
FSH Follicle stimulating hormone
FU Follow up
GCP Good Clinical Practice
G-GT Garnma-glutamyl transpeptidase
GI Gastro-Intestinal
GLP-1 Glucagon like peptide-1
GSO Global Safety Officer
HbA1c Glycated hemoglobin A1c
HBsAg Hepatitis B surface antigen
HCAb Hepatitis C antibody
HDL High density lipoprotein
HLGT High Level Group Term
HLT High Level Term
HRQoL Health related quality of life
ICH International Conference on Harmonization
1e Id est=that is
IEC Independent ethics committee
IMP Investigational medicinal product
IND Investigational new drug
INR International normalized ratio
IRB Institutional review board
ITT Intention-to-treat
IVRSIIWRS Interactive voice/web response system
IWQOL-lite Impact of weight on quality of life
kg Kilogram
LDL Low density lipoprotein
LOCF Last observation carried forward
LLOQ Lower Limit of Quantification
LLT Lower Level Term
MTC Medullary thyroid cancer
MedDRA Medical Dictionnary for Drug Regulatory Affairs
Met Metformin
MMRM Mixed-effect model with repeated measures
MRI Magnetic resonance imaging
μg Microgram
mITT Modified intention-to-treat
mL Milliliter
mmHg Millimeters of mercury
mmol Millimole
ms Millisecond
N Number
NGSP National glycohemoglobin standardization program
OAD Oral anti-diabetic
oc Observed cases
PCSA Potentially clinically significant abnormalities
pg Picogramme
PK Pharmacokinetic
pmol Picomole
PPG Postprandial plasma glucose
PRO Patient report outcome
PSAC Pancreatic safety assessment committee
PT Preferred term
PIC Product technical complaint
QD Quague die=once daily
QoL Quality of life
RBC Red blood cell count
s Second
S.C. Subcutaneous
SAE Serious adverse event
SAS Statistical Analysis System
SBP Systolic blood pressure
SD Standard deviation
SM PG Self-measured plasma glucose
soc System organ class
su Sulfonylurea
T2DM Type 2 diabetes mellitus
TEAE Treatment emergent adverse event
TRIM-D Treatment-related impact measure for diabetes
TSH Thyroid Stimulating Hormone
ULN Upper limit of normal range
v Visit
VAS Visual analogue scale
WBC White blood cell count
WHO World health organization
WHO-DD World health organization—Drug Dictionary

3 INTRODUCTION AND RATIONALE

The present Example will evaluate the efficacy and safety of the combination of basal insulin glargine (Lantus®) and the GLP-1 receptor agonist lixisenatide in patients with T2DM not sufficiently controlled on basal insulin.

Lixisenatide (AVEOO10) is a polypeptide with pronounced GLP-1 agonistic activities which has been approved in 2013 in the European Union, Japan, Mexico, and Australia (under tradename Lyxumia®) and has been filed in several other countries. The current approved indication of Lyxumia in EU is the treatment of adults with type 2 diabetes mellitus to achieve glycaemic control in combination with oral glucose-lowering medicinal products and/or basal insulin when these, together with diet and exercise, do not provide adequate glycaemic control.

Insulin glargine (HOE901 or Lantus®) an analogue of human insulin provides 24-hour basal insulin supply after single dose subcutaneous injection. Lantus® has been marketed since June 2000 in Europe and since May 2001 in the USA and other parts of the world. Lantus® is indicated for the treatment of adult and pediatric patients with TIDM or adult patients with T2DM who require basal (longacting) insulin for the control of hyperglycemia.

Since both lixisenatide and insulin glargine are efficacious when given once daily, and have similar physicochemical features such as good solubility at low pH, both components can be mixed as a defined fixed ratio formulation to be delivered by one single injection.

Type 2 Diabetes Mellitus (T2DM) is characterized by a gradual deterioration of glucose control. Even with multiple oral antidiabetic drugs (OADs), a substantial proportion of patients eventually needs the addition of insulin therapy to achieve and maintain glycated hemoglobin (HbA1c) targets. The transition from OADs to insulin is generally conducted by adding basal insulin to existing OADs and usually is an efficient step in controlling fasting plasma glucose (FPG) levels, when the beta cell still has enough function to cover meals with intrinsic insulin synthesis or secretion. Approximately 60% of T2DM patients treated with basal insulin do not reach HbA1c target of <7%. Further increasing the dose of basal insulin or adding other agents that also target FPG is often associated with weight gain and hypoglycemic events. These and other factors result in poor persistence and adherence to treatment in a sizable proportion of patients.

The combination of basal insulin with a GLP-1 receptor agonist (GLP-1 RA) might offer a significant advantage over existing modality of treatment intensification for patients not able to achieve good glycemic control with basal insulin. In addition to improving glycemic control in patients already being treated with basal insulin, the association of the two can maximize other benefits and at the same time minimize some of the limitations of each one. While the studies conducted to date are heterogeneous in their design, generally speaking, the combination promises to increase the number of patients at target with minimal weight gain or even weight loss while maintaining a manageable hypoglycemia profile. Therefore the combination of basal insulin with a GLP-1 receptor agonist may provide an improvement of the benefit/risk when compared to each one used individually.

As basal insulin products target primarily, although not exclusively, fasting hyperglycemia, and are often given once daily, the most desirable combination would be with a GLP-IRA such as lixisenatide, which, when given once daily, still effectively acts on post-prandial glycemia due to slowing down gastric emptying even when the ability to restore glucose sensitive insulin secretion is exhausted or limited.

There is still an unmet need in patients with uncontrolled type 2 diabetes despite basal insulin. A very significant proportion of patients were able to achieve FPG goals but not HbA1c goals. A therapeutic strategy targeting both FPG and PPG components of HbA1c could help to address this unmet medical need. The present Example intends to demonstrate this for the combination of insulin glargine and lixisenatide.

The lixisenatide standalone product has been developed and approved in the EU at a fixed dose of 20 µg QD. The dosing of lixisenatide in the combination will be variable and range from 5 to 20 µg QD.

In this combination insulin glargine and lixisenatide will be mixed in two fixed ratios solutions delivered by prefilled disposable pen injectors. The dose of the combination will be titrated depending on the insulin needs of the patient, from 10 U insulin glargine/5 µg lixisenatide to 60 U insulin glargine/20 µg lixisenatide. The 2 fixed ratios of the components are proposed to obtain a good pharmacological effect within established tolerability limits. The lower end of the dosing range of lixisenatide is defined by the minimum dose for efficacy, the upper end by available safety database. Data derived from studies in T2DM patients and healthy subjects demonstrate that doses of 5-10 µg lixisenatide could provide sufficient concentrations to stimulate glucose-sensitive insulin release and have demonstrated efficacy on HbA1c, while doses of 10 µg have also demonstrated a potent effect on inhibition of gastric emptying.

Based on the above considerations, the following two pens with 2 different strengths of the combination will be used in the present Example: Pen A will deliver a dose from 10 U insulin glargine/5 µg lixisenatide to 40 U insulin glargine/20 µg lixisenatide [2 (units) to 1 (µg) ratio], while pen B will deliver a dose from 30 U insulin glargine/10 µg lixisenatide to 60 U insulin glargine/20 µg lixisenatide [3 (units) to 1 (µg) ratio].

The dose of the combination will be titrated depending on the insulin glargine needs of the patient. Only the insulin glargine dose appears in the pen dosing window. The dose (µg) of lixisenatide does not appear in the dose window although lixisenatide is pre-mixed in the cartridge. The lixisenatide dose is increased or decreased concomitantly with any insulin glargine dose change and also depends on the insulin glargine/lixisenatide fixed ratio of the combination product. Pen A is intended to be used for patients requiring insulin glargine doses between 10 and 40 U, Pen B is intended to be used for patients requiring insulin glargine doses between 40 and 60 U. It may also be used for insulin glargine doses between 30 and 40 U either at initiation of treatment or during the treatment phase to allow temporary (≤5 days) dose decrease e.g. in case of hypoglycemia without necessitating a return to pen A.

The primary objective of the current Example is to demonstrate over 30 weeks the superiority on HbA1c reduction of the insulin glargine/lixisenatide combination to insulin glargine (±metformin for both treatments) in patients not sufficiently controlled on basal insulin±oral anti-diabetic treatments.

The secondary objectives are to assess the effects of the insulin glargine/lixisenatide combination versus insulin glargine on percentage of patients reaching HbA1c targets, glycemic control during a standardized meal test, body weight, composite endpoints of percentage of patients reaching HbA1c target (<7%) with no weight gain and/or documented symptomatic hypoglycemia, 7-point Self-Monitored Plasma Glucose (SMPG) profile, insulin glargine dose and fasting Plasma Glucose. Other endpoints include health related quality of life.

These endpoints focusing not only on glucose-lowering effects and HbA1c but also on other parameters such as weight and hypoglycemia are considered appropriate to demonstrate the expected benefits from the insulin glargine/lixisenatide fixed ratio combination.

Screened patients who satisfy all entry criteria, will enter a 6-week run-in phase for introduction and/or adjustment of insulin glargine doses (individually adapted according to investigators judgment based on the results of the fasting SMPG levels). Anti-diabetic treatment other than metformin will be stopped at entry in the run-in phase. Metformin treatment if previously taken will be continued.

At the end of this run-in phase, patients with HbA1c≥7% and ≤10%, a mean fasting SMPG calculated from the self-measurements for the 7 days prior to randomization visit ≤140 mg/dL (7.8 mmol/L) and a daily insulin glargine dose ≥20 U or ≤50 U, will enter a 30-week open-label randomized treatment period comparing the fixed ratio combination to insulin glargine. This treatment period duration is considered sufficient to allow an appropriate evaluation of the effect on HbA1c, plasma glucose levels, body weight and other secondary endpoints.

Patients having at randomization a daily insulin glargine dose <30 U will start the combination treatment with Pen A at a dose of 20 U of insulin glargine/10 µg of lixisenatide, those receiving 30 U or more will start the combination treatment with pen B at a dose of 30 U of insulin glargine/10 µg of lixisenatide. After a transition phase during the first 4 week(s) of treatment (see Section 7.2.4), doses will be titrated once a week to achieve glycemic targets [fasting self-monitored plasma glucose (SMPG) in the range of 80 to 100 mg/dL (4.4 to 5.6 mmol/L)] without hypoglycemia. In order not to go above a 20 µg daily dose of lixisenatide, the maximal daily dose of insulin glargine that can be administered in the fixed ratio combination treatment arm is 60 U. Therefore the maximal dose of insulin glargine allowed in the insulin glargine alone arm will also be 60 U/day in order to best investigate the additional impact of the lixisenatide component of the insulin glargine/lixisenatide fixed ratio combination on glucose control.

Both treatments should be administered once daily by deep subcutaneous injection. The insulin glargine/lixisenatide fixed ratio combination is to be injected within one hour prior to breakfast. Insulin glargine can be injected at any time of the day (but approximately at the same time every day). The injection time will be determined at Visit 2. This time injection should remain the same throughout the study (during run-in phase for all patients and also during the randomized treatment period for patients randomized to the insulin glargine treatment group). Patients randomized to the fixed ratio combination group and who previously received insulin glargine at another time of the day than morning will have to switch to an administration within one hour prior to breakfast. A procedure for transitioning time administration is proposed in Section 7.2.4.

Potential safety signals for acute pancreatitis had been identified in the post-marketing experience of other GLP-1 receptor agonists. (to be confirmed with GSO Elisabete) Therefore, patients enrolled in this study should be followed for any suspected pancreatitis, e.g. with symptoms and/or signs of acute abdominal distress or abnormal levels of pancreatic enzymes. Serum amylase and lipase concentrations are monitored routinely at screening, baseline and periodically during the study treatment period. As this monitoring may be difficult in patients who already have high values of amylase or lipase, patients with values above 3 times the upper limit of normal range at screening will not be included in the study. Guidance for Investigators on the follow-up of suspected pancreatitis is specified in the protocol. In addition, selected pancreatic events, including pancreatitis, pancreatic neoplasms and abnormal levels of amylase or lipase, will be reviewed by a panel of blinded, external experts (Pancreatic Safety Assessment Committee).

Information from Victoza® pre-clinical carcinogenicity studies has raised the issue of a potential increased risk of thyroid C-cell hyperplasia and neoplasm. Following a request of the health authorities concerning any clinical study longer than 3 months with a GLP-1 receptor agonist, serum calcitonin will be monitored in the present Example as a marker of thyroid C-cell hyperplasia and neoplasm, with specific monitoring implemented for patients with value 20 pg/mL (5.9 pmol/L). As this monitoring may be difficult in patients who already have high values, those with calcitonin values equal to or above 20 pg/mL (5.9 pmol/L) at screening will not be included in the study.

Conclusion on the Benefit Risk Assessment in this Study:

The insulin glargine/lixisenatide fixed ratio combination is the combination of two products with demonstrated glucose-lowering properties and which are approved in Europe for the treatment of adult patients with T2DM to improve glycemic control.

The type and incidence of adverse events observed in previous lixisenatide clinical studies covering daily doses of up to 60 µg, and in the insulin glargine/lixisenatide fixed ratio combination Phase 2 Study of Example 1 with daily doses up to 60 U of insulin glargine/30 µg of lixisenatide did not reveal findings or concerns precluding the continuation of clinical development. Given the safety profile observed in the completed studies, combined treatment of insulin glargine and lixisenatide in a fixed ratio solution can be considered well tolerated and no particular risk has been identified for the population to be included in the present Example. Therefore, the risk profile for patients participating in this study, using daily doses up to 60 U of insulin glargine/20 µg of lixisenatide is considered limited.

All patients entering this study will receive treatment with insulin glargine/lixisenatide fixed ratio combination or insulin glargine, which should improve their glycemic control. In addition, all patients will benefit from close management of their T2DM.

Rescue therapy is planned and described in the clinical study protocol for patients whose glycemia is poorly controlled.

Given the expected improvement of metabolic control and the additional measures to improve diabetes management, these benefits are considered to outweigh the limited risk associated with the insulin glargine/lixisenatide fixed ratio combination drug. Therefore the benefit-risk ratio for patients participating in the present Example is considered favorable.

4 STUDY OBJECTIVES

4.1 Primary

The primary objective of this study is to demonstrate over 30 weeks the superiority on HbA1c reduction of the insulin glargine/lixisenatide fixed ratio combination versus insulin glargine in type 2 diabetic patients with or without metformin.

4.2 Secondary

The secondary objectives of this study are

To assess over 30 weeks the effects of the insulin glargine/lixisenatide fixed ratio combination versus insulin glargine on:
  Percentage of patients reaching HbA1c targets;
  Glycemic control in relation to a meal as evaluated by glucose excursion and 2-hour Post-prandial Plasma Glucose (PPG) during a standardized meal test;
  Body weight;
  7-point Self-Monitored Plasma Glucose (SMPG) profile;
  Percentage of patients reaching HbA1c targets with no body weight gain and/or documented symptomatic hypoglycemia;
  Insulin glargine dose;
  Fasting Plasma Glucose (FPG).
To assess the safety and tolerability in each treatment group;
To assess the development of anti-insulin antibodies and anti-lixisenatide antibodies (fixed ratio combination treatment group for the latter);
To assess the total and active plasma concentration of lixisenatide before and following injection (fixed ratio combination treatment group);
To assess the treatment effects of each treatment group on Patient Reported Outcomes (PROs) measured by the following questionnaires:
  Treatment related impact measure-diabetes (TRIM-D),
  EuroQol-5D (EQ-5D),
  Impact of Weight on Quality of Life-Lite (IWQoL-Lite).

To assess patient's overall response to treatment for each treatment group using patient- and physician-rated global treatment effectiveness evaluation scales.

5 STUDY DESIGN

5.1 Description of the Protocol

This is an open-label, 1:1 randomized, active-controlled, 2-arm, 30-week treatment duration, parallel-group multinational and multicenter phase III study.

The study will recruit outpatients with T2DM. At baseline visit, the patient will be randomized to either one of the following two treatment groups:
Insulin glargine/lixisenatide fixed ratio combination group
Insulin glargine group The patients will be stratified by value of HbA1c at visit 5 (week −1) (<8%, 8%) and metformin use at screening (Y, N).

The study will comprise 3 periods:
An up-to 8-week screening period, which includes
An up to 2-week screening phase: Run-in visit can be performed less than 2 weeks after screening visit if the laboratory data are available.
A 6-week run-in phase: Switching to (if appropriate) and/or dose optimization of insulin glargine, continuing metformin (if appropriate) and stopping sulfonylurea, glinide, SGLT-2 inhibitor or DPP-4 inhibitor if previously taken at V2.
A 30-week open-label randomized treatment period
At the end of the screening period, patients whose HbA1c is ≥7% and ≤10%, whose mean fasting Self Monitored Plasma Glucose (SMPG) calculated from the self-measurements for the 7 days prior to randomization visit is ≤140 mg/dL (7.8 mmol/L) and whose insulin glargine daily dose is ≥20 U or ≤50 U, will enter a 30-week, open-label randomized treatment period comparing lixisenatide/insulin glargine fixed ratio combination to insulin glargine (±metformin for both treatments).
A 3-day post-treatment safety follow-up period for all the patients after permanent IMP discontinuation (except for patients who prematurely discontinue the study treatment; those patients should continue in the study up to the scheduled date of study completion)

5.2 Duration of Study Participation

5.2.1 Duration of Study Participation for Each Patient

The maximum study duration per patient will be approximately 39 weeks: an up to 8-week screening period (with an up to 2-week screening phase and a 6-week run-in phase), a 30-week randomized treatment period and 3 days post-treatment safety follow up period.

5.2.2 Determination of End of Clinical Trial (all Patients)

The end of the study is defined as being the "last patient last visit" planned with the protocol, including follow-up visit.

5.3 Interim Analysis

Please refer to Section 10.5.

5.4 Study Committees

5.4.1 Data Monitoring Committee

A Data Monitoring Committee (DMC) with members who are independent from the sponsor and the investigators will be used to make appropriate recommendations on the conduct of the clinical trial for ensuring the protection and the safety of the enrolled patients in the study. The DMC reviews and analyzes, on a regular basis, unblinded safety data provided by an independent statistical group throughout the study, as well as safety data from the other ongoing clinical studies conducted with lixisenatide (except the cardiovascular study). A detailed charter outlines the activities of the DMC.

5.4.2 Allergic Reaction Assessment Committee

Since lixisenatide is a peptide that may potentially generate allergic reactions an Allergic Reaction Assessment Committee (ARAC) has been set up. The ARAC is a committee of experts in the field of allergy, independent from the Sponsor and the Investigators, implemented to assess allergic reactions or allergic-like reactions that may occur during the study. The mission of the ARAC will be to adjudicate, in a timely manner, all allergic, or possible allergic events. The ARAC will review the cases in a blinded manner with regard to study treatment.

The ARAC will review the reported cases, determine the nature of the events, and confirm the allergic nature or alternative diagnosis based on the information reported by the Investigator. A detailed charter describes the ARAC procedures.

5.4.3 Cardiovascular Events Adjudication Committee

Following regulatory agency requirements to better assess the impact of newly developed diabetes treatments on cardiovascular events and to adjudicate significant cardiovascular events, an independent Cardiovascular events Adjudication Committee (CAC) has been set up. The CAC is a committee of experts in the field of cardiovascular or cerebrovascular diseases, independent from the Sponsor and the Investigators, implemented to adjudicate major cardiovascular events that may occur during the study. The CAC will review the cases in a blinded manner with regard to study treatment, at the latest before the database lock. A detailed Manual of Operations describes the CAC procedures.

5.4.4 Pancreatic Safety Assessment Committee

Potential safety signals for acute pancreatitis had been identified in the post-marketing experience of other GLP-1 receptor agonists. Specific monitoring for pancreatic events is planned in this study (see Section 9.6.4) and a Pancreatic Safety Assessment Committee (PSAC) has been set up. This is a committee of experts in the field of pancreatitis and pancreatic neoplasm, independent from the Sponsor and the Investigators, implemented to assess pancreatic events that may occur during the study. The PSAC will review selected pancreatic events, including pancreatitis, pancreatic neoplasms and abnormal levels of amylase or lipase. This review will be conducted in a blinded manner with regard to study treatment. A detailed charter describes the PSAC procedures.

6 SELECTION OF PATIENTS

6.1 Inclusion Criteria

Patients meeting all of the following inclusion criteria will be screened:

I 01. Patients with type 2 diabetes mellitus diagnosed at least 1 year before the screening visit.
I 02. Patients who have been treated with basal insulin for at least 6 months before the screening visit.
I 03. Patients who have been treated for at least 3 months prior to the screening visit with a stable basal insulin regimen (i.e. type of insulin and time/frequency of the injection).
I 04. The total daily basal insulin dose should be stable (±20%) and between 15 and 40 U/day for at least 2 months prior to the screening visit.
I 05. Patients who have been treated with basal insulin alone or in combination with a stable dose for at least 3 months before the screening visit of 1 to 2 OADs that can be: metformin (1500 mg/day or maximal tolerated dose), a sulfonylurea (SU), a glinide, a dipeptidyl-peptidase-4 (DPP-4) inhibitor or a SGLT-2 inhibitors.
I 06. Patients with FPG 180 mg/dL (10.0 mmol/L) at screening visit.
I 07. Signed written informed consent.

6.2 Exclusion Criteria

Patients who have met all the above inclusion criteria listed in Section 6.1 will be screened for the following exclusion criteria which are sorted and numbered in the following subsections:

6.2.1 Exclusion Criteria Related to Study Methodology

E 01. At screening visit, age under legal age of adulthood.
E 02. At screening visit, HbA1c: <7.5% and >10.0%.
E 03. At screening visit, Body Mass Index (BMI)≤20 or >40 kg/m$^2$
E 04. History of hypoglycemia unawareness.
E 05. History of metabolic acidosis, including diabetic ketoacidosis within 1 year prior to screening visit.
E 06. Use of other oral or injectable glucose-lowering agents than stated in the inclusion criteria in a period of 3 months prior to screening.
E 07. Previous use of insulin regimen other than basal insulin (e.g. prandial or pre-mixed insulin) more than 3 months ago.
  Note: Short term treatment due to intercurrent illness including gestational diabetes is allowed at the discretion of the investigator
E 08. Previous use of insulin regimen other than basal insulin (e.g. prandial or pre-mixed insulin) more than 3 months ago.
  Note: Short term treatment due to intercurrent illness including gestational diabetes is allowed at the discretion of the investigator
E 09. Discontinuation of a previous treatment with GLP-1 RAs due to safety/tolerability issue or lack of efficacy.
E 10. Use of systemic glucocorticoids (excluding topical and inhaled forms) for a total duration of 1 week or more within 3 months prior to screening visit.
E 11. Use of weight loss drugs within 3 months prior to screening visit.
E 12. Use of any investigational drug within 1 month or 5 half-lives, whichever is longer, prior to screening visit.
E 13. Patient who has previously participated in any clinical trial with lixisenatide or the insulin glargine/lixisenatide fixed ratio combination or has previously received lixisenatide.
E 14. Within the last 6 months prior to screening visit: history of stroke, myocardial infarction, unstable angina, or heart failure requiring hospitalization.
E 15. Planned coronary, carotid or peripheral artery revascularisation procedures to be performed during the study period.
E 16. Known history of drug or alcohol abuse within 6 months prior to the time of screening visit.
E 17. Uncontrolled or inadequately controlled hypertension (systolic blood pressure >180 mmHg or diastolic blood pressure >95 mmHg) at screening visit.
E 18. Conditions/situations such as:
  Patients with conditions/concomitant diseases making them non evaluable for the primary efficacy endpoint (e.g., hemoglobinopathy or hemolytic anemia, receipt of blood or plasma products within the last 3 months prior to the screening visit)
  Patients with conditions/concomitant diseases precluding their safe participation in this study (e.g. active malignant tumor, major systemic diseases, presence of clinically significant diabetic retinopathy or presence of macular edema likely to require treatment within the study period, etc.); Impossibility to meet specific protocol requirements (e.g., scheduled visits, patients unable to fully understand patient's study documents and to complete them, etc.);
  Uncooperative or any condition that could make the patient potentially non-compliant to the study procedures (e.g. patient unable or unwilling to do self-injections or blood glucose monitoring using the sponsor-provided blood glucose meter at home, etc.);
  Patient is the Investigator or any Sub-Investigator, research assistant, pharmacist, study coordinator, other staff or relative thereof directly involved in the conduct of the protocol.
E 19. Laboratory findings at the screening visit:
  Amylase and/or lipase: >3 times the upper limit of the normal (ULN) laboratory range, ALT or AST: >3 ULN, Total bilirubin>1.5 ULN (except in case of Gilbert's syndrome), Calcitonin ≥20 pg/mL (5.9 pmol/L),
  Hemoglobin <10.5 g/dL or neutrophils <1,500/mm$^3$ or platelets <100,000/mm$^3$,
  Positive test for Hepatitis B surface antigen and/or Hepatitis C antibody, Positive serum pregnancy test.
E 20. Any technical/administrative reason that makes it impossible to randomize the patient in the study.
E 21. Patient who withdraws consent during the screening period (screening phase and run-in phase).
E 22. The target number of randomized patients is reached.

6.2.2 Exclusion Criteria Related to the Active Comparator and/or Background Therapy E 23. Any contraindication to metformin use, according to local labeling. (e.g. renal impairment defined as creatinine >1.4 mg/dL in women, >1.5 mg/dL in men, or creatinine clearance <60 mL/min, etc.) if the patient is taking metformin.

E 24. Contraindication to use of insulin glargine according to local labeling. History of hypersensitivity to insulin glargine or to any of the excipients.

6.2.3 Exclusion Criteria Related to the Tested IMP (Insulin Glargine/Lixisenatide Fixed Ratio Combination)

E 25. Pregnancy or lactation.

E 26. Women of childbearing potential not protected by highly effective contraceptive method of birth control (as defined for contraception in the Informed Consent Form and/or in a local protocol addendum) and/or who are unwilling or unable to be tested for pregnancy.

"Woman of childbearing potential not protected by highly-effective method(s) of birth control (as defined for contraception in the Informed Consent Form and/or in a local protocol amendment in case of specific local requirement) and/or who are unwilling or unable to be tested for pregnancy."—whether to be changed is under confirmation.

E 27. Clinically relevant history of gastrointestinal disease associated with prolonged nausea and vomiting, including (but not limited to): gastroparesis, unstable (ie, worsening) or not controlled (i.e., prolonged nausea and vomiting) gastroesophageal reflux disease requiring medical treatment, within 6 months prior to the time of screening visit.

E 28. History of pancreatitis (unless pancreatitis was related to gallstones and cholecystectomy was already performed), chronic pancreatitis, pancreatitis during a previous treatment with incretin therapies, pancreatectomy, stomach/gastric surgery.

E 29. Personal or immediate family history of medullary thyroid cancer (MTC) or genetic conditions that predispose to MTC (eg, multiple endocrine neoplasia syndromes).

E 30. Patient who has a renal function impairment with creatinine clearance <30 mL/min (using the Cockroft and Gault formula) or end-stage renal disease for patients not treated with metformin.

E 31. Contraindication to use of lixisenatide (according to local labeling if appropriate). History of allergic reaction to any GLP-1 receptor agonists including lixisenatide in the past or to metacresol

6.2.4 Additional Exclusion Criteria at the End of Screening Period Before Randomization E 32. Use of sulfonylurea, glinide, SGLT-2 inhibitor, and DPP-4 inhibitor after start of run-in (from visit 2).

E 33. HbA1c<7% or >10% at visit 5 (week −1).

E 34. Mean fasting SMPG calculated from the self-measurements for 7 days the week before randomization visit (V6) is >140 mg/dL (7.8 mmol/L).

E 35. Average insulin glargine daily dose<20 U or >50 U calculated for the last 3 days the week before visit 6.

E 36. Amylase and/or lipase >3 ULN at visit 5 (week −1).

E 37. Patient with any AE, which, by the judgment of the Investigator would preclude the inclusion in the open-label randomized treatment period.

A patient should not enter the run-in phase or be randomized more than once. In cases where original screen failure was due to reasons expected to change at rescreening and based upon the Investigator's clinical judgment, the patient can be rescreened one time for this study.

7 STUDY TREATMENTS

7.1 Diet and Exercise

Lifestyle and diet therapy provided before the time of screening is to be continued during the study in a similar manner. Dietary and lifestyle counseling will be given by a healthcare professional at visit 2 and visit 6, which should be consistent with the recommendations of international or local guidelines (with regard to the distribution of calories among carbohydrates, proteins, and fats, exercise, etc.) for type 2 diabetic patients.

Compliance with the diet and lifestyle counseling will be assessed in case of insufficient glucose control (please refer to Section 7.4).

7.2 Investigational Medicinal Product(s)

Insulin glargine/lixisenatide fixed ratio combination and insulin glargine are considered as investigational medicinal products (IMPs).

7.2.1 Formulations

Insulin glargine/lixisenatide fixed ratio combination

Insulin glargine/lixisenatide fixed ratio combination is supplied as a sterile aqueous solution for subcutaneous (s.c.) injection in a pre-filled disposable SoloStar® pen-injector (100 U/mL insulin glargine with 50 μg/mL or 33 μg/mL lixisenatide depending on the pen (pen A or B respectively).

Insulin Glargine

Insulin glargine is supplied as a sterile aqueous solution for subcutaneous (s.c.) injection in a pre-filled disposable SoloStar® pen-injector (100 U/mL insulin glargine).

7.2.2 Injection Devices and Training for Injection Devices

7.2.2.1 Injection Devices

Insulin glargine/lixisenatide fixed ratio combination (Pen A or Pen B)

The combination product will be self-administered with a pre-filled disposable SoloStar® pen-injector.

The dose of the combination is titrated according to the patient's needs for insulin glargine. Note that only the dose of insulin glargine appears in the pen dosing window. The dose (μg) of lixisenatide does not appear in the dose window although lixisenatide is pre-mixed in the cartridge.

Two pens (A and B) with different insulin glargine/lixisenatide fixed ratios are available to allow insulin glargine titration over a range of 10 to 60 U/day while limiting the lixisenatide dose to a maximum of 20 μg/day:

Pen A (yellow label, yellow dose button): pre-filled disposable SoloStar® pen-injector containing 3 mL of a sterile solution of 100 U/mL insulin glargine and 50 μg/mL lixisenatide in ratio of 2:1 (2 units of insulin glargine per 1 μg lixisenatide). Each pen is specifically labeled for use in the study and contains in total 300 units insulin glargine and 150 μg lixisenatide in 3 ml. Printing on the number sleeve shows priming feature and doses from 10 to 40 U which is the intended dose range for pen A (Please see FIG. 16).

Doses can be set from 10 to 40 units in steps of 1 unit. Pen A allows administration of daily combination doses between 10 U/5 µg and 40 U/20 µg.

It would be theoretically possible to dial more than 40 U or less than 10 U insulin glargine (no mechanical upper or lower cap), but the dose is not marked on the pen outside the intended range of 10 to 40 U.

Pen B (red label, red dose button): pre-filled disposable SoloStar® pen-injector containing 3 mL of a sterile solution of 100 U/mL insulin glargine and 33 11 g/mL lixisenatide in ratio of 3:1 (3 units of insulin glargine per 1 11 g lixisenatide). Each pen is specifically labeled for use in the study and contains in total 300 units insulin glargine and 99 µg lixisenatide in 3 ml. Printing on the number sleeve shows priming feature and doses from 30 to 60 U. (Please see FIG. 16).

Doses can be set from 30 to 60 units in steps of 1 unit. Pen B allows administration of daily combination doses between 30 U/10 µg and 60 U/20 µg.

It would be theoretically possible to dial more than 60 U or less than 30 U insulin glargine (no mechanical upper or lower cap), but the dose is not marked on the pen outside the intended range of 30 to 60 U.

Pen B is intended mainly for use by patients requiring daily insulin glargine doses between 40 and 60 U. However, it may also be used for patients needing daily insulin glargine doses between 30 and 40 U either at initiation of treatment (see Section 7.2.4) or during the treatment phase to allow a temporary (5 or 7 days?) dose decrease in dos e.g. in case of hypoglycemia without the inconvenience of a change to pen A. But if the dose remains below 40 U for more than X days, then the patient should switch back to Pen A.

Patients who started treatment with Pen A and require a daily dose of insulin glargine above 40 U will be switched to Pen B.

Figure 16:
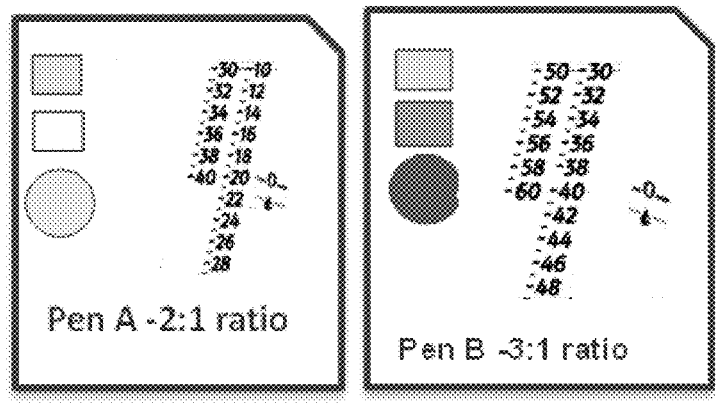
FIG. 16 shows the printing on the number sleeve (top) and the detailed doses (bottom) of Pen A and Pen B.

The lixisenatide dose is increased or decreased along with insulin glargine dose changes and also depends on which Pen (A or B) is used. For example, when the dose window in pen A (ratio of 2:1) shows 30 U, this is a dose of 30 U of insulin glargine and 15 µg of lixisenatide, while for pen B (ratio of 3:1) when the dose window shows 30 U, this is a dose of 30 U of insulin glargine and 10 µg lixisenatide. Detailed doses for pen A and pen B are shown in FIG. 16.

Insulin Glargine Only (Lantus®SoloStar®)

Disposable pre-filled pen-injectors Lantus® SoloSTAR® are provided to all patients at V2 and to patients randomized to the insulin glargine arm at V6 (week 0, Day 1) and thereafter. Each pen is specifically labeled for use in the study and contains 300 units insulin glargine in 3 ml. Doses can be set from 1 to 80 units in steps of 1 unit. However, in this study the maximum daily dose of insulin glargine is 60 U.

7.2.2.2 Training for Injection Devices

An instruction leaflet (including IMP leaflet?) will be provided which explains how to use the disposable pen-injectors. All patients will be trained by study staff in how to use the pen correctly, how to store it and how to change the needle for both the following pen-injector devices At V2 (week −6): all patients are trained using a training disposable Lantus® Solostar®.

At V6 (day 1): Patients who are randomized to receive the combination treatment are trained using a training disposable pen A and pen B.

Training will be repeated as often as deemed necessary by study site staff during the run-in phase and the treatment period.

The pens and leaflet that the patient will need to use during the run-in phase and treatment period will be dispensed according to the visit. Each patient is supplied with the appropriate number of pen-injectors according to the dispensing scheme indicated in the study flowchart (see Section 1.2).

The following commercial pen needles will be provided for use with the disposable injection pen devices:

BD Micro-Fine+31 G×8 mm

Pen-device related issues (malfunctions) should be reported to the sponsor on a Product Technical Complaint (PTC) form, which is described in a separate manual.

7.2.3 Dosage Schedule

Insulin Glargine/Lixisenatide Fixed Ratio Combination

The insulin glargine/lixisenatide fixed ratio combination should be self-administered once daily in the morning the hour (0 to 60 minutes) before breakfast, using Pen A or Pen B depending on the daily dose of insulin glargine.

Insulin Glargine

The insulin glargine should be self-administered once daily at any time of the day but at approximately the same time every day, using the Lantus® SoloSTAR®, during the run-in phase (all patients) and the open-label randomized treatment period (only for patients randomized to insulin glargine). The injection time will be selected at the discretion of patients and investigators at V2.

Injection Site

The IMP should be administered by deep subcutaneous injection, alternating between the left and tight anterolateral and left and right posterolateral abdominal wall or thighs or upper arms. Within a given area, location should be changed (rotated) at each time to prevent injection site skin reactions.

At days of on-site visits, the IMP which is to be administered before breakfast should be self-administered at the investigational site under the observation of site staff.

7.2.4 Starting Dose and Dose Adjustments

7.2.4.1 During Run-in Phase

Starting Dose of Insulin Glargine

From the start of run-in (visit 2), the only basal insulin allowed is insulin glargine. Patients receiving any basal insulin other than insulin glargine before screening will switch to once daily insulin glargine at visit 2.

Guidelines for transitioning patients' basal insulin doses from their pre-study to study regimens at V2 are offered below. These are guidelines only, and other changeover regimens may be employed if desired.

Patients should be informed at the time of the screening visit (V1) not to administer the morning dose of basal insulin at the day of V2, if at all possible.

Patients receiving more than 1 daily injection of basal insulin will change to one daily injection at V2.

The total basal insulin dose on the day before V2 will be used for the calculation of the starting dose according to the rules described in Table 1.

TABLE 1

Starting dose of insulin glargine at run-in visit

| Patients on | The daily dose (U) of glargine insulin will be equal |
|---|---|
| Insulin glargine | the total daily dose on the day prior to the visit 2 |
| Basal insulin other than insulin glargine once daily | the total daily dose on the day prior to the visit 2 |
| Basal insulin other than insulin glargine more than once daily | 80% of total daily dose (= total daily dose reduced by 20%) on the day prior to the visit 2 |

Insulin glargine can be injected at any time of the day but at the same time every day. The time of the once daily injection is at the discretion of the patient and investigator and will be decided at Visit 2 and should remain about the same throughout the study (during the run-in phase for all patients, and during the randomized treatment period for patients randomized to insulin glargine).

Adjustment of Insulin Glargine Dose

Doses will be adjusted based on daily measured fasting SMPG with the goal of improving fasting glycemic control and allowing patients to meet the randomization criteria (HbA1c at visit 5≥7% and ≤10%; mean fasting SMPG 140 mg/dL [7.8 mmol/L] measured for the 7 days before visit 6). The titration procedure to meet these criteria while avoiding hypoglycemia is at the discretion of the Investigator. Small decreases in dose are permitted if there is hypoglycemia, again at the discretion of the Investigator.

7.2.4.2 During Open-Label Randomized Treatment Period

7.2.4.2.1 Insulin Glargine/Lixisenatide Fixed Ratio Combination Group

Patients who received insulin glargine (Lantus) in the morning during the run-in phase:

Patients having the day before Visit 6 (D-1) a daily insulin glargine dose of
- <30 U will start the combination treatment with pen A at a dose of 20 U of insulin glargine/10 µg of lixisenatide
- ≥30 U will start the combination treatment with pen B at a dose of 30 U of insulin glargine/10 µg of lixisenatide The first injection will be done on site the morning of the randomization.

Patients who received insulin glargine at a time of day other than the morning, during the run-in phase:

These patients will have to switch to administration within the hour before breakfast. A procedure for transitioning time administration is offered below, but other change-over regimens may be employed if desired:
- The morning of the baseline visit after randomization (D1): injection while patient is on site, of an insulin glargine dose equal to −½-⅔ (to be decided by the investigator) of the dose injected the day before randomization (D-1)
- The next morning (D2), patients having the day before Visit 6 (D-1) a daily insulin glargine dose of
  - <30 U will start the combination treatment with pen A at a dose of 20 U of insulin glargine/10 µg of lixisenatide.
  - ≥30 U will start the combination treatment with pen B at a dose of 30 U of insulin glargine/10 µg of lixisenatide.

For all patients this first dose (either 20 U/10 µg or 30 U/10 µg) will be maintained stable for 2 weeks. For the next two weeks, any necessary dose increase will be limited to a maximum of +2 U not more often than once a week.

After the first 4 weeks, the doses will be titrated once a week according to the algorithm described in table 2 until the patient reaches a target fasting SMPG (80 to 100 mg/dL [4.4 to 5.6 mmol/L]) without hypoglycemia. Thereafter, until the end of the study, the dose will be adjusted as needed to maintain these fasting SMPG targets.

Patients who started the fixed ratio combination treatment using Pen A and then need a daily dose >40 U will be instructed to switch from Pen A to Pen B: e.g a patient receiving 40 U with pen A and having a median of fasting self-monitored plasma glucose (SMPG) values from preceding 3 days>140 mg/dL (>7.8 mmol/l) would need a dose adjustment of +4 U/day (according to table 1) to a daily dose of 44 U. Since the maximum dose to be delivered with Pen A is 40 U, the patient will use Pen B to self-inject the adjusted 44 U daily dose.

TABLE 2

Dose adjustment algorithm

| Median of fasting SMPG values from preceding 3 days | Insulin glargine dose adjustments (U/day)* |
|---|---|
| >140 mg/dL (>7.8 mmol/L) | +4 |
| >100 and ≤140 mg/dL (>5.6 and ≤7.8 mmol/L) | +2 |
| Glycemic target: 80 and 100 mg/dL (4.4 and 5.6 mmol/L), inclusive | No change |
| ≥60 and <80 mg/dL (≥3.3 and <4.4 mmol/L) | −2 |
| <60 mg/dL (<3.3 mmol/L) or occurrence of 2 (or more) symptomatic hypoglycemic episodes or one severe hypoglycemic episode (requiring assistance) documented in the preceding week. | −2 to −4 or at the discretion of the investigator or medically qualified designee |

*Dose adjustment should not be done more than once weekly.

7.2.4.2.2 Insulin Glargine Group

Time of injection should remain the same as determined at visit 2 for the run-in phase.

Patients randomized to insulin glargine will administer the same daily dose of insulin glargine on the day of randomization as the day before randomization, and then conduct insulin dose titration as necessary during the open-label randomized treatment period.

The dose will be titrated once a week following the same algorithm as the fixed ratio combination group (table 2), until the patient reaches the target fasting SMPG (80 to 100 mg/dL [4.4 to 5.6 mmol/L]) without hypoglycemia. Thereafter, until the end of the study, the dose will be adjusted as needed to maintain these fasting SMPG targets.

7.2.4.2.3 in Both Groups

Dose changes are based on a median of fasting SMPG values from last 3 days measured by the patient using glucometers and accessories supplied by the sponsor for this purpose.

The total daily insulin glargine dose will be capped at 60 U. If a dose >60 U of insulin glargine is needed to maintain HbA1c below predefined thresholds value, the dose should be kept at 60 U and a rescue therapy should be introduced (see Section 7.4). All assessments planned at the end of treatment visit must be performed before initiating rescue therapy.

Sound clinical judgment is to be exercised while titrating patients. Investigators may adjust or stop titration, or temporarily reduce dose if they believe further titration would be hazardous at that time.

Patients will be educated about the titration schedule so that they can monitor it with the assistance of the investigator or medically qualified designee. Patients will be allowed to increase the dose by themselves if necessary (i.e. median of fasting SMPG values from preceding 3 days>100 mg/dL), but not by more than +2 U and not more often than once a week. All other dose increases must be discussed between the patient and appropriate site personnel. All discussions must be properly documented in the patient's record. If needed, additional contacts will be made available for patients to discuss dose adjustments in between the scheduled visits. It is at the discretion of the investigator to allow well-trained patients to IMP insulin dose adjustments in between scheduled visits without prior consultation of the site personnel.

Doses may be reduced or modified at any time for hypoglycemia and according to the medical judgment of investigator. Patients who experience mild to moderate hypoglycemia as a result of a missed meal, unusual exercise or alcohol use will be advised how to correct their behaviour and will not necessarily have their insulin dose decreased (decision to be based on investigators clinical judgment).

7.3 Noninvestigational Medicinal Products

Metformin (If appropriate) is considered as a non-investigational medicinal product (NJMP). It (commercial metformin tablet) will be administered orally according to its locally approved label.

If patients are on metformin as background treatment, it should be at a stable dose of at least 1500 mg/day or maximal tolerated dose for at least 3 months prior to screening. This should be continued and the dose should remain stable throughout the study unless there is a specific safety issue related to this treatment. Sulfonylureas, glinides, SGLT-2i and DPP-4i, if previously taken, will be stopped at the start of run-in (Visit 2) and cannot be used during the run-in phase and the treatment period.

Rescue therapy (Section 7.4) if appropriate will be considered as NIMP(s) Metformin treatment dose or rescue therapy is to be reported in the e-CRF.

The cost of the background treatment metformin (if applicable) or rescue therapy not covered by health insurance will be reimbursed where permitted by local regulations.

7.4 Rescue Therapy

Routine fasting SMPG and central lab alerts on FPG (and HbA1c after week 12) are required to ensure that glycemic parameters remain under predefined thresholds values (see below). If all the fasting SMPG values in three consecutive days exceed the specific limit, the patient should contact the investigator and a central laboratory FPG measurement (and HbA1c after week 12) will be performed.

The thresholds values are defined as follows, depending on study period:
From Visit 13 (week 8) to Visit 15 (week 12) (excluding V15 value): FPG>240 mg/dL (13.3 mmol/L).
From Visit 15 (week 12) up to Visit 21 (week 30) (including V21 value): FPG>200 mg/dL (11.1 mmol/L) or HbA1c>8%.

In case of FPG or HbA1c above the threshold values, the investigator should ensure that no reasonable explanation exists for insufficient glucose control and in particular that:
Plasma glucose was measured when patient was fasting (i.e. after at least 8-hour fasting);
Treatment is being correctly titrated according to the protocol (up to a maximum daily dose of 60 U for both groups);
There is no intercurrent disease which may jeopardize glycemic control (e.g. infection)
Compliance to treatment is appropriate
Compliance to diet and lifestyle is appropriate.
If any of the above can reasonably explain the insufficient glycemic control, the investigator should undertake appropriate action, i.e.:
Assess plasma glucose in fasting condition (i.e., after at least 8 hours fasting);
Titrate insulin glargine or insulin glargine/lixisenatide fixed ratio combination according to the protocol (up to a maximum of 60 U for both groups);
Initiate an evaluation and treatment of any intercurrent disease (to be reported in AE/concomitant medication parts of the e-CRF and the medical record); Stress the absolute need to comply with treatment;
Schedule a meeting with the patient and a qualified nutrition professional to reinforce the absolute need to comply with diet and lifestyle recommendations;
Schedule a FPG/HbA1c assessment at the next visit (if the next visit is a phone call, it should be replaced by an on-site visit).
If none of the above reasons can be found, and/or appropriate actions fail, or if a dose >60 U is necessary to decrease FPG/HbA1c below threshold, a short/rapid-acting insulin may be added as rescue therapy; this should be started with a single daily administration to be given at any meal other than breakfast in the fixed ratio combination group, and at any meal for the insulin glargine group.

All assessments (including 2-hour standardized meal test but except for PK and antibody assessments) planned for the end of treatment visit are to be performed before initiating rescue therapy. After these assessments are completed and rescue therapy has been initiated, the patient will remain in the study and continue with study treatment (including background therapy). The planned visits and assessments (including PK and antibody assessments but except for meal test, and PRO assessments) should be performed until the last scheduled visit.

Note:

If the central laboratory results demonstrate an FPG and/or HbA1c above threshold value(s), the investigator will receive an alert from the central laboratory.

The decision to initiate rescue therapy should not be based on a single laboratory value. If FPG is incidentally found above threshold at a routine visit, the investigator should ensure that the criteria for rescue therapy are fulfilled (i.e. 3 consecutive fasting SMPG values above threshold confirmed by a central laboratory value) before initiating rescue therapy.

Short-term (up to 10 days maximum) use of short/rapid-acting insulin therapy (e.g., due to acute illness or surgery) will not be considered as rescue therapy. All such use of short/rapid-acting insulin therapy must be reported in the e-CRF and patient record.

7.5 Blinding Procedures

7.5.1 Methods of Blinding

This study is an open-label design.
Compensation for Lack of Blinding:

The investigator and the Sponsor will not have access to the data of the primary efficacy endpoint (ie, HbA1c) nor to the data of the standardized meal test endpoints obtained after baseline visit until V21 (week 30), or until End of Treatment visit in case of premature treatment discontinuation. However, the study team may review the data for the primary efficacy parameter in descriptive statistics with the name of the IMP treatment masked during data review meetings.

ARAC, CAC, and PSAC members will review and adjudicate events in a blinded manner (please also refer to Section 5.4).

The Data Monitoring Committee receives unblinded, closed reports from an independent statistician for review, which have to be handled strictly confidentially. None of these reports may be delivered to unauthorized persons (please also refer to Section 5.4.1).

7.6 Method of Assigning Patients to Treatment Group

Patients are randomized to receive during the 30-week open-label treatment period, once daily, either insulin glargine/lixisenatide fixed ratio combination or insulin glargine alone. The randomization ratio is 1:1. The randomization is stratified by HbA1c value (<8, %) at week −1 and screening metformin use (Y, N).

The randomization and the treatment allocation are performed centrally by an Interactive Voice/Web Response System (IVRS/IWRS). The randomized treatment kit number list is generated centrally by Sanofi, and the Study Biostatistician provides the randomization scheme (including stratification) to the IVRS/IWRS. Then, the IVRS/IWRS generates the patient randomization list according to which it allocates treatment arms to the patients.

The IMPs (insulin glargine/lixisenatide fixed ratio combination or insulin glargine alone) are provided in open-label boxes and are identified with treatment kit numbers.

At the screening visit the investigator or designee has to contact the IVRS/IWRS center to receive the patient number. The patient identification (patient number) is composed of 9-digit number containing the 3-digit country code, the 3-digit center code and the 3-digit patient chronological number (which is 001 for the first patient screened in a center, 002 for the second patient screened in the same center etc.).

On V6 (week 0), after V5 (week −1) assessment results are reviewed and baseline assessments are completed, the IVRS/IWRS is contacted for randomization and allocation of the treatment kits. For each randomized patient, the IVRS/IWRS will allocate a treatment kit number and a quantity of kit to be dispensed corresponding to the same treatment arm as assigned at randomization. After V6 (week 0) the IVRS/IWRS is contacted again each time a new treatment kit(s) allocation is necessary. The IVRS/IWRS will allocate treatment kits using their treatment kit number.

A randomized patient is defined as a patient who is registered and assigned to a randomized treatment arm by the IVRSIIWRS, as documented from IVRS/IWRS log file.

A patient cannot be randomized more than once in the study. Additionally, the patient cannot enter in the run-in phase more than once.

7.7 Packaging and Labeling

Packaging is in accordance with the administration schedule. The content of the labeling is in accordance with the local regulatory specifications and requirements.

The appropriate number of kits will be dispensed to cover up to the next dispensing visit. Storage conditions and use-by-end date are part of the label text.

Treatment labels will indicate the treatment number (used for treatment allocation and reported in the e-CRF). The patient number, visit number and date of dispensation will be entered manually by the site staff on the treatment box label prior to dispensing.

Insulin Glargine/Lixisenatide Fixed Ratio Combination

Pens A containing a 3 ml solution of Insulin glargine 100 U/ml and lixisenatide 50 ug/ml are supplied as open-label treatment kits containing 3 pre-filled pens.

Pens B containing a 3 ml solution of insulin glargine 100 U/ml and lixisenatide 33 ug/ml are supplied as open-label treatment kits containing 3 pre-filled pens.

Insulin glargine (Lantus® SoloSTAR®)

Insulin glargine pens (Lantus® SoloSTAR®) containing a 3 ml solution of insulin glargine 100 U/ml are supplied as open-label treatment kits containing 3 Lantus® SoloSTAR® pens.

7.8 Storage Conditions and Shelf Life

Investigators or other authorized persons (eg, pharmacists) are responsible for storing IMP in a secure and safe place in accordance with local regulations, labeling specifications, policies and procedures.

Control of IMP storage conditions, especially control of temperature (eg, refrigerated storage) and information on in-use stability and instructions for handling the Sanofi compound should be managed according to the rules provided by the Sponsor.

The expiry date is mentioned on the IMPs labels, and storage conditions are written on the IMPs labels and in the instruction leaflet.

Insulin Glargine/Lixisenatide Fixed Ratio Combination

Prior to the first use, the disposable fixed ratio combination pens have to be stored between +2° C. and +8° C., protected from light, and must not be frozen.

In-use disposable pen-injector has to be stored below +30° C. (not refrigerated) protected from light. Each pen should be replaced if not completely used within 14 days.

Insulin Glargine (Lantus® SoloSTAR®)

Prior to the first use, the disposable Lantus® SoloSTAR® pens have to be stored between +2° C. and +8° C., protected from light, and must not be frozen.

In-use disposable Lantus® SoloSTAR® pens have to be stored below +25° C. (not refrigerated) protected from light. Each pen should not be used for more than 28 days after the first use.

7.9 Responsibilities

The Investigator, the hospital pharmacist, or other personnel allowed to store and dispense the IMP will be responsible for ensuring that the IMP used in the clinical trial is securely maintained as specified by the Sponsor and in accordance with applicable regulatory requirements.

All IMPs will be dispensed in accordance with the Investigator's prescription and it is the Investigator's responsibility to ensure that an accurate record of IMP issued and returned is maintained.

Any quality issue noticed with the receipt or use of an IMP (deficiency in condition, appearance, pertaining documentation, labeling, expiration date, etc) should be promptly notified to the Sponsor. Some deficiencies may be recorded through a complaint procedure.

A potential defect in the quality of IMP may be subject to initiation of a recall procedure by the Sponsor. In this case, the Investigator will be responsible for promptly addressing any request made by the Sponsor, in order to recall IMP and eliminate potential hazards.

Under no circumstances will the Investigator supply IMP to a third party, allow the IMP to be used other than as directed by this clinical trial protocol, or dispose of IMP in any other manner.

7.9.1 Treatment Accountability and Compliance

The investigator checks the compliance to the study treatments based on the patient diary and by visually checking the returned fixed ratio combination pens or Lantus® SoloSTAR® pens and completes the appropriate "Treatment Log Form". Visual check on return has to be performed by site staff. In addition he/she also records the dosing information on the appropriate pages of the e-CRF.

For metformin (if appropriate), name, start and end date of treatment, total daily dose, etc, will be documented in the source documents. Compliance to metformin (if appropriate) will be checked by interviewing the patient and reviewing diary at each visit and be documented in the source documents and in the e-CRF.

7.9.2 Return and/or Destruction of Treatments

Patients have to return used and in-use IMPs (and corresponding leaflets if appropriate) at each on-site visit. Patients also return unused IMPs each time a re-supply is planned (see Section 1.2).

Patients have to return used, in-use and unused IMP at Visit 21 (or final assessment on-treatment visit in case of permanent premature discontinuation).

All partially used or unused treatments will be retrieved by the Sponsor. A detailed treatment log of the returned IMP will be established with the Investigator (or the pharmacist) and countersigned by the Investigator and the Monitoring Team.

For NIMP not provided by the sponsor, tracking and reconciliation has to be achieved by the investigator according to the system proposed by the sponsor.

7.10 Concomitant Medication

A concomitant medication is any treatment received by the patient concomitantly to any open-label IMP. (medications should also be reported during screening period and follow-up).

7.10.1 Allowed Concomitant Therapy

Any therapies or medications other than prohibited concomitant therapy in addition to the IMP should be kept to a minimum during the study. However, if these are considered necessary for the patients welfare and are unlikely to interfere with the IMP, they may be given at the discretion of the investigator, with a stable dose (when possible).

In the insulin glargine/lixisenatide fixed ratio combination treatment group, for oral medicinal products that are particularly dependent on threshold concentrations for efficacy, such as antibiotics, patients should be advised to take those medicinal products at least 1 hour before or 4 hours after lixisenatide injection. Gastro-resistant formulations containing substances sensitive to stomach degradation, should be administered 1 hour before or 4 hours after lixisenatide injection.

Specific treatments, which are ongoing before the study and/or prescribed or changed during the study, must be recorded in the e-CRF and Source Data (please refer to Section 9.2).

7.10.2 Concomitant Diabetes Therapy

Patients are enrolled with a background therapy consisting of a stable basal insulin regimen alone or in combination with a stable dose for at least 3 months of 1 to 2 OADs before the screening visit that can be: metformin (1500 mg/day or maximal tolerated dose), a sulfonylurea (SU), a glinide, a dipeptidyl-peptidase-4 (DPP-4) inhibitor or a SGLT-2 inhibitors.

From V2, all patients receive insulin glargine as basal insulin.

Previous OADs (SU, a glinide, DPP-4i or a SGLT-2i) other than metformin will be discontinued from visit 2. If taken, previous treatment with metformin is to be continued throughout the study. Metformin should be kept at stable dose throughout the study unless there is a specific safety issue related to this treatment. Metformin treatment dose changes are to be properly reported in patient record and in the eCRF. (see Section 7.3).

No other concomitant antidiabetic treatments except rescue therapy should be used in this study.

7.10.3 Prohibited Concomitant Therapy

The following drugs are not permitted during the screening period (including screening phase and run-in phase) and the randomized open-label treatment periods:
  Any glucose-lowering agents other than the IMP, authorized background anti-diabetic therapy (metformin if appropriate) and rescue therapy, if necessary. Note: Short time use (10 days) of short/rapid-acting insulin due to acute illness or surgery (eg, infectious disease) is allowed; Sulfonylurea, glinide, SGLT-2 inhibitor or DPP-JV inhibitor if previously taken should be stopped at V2.
  Systemic glucocorticoids for more than 10 days (topical or inhaled applications are allowed),
  Body weight loss drugs.
  During the 3-day follow-up period, any treatments (other than GLP-1 receptor agonists) are permitted, as deemed necessary by the Investigator.

8 ASSESSMENT OF INVESTIGATIONAL MEDICINAL PRODUCT

All biological efficacy and safety analysis will be performed by a Central Laboratory. Detailed information on samples drawing, management and analysis will be provided in a specific manual.

8.1 Primary Endpoint

8.1.1 Primary Efficacy Endpoint

Change in HbA1c from baseline to week 30

8.2 Secondary Endpoints

8.2.1 Secondary Efficacy Endpoint(s)

The continuous secondary efficacy endpoints are:
Change in 2-hour PPG and in blood glucose excursion during standardized meal test from baseline to week 30,
Change in body weight from baseline to week 30,
Change in 7-point SMPG profiles from baseline to week 30 (each time point and average daily value),
Change in daily dose of insulin glargine from baseline to week 30;
Change in FPG from baseline to week 30,
Change in 30-minute and 1-hour PPG and blood glucose excursion during standardized meal test from baseline to week 30.
The categorical secondary efficacy endpoints are:
Percentage of patients reaching HbA1c≤6.5% at week 30,
Percentage of patients reaching HbA1c<7% at week 30,
Percentage of patients reaching HbA1c<7% with no body weight gain at week 30,
Percentage of patients reaching HbA1c<7% at week 30 with no documented [PG 70 mg/dL (3.9 mmoJJL)] symptomatic hypoglycemia during the 30-week randomized treatment period,
Percentage of patients reaching HbA1c<7% with no body weight gain at week 30 and with no documented [PG 70 mg/dL (3.9 mmol/L)] symptomatic hypoglycemia during the 30-week randomized treatment period,
Percentage of patients requiring a rescue therapy during 30-week open-label treatment period.
Observation Period of Efficacy Endpoints
The on-treatment period for efficacy endpoints (primary and secondary efficacy endpoints) is defined as the time from the first injection of open-label IMP up to 14 days for HbA1c; 0 day for standardized meal test parameters, 7-point SMPG and insulin glargine dose; 1 day for FPG; and 3 days for body weight after the last injection of IMP or up to the introduction of rescue therapy, whichever is the earliest.
The baseline value for efficacy endpoints is the last available value prior to the first injection of IMP.

8.2.2 Safety Endpoints

The safety endpoints are assessed by:
Symptomatic hypoglycemia (documented, probable, severe symptomatic hypoglycemia),
Adverse events, serious adverse events and AESI, Safety laboratory values,
Vital signs and physical examination,
Electrocardiogram (ECG),
Immunogenicity (Antibody variables): Anti-lixisenatide antibodies and/or anti-insulin antibodies (fixed ratio combination group).
Observation Period of Safety Endpoints
The observation period of safety data will be divided into 3 segments:
The pre-treatment period is defined as the time between the date of the informed consent and the first injection of open-label IMP.
The on-treatment period is defined as the time from the first injection of open-label IMP up to 3 days (1 day for symptomatic hypoglycemia) after the last injection of IMP, regardless of the introduction of rescue therapy. The 3-day interval is chosen based on the half-life of the IMP (approximately 5 times the half-life of lixisenatide).
The post-treatment period is defined as the time starting 4 days after last injection of open-label IMP (after the on-treatment period).
The baseline value for safety endpoints will be the last available value prior to the first injection of IMP.

8.2.2.1 Symptomatic Hypoglycemia

Symptomatic hypoglycemia (documented, probable, severe symptomatic hypoglycemia) will be assessed. Please refer to Section 9.6.1 for details.

8.2.2.2 Adverse Events

AE including SAE and AESI will be assessed. Please refer to Section 9.4 to Section 9.7 for details.
Adverse event collection: Adverse events and serious adverse events will be collected from the time of informed consent signature and then at each visit until the end of the study.

8.2.2.3 Laboratory Safety Variables

All laboratory data listed in this section will be measured at a central laboratory. The laboratory data will be collected at designated visits in Section 1.2. Clinical laboratory values will be analyzed after conversion into standard international units. International units will be used in all listings and tables. The conventional unit will be presented if appropriate.
The following laboratory safety variables will be analyzed:
Hematology: blood count (erythrocytes, hemoglobin, hematocrit, leukocytes), differential blood count (neutrophils, lymphocytes, monocytes, eosinophils, basophils) and platelets.
Clinical chemistry: total bilirubin (and, in case of values above the normal range, differentiation in conjugated and non-conjugated bilirubin), AST, ALT, ALP, G-GT, creatinine, uric acid, sodium, potassium, calcium, phosphorus.
Lipid parameters (total cholesterol, HDL-cholesterol, LDL-cholesterol, triglycerides).
Serum amylase and lipase.
Serum calcitonin.
Urine albumin/creatinine ratio assessment (to be done on first morning urine sample).
In addition, the following laboratory data will also be collected at screening visit, baseline visit, and at on-site visits depending on item (see Section 1.2) for identifying patients with exclusion criteria, childbearing potential or safety consideration.
Hepatitis B surface antigen and hepatitis C antibody (only at screening).
Urine analysis (assayed by the central laboratory): pH, glucose, ketones, leucocytes, blood/hemoglobin, protein (only at screening).
Serum pregnancy test in females of childbearing potential.

Serum FSH and estradiol (only in females requiring confirmation of postmenopausal status, and only at screening).

In case of suspected acute pancreatitis, safety laboratory, including amylase and lipase should be performed in a timely manner. Please also refer to Section 9.6.4.

For patients concomitantly treated with oral anticoagulants the International Normalized Ratio (INR) values (measured by the patients usual laboratory) should be reported in the e-CRF each time they are available associated with the actual dose of the anticoagulant.

Notes: Any abnormal laboratory value should be immediately rechecked (whenever possible using the central laboratory) for confirmation before making a decision of permanent discontinuation of IMP for the concerned patient. Please also refer to Section 9.3 and Section 9.4.2.

8.2.2.4 Vital Signs

Clinical safety will be assessed by:
Physical examination
Vital signs (systolic and diastolic blood pressure, heart rate)

Blood pressure (mmHg) should be measured when the patient is quiet and seated and with their arm outstretched in line with mid-sternum and supported. Measurement should be taken under standardized conditions, approximately at the same time of the day, on the same arm, with the same device (after the patient has rested comfortably for at least five minutes) and the values are to be recorded in the e-CRF. Both systolic blood pressure and diastolic blood pressure should be recorded. Devices for blood pressure measurement should be regularly recalibrated according to manufacturers' instructions.

Determination of the Arm for Blood Pressure Measurements:

At visit 1 of the screening period, blood pressure has to be measured on both of the arms after 5 minutes in seated position and then again after two minutes in both arms in seated position. The arm with the higher diastolic pressure will be determined at this visit, identifying the reference arm for future measurements throughout the study. The highest value will be recorded in the e-CRF (all blood pressure values are to be recorded in the source data).

Heart rate (bpm) will be measured at the time of the measurement of blood pressure.

8.2.2.5 Electrocardiogram (ECG) Variables

The ECG assessment of "normal" or "abnormal" will be analyzed.

ECGs are measured automatically by the device from the investigator as automatic 12-lead ECG. ECG status of "normal" or "abnormal" will be reported in the e-CRF as determined by the Investigator.

The 12-lead ECGs should be performed after at least 10 minutes in supine position. The electrodes are to be positioned at the same place for each ECG recording throughout the study.

Each trace is analyzed in comparison with the screening recorded trace. The original trace is kept as source data.

Notes: Any abnormal ECG parameter should be immediately rechecked for confirmation before making a decision of permanent discontinuation of treatment with IMPs for the concerned patient. Please also refer to Section 9.3 and Section 9.4.2.

8.2.2.6 Immunogenicity

Antibody Variables

For insulin glargine/lixisenatide fixed ratio combination group: anti-lixisenatide antibody status (Positive, Negative) and concentration.

For both treatment groups: anti-insulin glargine antibody status (Positive, Negative) and titer and the change from baseline during the course of the clinical study, with additional determination of cross reactivity to human insulin for anti-insulin glargine positive patients.

Anti-lixisenatide antibodies and/or anti-insulin antibodies will be measured at Day 1 and at Week 30.

Sampling Time

Blood samples for anti-insulin and anti-lixisenatide antibody determination will be taken before injection of IMP, at Day 1 and week 30, in both treatment groups for anti-insulin antibody and from all patients treated with lixisenatide for anti-lixisenatide antibody. Samples will also be taken in case of premature discontinuation from IMP, if possible (see Section 9.3).

Note: One sample will also be taken at Week 30 (V21) for potential additional measurements of immunogenicity.

Anti-Lixisenatide and Anti-Insulin Antibodies Handling Procedures

Detailed procedures of sample preparation, storage and shipment will be described in the specific laboratory manual.

Bioanalyticalmethod

Anti-insulin antibodies and anti-lixisenatide antibodies will be determined at centralized laboratories using validated assay methodologies.

8.3 Other Endpoint(s)

8.3.1 Pharmacokinetics

8.3.1.1 Pharmacokinetics Parameters

Total and active plasma concentrations of lixisenatide will be assessed in the time frame from 1 to 4 hours post-injection at Day 1 of the treatment phase and prior to injection as well as in the time frame from 1 to 4 hours post-injection at Week 30 (for patients in the insulin glargine/lixisenatide fixed ratio combination).

8.3.1.2 Sampling Time

Lixisenatide PK Sampling:

For total and active concentrations of lixisenatide, respectively, three blood samples are to be taken for patients from the insulin glargine/lixisenatide fixed ratio combination arm: at baseline and at end of treatment visits, as described in the flowchart. One sample will be taken immediately before IMP injection at week 30 and each one sample will be taken in the time period from 1 to 4 hours post injection at Day 1 and week 30. Samples will also be taken in case of premature discontinuation from IMP or rescue therapy, if possible.

8.3.1.3 PK Handling Procedure

Detailed procedure of sample preparation, storage and shipment are described in the specific lab manual.

8.3.1.4 Bioanalytical Method

Lixisenatide Total Concentration

For determination of total concentrations of lixisenatide (bound and unbound to anti-lixisenatide antibodies) plasma samples will be analyzed using a validated ELISA with a lower limit of quantification of 5.5 µg/mL.

Lixisenatide Active Concentration

For determination of active concentrations of lixisenatide, plasma samples will be analyzed using a validated cell-based assay with a lower limit of quantification of 40 µg/mL.

Active concentrations will be analyzed for at least 100 patients from the insulin glargine/lixisenatide fixed ratio combination although blood sample in all patients in this group will be drawn.

8.3.2 Patient Reported Outcomes

Patient reported outcomes (PROs) questionnaires include TRIM-D, EQ-5D and IWQoL-Lite describe further in this section. These three PROs measures will be administered at baseline, week 12 and end of the treatment. Patient-rated and physician-rated global treatment effectiveness evaluation scales will be administered at the end of the study.

TRIM-D, EQ-5D and IWQoL: the patients will be requested to complete the questionnaires by themselves during selected clinical visits (see study flow chart) in specific booklets, independently from Investigator, site staff and any help from friends or relatives. For validity purposes, patients will be asked to answer to all the questions of these questionnaires at the start of the visit in a quiet place, and while on site to return the completed questionnaires to the investigator or his/her designed on the same day. Schedule of questionnaires is specified in the study flowchart (Section 1.2). The questionnaires are shown in FIGS. 23, 24 and 25.

PROs questionnaires will be analyzed using assessments obtained during the period from the first injection of open-label randomized IMP up to 3 days after the last injection of IMP or up to the introduction of rescue therapy, whichever is the earliest.

8.3.2.1 Treatment-Related Impact Measure for Diabetes (TRIM-D)

The general treatment-related impact on patients' health related quality of life, treatment satisfaction and treatment behavior will be assessed using the TRIM-D questionnaire.

The TRIM-D questionnaire (see FIGS. 23, 24 and 25) is a 28-item measure with 5 domains assessing Treatment Burden, Daily Life, Diabetes Management, Compliance and Psychological Health. This PRO measure can be scored independently for each domain or as a total score.

The five-point Likert like response options, for all items, range from (1) Not at all satisfied/convenient, Never to Extremely/Almost always, Always or Extremely dissatisfied/inconvenient to (5) Extremely satisfied/convenient, depending upon the item stem and are scored on a scale of 0 to 100 so that a higher score indicates a better health state (less negative impact).

The TRIM-D variables include response to each item and the change in TRIM-D scores (total score and separate score for each of the five domains) from baseline to endpoint.

A domain score is calculated if a respondent answers at least half of the items in a multi-item domain (or half plus one in the case of domains with an odd number of items).

8.3.2.2 EuroQoL Five Dimension (EQ-5D)

Patients' health related quality of life (HRQoL) will be assessed using the EQ-5D questionnaire.

Figure 27:
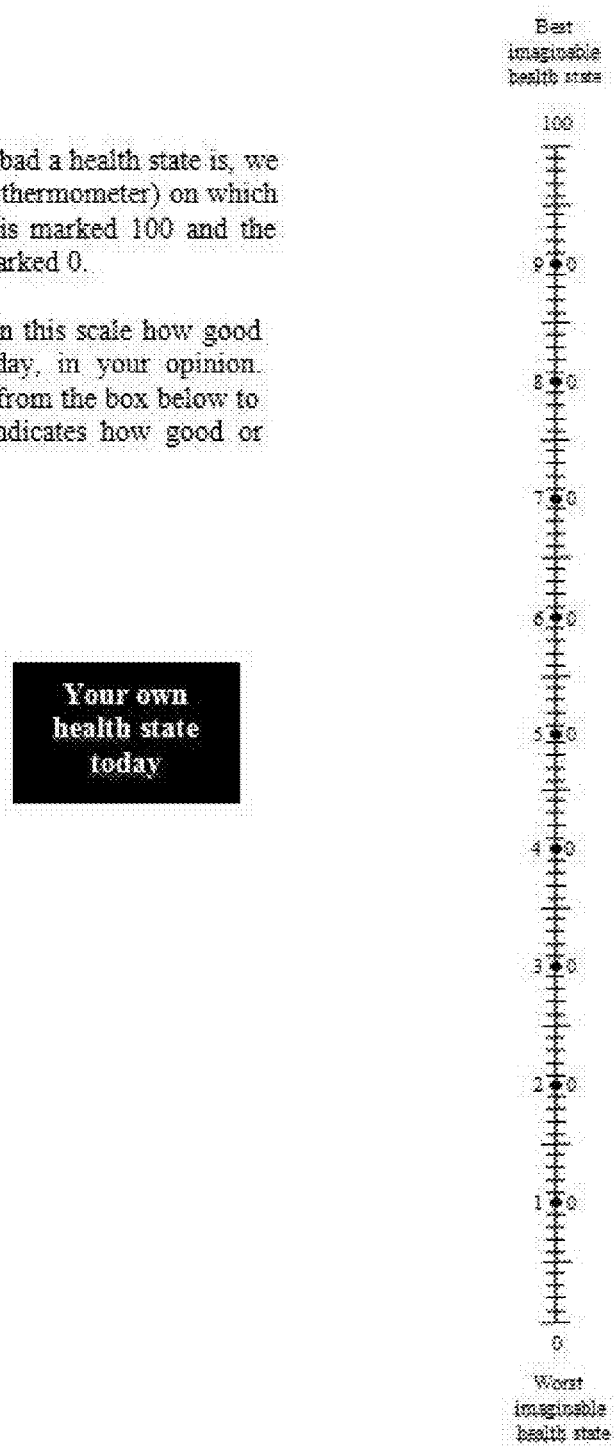
FIG. 27 shows page 2 of the EuroQoL Five Dimension (EQ-5D) questionnaire.

The EQ-5D questionnaire (see FIGS. 26 and 27) is a 6 item, self-administered instrument comprised of 2 components: a descriptive profile and a single index visual analogue scale (VAS). The descriptive profile assesses health status on 5 dimensions: mobility, self-care, usual activities, pain/discomfort, and anxiety/depression. Respondents were asked to indicate whether they have 1) no problems; 2) some/moderate problems; or 3) extreme problems with each of the 5 dimensions. Their responses were then mapped to previously derived utility weights for each of the 243 possible combinations. These utility weights are intended to represent society's ratings of the desirability of a given health state. Utility weights have been derived from general populations in the United Kingdom and the United States.

The VAS records the patient's personal perspective of their current health status on a vertical rating scale with scores ranging from 0 to 100, with 0 representing the worst imaginable health status and 100 representing the best imaginable health state. The VAS has been considered a representation of patients' overall HRQoL.

The EQ-5D variables include response to each item, change in score of the 5 dimensions from baseline to endpoint, change in single utility index from baseline to endpoint, and change in perceived health status on VAS from baseline to endpoint.

EQ-5D score and single utility index will be calculated only if all 5 dimensions of the descriptive profile are responded correctly.

8.3.2.3 Impact of Weight on Quality of Life-Lite (IWQOL-Lite)

Patients' weight related quality of life will be assessed using the IWQOL-Lite questionnaire.

IWQOL-Lite questionnaire (see FIGS. 28 and 29) is a 31-item self-reported instrument that reliably measures how a patient's weight affects his/her quality of life. The five domains of the IWQOL-Lite are physical function, self-esteem, sexual life, public distress, and work. IQWOL-Lite scores (total score and separate scores for each of the five domains) range from 0 to 100, with 0 representing the worst outcome and 100 representing the best.

The IQWOL-Lite variable includes response to each item and the change in IWQOL-Lite scores (total score and separate score for each of the five domains) from baseline to endpoint.

The score for each domain is calculated only if a respondent answers at least half of the items in a multi-item domain (or half plus one in the case of domains with an odd number of items), and for the total score only if 75% of the items answered.

8.3.2.4 Patient- and Physician-Rated Global Evaluation Scales

Patient- and physician-rated global treatment effectiveness evaluation scales are self-administered instruments that will be measuring whether patient's overall response to treatment is excellent, good, moderate, poor or whether the patient's condition is worsening. The variables related to these patient-rated and physician-rated global treatment effectiveness scales include the response to each question at end of treatment.

8.3.3 Pharmacogenetic Assessment

Pharmacogenetic sampling is optional for the patient. For those patients who signed the specific informed consent form, a single blood sample of 6 ml will be collected preferably at baseline (V6; Day 1), but the sample could also be collected at any later visit.

The data from genetic material can be used to determine a possible relationship between genes and responses to treatment with lixisenatide. DNA will be stored for up to 15 years from the completion of the Clinical Study Report.

Procedures for sampling, storage and shipping of pharmacogenetic samples are described in a specific document included in the central laboratory manual.

The Sponsor has included safeguards for protecting patient confidentiality. The blood sample and DNA that is extracted will be assigned a second number, a Genetic ID (de-identification code) that is different from the Subject ID. This "double coding" is performed to separate a patients medical information and DNA data. The clinical study data (coded by Subject ID) will be stored in a distinct database at a different location from the database containing the pharmacogenetic data (coded by Genetic ID). The key linking Subject ID and Genetic ID will be maintained by a third party, under appropriate access control. The matching of clinical data and pharmacogenetic data, for the purpose of data analysis, will be possible only by using this key, which will be under strict access control. All data will be reported only in coded form in order to maintain confidentiality.

8.4 Efficacy Assessment Methods

8.4.1 HbA1c Measurement

For the eligibility and efficacy assessments of the study, HbA1c is measured by a certified level I "National Glycohemoglobin Standardization Program" (NGSP) central laboratory.

8.4.2 Standardized Meal Test

Patients will undergo a standardized meal challenge to assess fasting and postprandial glucose (central laboratory), as well as plasma glucose excursion.

The standardized meal contains approximately 600 kcal and is composed of 50 to 55% carbohydrate, 15 to 20% protein and 25 to 30% fat.

The composition and the quantity of the standardized meal must be identical throughout the study. If the patient needs to receive a rescue antidiabetic medication, the standardized meal test should be performed before the introduction of the rescue medication and will not be performed at the final on-treatment visit.

In case of permanent discontinuation of the treatment with IMP, the standardized meal test should be performed only in case the patient receives IMP, on the day of the visit.

On the day of the standardized meal test, the patients will come to the investigational site in the morning, in fasting conditions for at least 8 hours and must not eat any food or drink, except water, before the scheduled standardized meal test. Injection of insulin glargine/lixisenatide fixed ratio combination at V21 (week 30) should be done at the investigational site in the presence of the investigational staff 30 minutes before the start of the standardized meal. Patient in insulin glargine group will inject their insulin glargine at their usual injection time.

The standardized meal for all patients should be consumed within a 15-minute period. Blood for plasma glucose is drawn 5 times:

30 minutes prior to the start of the meal and before IMP administration if the IMP is injected before breakfast;

Just before the start of the standardized meal (0 minute),
30 minutes after the start of the standardized meal,
60 minutes after the start of the standardized meal,
120 minutes after the start of the standardized meal.

The exact times of the IMP injection and the standardized meal intake and the blood draws are to be documented.

8.4.3 Self-Monitored Plasma Glucose Profiles (SMPG) and Glucometer, Patient's Diaries and Training

8.4.3.1 Self-Monitored Plasma Glucose Profiles (SMPG)

SMPG measurements include the followings:
Fasting SMPG:

Fasting SMPG will be used by the investigator and patients if appropriate to titrate and adjust insulin glargine dose or the combination dose and to monitor glycemic control (Section 8.4). The fasting SMPG should be measured by the patient before breakfast and before the administration of the glucose-lowering agents (IMP or metformin if appropriate) once a day from visit 2 to the end of the treatment.

Daily fasting SMPG values should be recorded in patient diary. The following daily fasting
SMPG values will be entered in the e-CRF:
The values on the last 3 days leading to insulin dose change
The values measured during 7 days the week prior to visit 6 (used to assess eligibility for randomization).
7-Point SMPG Profile:

The 7-point SMPG profile should be measured at the following 7 points: pre-prandial and 2 hours postprandial for breakfast, lunch, dinner and at bedtime. Two hours postprandial (breakfast, lunch and dinner) is defined as 2 hours after the start of the meal.

The patients are requested to perform 7-point SMPG profile measurement over a single 24-hour period on 2 different days in the week before V6 (week 0), V15 (week 12), and V21 (week 30, end of treatment assessment visit). All SMPG values measured on these days will be recorded in diary and transferred into the e-CRF.

On the 7-point profile days, information on times of meals and bedtime, injection time and doses of IMP should be recorded in the patient's diary and entered in the e-CRF.
SMPG During Episodes of Symptomatic Hypoglycemia:

Whenever the patient feels hypoglycemic symptoms, plasma glucose should be measured by the patient (or others, if applicable), if possible. Patients should be instructed to measure plasma glucose levels prior to the administration of glucose or carbohydrate intake whenever symptomatic hypoglycemia is suspected (Section 9.6.1), unless safety considerations necessitate immediate glucose/carbohydrate rescue prior to confirmation. The SMPG values are to be entered in the patient's diary and entered in the e-CRF.
Further SMPG:

The investigator may decide to request more frequent self-monitoring of plasma glucose if he/she considers necessary for the patient. The SMPG values are to be entered in the patients diary.

8.4.3.2 Glucometer, Patient's Diaries and Training

All the patients are supplied with a glucometer, the corresponding supplies (lancets, test strips, etc.), a leaflet, and with diaries at visit V2 (week-6) in order to perform self-measurement of plasma glucose and its recording. The patients will be instructed to bring their glucometers and patient diaries with them to each site visit.

The glucometers should be calibrated according to instructions given in the package leaflet and the study site should also check the glucose meters regularly using the provided control solutions for data validity.

At visit V2 (week −6) patients are trained to accurately measure plasma glucose values with the glucometer and to correctly record the values and other requested information in the patient's diaries. It is the investigators responsibility to explain the need to measure glucose at the times requested and to correctly record all SMPG values in the patient's diaries to patients. Training is repeated as often as necessary at the study visits.

Instruction on how to complete the patient diary on a daily basis will be done by site staff. At each on site visit:
  The study site staff reviews the patient's diary,
  SMPG values stored in the glucose meter memory will be downloaded, printed out, dated, signed and filed into the patient file. This information will help the Investigator to assess treatment effects, adjust insulin doses and compliance.

Note: The SMPG values recorded into the diary, which have to be entered in the e-CRF, have to be checked for consistency with the information from the glucose meter. In case of inconsistency, the reason for inconsistency has to be documented. If needed, the resulting action (e.g., training of the patient on correct documentation of the values) is also to be documented. The confirmed values will be entered into e-CRF by the investigator or designee based on the glucometer output values.

The patient diary includes but not limited to the following information:
  Time and dose of IMP (insulin glargine/lixisenatide combination or insulin glargine) injections,
  Missed IMP injection (including start date and end date).
  Time and value of fasting SMPG,
  Time of start of meals and SMPG measurements as well as plasma glucose values the day of the 7-point profile,
  Potential changes in metformin treatment,
  Adverse events, including signs and symptoms suggesting occurrence of hypoglycemia and local injection site reactions, if any.

8.4.4 Body Weight

Body weight should be obtained with the patient wearing undergarments or very light clothing and no shoes, and with an empty bladder. The same scale should be used throughout the study, and calibrated on a regular basis as recommended by the manufacturer.

The use of balance scales is recommended; if digital scales are used, testing with standard weights is of particular importance. The floor surface on which the scale rests must be hard and should not be carpeted or covered with other soft material. The scale should be balanced with both weights at zero and the balance bar aligned. The patient should stand in the center of the platform as standing off-center may affect measurement. The weights are moved until the beam balances (the arrows are aligned). The weight is read and recorded in the e-CRF and Source Data. Self-reported weights are not acceptable; patients must not read the scales themselves.

8.4.5 Dose of IMP

The patients document daily their IMP dose or any missed IMP injection in the patient diary. The following values will be entered in the e-CRF:

The daily doses of IMP used on last 3 days per week until week 12 and then the dose used in the last 3 days before each visit (including each phone call visit);
The daily doses of IMP used on the 7-point blood glucose profile days;
Missed IMP injections In case of premature discontinuation or rescue therapy, data on the last 3 days in the week before the time of discontinuation or rescue therapy should be entered in the e-CRF.

8.4.6 Fasting Plasma Glucose

FPG is measured at a central laboratory. At V5 and V21, FPG will be part of the standardized meal test.

8.5 Appropriateness of Measurements

The combination of basal insulin with a GLP-1 receptor agonist (GLP-IRA) is expected to lower HbA1c, as a complementary action on both fasting and postprandial glucose, with no weight gain or even weight loss, and a limited increased risk of hypoglycemia in a single daily injection.

The primary efficacy analysis of this study comparing insulin glargine fixed ratio combination to insulin glargine will be based on primary variable: change in HbA1c from baseline to week 30.

The concentration of HbA1c reflects the glycemic history of the previous 120 days and is thus an index of mean glycemia, documenting glycemic control over the past 2- to 3-month period. HbA1c has also been shown to correlate with the development of long-term complications of diabetes, and reduction of HbA1c is known to reduce the risk of long-term microvascular complications. Therefore, HbA1c is considered to be an appropriate primary endpoint for assessing the effect of a treatment on glycemic control. In addition to the analysis of the change from baseline in HbA1c, the responder analysis allows the clinical relevance of the reduction observed in HbA1c to be demonstrated. The duration of study treatment is considered to be sufficient for achieving stable conditions with IMP after titrating insulin dose and for enabling an adequate assessment of time-dependent changes in HbA1c and the concomitant risk of hypoglycemia.

The problem of weight gain in type 2 diabetes is widely recognized. More than 80% of individuals with type 2 diabetes are overweight, many at the time of diagnosis. Consequently, iatrogenic weight gain is not only unwelcome, but represents an important clinical issue that can become a barrier to the successful management of glycaemic control. Body weight control is one of the reasons to choose a GLP-1 receptor agonist instead of rapid-acting insulin to intensify basal insulin therapy in this overweight or obese type 2 diabetes population. Taking into account the major impact of insulin-related body weight gain, it seems appropriate to include body weight change as secondary efficacy endpoint.

Insulin glargine targets primarily, although not exclusively, fasting hyperglycemia, and lixisenatide effectively acts on post-prandial glycemia mainly by slowing down gastric emptying. Therefore assessment of both fasting and post-prandial glucose (after a standardized meal) is relevant in this study. These 2 blood glucose parameters are also considered by regulatory agencies to be a supportive measure of efficacy of an antidiabetic agent.

Safety will be evaluated by standard clinical and laboratory measurements. Specific safety parameters of interest for a glucose lowering injectable peptide such as symptomatic hypoglycemia, injection site reactions and potential allergic reactions will also be assessed. In addition, lixisenatide being a GLP1-receptor agonist, pancreatic enzymes (amylase and lipase) and serum calcitonin concentration will be monitored and reported over the study course according to specific procedures (Section 9.6)

9 STUDY PROCEDURES

This section is to summarize information not presented in the flow chart or in Section 9.

9.1 Visit Schedule

The visit schedule and procedures/assessments listed in the "Study Flow Chart" in Section 1.2 are not repeated in this section. The aim of this section is to provide details on how some of the procedures/assessments have to be performed.

This is an outpatient study and consists of 11 on-site visits and 11 phone-call visits. Additional, optional phone call visits to monitor insulin titration should be scheduled whenever considered necessary by the investigator.

The patient has to be in fasting conditions for all on-site visits. For all these visits, the patient should be seen in the morning, approximately at the same time, as much as possible. The patient should take metformin treatment and inject the insulin glargine/lixisenatide fixed ratio combination or insulin glargine (if appropriate) at the investigational site after the fasting blood sample has been drawn. Insulin glargine will be injected at usual time fixed at V2 even if it falls in the period of the 8-hour fasting.

The fasting condition is defined as an overnight fast no less than 8 hours that consisted of no food or liquid intake, other than water. IMP and other glucose-lowering agents (i.e. metformin if appropriate) should be administered after fasting blood sample is drawn for all laboratory tests on the study site.

Note: If the patient is not in fasting condition at the visits specified above, the blood sample is not collected and a new appointment should be given to the patient for the following day, if possible, with instruction to be fasted.

Visit window: For the run-in phase a visit window of ±3 days is acceptable using the date of visit 2 as reference. During the open-label treatment period a visit window of ±3 days for visit 7 to visit 15, and ±5 days for visit 16 to Visit 21 is acceptable using day 1 (the day of visit 6) as reference. A visit window of −1 day or +3 days for the post-treatment follow-up visit (V22) is acceptable using the day of Visit 21 as reference. If one visit date is changed, the next visit should take place according to the original schedule.

9.1.1 Screening Period (Week −8 to Week 0)

Only patients meeting all the inclusion criteria are candidates for the screening. The screening period is about 8 weeks and includes screening phase which is up to two weeks from screening visit (V1, week −8) to run-in visit (V2, week −6) and run-in phase which is from run-in visit (V2, week −6) to baseline visit (V6, week 0).

Only patients who meet the inclusion criteria as noted in Section 6.1 may be screened. It will be the investigators responsibility to confirm the diagnosis of T2DM.

The background metformin treatment (if appropriate) at a stable dose should be continued during the screening period.

All laboratory tests measured at a central laboratory that are needed for checking the exclusion criteria of the patients, are performed at the screening visit. At V2 (week −6), depending on the availability of the laboratory parameters, eligible patients can enter into the run-in phase. Run-in visit (V2) can be performed less than 2 weeks after screening visit if laboratory data is available. After the screening period, patients who meet the selection criteria at the end of screening period as noted in Section 6.2.4 can enter into the open-label randomized treatment period.

9.1.1.1 on-Site Visits: V1 (Screening Visit, Week-8); V2 (Run-in Visit, Week −6); V5 (Week −1)

For the complete list and contents of procedures/assessments scheduled for the visits, please refer to the "Study Flow Chart" in Section 1.2 and for detailed description of assessments to Section 8 and Section 9.6.

The details of the procedures/assessments to be performed at on-site visits during screening period and which are not described elsewhere are provided below:

Informed Consent

The patient will receive verbal information concerning the aims and methods of the study, its constraints and risks and the study duration at the screening visit. Written information will be provided to the patient and must be signed by the patient and investigator prior to any investigations.

Demography, diabetes and medical/surgical history, cardiovascular & allergy history, alcohol and smoking habits, and medications Demography data such as birth date, gender and race will be collected. Collection of diabetes history will include documentation of duration of diabetes, history of microvascular complications (retinopathy, neuropathy, and nephropathy), and history of gestational diabetes if applicable. Medical/surgical history including patients cardiovascular and allergy history and patient's family allergy history will be recorded. Data for alcohol habits during the last 12 months before screening visit and smoking habit will be collected.

Check of previous medication refers to documentation of medication including the glucose-lowering agents and over-the-counter medications. In women of childbearing potential, the contraceptive methods have to be documented.

Diet and Lifestyle Counseling

Please see Section 7.1.

IVRS/IWRS Contact

IVRS/IWRS will be contacted for notification of screening and patient number allocation (Section 7.6). Please note that it is important to have the IVRS/IWRS contact before any blood sample is drawn because the patient number is given by IVRS/IWRS and it must be reported on the laboratory requisition forms.

Training on Self-Injection Devices and Dispensation of Insulin Glargine:

One injection pen device with the instruction leaflet is dispensed. The patient is instructed by the study staff how to use properly the pen, how to store it, and instruction on self-injection technique is also given. Please refer to Section 7.2.2

Compliance Check

Compliance check includes compliance to metformin (if appropriate), insulin treatment, and use of glucometer, review of daily fasting SMPG values and patient diary.

Glucometer Dispensation and Training
Please see Section 8.4.3.2

Insulin Glargine Starting Dose and Dose Adjustment

Eligible patients will enter a 6-week run-in phase with switch to (if appropriate) and/or dose optimization of insulin glargine (see details in Section 7.2.4).

Central laboratory testing

Blood sample is drawn for all central laboratory tests needed for checking the exclusion criteria.

Provide patients with a urine container and instruct them how to collect at home in the morning of their first morning urine and to bring the urine sample to the site at planned visit.

An appointment is given to the patient for next visit (on-site visit or phone call visit). Patients are instructed to return to the site in the morning and to bring the glucose meter, the diary and insulin glargine pens.

9.1.1.2 Phone Call Visits: V3 (Week-4) and V4 (Week 2)

The patient is called by the investigator or qualified designee at a scheduled time. If the call has been completed by site staff other than the investigator, the investigator has to be consulted if AE/SAE is suspected and informed in case AE/SAE occurred. A phone call visit can optionally be performed as a clinical visit in case of symptomatic hypoglycemia/AE or other reasons.

During the phone call, the following questions are to be asked:
Did you experience any new medical event, disease or symptom since the last visit?
Did you experience any changes in a pre-existing medical condition, disease or symptom since the last visit?
Did you miss, change, take or add any medications (including OAD if appropriate) since the last visit?
Did you experience any symptoms or events of hypoglycemic and AE?
Do you feel comfortable in handling the diary, glucose meter and IMP injection device or do you need any more explanation?

The phone visits will also include:
Asking patient fasting pre-breakfast SMPG and insulin dose on the last 3 days including day of visit.
Adjustment of the dose of insulin glargine as necessary.
Recording of AE and symptomatic hypoglycemia events (if any).
Recording of the use or change of any medication.

The patient will be instructed to:
Perform required SMPG measurements
Complete daily the diary.
Self-inject once daily insulin glargine at the dose prescribed by the investigator.
Contact the site in case of occurrence of adverse event, record the event in the patients diary and return to the site as deemed appropriate.

Give an appointment to the patient for subsequent visits (on-site visit or phone call visit) and remind them to come fasting if planned at next on-site visit.

9.1.2 Open-Label Randomized Treatment Period (Week 0 to Week 30)

Patients meeting all inclusion criteria and with no exclusion criteria at the end of the screening period are eligible to be enrolled into the open-label randomized treatment period. The duration of the open-label treatment period is 30 weeks±5 days from baseline visit (V6, week 0) to the end of treatment visit (V21, week 30).

Each patient self-administers IMP once daily during the open-label treatment period. The IMP dose will be adjusted according to fasting SMPG values documented in the patient diary (Section 7.2.4.2).

9.1.2.1 Baseline Visit (V6, Week 0, Day 1)

For the complete list and contents of procedures/assessments scheduled for the visit, please refer to the "Study Flow Chart" in Section 1.2 and for detailed description of assessments to Section 8 and Section 9.6.

The details of the procedures/assessments to be performed at this visit and which are not described elsewhere are provided below:

At this visit, the patient must return to the investigation site in the morning after 8 hours fasting not having injected their insulin or administered metformin (if appropriate) at home. Patients will visit the site with the blood glucometer, the diary, and the used, unused and in-use pens of insulin glargine.

Compliance Check

Compliance check includes compliance to insulin glargine and metformin treatment (if appropriate) and use of glucometer, review of daily fasting SMPG values, and the 7-point SMPG profile and patient diary. If patient is not compliant enough with the study procedures, the training will be repeated by the site staff.

IVRS/IWRS Contact

After the baseline assessments are completed and eligibility confirmed, the investigator contacts IVRS/IWRS for randomization. The treatment arm (i.e., insulin glargine/lixisenatide fixed ratio combination or insulin glargine) is notified by IVRS/IWRS.

Training on Self-Injection Devices and Dispensation of IMP:

Patients randomized to the combination group are instructed by the study staff how to use properly the combination Pen A and Pen B and to store it. Instructions on self-injection technique are also given. Injection pen device with the instruction leaflet is dispensed.

Patients randomized to the insulin glargine group will continue to use the insulin glargine pen (SoloStar®). Training on SoloStar® pen-injector might be repeated if necessary. Injection pen device is dispensed. Please refer to Section 7.2.2.

Starting Dose and Dose Adjustment of IMP

Eligible patients will enter a 30-week open-label randomized treatment period to receive either insulin glargine/lixisenatide fixed ratio combination or insulin glargine (see details in Section 7.2.4).

An appointment for one week later is given to the patient for next phone call visit.

9.1.2.2 Phone Call Visits: V7 (Week 1); V9 (Week 3); V11 (Week 5); V12 (Week 6); V14 (Week 10); V16 (Week 15); V18 (Week 21); V20 (Week 27)

The patient is called by the investigator or qualified designee at a scheduled time. If the call has been completed by site staff other than the investigator, the investigator has to be consulted if AE/SAE is suspected and informed in case AE/SAE occurred. A phone call visit can optionally be performed as a clinical visit in case of symptomatic hypoglycemia/AE or other reasons.

During the phone call, the following questions are to be asked:
Did you experience any new medical event, disease or symptom since the last visit?
Did you experience any changes in a pre-existing medical condition, disease or symptom since the last visit?
Did you miss, change, take or add any medications (including OAD if appropriate) since the last visit?
Did you experience any symptoms or events of hypoglycemic and AE?
Do you feel comfortable in handling the diary, glucose meter and IMP injection device or do you need any more explanation?
Did you adjust IMP since last visit? If appropriate, what is your IMP dose?
Did you measure any fasting SMPG value outside of the range 80 to 100 mg/dL (4.4 to 5.6 mmol/L)?
Did you measure any fasting SMPG value above:
From Visit 13 (week 8) to Visit 15 (week 12) (excluding V15 value): FPG>240 mg/dL (13.3 mmol/L).
From Visit 15 (week 12) up to Visit 21 (week 30) (including V21 value): FPG>200 mg/dL (11.1 mmol/L).
The phone visits will also include:
Asking patient fasting pre-breakfast SMPG and insulin dose on the last 3 days including day of visit.
Adjustment of the dose of IMP (insulin glargine or insulin glargine/lixisenatide combination) to continue treatment toward the target fasting SMPG between 100 and 80 mg/dL (5.6 and 4.4 mmol/I), inclusive.
Recording of AE and symptomatic hypoglycemia events (if any).
Recording of the use or change of any concomitant medication.
The patient will be instructed to:
Perform required SMPG measurements
Complete daily the diary.
Self-inject once daily IMP at the dose prescribed by the investigator.
Contact the site in case of occurrence of adverse event, record the event in the patient's diary and return to the site as deemed appropriate.
Give an appointment to the patient for subsequent visits (on-site visit or phone call visit) and remind them to come fasting if planned at next on-site visit.

9.1.2.3 on-Site Visits: VB (Week 2); V10 (Week 4); V13 (Week 8); V15 (Week 12); V17 (Week 18); V19 (Week 24)

For the complete list and contents of procedures/assessments scheduled for the visits, please refer to the "Study Flow Chart" in Section 1.2 and for detailed description of assessments to Section 8 and Section 9.6.
The details of the procedures/assessments to be performed at visits and which are not described elsewhere are provided below.
Compliance Check
Compliance check includes compliance to IMP and metformin treatment (if appropriate) and use of glucometer, review of daily fasting SMPG values, and the 7-point SMPG profile and patient diary. If patient is not compliant to the study well, the training has to be repeated by the site staff.
Patients are instructed to return to the site in the morning in fasting condition for all on-site visit with the glucose meter and the diary for each on-site visit. Patients will return used pens/in-use pens at each on-site visit and with the unused pens for the visits where a re-supply is planned.
Upon completion of each on-site visit, an appointment for the next visit (on-site visit or phone call visit) will be made.

9.1.2.4 Final on-Treatment Assessment/End of Treatment Visit (V21, Week 30)

For the complete list and contents of procedures/assessments scheduled for the visit, please refer to the "Study Flow Chart" in Section 1.2 and for detailed description of assessments to Section 8 and Section 9.6.
The same procedures/assessments including IVRS/IWRS contact as planned at Visit 21 (week 30) have to be performed in case of prematurely permanent treatment discontinuation (Section 9.3.2). The IVRS/IWRS has to be contacted in order to register the end of treatment.
An appointment for the post-treatment follow-up phone call visit will be made.

9.1.3 Post-Treatment Follow-Up Phone Call Visit (V22)

Following the last injection of insulin glargine or insulin glargine/lixisenatide fixed ratio combination either as scheduled or prematurely, a post-treatment follow-up visit is performed 3 (−1/+3) days. This visit can be a phone call visit, or an on-site visit in case of ongoing or new adverse event during the post-treatment period, if necessary.
The patient is called by the investigator or medically qualified designee at certain, previously agreed time point.
During the phone call, the following questions are to be asked:
Did you experience any new medical event, disease or symptom since the last visit?
Did you experience any changes in a pre-existing medical condition, disease or symptom since the last visit?
Did you change, take or add any new medications since the last visit?
All reports of hypoglycemic events (if any) or any adverse events are recorded. The use or change of any concomitant medications, including rescue therapy, is recorded.
IVRS/IWRS is contacted for notification of the end of study.

9.2 Definition of Source Data 9.2.1 Source Data to be Found in the Patient's Files Evaluations that are reported in the e-CRF must be supported by appropriately signed identified source documentation related but not limited to the following:
Agreement and signature of informed consent mentioning the study identification,
Patient identification, last participation in a clinical trial, medical history, associated diseases, and data related to the studied pathology,
Contraception method for women of childbearing potential,
Reason for lack of childbearing potential for concerned women (e.g. postmenopausal, history of hysterectomy)
Previous and concomitant medication (including background metformin and rescue therapy), Study identification, Treatment kit number, dates of administration and doses of insulin glargine/lixisenatide fixed ratio combination or insulin glargine alone (Lantus® Solostar® pen, pen A and pen B), Compliance to metformin if appropriate assessed by interview and patient's diary Dates of visits and assessments including the examination report, Vital signs, height, body weight, Faxed central lab reports and original report received at site (dated and signed by the Principal Investigator or Sub-Investigator), IVRSIIWRS confirmation notifications by fax or e-mail (screening, screen failure, run-in, run-in failure, randomization, treatment reallocation, treatment/study discontinuation, end of study, treatment replacement if applicable, etc.), ECG records signed and dated, Adverse events and follow-up:

In case of SAE, increased lipase/amylase >2 ULN, increased calcitonin the site should file in the source document at least copies of the hospitalization reports and any relevant examination reports (eg, imaging reports, specialists' reports, etc.) documenting the follow-up of the SAE or AESI.

Date of premature study discontinuation (if any) and reason.

Source documentation may be found in the following:

Patients identity,

Medical history,

Nursing notes,

Dietician's notes,

Physician's notes,

Patients diaries.

Dated and signed print-outs with SMPG downloaded from glucose meter.

9.2.2 Source Data Verification Requirements for Patients not Randomized

For patients not randomized, the source data that must be checked include the patient's identification details, the informed consent signed by the patient, the study identification, the dates of study visits and the main reasons preventing randomization.

9.3 Handling of Patient Temporary or Permanent Treatment Discontinuation of Patient Study Discontinuation The IMP should be continued whenever possible. In case the IMP is stopped, it should be determined if the stop can be made temporarily; permanent IMP discontinuation should be a last resort. Any IMP discontinuation should be fully documented in the e-CRF. In any case, the patient should remain in the study as long as possible.

9.3.1 Temporary Treatment Discontinuation with Investigational Medicinal Product(s)

Temporary treatment discontinuation may be considered by the investigator because of suspected AEs or for other reasons. In case of treatment interruption due to an AE, reinitiating of treatment with the IMP will be done under close and appropriate clinical/and or laboratory monitoring once the Investigator will have considered according to his/her best medical judgment that the responsibility of the IMP(s) in the occurrence of the concerned event was unlikely and if the selection criteria for the study are still met (refer to Section 6).

All temporary treatment discontinuation, duration should be recorded by the Investigator in the appropriate e-CRF pages when considered as confirmed

9.3.2 Permanent Treatment Discontinuation with Investigational Medicinal Product(s)

Permanent treatment discontinuation is any treatment discontinuation associated with the definitive decision from the Investigator or the patient not tore-expose the patient to the IMP at any time.

9.3.3 List of Criteria for Definitive Treatment Discontinuation

The patients may withdraw from treatment with IMP if they decide to do so, at any time and irrespective of the reason, or this may be the Investigator's decision. All efforts should be made to document the reasons for treatment discontinuation and this should be documented in the e-CRF.

The patients may withdraw from treatment with IMP in case of the following:

At patients own request;

If, in the Investigator's opinion, continuation with the administration of IMP would be detrimental to the patient's well-being;

At the specific request of the Sponsor.

A patient must withdraw from treatment with IMP in either of the following cases:

Intercurrent condition that requires discontinuation of IMP: e.g. laboratory abnormalities (see decision tree and general guidance for the follow up of laboratory abnormalities in Appendix B), diagnosis of acute pancreatitis confirmed by gastroenterologic evaluation and imaging (Section 9.6.4) calcitonin value 50 µg/mL (see Section 9.6.6).

Pregnancy.

Any abnormal laboratory value or ECG parameter will be immediately rechecked for confirmation before making a decision of permanent discontinuation of the IMP for the concerned patient.

9.3.4 Handling of Patients after Permanent Treatment Discontinuation

Patients will be maintained in the study as much as possible and followed-up according to procedures specified in this protocol (except 3-day safety post-treatment follow-up, PK and antibody assessment, meal test, and PRO assessments) up to the scheduled date of study completion, or recovery or stabilization of any AE requiring followed-up as specified in this protocol, whichever comes last.

If possible, after the permanent discontinuation of treatment regardless of the reason, the patients will be as soon as possible assessed using the procedure normally planned for the last IMP dosing day (End of treatment visit), including PK and antibody samples, PRO assessments, if appropriate.

Test meal will only be performed if the IMP has not been stopped, and if the patient is not on rescue therapy. The two PK samples normally planned for the end of treatment visit, should only be taken if the last dose is administered at visit, otherwise one PK sample is sufficient.

All cases of permanent treatment discontinuation should be recorded by the Investigator in the appropriate pages of the CRF and in the patient's medical records when confirmed. IVRS/IWRS should be notified when a patient prematurely discontinues treatment.

9.3.5 Procedure and Consequence for Patient Withdrawal from Study

The patients may withdraw from the study before study completion if they decide to do so, at any time and irrespective of the reason. If possible, the patients are assessed using the procedure normally planned for the end-of-study visit including PK and antibody samples, and PRO assessments, if appropriate.

For patients who fail to return to the site, the Investigator should make the best effort to re-contact the patient (eg, contacting patient's family or private physician, reviewing available registries or health care databases), and to determine his/her health status, including at least his/her vital status. Attempts to contact such patients must be documented in the patients records (eg, times and dates of attempted telephone contact, receipt for sending a registered letter).

The statistical analysis plan will specify how these patients lost to follow-up for their primary endpoints will be considered.

Patients who have withdrawn from the study cannot be re-randomized (treated) in the study. Their inclusion and treatment numbers must not be reused.

9.4 Obligation of the Investigator Regarding Safety Reporting

9.4.1 Definitions of Adverse Events

9.4.1.1 Adverse Event

An adverse event (AE) is any untoward medical occurrence in a patient or clinical investigation patient administered a pharmaceutical product and which does not necessarily have to have a causal relationship with this treatment.

9.4.1.2 Serious Adverse Event

A serious adverse event (SAE) is any untoward medical occurrence that at any dose:
Results in death, or
Is life-threatening, or
  Note: The term "life-threatening" in the definition of "serious" refers to an event in which the patient was at risk of death at the time of the event; it does not refer to an event which hypothetically might have caused death if it were more severe.
Requires inpatient hospitalization or prolongation of existing hospitalization, or
Results in persistent or significant disability/incapacity, or
Is a congenital anomaly/birth defect
Is a medically important event
  Medical and scientific judgment should be exercised in deciding whether expedited reporting is appropriate in other situations, such as important medical events that may not be immediately life-threatening or result in death or hospitalization but may jeopardize the patient or may require medical or surgical intervention (ie, specific measures or corrective treatment) to prevent one of the other outcomes listed in the definition above.
  Note: The following list of medically important events is intended to serve as a guideline for determining which condition has to be considered as a medically important event. The list is not intended to be exhaustive:
  Intensive treatment in an emergency room or at home for:
  Allergic bronchospasm
  Blood dyscrasias (ie, agranulocytosis, aplastic anemia, bone marrow aplasia, myelodysplasia, pancytopenia, etc),
  Convulsions (seizures, epilepsy, epileptic fit, absence, etc). Development of drug dependence or drug abuse
  ALT>3 ULN+total bilirubin >2 ULN or asymptomatic ALT increase >10 ULN
  Suicide attempt or any event suggestive of suicidality
  Syncope, loss of consciousness (except if documented as a consequence of blood sampling)
  Bullous cutaneous eruptions
  Cancers diagnosed during the study or aggravated during the study (only if judged unusual/significant by the Investigators in oncology studies)
  Chronic neurodegenerative diseases (newly diagnosed) or aggravated during the study (only if judged unusual/significant by the Investigators in studies assessing specifically the effect of a study drug on these diseases).

9.4.1.3 Adverse Event of Special Interest

An adverse event of special interest (AESI) is an AE (serious or non-serious) of scientific and medical concern specific to the Sponsors product or program, for which ongoing monitoring and immediate notification by the Investigator to the Sponsor is required. Such events may require further investigation in order to characterize and understand them. AES is may be added or removed during a study by protocol amendment.

All AESIs will be reported to the Sponsor in the same timeframe as SAEs, ie within 24 hours as detailed in Section 10.4.1.2.

The AESIs are listed below:
ALT increase (see FIG. 19)
Pregnancy occurring in a female patient entered in the study as well as pregnancy occurring in a female partner of a male patient entered in a study with IMP/NIMP;
  Pregnancy will be recorded as an AESI in all cases.
  It will be qualified as an SAE only if it fulfills one of the seriousness criteria (see Section 9.4.1.2).
  In the event of pregnancy in a female participant, IMP should be discontinued.
  Follow-up of the pregnancy in a female participant or in a female partner of a male participant is mandatory until the outcome has been determined.
Symptomatic overdose (serious or non-serious) with IMP/NIMP
  An overdose (accidental or intentional) with the IMP/NIMP is an event suspected by the Investigator or spontaneously notified by the patient (not based on systemic pills counts) and defined as follows:

For insulin glargine/lixisenatide combination: any dose corresponding to a lixisenatide daily dose greater than 40 μg (i.e. >80 U for pen A, >120 U for pen B).

For insulin glargine: any dose administration which, in the Investigator's opinion based on clinical judgment is considered significantly greater than the prescribed dose of insulin.

An overdose with OADs (e.g. metformin) is defined as at least twice of the intended dose within the intended/planned therapeutic interval.

The circumstances of the overdose (ie, accidental or intentional) should be clearly specified in the verbatim and symptoms, if any, entered on separate AE forms.

Note:

Asymptomatic overdose with IMP does not need immediate notification: the definition is the same as described above. Asymptomatic overdose is to be reported in the standard AE page in the e-CRF.

9.4.1.4 Other AEs Requiring Specific Monitoring and Reporting on Specific e-CRFs The following AEs require specific monitoring and should be reported on the specific e-CRF completion. These AEs will only qualify for expedited reporting when Serious (fulfilling SAE criteria).

Suspected allergic reactions (please refer to Section 9.6.3),

Monitoring of patients with increased pancreatic enzymes >2 ULN/suspected pancreatitis (please refer to Section 9.6.4), Major cardiovascular events (please refer to Section 9.6.5), Monitoring of patients with increased calcitonin 2:20 pg/mL (please refer to Section 9.6.6).

9.4.2 General Guidelines for Reporting Adverse Events

All AEs, regardless of seriousness or relationship to IMP/NIMP, spanning from the signature of the informed consent form until the end of the study as defined by the protocol for that patient, are to be recorded on the corresponding page(s) or screen(s) of the e-CRF.

Whenever possible, diagnosis or single syndrome should be reported instead of symptoms. The Investigator should specify the date of onset, intensity, action taken with respect to IMP, corrective treatment/therapy given, additional investigations performed, outcome, and his/her opinion as to whether there is a reasonable possibility that the AE was caused by the IMP or NIMP or by the study procedure(s).

For the IMP (lixisenatide/insulin glargine combination) the causal relationship assessment is for the combined product.

The Investigator should take appropriate measures to follow all AEs until clinical recovery is complete and laboratory results have returned to normal, or until progression has been stabilized, or until death, in order to ensure the safety of the patients. This may imply that observations will continue beyond the last planned visit per protocol, and that additional investigations may be requested by the monitoring team up to as noticed by the Sponsor.

When treatment is prematurely discontinued, the patients observations will continue until the end of the study as defined by the protocol for that patient.

Laboratory, vital signs or ECG abnormalities are to be recorded as AEs only if:

Symptomatic and/or

Requiring either corrective treatment or consultation, and/or

Leading to IMP discontinuation or modification of dosing, and/or

Fulfilling a seriousness criterion, and/or

Defined as an AESI.

9.4.3 Instructions for Reporting Serious Adverse Events

In the case of occurrence of a SAE, the Investigator must immediately:

ENTER (within 24 hours) the information related to the SAE in the appropriate screens of the e-CRF; the system will automatically send the notification to the Monitoring Team after approval of the Investigator within the e-CRF or after a standard delay.

SEND (preferably by fax or e-mail) the photocopy of all examinations carried out and the dates on which these examinations were performed, to the representative of the Monitoring Team whose name, fax number and email address appear on the Clinical Trial Protocol. Care should be taken to ensure that the patient's identity is protected and the patient's identifiers in the Clinical Trial are properly mentioned on any copy of source document provided to the Sponsor. For laboratory results, include the laboratory normal ranges.

All further data updates should be recorded in the e-CRF as appropriate, and further documentation as well as additional information (for Lab data, concomitant Medication, patient status . . . ) should be sent (by fax or e-mail) to the Monitoring Team within 24 hours of knowledge. In addition, any effort should be made to further document each Serious AE that is fatal or life threatening within the week (7 days) following initial notification.

A back-up plan is available and should be used (using paper CRF process) when thee-CRF system does not work (please see Appendix C).

Any SAE brought to the attention of the Investigator at any time after the end of the study for the patient and considered by him/her to be caused by the IMP with a reasonable possibility, should be reported to the monitoring team.

9.4.4 Guidelines for Reporting Adverse Events of Special Interest

For AES is, the Sponsor must be informed immediately (ie, within 24 hours), as per SAE notification guidelines described in Section 9.4.3, even if not fulfilling a seriousness criterion, using the corresponding pages of the CRF (to be sent) or screens in the e-CRF.

Instructions for AE reporting are summarized in Table 3.

9.4.5 Guidelines for Management of Specific Laboratory Abnormalities

Decision trees for the management of certain laboratory abnormalities by Sanofi are provided in Appendix B.

The following laboratory abnormalities should be monitored, documented, and managed according to the related flow chart in protocol Appendix B.
Neutropenia
Thrombocytopenia
Increase in ALT
Acute renal failure
Suspicion of rhabdomyolysis

TABLE 3

Summary of Adverse Event Reporting Instruction

| Event Category | Reporting Timeframe | Specific Events in This Category | Case Report Form Completion | | |
|---|---|---|---|---|---|
| | | | AE form | Safety Complementary Form | Other Specific Forms |
| Adverse Event (non-SAE, non-AESI) | Routine | Any AE that is no SAE or AESI | Yes | No | No |
| Serious Adverse Event (non-AESI or AESI) | Expedited (within 24 hours) | Any AE meeting seriousness criterion per Section 9.4.1.2 | Yes | Yes | No |
| Adverse Event of Special Interest (non-SAE) | Expedited (within 24 hours) | Pregnancy of female patient/subject | Yes | Yes | No |
| | | Pregnancy of female partner of male patient/subject | | | |
| | | Symptomatic overdose with IMP/NIMP* | Yes | Yes | No |
| AEs requiring specific monitoring (non-SAE) | Routine | Increase in ALT | Yes | No | Yes |
| | | Suspected allergic reactions | Yes | No | Yes |
| | | Increased amylase/lipase >2 ULN | Yes | No | Yes |
| | | Major cardiovascular events | Yes | No | Yes |
| | | Increased calcitonin ≥20 pg/mL | Yes | No | Yes |
| Laboratory, vital sign, or ECG abnormality, asymptomatic overdose recorded as AE (non-SAE, non-AESI) | Routine | Neutropenia | Yes | No | No |
| | | Thrombocytopenia | Yes | No | No |
| | | Acute renal insufficiency | Yes | No | No |
| | | Suspicion of rhabdomyolysis | Yes | No | No |
| | | Others (e.g. leading to IMP discontinuation) | Yes | No | Yes/No |

Footnote:
Hypoglycemia will be reported on the dedicated hypoglycemia event page.
*Asymptomatic overdose is reported in the AE form and does not require expedited reporting.

9.5 Obligations of the Sponsor

During the course of the study, the Sponsor will report in an expedited manner:
All SAEs that are both unexpected and at least reasonably related to the IMP (SUSAR), to the regulatory authorities, IECs/IRBs as appropriate and to the Investigators.
All SAEs that are expected and at least reasonably related to the IMPs to the regulatory authorities, according to local regulations.

Any other AE not listed as an expected event in the lixiseantide/insulin glargine combination product Investigator's Brochure (IB) will be considered as an unexpected event.

In this study, some AEs considered related to the underlying condition (e.g. blood glucose increased) will not be considered unexpected as given in the Investigator's Brochure.

The Sponsor will report all safety observations made during the conduct of the trial in the clinical study report (CSR).

9.6 Safety Instructions

The study-specific safety instructions are given in this Section.

9.6.1 Symptomatic Hypoglycemia

Symptomatic hypoglycemia events will be categorized as follows:
Severe Symptomatic Hypoglycemia
Severe symptomatic hypoglycemia is an event requiring assistance of another person to actively administer carbohydrate, glucagon, or other resuscitative actions. These episodes may be associated with sufficient neuroglycopenia to induce seizure, unconsciousness or coma. Plasma glucose measurements may not be available during such an event, but neurological recovery attributable to the restoration of plasma glucose to normal is considered sufficient evidence that the event was induced by a low plasma glucose concentration.

The definition of severe symptomatic hypoglycemia includes all episodes in which neurological impairment was severe enough to prevent self-treatment and which were thus thought to place patients at risk for injury to themselves or others.

Note that "requires assistance" means that the patient could not help himself or herself. Assisting a patient out of kindness, when assistance is not required, should not be considered a "requires assistance" incident.

Severe symptomatic hypoglycemia will be qualified as an SAE only if it fulfills SAE criteria. All events of seizure, unconsciousness or coma must be reported as SAEs.

Documented Symptomatic Hypoglycemia

Documented symptomatic hypoglycemia is an event during which typical symptoms of hypoglycemia are accompanied by a measured plasma glucose concentration of ≤70 mg/dL (3.9 mmol/L). In addition, hypoglycemia episodes with a plasma glucose of <60 mg/dL (3.3 mmol/L) will be analyzed.

Clinical symptoms that are considered to result from a hypoglycemic episode can include (but not necessarily limited to): increased sweating, nervousness, asthenia, tremor, dizziness, increased appetite, palpitations, headache, sleep disorder, confusion, seizures, unconsciousness, and coma.

Probable Symptomatic Hypoglycemia

Probable symptomatic hypoglycemia is an event during which symptoms of hypoglycemia are not accompanied by a plasma glucose determination, but was presumably caused by a plasma glucose concentration less than or equal to 70 mg/dL (3.9 mmol/L); symptoms treated with oral carbohydrate without a test of plasma glucose.

Patients will be instructed to measure finger stick plasma glucose levels prior to the administration of carbohydrates whenever symptomatic hypoglycemia is suspected, unless safety considerations necessitate immediate glucose rescue prior to confirmation, and then a glucose measurement should be performed as soon as safe, with appropriate diary documentation. Details on hypoglycemia episodes will be captured in the patient diaries, and patients will contact the sites as soon as possible following severe events to review the details and decide on any necessary measures to be taken.

Symptomatic hypoglycemia episodes will be documented on the dedicated hypoglycemia event page in the e-CRF. Symptomatic hypoglycemia events fulfilling the criteria of a SAE will also be documented on AE and SAE complementary forms form in the e-CRF.

9.6.2 Local Tolerability at Injection Site

In case the investigator or the patient recognizes any signs of local intolerability at injection site this should be recorded on the standard AE page in the e-CRF.

9.6.3 Allergic or Allergic-Like Reaction

In case a patient experiences an allergic reaction or an allergic-like reaction this has to be reported as an adverse event and recorded in the e-CRF on the specific AE form for suspected allergic event. Additional information is collected on specific allergic reaction complementary form. Allergic reaction or possible allergic reaction will be adjudicated by the ARAC (Section 5.4.2).

Virtually all symptoms listed on the allergic reaction complementary form are possible adverse reactions that may be allergic in nature and may need to be addressed after medical judgment, excluding another etiology than allergy.

Sometimes transient injection site reactions, irritant in nature may occur requiring no intervention and are of dubious significance. These reactions would not be considered to be allergic reactions. Adverse events that are obviously not of allergic origin (e.g. local injection site reactions) should not be recorded on the Allergic Reaction Complementary Form.

9.6.4 Monitoring of Patients with Increased Lipase and/or Amylase >2 ULN

Potential safety signals for acute pancreatitis had been identified in the post-marketing experience of other GLP-1 receptor agonists. Therefore, patients enrolled in this study should be followed for any suspected pancreatitis, e.g. with symptoms and/or signs of acute abdominal distress or abnormal levels of pancreatic enzymes. Serum amylase and lipase concentrations are monitored routinely at screening, baseline and periodically during the study treatment period.

In the presence of clinical signs and/or symptoms evocative of pancreatitis, eg, persistent abdominal pain, which can radiate to the back, often with characteristic positional features, with possible occurrence of nausea, vomiting, fever and leucocytosis, further measurement of amylase and lipase should be performed. The clinical signs and/or symptoms should be documented in the source data.

(1) Elevation of Amylase and/or Lipase >2 ULN without Clinical Signs and/or Symptoms In any case where amylase and/or lipase are >2 ULN, a retest (centrally assessed as far as possible) must be performed as follows:
  If value(s) is/are >2-3 ULN: retest within 7 days,
  If value(s) is/are >3 ULN: retest within 48 hours,
  If the value(s) remain(s) >2 ULN upon retesting: amylase and/or lipase levels should be retested weekly until values are <2 ULN.

In case a retest is >2 ULN a gastroenterological evaluation and imaging (ultrasound and/or CT or MRI with contrast, as appropriate) must be performed. Please document in the source data the absence of clinical signs and/or symptoms (if clinical signs and/or symptoms develop, please see (2) below).

Best clinical judgment is to be used when interpreting elevated serum amylase and lipase levels in asymptomatic patients. Temporary discontinuation of the IMP may be considered in these cases if deemed necessary by the Investigator.

(2) Elevation of Amylase and/or Lipase >2 ULN with Clinical Signs and/or Symptoms In the presence of clinical signs and/or symptoms evocative of pancreatitis (as described above) associated with elevated amylase and/or lipase, treatment with the IMP should be promptly and at least temporarily discontinued pending further clinical evaluation and diagnosis confirmation.

Clinical signs and/or symptoms are to be documented in the source data. A laboratory determination of amylase and lipase has to be obtained at the time of the event and again within 48 hours or earlier as clinically indicated. If the value(s) remain(s) >2 ULN, then amylase and/or lipase levels should be retested as described in (1) above, or more often if clinically indicated.

A gastroenterologic evaluation and imaging (ultrasound and/or CT or MRI with contrast, as appropriate) must be performed. If a diagnosis of pancreatitis is confirmed, IMP should not be restarted and should be permanently discontinued.

In both cases as described above under (1) and (2), all laboratory or clinical documentations are to be collected. If the retest confirms lipase and/or amylase values are >2 ULN, the event must be reported in the eCRF on the specific AE form for "Increased Lipase and/or Amylase >2 ULN" and the specific forms, using the appropriate verbatim: eg, "increased amylase and/or lipase" in case of isolated enzyme elevation, "suspected pancreatitis" in the presence of clinical signs evocative of pancreatitis if the diagnosis is suspected but cannot be confirmed or excluded, and "pancreatitis" if the diagnosis has been confirmed.

The PSAC will review selected pancreatic events, including pancreatitis, pancreatic neoplasms and abnormal levels of amylase or lipase.

9.6.5 Major Cardiovascular Events

In case a patient experiences a major cardiovascular event, the investigator, in addition to adverse event reporting on specific AE forms for cardiovascular events, has to collect more detailed information on specific complementary forms. Major cardiovascular events will be adjudicated by the CAC in a blinded manner at the latest before the database lock. Please also refer to Section 5.4.3.

9.6.6 Management of Patients with Increased Calcitonin Values

During the course of the study, if calcitonin value is found 2:20 pg/mL (5.9 pmol/L):
  A retest should be performed by the central laboratory within 7 days. In addition, blood should be collected and sent to the central laboratory for measurement of: calcium, phosphorus, gastrin, Thyroid Stimulating Hormone (TSH), and anti-thyroid peroxidase (anti-TPO) antibodies.
  The clinical and laboratory documentations listed below are to be collected and recorded in source documents as soon as possible:
    Potential false positive circumstances: smoking status, proton-pump inhibitor treatments (eg, omeprazole), autoimmune thyroid diseases (Hashimoto's thyroiditis or Grave's disease), differentiated thyroid cancer, hypercalcemia, hypergastrinemia, chronic renal insufficiency (not on dialysis), other neuro-endocrine tumors (lung small cell cancer, intestinal carcinoid), acute pulmonary inflammatory conditions, or sepsis;
    Specific personal and/or familial medical history in relation to thyroid or other endocrine diseases;
    Specific physical examination (neck, thyroid gland).
  If the retest confirms that the calcitonin value is 20 μg/mL:
  The event must be reported in the e-CRF on the specific AE form and specific complementary form for "increased calcitonin 20 μg/mL" with all appropriate clinical and laboratory documentation.
  An ultrasound scan of the thyroid should be performed and the patient may be referred to a thyroid specialist if judged necessary.
  The patient should continue to be followed according to protocol schedule (including planned calcitonin measurements). The specific AE form "increased calcitonin ≥20 pg/mL (5.9 pmol/L)" should be updated with any new information collected during the follow up.
  If a calcitonin value ≥50 pg/mL (14.75 pmol/L) is found at any time during further follow up, the patient should be permanently discontinued from IMP (see Section 9.6.6) and referred to a specialist. As far as possible, blood should be collected 1 to 2 weeks after IMP discontinuation and sent to the central laboratory for calcitonin measurement.
  If at any time during follow-up a calcitonin value ≥20 pg/mL increases by 20% or more between 2 assessments (while remaining below 50 pg/mL), a repeated measurement should be performed earlier than scheduled in the protocol, ie, 1 month later. Once results are available, discussion with Sponsor should be initiated without delay for further guidance.

9.6.7 Monitoring of Renal Function in Case of Prolonged and Severe Nausea and Vomiting In case of prolonged or severe nausea and vomiting, if clinically indicated, serum creatinine measurement has to be centrally performed. If there is an acute increase of serum creatinine, metformin (if taken) has to be discontinued until resolution of renal dysfunction.

9.6.8 Follow-Up of Laboratory Abnormalities

Figure 17:
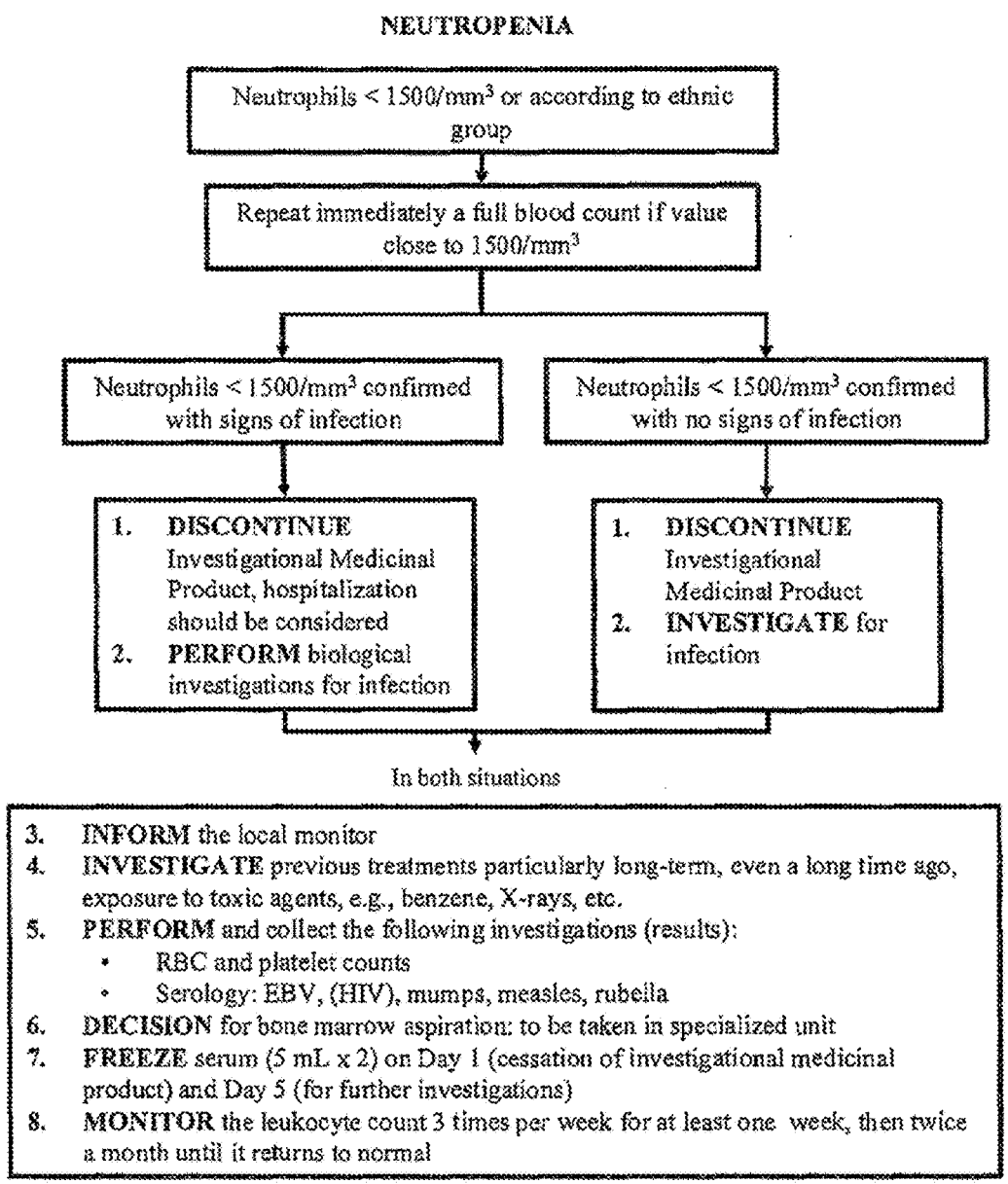
FIG. 17 shows the follow-up guidance for neutropenia.
Figure 18:
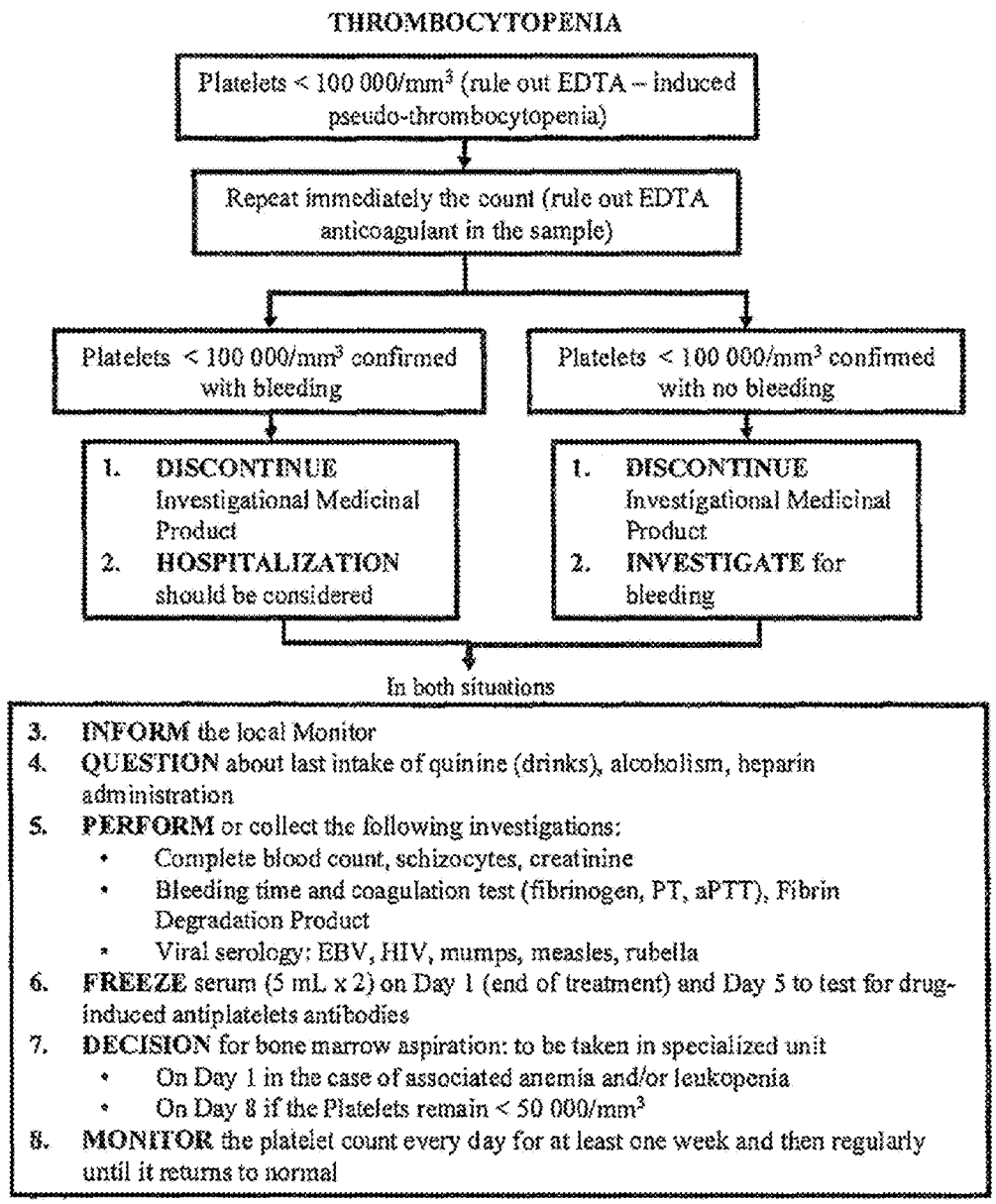
FIG. 18 shows the follow-up guidance for thrombocytopenia.

Decision trees for the management of certain laboratory abnormalities are provided in Appendix B (See FIG. 17 and FIG. 18).

9.7 Adverse Events Monitoring

All events will be managed and reported in compliance with all applicable regulations, and included in the final clinical study report.

10 STATISTICAL CONSIDERATIONS

10.1 Determination of Sample Size

The sample size calculations are based on the primary efficacy variable change in HbA1c from baseline to Week 30, with the following assumptions:
  A common standard deviation of 1.1%,
  A 0.4% mean difference between insulin glargine/lixisenatide fixed ratio combination and insulin glargine in change in HbA1c from baseline to Week 30,
  A t-test at a 2-sided 5% significance level with at least 95% power.
Based on the above assumptions, 350 patients per arm are needed for this study.
Calculations were made using nQuery Advisor 7.0.

10.2 Disposition of Patients

The total number of patients for each of the following categories will be presented in the CSR:
  Screened patients: patients who have signed the informed consent,
  Run-in patients: patients who had a run-in record in IVRS/IWRS database,
  Randomized patients: patients with a treatment kit number allocated and recorded in IVRS/IWRS database, and regardless of whether the treatment kit was used or not.
  The safety population (ie, randomized and treated patients),
  The modified intent-to-treat (mITT) population (as defined in Section 10.3.1.1 and analyzed as randomized),
  The pharmacokinetic (PK) population (as defined in Section 10.3.3),
  The randomization strata [HbA1c at Visit 5 (<8%, 2:8%) and metformin use at screening (Yes, No)] assigned by IVRS/IWRS will be summarized. The discrepancy between the strata assigned by IVRS/IWRS and the information reported on electronic Case Report Form (eCRF) will be listed for all randomized patients, Patients who have completed the 30-week treatment period, Patients who discontinued the IMP during the 30-week treatment period, and the reasons for treatment discontinuation.

For all categories of patients except screened and run-in patients, percentages will be calculated using the number of randomized patients as denominator for each treatment group.

A list of patients prematurely discontinued from the treatment, along with reasons for discontinuation, will be provided.

Patients treated but not randomized, patients randomized but not treated and patients randomized but not treated as randomized will be identified and described in separate listings. Only the patients of the third category (randomized and not treated as randomized) will be part of efficacy and safety analyses.

For any patient randomized more than once, only the data associated with the first randomization will be used in any analysis population. The safety experience associated with any later randomization will be assessed separately.

The safety experience of patients treated and not randomized will be reported separately, and these patients will not be in the safety population.

10.3 Analysis Populations

10.3.1 Efficacy Populations

Efficacy analyses will be based on the treatment arm allocated by the IVRS/IWRS according to the randomization schedule at randomization visit (as randomized), irrespective of the treatment arm actually received.

10.3.1.1 Modified Intent-to-Treat Population

Efficacy analyses will be based on the modified intent-to-treat (mITT) population, defined as all randomized patients who receive at least one dose of open-label IMP and have both a baseline assessment and at least one post-baseline assessment of any primary or secondary efficacy variables, irrespective of compliance with the study protocol and procedures. Patients will be analyzed for efficacy analyses according to the treatment group to which they are randomized.

10.3.2 Safety Population

Safety analyses will be based on the safety population, defined as all randomized patients who receive at least one dose of open-label IMP (regardless of the amount of treatment administered). Patients will be analyzed for safety analyses according to the treatment actually received.

In addition:

Nonrandomized but treated patients will not be part of the safety population, but their safety data will be presented separately.

Randomized patients for whom it is unclear whether they took the study medication will be included in the safety population as randomized.

When a patient is exposed to both insulin glargine/lixisenatide fixed ratio combination and insulin glargine, the patient will be analyzed in the treatment group (insulin glargine/lixisenatide fixed ratio combination or insulin glargine) in which he/she is treated longer.

Patients will be excluded from the safety population only if there is documented evidence (ie, all study dates recorded as no medication taken) that patients have not taken the study medication.

10.3.3 Pharmacokinetic Population

For pharmacokinetic (PK) analyses, the PK population is defined as all randomized and treated patients who contribute with at least one valid plasma analysis of lixisenatide.

10.4 Statistical Methods

Continuous data will be summarized by treatment group using the number of observations available (N), mean, standard deviation (SD), minimum, median, and maximum.

Categorical data will be summarized by treatment group 'using count and percentage.

In general, descriptive statistics of quantitative efficacy and safety parameters (result and change from baseline) by scheduled visits will be provided on observed cases (OC), i.e., inclusion of only patients having non-missing assessments at a specific visit.

10.4.1 Demographic and Baseline Characteristics

The baseline value is defined as the last available value before the first injection of open-label Investigational Medicinal Product (IMP). Derived parameters will be computed by the sponsor.

Demographic characteristics to be summarized are:

Age (years) derived as: (Date of informed consent−Date of birth)/365.25,

Age categories (<50, 20 to <65, 65 to <75, 75 years of age), Gender (Male, Female), Race (Caucasian/White, Black, Asian/Oriental, Other), Ethnicity (Hispanic, Not Hispanic), HbA1c (%) at Visit 5 (Week −1), Randomization strata of HbA1c (<8, 2%) at Visit 5 (Week −1), Randomization strata of metformin use (Yes, No) at screening, Baseline BMI (kg/m$^2$) derived as: (Weight in kg)/(Height in meters)2, Baseline BMI categories (<30, 20 kg/m$^2$)

Country

Diabetes history includes

Duration of diabetes (years) derived as: (Date of informed consent−Date of diagnosis of diabetes+1)/365.25, Age at onset of diabetes (years) derived as: (Date of diagnosis of diabetes−Date of birth+1)/365.25, Duration of basal insulin treatment (years) derived as: (Date of informed consent-Date of first dose of basal insulin+1)/365.25, Averaged daily dose of basal insulin at Visit 2 (Week −6) and Averaged daily dose of insulin glargine at randomization Visit 6 (Week 0), Averaged daily dose of basal insulin within the 3 days immediately before screening at Visit 2 (Week −6) and Averaged daily dose of insulin glargine within the 3 days immediately before randomization at Visit 6, Percentage of patients who used metformin at screening,
Duration of metformin treatment (years) (for patients who used metformin at screening) derived as: (Date of informed consent−Date of first dose of metformin+1)/365.25,
Daily dose of metformin (mg) at baseline,
Categorized daily dose of metformin at baseline (<1500, 1500 to <2500, 2500 to <3000, 2000 mg),
Percent of patients with number of OAD use at screening (no OAD use, one OAD use, two OADs use),
Percent of patients with OAD use by class (i.e. metformin, sulfonylurea, glinide, dipeptidylpeptidase4 inhibitor or SGLT-2 inhibitor alone, or in combination of any two of them),
Duration of first OAD (years) (for patients who used OAD at screening) derived as: (Date of informed consent−Date of first dose of OAD+1)/365.25,
Duration of second OAD (years) (for patients who used OAD at screening) derived as: (Date of informed consent−Date of first dose of OAD+1)/365.25,
Prior use of GLP-1 receptor agonist (Yes, No),
Baseline diabetic microvascular complications (Yes, No) (ie, diabetic retinopathy, diabetic sensory or motor neuropathy, diabetic autonomic neuropathy, and diabetic nephropathy including the most recent event categories).
Baseline urine albumin/creatinine ratio categories (<30 µg/mg [Normal], 20 to <300 µg/mg [Microalbuminuria], and 200 [Macroalbuminuria]),
Calculated creatinine clearance at screening (ml/min),
Calculated creatinine clearance categories at screening (<30 ml/min [Severe renal impairment], ≥30 to <50 ml/min [Moderate renal impairment], ≥50 to ≤80 ml/min [Mild renal impairment], and >80 ml/min [No renal impairment]).
The baseline efficacy variables include:
HbA1c,
During standardized meal test:
  2-hour postprandial plasma glucose (PPG) and glucose excursion,
  30-minute and 1-hour PPG and the corresponding glucose excursion. Note: 30-minute, 1-hour or 2-hour plasma glucose excursion=30-minute, 1-hour or 2-hour postprandial value-value obtained 30 minutes prior to the start of meal and before IMP administration if IMP is injected before breakfast)
7-point (average) Self-Monitored Plasma Glucose,
Body weight.
Fasting plasma glucose (by central laboratory),
Medical history and medical findings include:
Physical examination,
Medical or surgical history,
Medical history of cardiovascular and cerebrovascular events,
Medical history of allergies,
Subject family allergy history,
Alcohol habits within the last 12 months,
Smoking habits.
Medical and surgical history will be coded using the version of Medical Dictionary for Regulatory Activities (MedDRA) currently in effect at sanofi at the time of database lock.
No statistical test will be performed for the between-group difference on demographic and baseline characteristics (including medical history and baseline efficacy data).

Demographic and baseline disease characteristics, baseline efficacy variables and medical history and medical findings will be summarized with appropriate descriptive statistics by treatment group and overall. Pathologies associated with past medical or surgical history will be summarized by primary SOC and HLT. These summaries will be provided on randomized patients.

10.4.2 Prior and Concomitant Medications

All medications will be coded using the version of World Health Organization-Drug Dictionary (WHO-DD) currently in effect at sanofi at the time of database lock.
Medications will be classified into the following three groups:
  Prior medications are those the patient took prior to the first injection of open-label IMP.
  Concomitant medications are those the patient continued or started on or after the first injection of open-label IMP up to 3 days after the last injection of IMP.
  Post-treatment medications during the follow-up period are those the patient continued or started on or after 4 days after the last injection of open-label IMP.
A given medication can be classified in several groups. Medications will be summarized according to the WHO-DD dictionary, considering the first digit of the ATC class (anatomic category) and the first three digits of the ATC class (therapeutic category). All ATC codes corresponding to a medication will be summarized, patients will be counted once in each ATC categories (anatomic or therapeutic) linked to the medication, therefore patients may be counted several time for the same medication.
Summaries of prior, concomitant and post-treatment medications will be presented on randomized patients for each treatment group (and overall for the summary of prior medications), using counts and percentages. No statistical test for the between-group difference will be performed.

10.4.3 Extent of Study Treatment Exposure and Compliance

The extent of study treatment exposure and compliance will be assessed and summarized by actual treatment received in the safety population.

10.4.3.1 Extent of Investigational Medicinal Product Exposure

The extent of study treatment exposure will be assessed by the duration of treatment exposure during the study.
The duration of treatment exposure will be the total number of days of administration of the open-label investigational medicinal product, regardless of unplanned intermittent discontinuations. The duration of IMP exposure will be calculated as: (Date of the last open-label IMP injection−Date of the first open-label IMP injection)+
The number (%) of patients randomized and exposed to the open-label IMP will be presented by specific time periods for each treatment group in the safety population. The time periods of interest are grouped as follows:
  1 to 14 days,
  15 to 28 days,
  29 to 56 days,
  57 to 84 days,
  85 to 126 days,
  127 to 168 days,
  169 to 210 days,
  >210 days.

Descriptive statistics of duration of treatment exposure (number, mean, SD, minimum, median, and maximum) and cumulative exposure in patient year will also be presented by treatment group in the safety population.

10.4.3.2 Compliance

Overall treatment compliance is defined as the actual number of days with any IMP injection compared to the planned number of days with IMP injection during the open-label treatment period, up to treatment discontinuation. It is calculated according to the following formula:

$$\text{Compliance rate (\%)} = \left[\frac{\text{Total number of days with at least one } IMP \text{ injection}}{\text{Planned number of days with } IMP \text{ injection}}\right] \times 100.$$

Treatment compliance will be summarized by treatment group using mean, SD, median, and range for the safety population. In addition, the percentage of patients who have <60%, ≥60 to <80%, ≥80 to 100%, and >100% compliance will be summarized by treatment group.

10.4.4 Analyses of Efficacy Endpoints

Efficacy analyses will be performed on the mITT population using efficacy assessment obtained during the on-treatment period (Section 8.1 and Section 8.2.1), unless otherwise specified.

For a patient to be included in a change from baseline analysis (endpoint-baseline) or a baseline adjusted analysis of an endpoint, the patient must have both a baseline and a post-baseline on-treatment measure for that endpoint.

10.4.4.1 Analysis of Primary Efficacy Endpoint(s)

The statistical test will be two-sided tests at a nominal 5% significance level.

The primary endpoint, change in HbA1c from baseline to Week 30, will be analyzed using a mixed-effect model with repeated measures (Mt\11RM), under the missing at random framework. The MMRM model will include treatment group (insulin glargine/lixisenatide fixed ratio combination or insulin glargine), randomization strata of HbA1c (<8, 2:8%) at Visit 5 (Week −1), randomization strata of metformin use (Yes, No) at screening, visit (Week 8, Week 12, Week 24, and Week 30), treatment-by-visit interaction and country as fixed effects, and baseline HbA1c value-by-visit interaction as a covariate. The adjusted mean change in HbA1c from baseline to Week 30 for each treatment group will be estimated in the framework of this model, as well as the between-group difference and the 95% CI for the adjusted mean.

The MMRM model will be implemented using SAS® (Version 9.2 or higher) MIXED procedure (PROC MIXED) with an unstructured correlation matrix to model the within-patient errors. Parameters will be estimated using the restricted maximum likelihood method with the Newton-Raphson algorithm. Denominator degree of freedom will be estimated using the Kenward-Roger approximation by fitting values from post-randomization scheduled visits during the on-treatment period.

Primary analysis will be performed using the mITT population and including all scheduled HbA1c measurements collected during the on-treatment period.

Sensitivity Analyses

The following sensitivity analyses will be performed for the primary endpoint.

In order to assess the impact of rescue therapy, a sensitivity analysis in a multilevel model with random slopes and intercepts, will be performed using all HbA1c data collected until the treatment cessation plus 14 days (including data collected after the introduction of rescue therapy). A multilevel model with random slopes and intercepts will be used to adjust for the effect of rescue medication on the change from baseline in HbA1c. This model will include treatment (insulin glargine/lixisenatide fixed ratio combination or insulin glargine), randomization strata of HbA1c (<8, 8%) at Visit 5 (Week −1), randomization strata of metformin use (Yes, No) at screening, visit (Week 8, Week 12, Week 24, and Week 30), treatment-by visit interaction, country as fixed-effect factors, and baseline HbA1c-by-visit interaction, and the number of days spent on rescue medications as covariates. The multilevel model will be implemented via PROC MIXED. Parameters will be estimated using the restricted maximum likelihood method with the Newton-Raphson algorithm. Denominator degrees of freedom will be estimated using the Kenward-Reger approximation by fitting values from all post-randomization visits in the on-treatment period.

An analysis of covariance (ANCOVA) with the missing data imputed by the Last Observation Carried Forward (LOCF) will be performed on the primary efficacy variable. Each patients last available post-baseline on-treatment HbA1c measurement (before the rescue medication is taken in the event of rescue therapy) will be modeled with treatment groups (insulin glargine/lixisenatide fixed ratio combination or insulin glargine), randomization strata of HbA1c (<8, 8%) at Visit 5 (Week −1), randomization strata of metformin use (Yes, No) at screening, and country as fixed effects and using the baseline HbA1c value as a covariate. Adjusted mean estimates by treatment and the difference of these estimates (insulin glargine/lixisenatide fixed ratio combination versus insulin glargine) will be provided as well as 95% confidence intervals (CI) of the differences and p-value.

A sensitivity analysis will also be conducted on the 30-week completers in mITT population (ie, all mITT patients who completed the 30-week open-label treatment period and did not start any rescue therapy before the end of the 30 week treatment period) using the observed Week 30 values and the same MMRM model as described in the primary analysis above.

Assessment of Treatment Effect by Subgroup

Descriptive analyses will be performed on the primary endpoint to summarize the treatment effects across subgroups defined by the following baseline or screening factors:

Race,
Ethnicity (Hispanic, Not Hispanic),
Age group (<50, ≥50 to <65, ≥65 years of age),
Gender,
Baseline BMI level (<30, ≥30 kg/m$^2$),
Baseline HbA1c (<8, ≥8%),
Metformin use (Yes, No) at screening,
Country.
Number of OAD use at screening (no OAD use, one OAD use, two OADs use).

The treatment effects across the subgroups defined for each of these factors will be estimated for the change from baseline to Week 30 in HbA1c in the mITT population excluding the assessments done after the introduction of a rescue medication, and using the MMRM approach with treatment group (insulin glargine/lixisenatide fixed ratio combination or insulin glargine), randomization strata of HbA1c (<8, ≥8%) at Visit 5 (Week −1), randomization strata of metformin use (Yes, No) at screening, visit, subgroup factor, treatment-by-visit, treatment-by-subgroup factor, visit-by-subgroup factor, treatment-by-visit-by-subgroup factor, and country as fixed effects and using baseline HbA1c value-by-visit interaction as a covariate. The adjusted estimates of treatment mean differences (insulin glargine/lixisenatide fixed ratio combination versus insulin glargine alone and versus lixisenatide alone) with standard errors and 95% confidence intervals will be provided as appropriate across the subgroups.

In case that the subgroup factor is identical or similar to a randomization strata factor (e.g. baseline HbA1c category or metformin use), only the subgroup factor will be included in the model in order to avoid collinearity issue in the analysis.

A similar MMRM model will also be used to estimate the within-group treatment effect for the change from baseline to Week 30 in HbA1c for the following subgroups:
  Anti-lixisenatide antibody status (positive, negative) at the end of 30-week treatment,
  Anti-insulin glargine antibody status (positive, negative) at the end of 30-week treatment,
  Anti-lixisenatide antibody concentration at the end of 30-week treatment: <lower limit of quantification (LLOQ), ≥LLOQ to 100, >100 nmol/L.

The adjusted means for each treatment group will be provided across the subgroups as appropriate, as well as the associated standard errors and 95% confidence intervals.

The change of HbA1c from baseline over time by visit will be evaluated by descriptive statistics (mean, standard deviation, median and ranges).

10.4.4.2. Analyses of Secondary Efficacy Endpoints

Descriptive statistics (number, mean, standard deviation, median, minimum, and maximum) will be provided by treatment for all continuous secondary variables at the scheduled visits.

Except for 30-minute, 1-hour, 2-hour PPG and glucose excursion, all continuous secondary efficacy endpoints at Week 30 defined in Section 8.2.1 will be analyzed using the same MMRM approach as described in Section 10.4.4.1 to compare insulin glargine/lixisenatide fixed ratio combination with insulin glargine. This model will include fixed effect terms including treatment group (insulin glargine/lixisenatide fixed ratio combination or insulin glargine), randomization strata of HbA1c (<8, 2:8%) at Visit 5 (Week −1), randomization strata of metformin use (Yes, No) at screening, scheduled visit, treatment-by-visit interaction, and country, and the covariate baseline value-by-visit interaction (except for insulin glargine dose at week 30, for which the MMRM model will not be adjusted on the baseline value). Means and adjusted means of each treatment group will be provided, as well as adjusted mean and associated two-sided 95% CI of the differences between treatment groups. The statistical tests for between-group differences will be two-sided at the alpha level of 0.05. The analyses include all scheduled measurements collected during the on-treatment period.

Thirty-minute, 1-hour, 2-hour PPG and glucose excursion, for which only one on-treatment assessment is scheduled, will be analyzed using the similar ANCOVA with the missing data imputed by LOCF as described in Section 10.4.4.1 to compare insulin glargine/lixisenatide fixed ratio combination with insulin glargine. This model will include fixed effect terms including treatment groups, randomization strata of HbA1c (<8, 2:8%) at Visit 5 (Week −1), randomization strata of metformin use (Yes, No) at screening, and country, and a covariate using the corresponding baseline value. Means and adjusted means of each treatment group will be provided, as well as adjusted mean and associated two-sided 95% CI of the difference between treatment groups. In case of discontinuation of study drug before Week 30, 30-minute, 1-hour, 2-hour PPG and glucose excursion will be assessed at the time of discontinuation. The LOCF procedure will be used by taking this last available post-baseline on-treatment measurement (before the rescue medication is taken in the event of rescue therapy) as the value at Week 30.

All categorical secondary efficacy endpoints defined in Section 8.2.1 will be analyzed using a Cochran-Mantel-Haenszel (CMH) method stratified on randomization strata of HbA1c (<8, 8%) at Visit 5 (Week −1) and randomization strata of metformin use (Yes, No) at screening. The proportion in each treatment group will be provided, as well as the difference of proportions between groups with associated 2-sided 95% CI. For HbA1c responders at Week 30 (6.5%, <7% respectively), patients who had no assessments at Week 30 during the on-treatment period will be treated as failures (non-responders) in the analysis, including those who discontinue study treatment before Week 30, start rescue medication before Week 30, or have no on-treatment assessments at all in mITT population. For each categorical composite endpoint, a patient will be treated as a responder only if the criterion is met for each component of the composite endpoint.

10.4.4.3 Multiplicity Considerations (to be Determined)

To control the Type I error, a step-down testing procedure will be applied.

For the primary variable (change from baseline to Week 30 in HbA1c), no multiplicity adjustment is needed to control the Type I error since only one comparison of insulin glargine/lixisenatide fixed ratio combination versus insulin glargine will be performed.

If the primary variable is statistically significant at the 5% level, a hierarchical testing procedure will be performed to test the following secondary efficacy variables in the following prioritized order. Testing will stop when an endpoint is found not to be statistically significant at the 5% level:
  1. Change in 2-hour blood glucose excursion during the standardized meal test from baseline to Week 30,
  2. Change in body weight from baseline to Week 30,
  3. Change in the daily average of the 7-point SMPG from baseline to Week 30,
  4. Percentage of patients reaching HbA1c<7% with no body weight gain at week 30,
  5. Change in daily dose of insulin glargine from baseline to Week 30, Multiplicity adjustment will not be performed on the secondary efficacy variables that are not included in the above list.

10.4.5 Analyses of Safety Data

The summary of safety results will be presented by treatment group.

All safety analyses will be perfomled on the Safety population as defined in Section 10.3.2 using the following common rules:

The baseline value is defined generally as the last available value before randomization.

The following definitions will be applied to laboratory parameters and vital signs.

The potentially clinically significant abnormality (PCSA) values for clinical laboratory tests and vital signs are defined as abnormal values considered medically important by the Sponsors Global Pharmacovigilance and Epidemiology department and in effect at the time of the final SAP approval. PCSA criteria for parameters not cited in the protocol as safety parameters will not be analyzed.

PCSA criteria will determine which patients had at least 1 PCSA during the on-treatment period, taking into account all evaluations performed during the on-treatment period, including unscheduled or repeated evaluations. The number of all such patients will be the numerator for the on-treatment PCSA percentage.

The "observation period" defined in Section 8.2.2 are applicable for classification of AEs, determination of on-treatment PCSA values and the last on-treatment value for the laboratory, vital sign and ECG parameters.

10.4.5.1 Analyses of Symptomatic Hypoglycemia

The number (%) of patients and rate in patient years (2 types: the number of patients with events or the total number of events per 100 patient-year) of each type of symptomatic hypoglycemia (severe, documented and probable symptomatic hypoglycemia) will be summarized by treatment group. The pattern of symptomatic hypoglycemia occurrence over time will also be assessed, as appropriate.

In addition to the threshold of less than or equal to 70 mg/dL (3.9 mmol/L) (please refer to Section 9.6.1 symptomatic hypoglycemia episodes with a plasma glucose of <60 mg/dL (3.3 mmol/L) will be analyzed separately.

10.4.5.2 Analyses of Adverse Events

Pre-treatment AEs are AEs that developed or worsened or became serious during the pre-treatment period.

Treatment-emergent AEs (TEAEs) are AEs that developed or worsened (according to the investigators opinion) or became serious during the on-treatment period.

Post-treatment AEs are AEs that developed or worsened or became serious during the post-treatment period.

The primary focus of AE reporting in the CSR will be on TEAEs. Pre- and post-treatment AEs will be described separately.

All Adverse Events

Adverse event incidence tables will present by system organ class (SOC) (sorted by internationally agreed order), high-level group term (HLGT), high level term (HLT) and preferred term (PT) sorted in alphabetical order for each treatment group, the number (n) and percentage (%) of patients experiencing an AE. Multiple occurrences of the same event in the same patient will be counted only once in the tables within a treatment phase. The denominator for computation of percentages is the safety population within each treatment group.

Summaries of all TEAEs in each treatment group will include:
The overview of AEs, summarizing number (%) of patients with any
TEAE,
serious TEAE,
TEAE leading to death,
TEAE leading to permanent treatment discontinuation.
The number (n) and percentage (%) of patients with at least one TEAE by primary SOC, HLGT, HLT and PT,
Summary of TEAEs by maximal severity (severe, moderate, mild), presented by primary SOC and PT,
Summary of TEAEs possibly related to open-label IMP, presented by primary SOC, HLGT, HLT and PT.

A detailed listing of TEAE summaries will be provided in the statistical analysis plan.

Death and Serious Adverse Events

Death and treatment-emergent SAEs will be summarized and presented as number and percent of patients in each treatment group.

The following deaths summaries will be generated:
Number (%) of patients who died by study period (TEAE, on-study) summarized on the safety population by treatment received
Death in nonrandomized patients or randomized and not treated patients
TEAE leading to death (death as an outcome on the AE e-CRF page as reported by the Investigator) by primary SOC, HLGT, HLT and PT showing number (%) of patients sorted by internationally agreed order of SOC and alphabetic order of HLGT, HLT, and PT.

Adverse Events Leading to Permanent Treatment Discontinuation

TEAEs leading to permanent treatment discontinuation will be summarized and presented as number and percent of patients in each treatment group.

Local Tolerability at Injection Site

AEs related to local intolerability at the injection site will be identified by searching the term "injection site" in either the PTs coded from the investigator reported terms or the PTs coded from the ARAC diagnosis terms. The number (%) of patients with related events will be summarized by treatment group.

Allergic Reactions

The number (%) of patients with events adjudicated as allergic reactions by ARAC and with events adjudicated by ARAC as possibly related to the IMP will be summarized by treatment group. All the allergic events reported by the investigators on the AE form for suspected allergic event and its associated complementary forms (confirmed or not confirmed by ARAC) will be listed.

Increased Pancreatic Enzymes >2 Times ULN

The number (%) of patients with events reported on the AE form for increased lipase and/or amylase >2 times ULN and its associated complementary forms will be summarized by PTs for each treatment group.

Major Cardiovascular Events

Major cardiovascular events positively adjudicated and confirmed by CAC will not be summarized in the CSR. All events reported by the Investigators on the AE forms for cardiovascular events and the associated complementary forms (confirmed or not confirmed by CAC) will be listed along with the adjudication outcome.

Increased Calcitonin Values

The number (%) of patients with events reported on the AE form for increased calcitonin 220 µg/mL and its associated complementary forms will be summarized by PTs for each treatment group.

ALT Increase

The number (%) of patients with events reported on the AE form for ALT increase and its associated complementary forms will be summarized by PT for each treatment group.

10.4.5.3 Analyses of Laboratory Variables

The number and percentage of patients with PCSA at any evaluation during the on-treatment period will be summarized for each clinical laboratory test within each treatment group. The summaries will include patients in the safety population who have at least one laboratory test performed during the on-treatment period and, when required by the definition of the abnormality, with an available baseline value and available laboratory normal ranges.

Descriptive statistics will be used to summarize the laboratory results and the changes from baseline by visit and for the last on-treatment value within each treatment group.

Shift tables and other tabular and graphical methods may be used to present the results for laboratory tests of interest.

Listings will be provided with flags indicating the out of laboratory range values as well as the PCSA values.

Drug-Induced Liver Injury

The liver function tests, namely AST, ALT, alkaline phosphatase and total bilirubin are used to assess possible drug induced liver toxicity. The proportion of patients with PCSA values at any post baseline visit by baseline status will be displayed by treatment group for each parameter. The proportion of patients with PCSA values at any post baseline visit will also be displayed by duration of exposure for each treatment group only if a tabulation summary is necessary.

A listing will be provided of possible Hy's Law cases identified by treatment group (eg, patients with any elevated ALT>3×ULN, and associated with an increase in total bilirubin 2:2×ULN) with liver-related TEAEs, ALT, AST, ALP, total bilirubin and the following complementary parameters, if available: Conjugated Bilirubin and Prothrombin Time/INR, creatine phosphokinase, serum creatinine, complete blood count, Immunoglobin M (IgM) antibodies to Hepatitis A virus, IgM antibodies to Hepatitis B core antigen, antibodies to Hepatitis C Virus, and Hepatitis C ribonucleic acid, IgM antibodies to Cytomegalovirus, and IgM antibodies to Hepatitis E virus, Auto-antibodies: anti-nuclear, anti-deoxyribonucleic acid, anti-smooth muscle, Epstein-Barr virus, Herpes viruses and anti-liver/kidney microsomes.

10.4.5.4 Analyses of Vital Sign Variables

The number and percentage of patients with PCSA at any evaluation during the on-treatment period will be summarized for each vital sign parameter within each treatment group. The summaries will include patients in the safety population who have at least one parameter to be analyzed during the on-treatment period. When the PCSA definition involves the change from the baseline value, patients need also to have a baseline value to be included in the summaries.

Descriptive statistics will be used to summarize the results and the changes from baseline by visit and for the last on-treatment value within each treatment group.

Tabular and graphical methods may be used to present the results for parameters of interest.

Listings will be provided with flags indicating the PCSA values.

10.4.5.5 Analyses of 12 Lead ECG Status

A shift table will be provided to present the ECG on-treatment status according to the baseline status within each treatment group

10.4.5.6 Analyses of Anti-Drug Antibody Variables

Analyses of antibody variables will be performed on the safety population (ie, in patients from both treatment groups for anti-insulin glargine antibody; in patients from the insulin glargine/lixisenatide fixed ratio combination group only for anti-lixisenatide antibody).

The number and percentage of patients by antibody status will be listed and summarized by treatment group and visit, as well as the percentage of conversion from negative to positive status from baseline to Week 30. For anti-insulin antibodies, the number and percentage of patients with cross reactivity to human insulin will also be summarized by treatment group and visit in anti-insulin glargine positive patients.

Antibody levels (titer or concentration), as well as respective percent changes from baseline for anti-insulin glargine antibodies, will be listed and summarized by treatment group and visit using descriptive statistics by N, geometric mean, coefficient of variation, median, minimum and maximum.

10.4.6 Analyses of Pharmacokinetic Variables

Lixisenatide plasma concentrations (total and active) of patients in the insulin glargine/lixisenatide fixed ratio combination group will be listed and summarized by visit and time window and by anti-lixisenatide antibody status in the PK population, using descriptive statistics by N, geometric mean, coefficient of variation, median, minimum and maximum.

Population PK modeling might be pursued for exploratory purpose.

10.4.7 Analyses of Patient Reported Outcomes Variables

The analyses of TRIM-D, EQ-5D and IWQoL-Lite will be performed on the mITT population.

The change in all computed PRO scores (global and for each domain of the different questionnaires) from baseline to endpoint will be analyzed using a similar MMRM model than the one of the primary endpoint.

Descriptive statistics (mean, median, standard deviation and range) for absolute values and for changes from baseline will be presented by treatment group per visit for each score (global and for each domain of each questionnaire) as well as for each item.

Moreover, the responses of each EQ-5D item will be presented by visit for each treatment group. The tables will contain information on the frequency and proportion of the population reporting level 1 (no problems), level2 (some problems) and level3 (extreme problems) per item, by treatment group and by visit.

The analyses of the patient-rated and physician-rated global treatment effectiveness evaluation scales will be performed on the mITT population. Descriptive statistics (mean, median, standard deviation and range) for patient- and physician-rated global evaluation scales will also be presented by treatment group at the end of the study.

10.5 Interim Analysis

No formal interim analysis for efficacy is planned for this study. The study will not be terminated early for excellent efficacy.

An independent Data Monitoring Committee (DMC) will monitor and assess the safety of patients from this trial through periodic review of the accumulated safety data provided by an independent statistical group. Related details are provided in separate documents (DMC charter and DMC statistical analysis plan).

11 APPENDICES

Appendix A: Calculation of creatinine-clearance by Cockroft and Gault

| Calculation Name Formula | Creatinine Clearance Units | Decimal Places |
|---|---|---|
| Conventional:<br>Male: ((140-age) × (weight (kg))/((72 × serum Creatinine (mg/dL))<br>Female: [(0.85 × (140-age) × (weight (kg)]/ [72 ×serum Creatinine (mg/dL)] | mL/min | 0 |
| SI:<br>Male: [(140-age) × (weight (kg))]/[72 × serum Creatinine (µmol/L) × 0.6786)]<br>Female: [0.85 × (140-age) × (weight (kg))]/ [(72 ×serum Creatinine (µmol/L) × 0.6786)] | mL/sec | 2 |

Appendix B: General Guidance for the Follow-Up of Laboratory Abnormalities by Sanofi (See FIG. 17 and FIG. 18)

Note on Naeutropenia (FIG. 17):
The procedures described in the above flowchart are to be discussed with the patient only in case the event occurs. If applicable (according to local regulations), an additional consent (e.g., for HIV testing) will only be obtained in the case the event actually occurs.
For individuals of African descent, the relevant value of concern is <1000/mm3 Neutropenia are to be recorded as AE only if they are:
Symptomatic, and/or
Requiring either corrective treatment or consultation, and/or
Leading to IMP discontinuation or modification of dosing, and/or
Fulfilling a seriousness criterion [in that case, the event (SAE) should be notified within 24 hours to the MT], and/or
Defined as an Adverse Event of Special Interest (AESI)

Note on Thrombocytopenia (FIG. 18):
The procedures described in the above flowchart are to be discussed with the patient only in case the event occurs. If applicable (according to local regulations), an additional consent (e.g., for HIV testing) will only be obtained in the case the event actually occurs. Thrombocytopenia are to be recorded as AE only if they are:
Symptomatic, and/or
Requiring either corrective treatment or consultation, and/or
Leading to IMP discontinuation or modification of dosing, and/or
Fulfilling a seriousness criterion [in that case, the event (SAE) should be notified within 24 hours to the MT], and/or
Defined as an Adverse Event of Special Interest (AESI)

Figure 19:
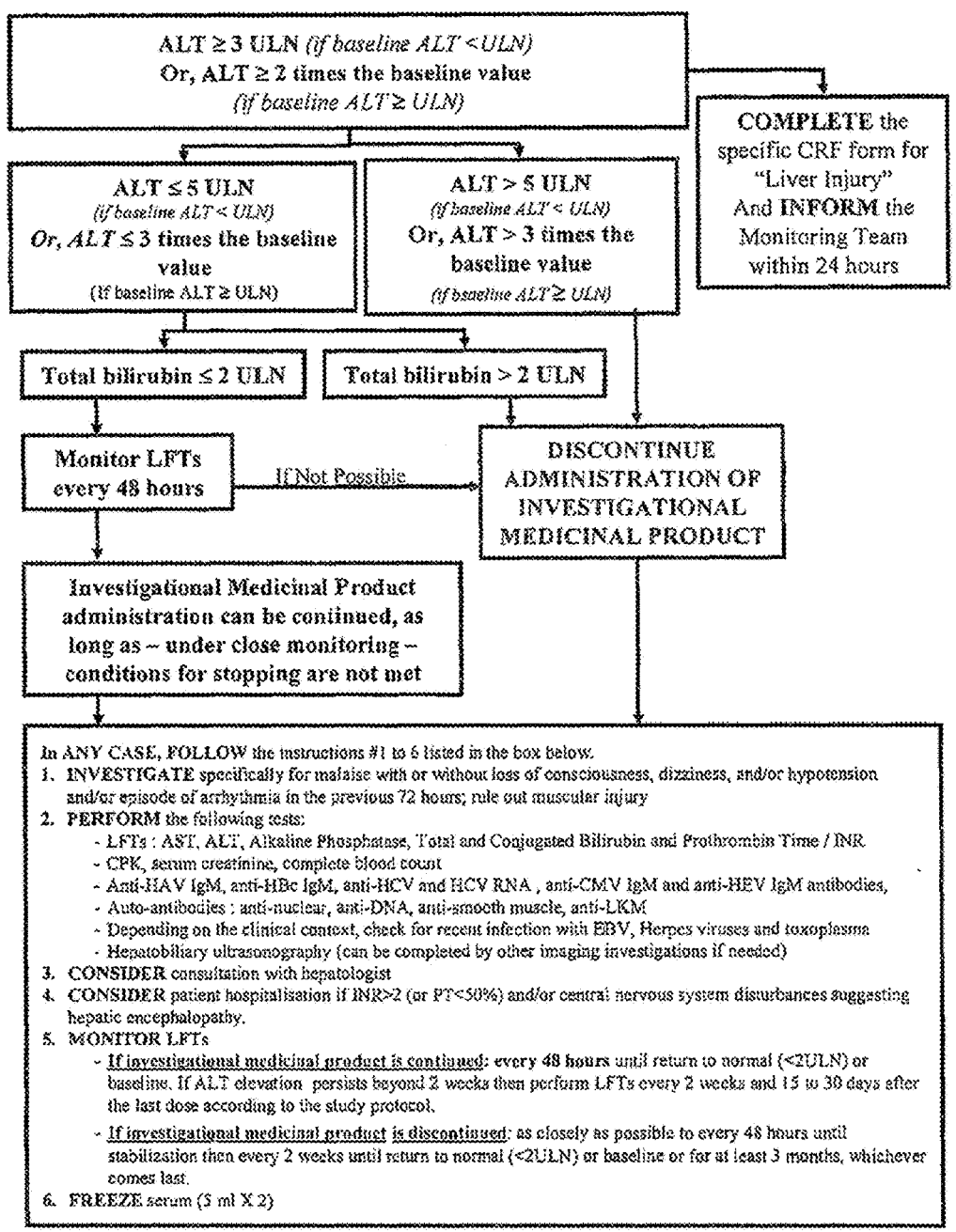
FIG. 19 shows the follow-up guidance for increase in ALT.

Note on FIG. 19:
In addition, as soon as a seriousness criterion is met, the event should be notified within 24 hours to the monitoring team.

Figure 20:
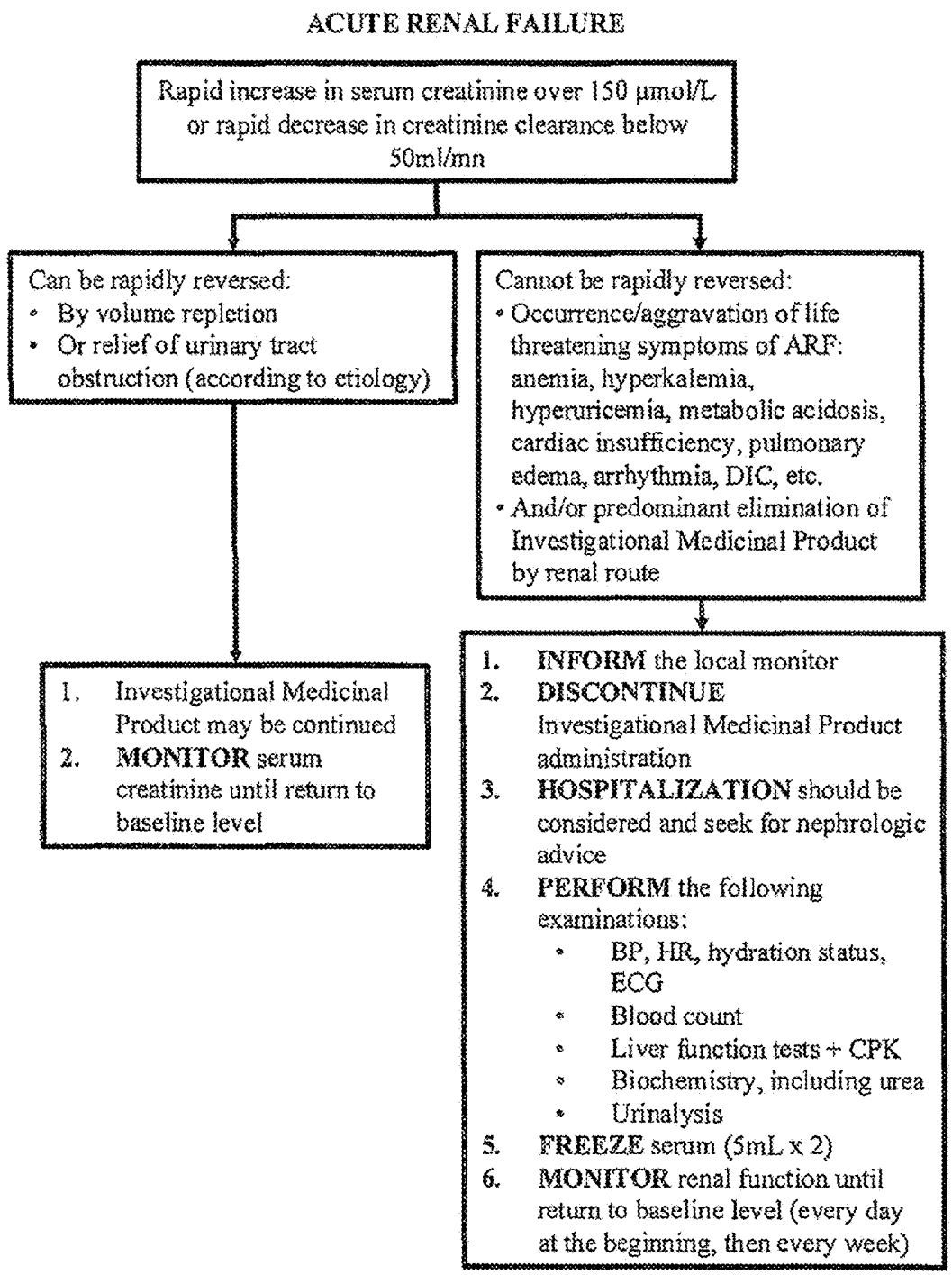
FIG. 20 shows the follow-up guidance for acute renal failure.

Notes on Acute Renal Failure (FIG. 20)
Acute renal failure is to be recorded as an AE only if it is:
Symptomatic, and/or
Requiring either corrective treatment or consultation, and/or
Leading to IMP discontinuation or modification of dosing, and/or
Fulfilling a seriousness criterion [in that case, the event (SAE) should be notified within 24 hours to the MT], and/or
Defined as an Adverse Event of Special Interest (AESI)

Figure 21:
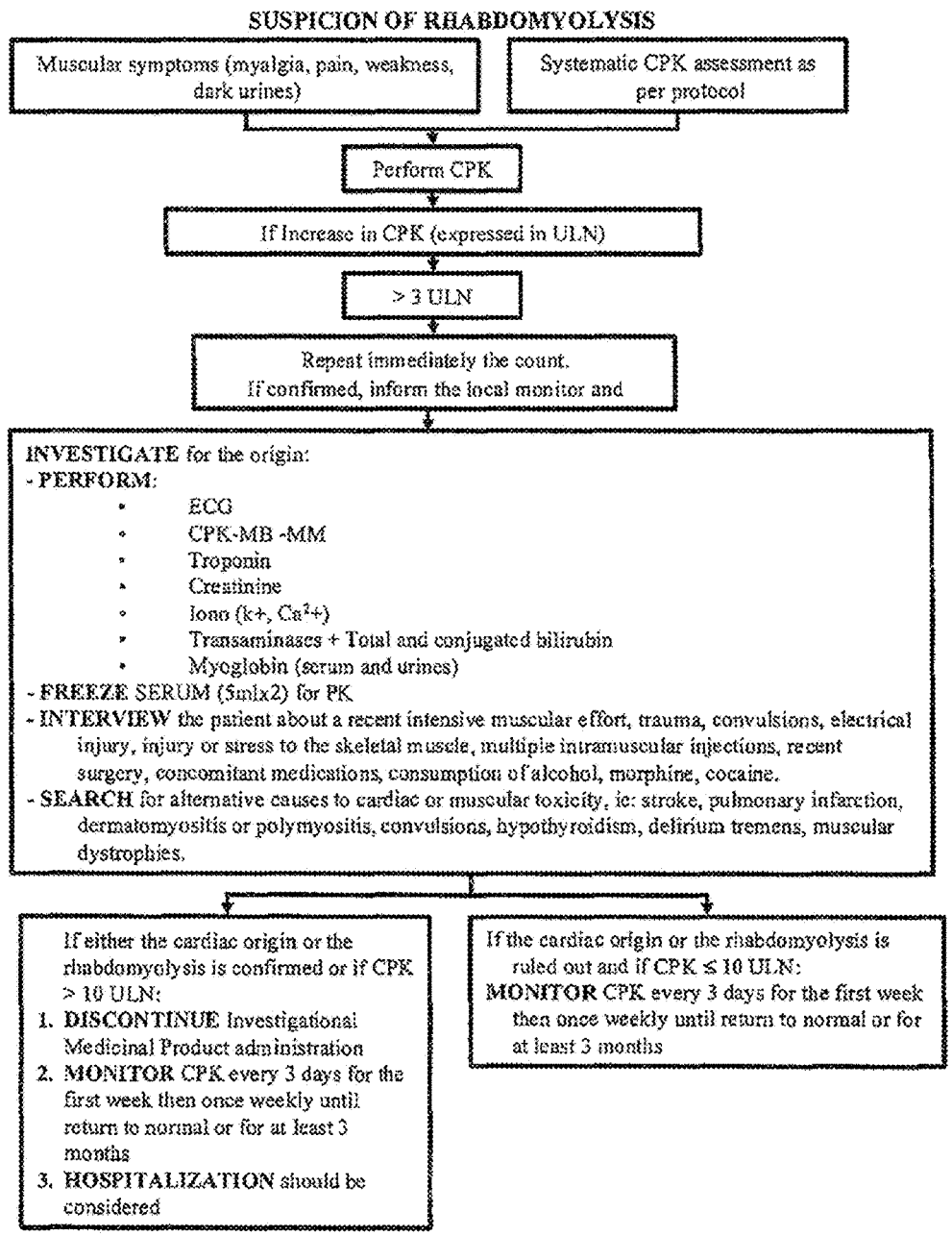
FIG. 21 shows the follow-up guidance for suspicion of rhabdomyolysis.

Notes on Suspicion of Rhabdomyolysis (FIG. 21)
Suspicion of rhabdomyolysis is to be recorded as an AE only if it is:
Symptomatic, and/or
Requiring either corrective treatment or consultation, and/or
Leading to IMP discontinuation or modification of dosing, and/or
Fulfilling a seriousness criterion [in that case, the event (SAE) should be notified within 24 hours to the MT], and/or
Defined as an Adverse Event of Special Interest (AESI)

Figure 22:
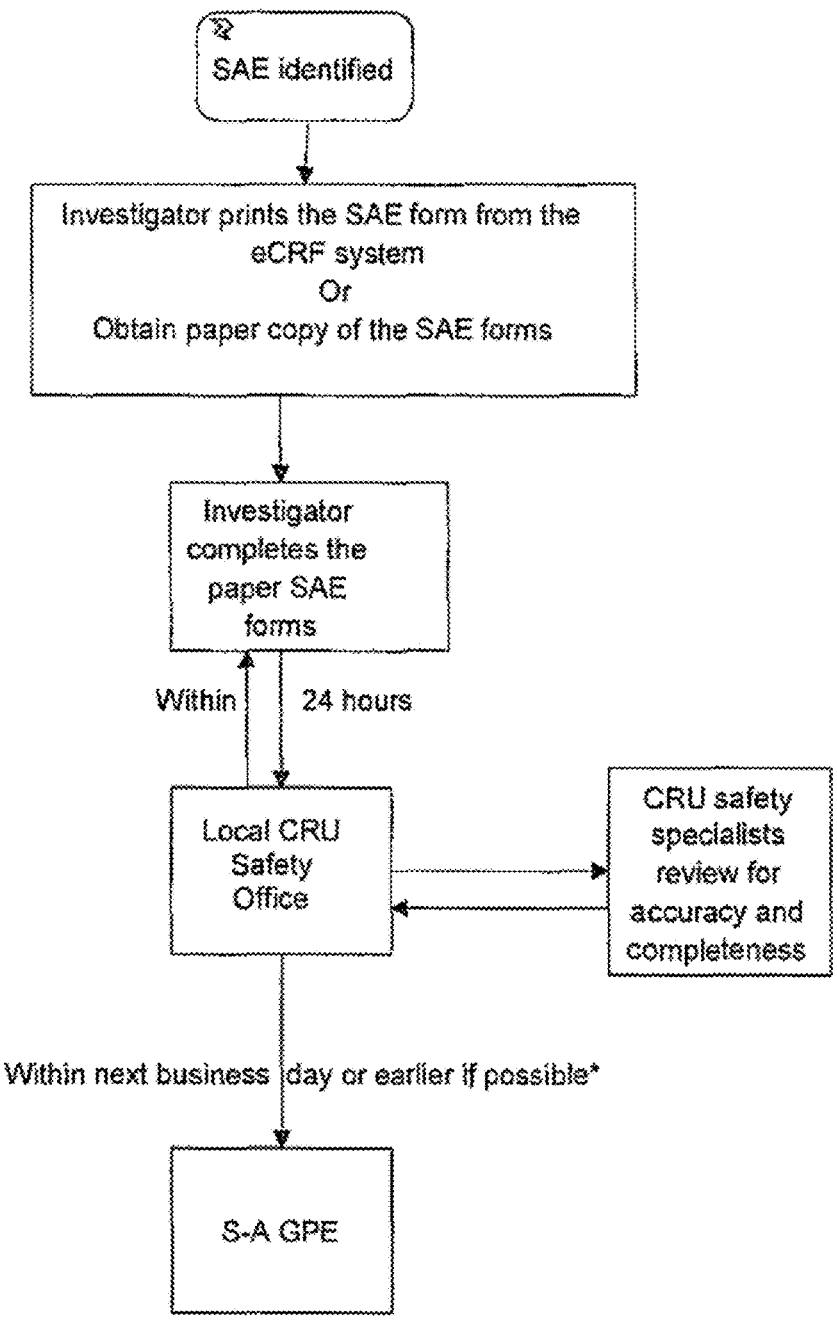
FIG. 22 shows the back-up plan for SAE and other Investigator Expedited Events reporting process when the e-CRF system fails.

Appendix C: Back-Up Plan for SAE and Other Investigator Expedited Events Reporting Process when the e-CRF System Fails (See FIG. 22)

Appendix D: Treatment-Related Impact Measure for Diabetes (TRIM-D) (See FIGS. 23, 24 and 25)

Appendix E: EuroQoL Five Dimension (EQ-5D) (See FIGS. 26 and 27)

Appendix F: Impact of Weight on Quality of Life-Lite (IWQOL-Lite) (See FIGS. 28 and 29)

EXAMPLE 2

A randomized, 30-week, active controlled, open label, 3-treatment arm, parallel-group multicenter study comparing the efficacy and safety of insulin glargine/lixisenatide fixed ratio combination to insulin glargine alone and to lixisenatide alone on top of metformin in patients with Type 2 diabetes mellitus (T2DM)

1 ABBREVIATIONS

AE: Adverse event
ALT: Alanine aminotransferase
ANCOVA: Analysis of covariance
ARAC Allergic Reaction Assessment Committee
BMI: Body mass index
CI: Confidence interval
CMH: Cochran-Mantel-Haenszel
FPG: Fasting plasma glucose
IMP: Investigational medicinal product
LS: Least squared
mITT: Modified Intent-To-Treat
PPG: Postprandial plasma glucose PT: Preferred term
SAE: Serious adverse event
SMPG: Self-monitored plasma glucose
SOC: System organ class
T2DM Type 2 diabetes mellitus
TEAE: Treatment-emergent adverse event

2 SYNOPSIS

Title of the Study:
 A randomized, 30-week, active-controlled, open label, 3-treatment arm, parallel-group multicenter study comparing the efficacy and safety of insulin glargine/lixisenatide fixed ratio combination to insulin glargine alone and to lixisenatide alone on top of metformin in patients with Type 2 diabetes mellitus (T2DM)
Study Center(s):
 Multicenter (240 centers in 23 countries)
Publications (Reference):
 NA
Phase of Development:
 Phase 3
Objectives:
Primary Objective:
 To demonstrate the superiority of the insulin glargine lixisenatide fixed ratio combination to lixisenatide in glycosylated hemoglobin A1c (HbA1c) change from baseline to Week 30.
 To demonstrate the non-inferiority of the insulin glargine/lixisenatide fixed ratio combination to insulin glargine in HbA1c change from baseline to Week 30.
Secondary Objectives:
 To assess the effects of the insulin glargine/lixisenatide fixed ratio combination in comparison with insulin glargine and lixisenatide alone over 30 weeks on:
  Percentage of patients reaching HbA1c targets;
  Glycemic control in relation to a meal as evaluated by glucose excursion and 2-hour postprandial plasma glucose (PPG)
   during a standardized meal test;
  Body weight;
  Fasting plasma glucose (FPG)
  7-point Self-Monitored Plasma Glucose profile
  Percentage of patients reaching HbA1c targets with no body weight gain and/or documented symptomatic hypoglycemia;
  Insulin glargine dose (in the combination and insulin glargine groups).
 To assess the safety and tolerability in each treatment group.
Methodology:
 This was an open-label, 2:2:1 randomized, active-controlled, 3-group, 30-week treatment duration, parallel-group multinational and multicenter study. Randomization was stratified by values of HbA1c at visit 4 (<8%, 8%) and second oral anti-diabetic (OAD) use at screening (Yes, No).
 The study comprised 3 periods: (1) An up to 6-week screening phase (including an up to 2-week screening phase and a 4-week run-in phase where a sulfonylurea (SU), glinide, sodium glucose co-transporter-2 (SGLT-2) inhibitor, or dipeptidyl peptidase-4 (DPP-4) inhibitor if previously taken were discontinued and metformin treatment optimized up to a daily dose of at least 2000 mg or the maximal tolerated dose (1500 mg/day)); (2) a 30-week open-label randomized treatment period; and (3) a 3-day post-treatment safety follow-up period.

| Number of patients: | Planned: 1125 |
|---|---|
|  | Randomized: 1170 |
|  | Treated: 1169 |
| Evaluated: | Efficacy: 1167 |
|  | Safety: 1169 |

Diagnosis and criteria for inclusion: Inclusion criteria: Patients with type 2 diabetes mellitus (T2DM) diagnosed for at least 1 year before the screening visit, treated for at least 3 months prior to Visit 1 with metformin alone or metformin and a second oral anti-diabetic treatment that could be a SU, a glinide, a SGLT-2 inhibitor, or a DPP-4 inhibitor, and who were not adequately controlled with this treatment. Key exclusion criteria at screening: HbA1c<7.5% or >10.0% for patients previously treated with metformin alone; HbA1c<7.0% or >9.0% for patients previously treated with metformin and a second oral anti-diabetic treatment; Body Mass Index (BMI)≤20 or >40 kg/m2.
Study Treatments
Investigational Medicinal Product(s) (IMPs):
 Tested drug: Insulin glargine/lixisenatide fixed ratio combination; Controlled drugs: Insulin glargine (Lantus®) and lixisenatide
Formulation:
Insulin Glargine/Lixisenatide Fixed Ratio Combination
 Insulin glargine/lixisenatide fixed ratio combination (hereafter referred to as fixed ratio combination) was supplied as a sterile aqueous solution in a pre-filled disposable SoloStar® pen-injector.
 Two pens (A and B) with different fixed ratios were available to allow insulin glargine titration over a range of 10 to 60 U/day while limiting the lixisenatide dose to a maximum of 20 μg/day:
  Pen A contained 100 U/mL of insulin glargine and 50 μg/mL of lixisenatide in ratio of 2:1 (2 units of insulin glargine per 1 μg lixisenatide). Doses could be set from 10 to 40 units in steps of 1 unit, allowing administration of daily combination doses between 10 U/5 μg and 40 U/20 μg.
  Pen B contained 100 U/mL insulin glargine and 33 μg/mL lixisenatide in a ratio of 3:1. Doses could be set from 30 to 60 units in steps of 1 unit, allowing administration of daily combination doses between 30 U/10 μg and 60 U/20 μg.
 The maximum daily dose was 60 units (60 units insulin glargine and 20 μg lixisenatide).
Insulin Glargine
 Insulin glargine was suppled as a sterile aqueous solution in a pre-filled disposable Lantus® SoloStar® pen-injector (100 U/mL).
 Doses could be set from 1 to 80 units in steps of 1 unit. However, in this study the maximum insulin glargine daily dose allowed was 60 U.
Lixisenatide
 Lixisenatide was supplied as a disposable pre-filled pen (lixisenatide pen):
  10 μg initiation dose: disposable pen-injector device containing 3 mL of a sterile aqueous solution with 150 μg of the active ingredient (50 μg/mL)
  20 μg maintenance dose: disposable pen-injector device containing 3 mL of a sterile aqueous solution with 300 μg of the active ingredient (100 μg/mL)
Route(s) of Administration:
 Subcutaneous injection for all IMPs. The fixed ratio combination was self-administered with a pre-filled disposable SoloStar® pen-injector. Insulin glargine was self-administered with a pre-filled disposable Lantus® SoloStar® pen-injector. Lixisenatide was self-administered with a pre-filled disposable pen (lixisenatide pen).

Dose Regimen:

Fixed Ratio Combination

The fixed ratio combination was self-administered once daily in the morning, in the hour (0 to 60 minutes) before breakfast. Treatment was initiated with Pen A at a daily dose of 10 U of insulin glargine/5 µg of lixisenatide.

Insulin Glargine

Insulin glargine was self-administered once daily at any time of the day but at about the same time every day. The initial daily dose of insulin glargine during the first week of treatment was 10 U.

Dose Adjustment (Fixed Ratio Combination and Insulin Glargine)

The same dose adjustment algorithm was recommended for fixed ratio combination and insulin glargine and was based on patient's need for insulin. After the first week, the dose was titrated once a week to reach and maintain a target fasting self-monitored plasma glucose (SMPG) of 80 to 100 md/dL (4.4 to 5.6 mmol/L) while avoiding hypoglycemia.

In the combination group, Pen A was to be used for total daily doses between 10 and 40 units/day, and Pen B was to be used for total daily doses between 41 and 60 units/day Lixisenatide Lixisenatide was self-administered once daily in the hour (0 to 60 minutes) before breakfast or the evening meal.

Lixisenatide started with once daily injection of 10 µg for 2 weeks, and then was continued with the maintenance dose of 20 µg once daily from week 2 up to the end of the treatment period.

Non Investigational Medicinal Product(s) (NIMPs):

Background treatment: Metformin

Formulation:

Metformin tablets

Route(s) of Administration:

Administered orally according to its locally approved label

Metformin was a mandatory background therapy. If taken, previous oral antidiabetic treatments other than metformin were discontinued from Visit 2. Patients in all 3 treatment groups continued metformin during the study. Daily metformin dose was increased weekly during the run-in phase by increments of up to 500 mg to a final daily dose of at least 2000 mg or up to the maximal tolerated dose, which had to be 500 mg/day to allow randomization. After randomization (during the treatment period), this dose was maintained until the end of the study unless there was a specific safety issue related to this treatment.

Rescue Therapy:

Routing measurements and central lab alerts were set up to ensure that glycemic parameters remained under thresholds values predefined for rescue therapy. If values were above these thresholds, and no explanations were found, or appropriate actions failed, or a dose >60 U was necessary to decrease glycemic parameters below the threshold values, rescue therapy was to be introduced along with IMP and metformin (if taken). Newly initiated anti-diabetic medications, or an increase from baseline in background metformin dose were considered as rescue therapy.

Duration of Treatment:

Up to 30 weeks

Duration of Observation:

Up to 37 weeks (up to 6-week screening period+30-week randomized treatment period+3-day post treatment safety follow-up period)

Criteria for Evaluation:

Efficacy:

Primary Efficacy Endpoint:

Change in HbA1c from baseline to Week 30

Key Secondary Efficacy Endpoints:

percent of patients with Hb1Ac<7% or 6.5% at Week 30, change from baseline to Week 30 plasma glucose (FPG), body weight, and average 7-point SMPG, percentage of patients reaching HbA1c<7% with no body weight gain at Week 30; percentage of patients reaching HbA1c<7% with no body weight gain at Week 30 and no documented symptomatic hypoglycemia during the treatment period; insulin glargine dose at Week 30.

Safety:

Symptomatic hypoglycemia

Documented: typical symptoms of hypoglycemia with a plasma glucose concentration 70 mg/dL (3.9 mmol/L).

Probably: symptoms of hypoglycemia without plasma glucose determination, but presumably caused by a plasma glucose concentration 70 mg/dL (3.9 mmol/L)

Severe: event requiring assistance of another person to actively administer carbohydrate, glucagon, or other resuscitative actions Treatment-emergent adverse events (TEAE): serious TEAEs, TEAEs leading to death, TEAEs leading to treatment discontinuation, adverse events of special interest (i.e., alanine aminotransferase [ALT] increase, pregnancy, symptomatic overdose with IMP/NIMP), major cardiovascular events, potential allergic reactions, pancreatic events (confirmed increased amylase/lipase >2×ULN, pancreatitis, pancreatic neoplasm), events of confirmed increased calcitonin ≥20 pg/mL (5.9 pmol/L), pen-related events Safety laboratory data (hematology, clinical chemistry, lipase/amylase and calcitonin)

Statistical Methods:

Efficacy analysis was based on modified intent-to-treat (mITT) population using efficacy assessments collected during the study, including those obtained after IMP discontinuation or introduction of rescue therapy. The mITT population consisted of all randomized patients who had both a baseline assessment and at least one post-baseline assessment of any primary or secondary efficacy variables.

The primary efficacy endpoint was analyzed using a mixed-effect model with repeated measures (MMRM). The MMRM model included the treatment groups, randomization strata, visit, treatment-by-visit interaction, and country as fixed-effect factors, and the baseline HbA1c-by-visit interaction as covariate. The adjusted mean change in HbA1c from baseline to Week 30 for each treatment group was estimated in the framework of this model, as well as the between-group difference and the 95% confidence interval (CI for the adjusted mean?.

Similar MMRM method or ANCOVA was applied on continuous secondary efficacy endpoints and Cochran-Mantei-Haenszel method stratified by randomization strata was applied on categorical efficacy endpoints.

A step-down testing procedure was applied in order to control the type 1 error. Once the co-primary hypotheses of statistical superiority of insulin glargine/lixisenatide fixed ratio combination to lixisenatide alone and the non-inferiority of insulin glargine/lixisenatide fixed ratio combination to insulin glargine alone were both established for the primary efficacy endpoint, testing was performed according to the following order: 2-hour glucose excursion and body weight compared to insulin glargine, FPG and daily average of the 7-point SMPG compared to lixisenatide, superiority test compared to insulin glargine for the percentage of patients reaching HbA1c<7% with no body weight gain, HbA1c, daily average of the 7-point SMPG, percentage of patients reaching HbA1c<7% with no body weight gain and no documented symptomatic hypoglycemia, insulin glargine dose, and FPG. When a test was not statistically significant at the 5% level, subsequent tests were not performed.

SUMMARY

Population Characteristics:

A total of 1170 patients were randomized to one of the three treatment groups (469 in the insulin glargine/lixisenatide fixed ratio combination group, 467 in the insulin glargine group and 234 in the lixisenatide group).

One randomized patient was not exposed to the study treatment (patient's request) and 3 randomized patients were not included in the mITT population due to a lack of post baseline efficacy data. Demographics and baseline characteristics were generally similar across the three treatment groups. The median age was 59.0 years, the mean diabetes duration was 9 years and the mean BMI was 32 kg/m$^2$. The study population was primarily Caucasian (90.1%), and 49.4% of the population were female patients (Table 3).

Efficacy Results:

Primary Efficacy Endpoint:

The primary objectives of the study were met as the non-inferiority and superiority of the fixed ratio combination compared to insulin glargine on HbA1c change from baseline to Week 30 was demonstrated as well as statistical superiority of the fixed ratio combination over lixisenatide.

The least squared (LS) mean changes from baseline to Week 30 in HbA1c were −1.63% for the fixed ratio combination group, −1.34% for the insulin glargine group, and −0.85% for the lixisenatide group, reaching mean HbA1c levels of 6.5%, 6.8% and 7.3% at Week 30, respectively.

Statistical superiority of the fixed ratio combination over lixisenatide was demonstrated for the co-primary end point (LS mean difference versus lixisenatide=−0.78%; 95% CI= [−0.898% to −0.665%]). p<0.0001).

LS mean difference between the combination group and insulin glargine group was −0.29%, 95% CI=[−0.384% to −0.194%]. Based on the pre-specified primary analysis, the non-inferiority of the combination group compared to the insulin glargine group was demonstrated, as the upper bound of the 2-sided 95% CI of the LS mean difference was less than the predefined non-inferiority margin of 0.3%. Statistical superiority of the combination over insulin glargine was also demonstrated for this co-primary end point (LS mean difference versus insulin glargine group=−0.29%; p-value <0.0001) based on the step-down testing procedure.

Secondary Efficacy Endpoints:

Significantly more patients treated with the fixed ratio combination reached an HbA1c<7% compared to those receiving insulin glargine or lixisenatide: 73.7%, 59.4% and 33%, respectively. The proportion difference (95% CI) versus insulin glargine was 14.31% (8.37% to 20.25%) and 40.61% (33.63% to 47.59%) versus lixisenatide. In addition, the proportion of patients reaching HbA1c≤6.5% was significantly higher in the combination group (55.8%) than in the insulin glargine group (39.5%) and the lixisenatide group (19.3%). The proportion difference (95% CI) versus insulin glargine was 16.35% (10.13% to 22.58%) and 36.38% (29.81% to 42.95%) versus lixisenatide.

Treatment with the combination significantly improved postprandial glycemic control during a standardized liquid breakfast meal in comparison to insulin glargine as shown by the results for the 2-hour glucose excursion (LS mean change was −2.31 and −0.18 mmol/L, respectively; LS mean difference (95% CI] versus insulin glargine=−2.13 mmol/L [−2.498 mmol/L to −1.770 mmol/L], p<0.0001). For the 2-hour PPG assessment the LS mean change was −5.68 and −3.31 mmol/L, respectively; and the LS mean difference [95% CI] versus insulin glargine was −2.38 mmol/L, [−2.794 mmol/L to −1.963 mmol/L]). The corresponding results for the lixisenatide group were −3.23 mmol/L for the LS mean change in 2-hour glucose excursion and −4.58 mmol/L for the LS mean change in 2-hour PPG; LS mean difference [95% CI] between combination and lixisenatide=0.91 mmol/L [0.448 mmol/L to 1.377 mmol/L] and −1.10 mmol/L[−1.627 mmol/L to −0.573 mmol/L]) respectively.

Body weight decreased in the fixed ratio combination and lixisenatide groups and increased in the insulin glargine group with a LS mean body weight change from baseline to Week 30 of −0.29, −2.30 and +1.10 kg for each group respectively. A statistically significant difference in the body weight change from baseline to Week 30 was found between the fixed ratio combination group and the insulin glargine group (LS mean difference=−1.40 kg; 95% CI: [−1.891 to −0.910]; p<0.0001).

The LS mean reductions from baseline to Week 30 in FPG were similar in the fixed ratio combination (−3.46 mmol/L) and the insulin glargine group (−3.27 mmol/L), and it was lower (−1.50 mmol/L) in the lixisenatide group. The LS mean difference of the fixed ratio combination group versus insulin glargine was −0.19 mmol/L, 95% CI: [−0.420 to 0.038], p=0.1017), and versus lixisenatide it was significantly greater (LS mean difference −1.96 mmol/L, 95% CI: [−2.246 to −1.682], p<0.0001).

Figure 6:
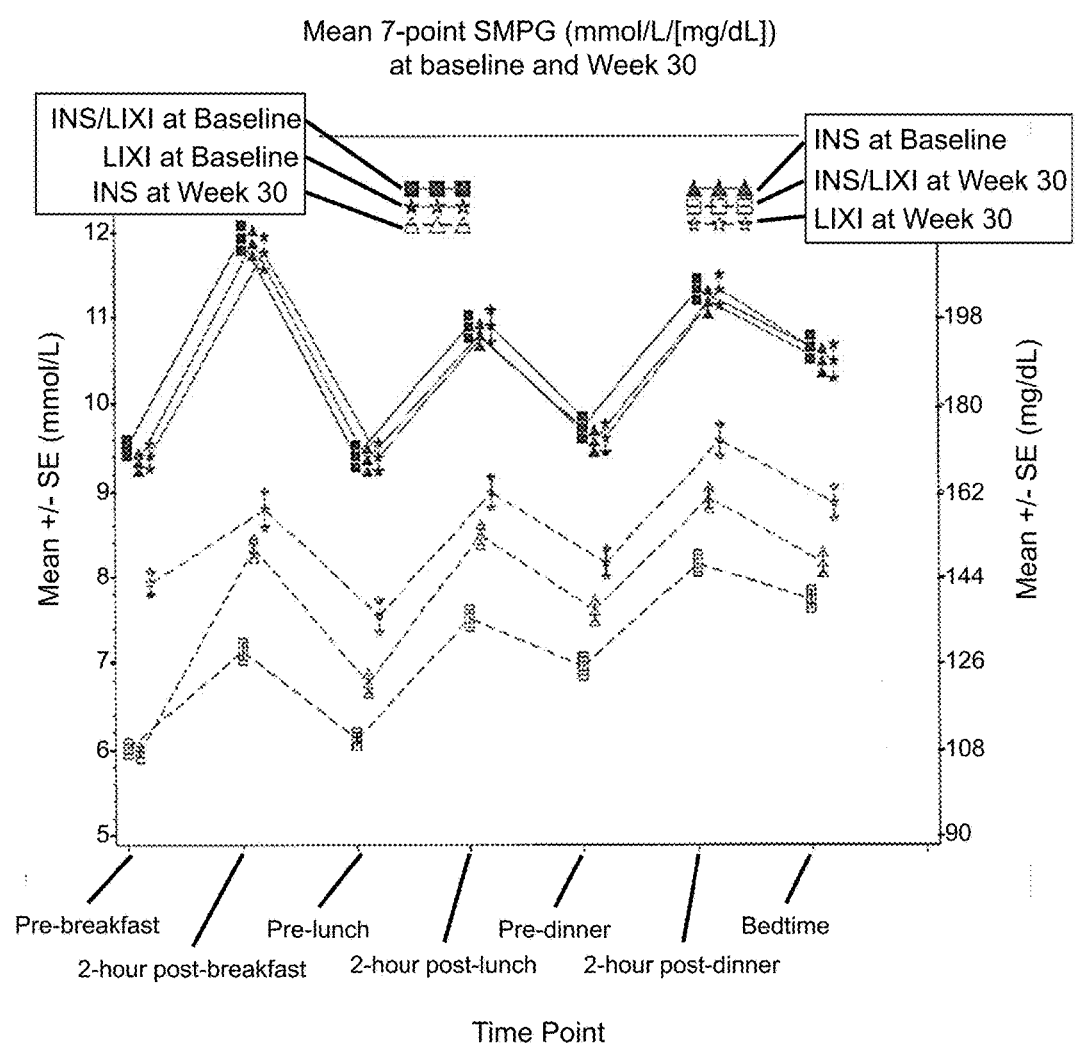
FIG. 6—Mean 7-point SMPG (mmol/L/[mg/dL]) at baseline and Week 30. SMPG=Self-monitored plasma glucose. INS/LIXI=Fixed Ratio Combination, INS=Insulin Glargine, LIXI=Lixisenatide. The analysis included all scheduled measurements obtained during the study, including those obtained after IMP discontinuation or introduction of rescue therapy.

Patients treated with fixed ratio combination had a statistically significant greater decrease in average 7-point SMPG profile compared to patients treated with insulin glargine and patients treated with lixisenatide respectively (LS mean difference versus insulin glargine=−0.69 mmol/L, 95% CI: [−0.892 to −0.495], p<0.0001; LS mean difference versus lixisenatide=−1.40 mmol/L, 95% CI: [−1.645 to −1.158], p<0.0001). Graphical presentation of the 7-point SMPG profiles showed a marked decrease in mean plasma glucose at all time-points at Week 30 compared with the baseline in all treatment groups. After 30 weeks of treatment, the 7-point SMPG profiles showed that the mean values at all time-points were lower in the fixed ratio combination group compared to the insulin glargine group (except for the similar pre-breakfast value) and the lixisenatide group, respectively (FIG. 6).

A higher proportion of patients reached the composite endpoint of HbA1c<7.0% with no body weight gain at Week 30 in the fixed ratio combination group (43.2%) compared to the insulin glargine group (25.1%) and the lixisenatide group (27.9%), respectively (proportion difference versus insulin glargine=18.08%, 95% CI=[12.15% to 24.01%], p<0.0001; proportion difference versus lixisenatide=15.22%, 95% CI=[8.05% to 22.39%]), and the difference between the combination group vs. insulin glargine was statistically significant. More patients reached the triple composite endpoint of HbA1c<7.0% with no body weight gain at Week 30 and with no documented (plasma glucose concentration 70 mg/dL [3.9 mmol/L]) symptomatic hypoglycemia during the study in the combination group (31.8%) compared to the insulin glargine group (18.9%) and the lixisenatide group (26.2%), respectively (proportion difference versus insulin glargine=12.98%, 95% CI=[7.50% to 18.45%], p<0.0001; proportion difference versus lixisenatide=5.61%, 95% CI=[−1.33% to 12.55%], and the difference between the combination group vs. insulin glargine was statistically significant.

Figure 7:
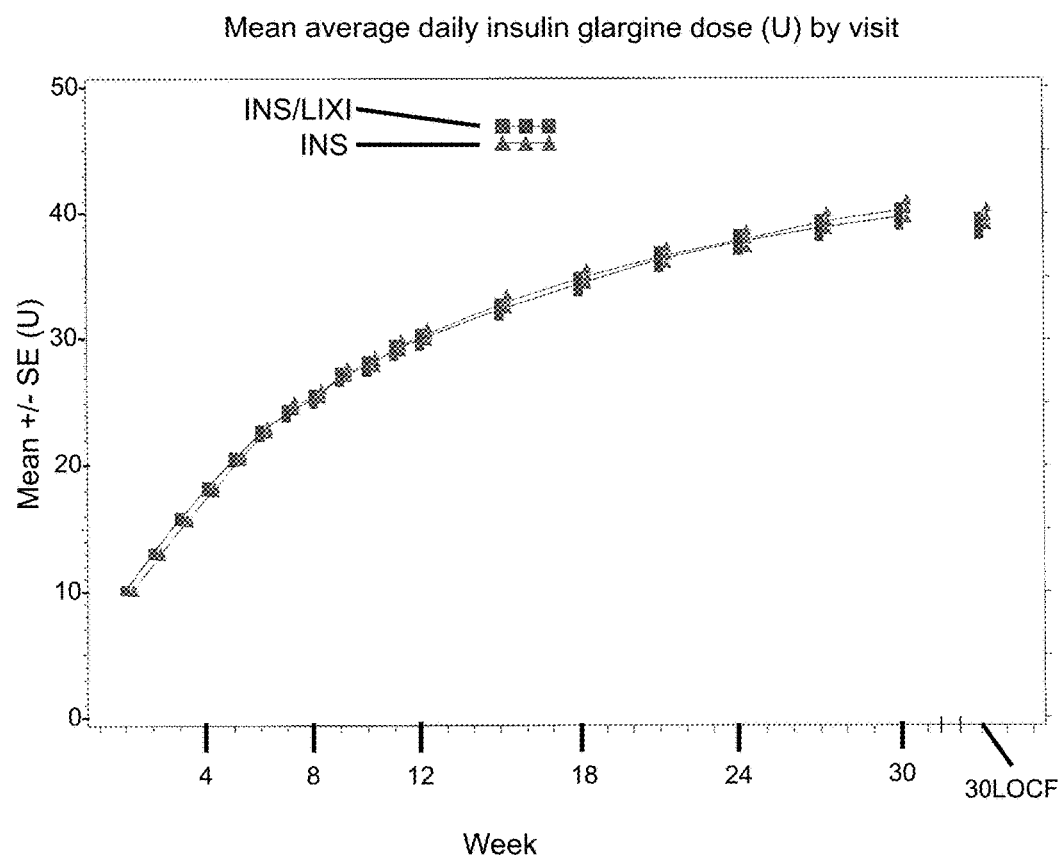
FIG. 7—Mean average daily insulin glargine dose (U) by visit. LOCF=Last observation carried forward. INS/LIXI=fixed ratio combination, INS=Insulin Glargine, LIXI=Lixisenatide. The analysis included scheduled measurements obtained up to the date of last injection of the IMP, including those obtained after introduction of rescue therapy.

At Week 30, the mean daily insulin glargine dose was similar in the fixed ratio combination group and in the insulin glargine group (fixed ratio combination: 39.77 U, insulin glargine: 40.46 U; LS mean difference=−0.69 U; 95% CI=[−2.632 to 1.252]; p=0.4857) (FIG. 7).

Seventeen (3.6%) patients in the fixed ratio combination group, 16 (3.4%) patients in the insulin glargine group and 29 (12.4%) patients in the lixisenatide group received rescue therapy.

Safety Results:

The fixed dose combination was well tolerated during the 30-week on-treatment period; the safety profile of the combination arm reflected those of its components.

A total of 267 (56.9%) patients in the combination group, 227 (48.6%) in the insulin glargine group, and 157 (67.4%) in the lixisenatide group reported treatment-emergent adverse events.

The most frequently occurring adverse events (AE) (PT≥15%) in the fixed ratio combination and the insulin glargine and lixisenatide groups were nausea (9.6%, 3.6% and 24%), diarrhea (9.0%, 4.3% and 9.0%) and upper respiratory tract infection (7.0%, 4.9% and 5.2%).

The overall incidence of gastrointestinal adverse events was 21.7%, 12.6% and 36.9 in the combination, insulin glargine and lixisenatide groups, respectively. Overall, 45 (9.6%) patients in the combination group experienced nausea, compared with 17 (3.6%) in the insulin glargine group and 56 (24%) in the lixisenatide group.

Overall, 6 patients experienced at least 1 TEAE leading to death: 2 from the fixed ratio combination group (PTs: Metastatic lung cancer; Congestive cardiac failure), 3 from the insulin glargine group (PTs: Acute myocardial infarction and Acute pulmonary edema; Squamous cell carcinoma of the oral cavity) and 1 from the lixisenatide group (PT: Death) (Table 21).

Serious TEAEs were reported by a similar proportion of patients in each treatment group: 18 (3.8%) patients in the combination group, 19 (4.1%) in the insulin glargine group and 9 (3.9%) in the lixisenatide group (Table 22).

A higher number of patients withdrew from treatment due to TEAEs in the lixisenatide group (9.0%) than from the combination (2.6%) or insulin glargine (1.9%) groups. Most of these withdrawals were caused by gastrointestinal adverse events in the lixisenatide group (5.2%) compared to the combination (0.9%) and insulin glargine (0.2%) groups (Table 23).

Injection site reactions during the on-treatment period were reported by similarly low percentages of patients across the three treatment groups (fixed ratio combination: (2.6%), insulin glargine: (1.7%), and lixisenatide: (3.0%)) (Table 24). None were considered serious. One patient in the lixisenatide group had injection site erythema that led to treatment discontinuation.

Adverse events adjudicated as allergic reactions possibly related to IMP by the Allergic Reaction Assessment Committee (ARAC) were reported in 3 patients (0.6%) (PTs: Urticaria) in the fixed ratio combination group, in 2 patients (0.9%) (PTs: Anaphylactic reaction and Urticaria) in the lixisenatide group and none in the in the insulin glargine group. Three patients (0.6%) reported angioedema, all in the fixed ratio combination group, which were adjudicated by the ARAC as allergic reactions not related to IMP (Table 25).

There were no cases of pancreatitis positively adjudicated by the Pancreatic Safety Assessment Committee (PSAC) (Table 26).

Two patients (0.4%) in the fixed ratio combination group, 7 patients (1.5%) in the insulin glargine group and 2 patients (0.9%) in the lixisenatide group experienced TEAEs adjudicated as major cardiovascular events by CAC during the on-treatment period (Table 27).

One case of pancreatic cancer was reported in the in insulin glargine group. No thyroid carcinomas were reported in any treatment group. One patient in the insulin glargine group reported a TEAE of increased calcitonin (20 µg/mL) versus none in either the fixed ratio combination group or the lixisenatide group (Table 28).

No symptomatic overdose with IMP was reported in any treatment group during the on-treatment period.

One patient in the insulin glargine/lixisenatide fixed ratio combination group, 2 patients in the insulin glargine group and 1 patient in the lixisenatide group experienced an AE of ALT increase during the on-treatment period (Table 29). None of the events met the definition for Hy's Law.

A total of 44 patients (fixed ratio combination: 25 (5.3%), insulin glargine: 10 (2.1%) and lixisenatide: 9 (3.9%)) reported 54 pen-related events in the pen-related event questionnaire during the on-treatment period. None was associated with a clinical event (i.e., symptomatic hypoglycemic event, hyperglycemic adverse event or other adverse event) (Table 30).

27.3% of patients treated with the fixed ratio combination, 25.5% patients treated with insulin glargine, and 6.4% patients treated with lixisenatide reported 409, 338, and 46 symptomatic hypoglycemia events according to protocol definition on the specific hypoglycemia page (Table 31). The number of symptomatic events per patient-year was 1.55 in the fixed ratio combination group, 1.29 in the insulin glargine group and 0.37 in the lixisenatide group. When considering documented (70 mg/dL) symptomatic hypoglycemia, the incidence was 25.6% in the combination group, 23.6% in the insulin glargine group and 6.4% in the lixisenatide group with a corresponding event rate per patient-year of 1.44, 1.22 and 0.34 respectively.

Only 1 event of severe symptomatic hypoglycemia was reported during the study and occurred in the insulin glargine group.

Preliminary Conclusions:

In conclusion, the primary objectives of the study were met as the non-inferiority and superiority of the fixed ratio combination compared to insulin glargine on HbA1c change from baseline to Week 30 was demonstrated as well as statistical superiority of the fixed ratio combination over lixisenatide. The fixed ratio combination added to metformin for patients not well controlled with metformin with or without a second OAD significantly improved HbA1c and reduced 2-hour glucose excursions and 2-hour PPG, average 7-point SMPG and body weight in comparison to insulin glargine. The combination also significantly improved HbA1c, FPG, and average 7-point SMPG in comparison with lixisenatide.

In summary the fixed ratio combination was well tolerated. Nausea was the most frequently reported adverse event in the combination group but was reported less frequently than in the lixisenatide group. The incidence of symptomatic hypoglycemia was similar in the combination and insulin glargine treatment groups and lower in the lixisenatide group, as expected. The safety profile of the combination group reflected those of its component parts.

The advantages of starting with the fixed ratio combination compared to starting with each component alone in patients not well controlled on OAD is therefore evidenced based on the advantages demonstrated for HbA1c and body weight vs insulin glargine, and for HbA1c, FPG and gastrointestinal tolerability (descriptive analysis) in comparison to lixisenatide.

3 RESULTS

3.1 Study Patients

3.1.1 Patient Accountability

Of the 2457 patients screened, 1170 were randomized to one of the three treatment groups (469 in the combination group, 467 in the insulin glargine group and 234 in the lixisenatide group) in 240 centers distributed among 23 countries (Australia, Belgium, Canada, Chile, Czech Republic, Denmark, Estonia, France, Germany, Hungary, Italy, Latvia, Lithuania, Mexico, Poland, Romania, Russian federation, South Africa, Spain, Sweden, Ukraine, United Kingdom and United States of America). The main reason for screening failure was HbA1c value at screening visit out of the protocol defined range (653 [26.6%] out of 2457 screened patients).

A total 1169 randomized patients were exposed to open-label treatment and 1167 patients were included in the mITT population for efficacy analyses (Table 1). One patient was randomized but not treated by the patient request. Three randomized patients (1 in each treatment group) were not included in the mITT population because they did not have any post baseline efficacy data.

TABLE 1

| Analysis populations | | | | |
|---|---|---|---|---|
| | Fixed Ratio Combination | Insulin Glargine | Lixisenatide | All |
| Randomized population | 469 (100%) | 467 (100%) | 234 (100%) | 1170 (100%) |
| Efficacy population | | | | |
| Modified Intent-to-Treat (mITT) | 468 (99.8%) | 466 (99.8%) | 233 (99.6%) | 1167 (99.7%) |
| Safety population | 469 | 467 | 233 | 1169 |

Note:
The safety population patients are tabulated according to treatment actually received (as treated).

For the efficacy population, patients are tabulated according to their randomized treatment.

There is no patient randomized in a group and taking another study treatment.

Figure 8:
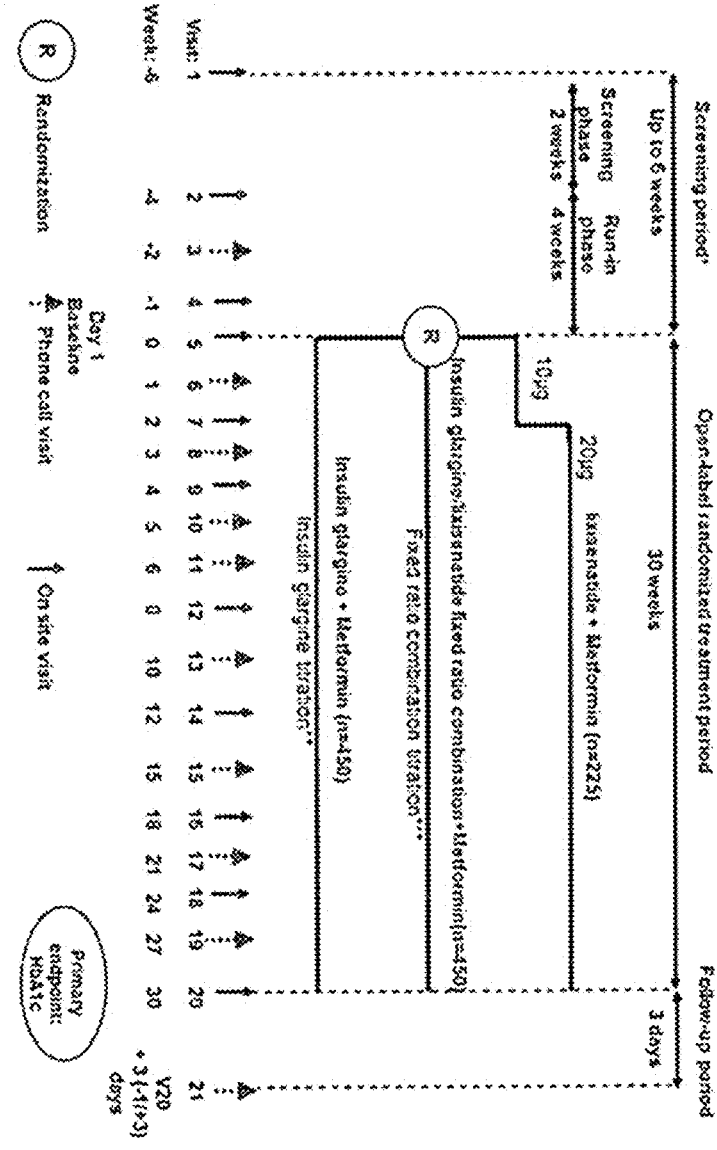
FIG. 8—Graphical Study Design.

The study design is described in FIG. 8.

3.1.2 Study Disposition

TABLE 2

| Patient disposition - Randomized population | | | |
|---|---|---|---|
| | Fixed Ratio Combination (N = 469) | Insulin Glargine (N = 467) | Lixisenatide (N = 234) |
| Randomized and treated | 469 (100%) | 467 (100%) | 233 (99.6%) |
| Completed the open-label study treatment period | 440 (93.8%) | 440 (94.2%) | 205 (87.6%) |
| Did not complete the open-label study treatment period | 29 (6.2%) | 27 (5.8%) | 28 (12.0%) |
| Subject's decision for treatment discontinuation | 25 (5.3%) | 17 (3.6%) | 18 (7.7%) |
| Reason for study treatment discontinuation | | | |
| Adverse event | 12 (2.6%) | 9 (1.9%) | 21 (9.0%) |
| Lack of efficacy | 1 (0.2%) | 0 | 3 (1.3%) |
| Poor compliance to protocol | 8 (1.7%) | 9 (1.9%) | 4 (1.7%) |
| Lost to follow-up | 0 | 0 | 0 |
| Other reasons | 8 (1.7%) | 9 (1.9%) | 0 |
| Status at last study contact | | | |
| Alive | 467 (99.6%) | 462 (98.9%) | 233 (99.6%) |
| Dead | 2 (0.4%) | 4 (0.9%) | 1 (0.4%) |
| Lost to follow-up | 0 | 1 (0.2%) | 0 |

Note:
Percentages are calculated using the number of patients randomized as denominator.

3.1.3 Demographics and Baseline Characteristics

TABLE 3

| Demographics and patient characteristics at screening or baseline - Randomized population | | | | |
|---|---|---|---|---|
| | Fixed Ratio Combination (N = 469) | Insulin Glargine (N = 467) | Lixisenatide (N = 234) | All (N = 1170) |
| Age (years) | | | | |
| Number | 469 | 467 | 234 | 1170 |
| Mean (SD) | 58.2 (9.5) | 58.3 (9.4) | 58.7 (8.7) | 58.4 (9.3) |
| Median | 59.0 | 59.0 | 59.0 | 59.0 |
| Min:Max | 18:79 | 25:82 | 31:80 | 18:82 |
| Age group (years) [n (%)] | | | | |
| Number | 469 | 467 | 234 | 1170 |
| <50 | 86 (18.3%) | 82 (17.6%) | 28 (12.0%) | 196 (16.8%) |
| ≥50 to <65 | 250 (53.3%) | 271 (58.0%) | 147 (62.8%) | 668 (57.1%) |
| ≥65 to <75 | 121 (25.8%) | 97 (20.8%) | 53 (22.6%) | 271 (23.2%) |
| ≥75 | 12 (2.6%) | 17 (3.6%) | 6 (2.6%) | 35 (3.0%) |

TABLE 3-continued

Demographics and patient characteristics at screening or baseline - Randomized population

|  | Fixed Ratio Combination (N = 469) | Insulin Glargine (N = 467) | Lixisenatide (N = 234) | All (N = 1170) |
|---|---|---|---|---|
| Gender [n (%)] | | | | |
| Number | 469 | 467 | 234 | 1170 |
| Male | 222 (47.3%) | 237 (50.7%) | 133 (56.8%) | 592 (50.6%) |
| Female | 247 (52.7%) | 230 (49.3%) | 101 (43.2%) | 578 (49.4%) |
| Race [n (%)] | | | | |
| Number | 469 | 467 | 234 | 1170 |
| Caucasian | 417 (88.9%) | 421 (90.1%) | 216 (92.3%) | 1054 (90.1%) |
| Black | 33 (7.0%) | 33 (7.1%) | 12 (5.1%) | 78 (6.7%) |
| Asian/Oriental | 8 (1.7%) | 7 (1.5%) | 3 (1.3%) | 18 (1.5%) |
| Other | 11 (2.3%) | 6 (1.3%) | 3 (1.3%) | 20 (1.7%) |
| Ethnicity [n (%)] | | | | |
| Number | 469 | 467 | 234 | 1170 |
| Hispanic | 85 (18.1%) | 87 (18.6%) | 51 (21.8%) | 223 (19.1%) |
| Not Hispanic | 384 (81.9%) | 380 (81.4%) | 183 (78.2%) | 947 (80.9%) |
| HbA1c (%) at visit 1 (week-6) | | | | |
| Number | 469 | 467 | 233 | 1169 |
| Mean (SD) | 8.17 (0.70) | 8.20 (0.68) | 8.28 (0.70) | 8.20 (0.69) |
| Median | 8.10 | 8.10 | 8.20 | 8.10 |
| Min:Max | 6.8:10.4 | 7.0:10.0 | 7.0:10.0 | 6.8:10.4 |
| HbA1c (%) at visit 4 (week-1) | | | | |
| Number | 469 | 467 | 234 | 1170 |
| Mean (SD) | 8.11 (0.67) | 8.13 (0.65) | 8.16 (0.69) | 8.13 (0.67) |
| Median | 8.10 | 8.00 | 8.10 | 8.10 |
| Min:Max | 7.0:9.8 | 7.0:10.0 | 7.0:10.0 | 7.0:10.0 |
| Randomization strata of HbA1c (%) at visit 4 (week-1) [n (%)] | | | | |
| Number | 469 | 467 | 234 | 1170 |
| <8 | 207 (44.1%) | 207 (44.3%) | 103 (44.0%) | 517 (44.2%) |
| ≥8 | 262 (55.9%) | 260 (55.7%) | 131 (56.0%) | 653 (55.8%) |
| Randomization strata of second OAD use at screening [n (%)] | | | | |
| Number | 469 | 467 | 234 | 1170 |
| Yes | 291 (62.0%) | 288 (61.7%) | 146 (62.4%) | 725 (62.0%) |
| No | 178 (38.0%) | 179 (38.3%) | 88 (37.6%) | 445 (38.0%) |
| Baseline BMI (kg/m$^2$) | | | | |
| Number | 469 | 467 | 234 | 1170 |
| Mean (SD) | 31.64 (4.40) | 31.66 (4.51) | 31.99 (4.39) | 31.72 (4.44) |
| Median | 31.40 | 31.45 | 32.09 | 31.53 |
| Min:Max | 18.9:40.1 | 21.0:41.5 | 20.2:40.3 | 18.9:41.5 |
| Baseline BMI categories (kg/m$^2$) [n (%)] | | | | |
| Number | 469 | 467 | 234 | 1170 |
| <30 | 174 (37.1%) | 179 (38.3%) | 75 (32.1%) | 428 (36.6%) |
| ≥30 | 295 (62.9%) | 288 (61.7%) | 159 (67.9%) | 742 (63.4%) |

BMI = Body Mass Index, OAD = Oral anti-diabetic drug.

TABLE 4

Disease characteristics at screening or baseline - Randomized population

|  | Fixed Ratio Combination (N = 469) | Insulin Glargine (N = 467) | Lixisenatide (N = 234) | All (N = 1170) |
|---|---|---|---|---|
| Duration of diabetes (years) | | | | |
| Number | 469 | 467 | 234 | 1170 |
| Mean (SD) | 8.89 (5.51) | 8.66 (5.59) | 8.89 (6.26) | 8.80 (5.69) |

TABLE 4-continued

Disease characteristics at screening or baseline - Randomized population

|  | Fixed Ratio Combination (N = 469) | Insulin Glargine (N = 467) | Lixisenatide (N = 234) | All (N = 1170) |
|---|---|---|---|---|
| Median | 8.14 | 7.60 | 7.65 | 7.69 |
| Min:Max | 1.0:34.2 | 1.0:39.7 | 1.0:44.5 | 1.0:44.5 |
| *Age at onset of Type 2 diabetes (years)* | | | | |
| Number | 469 | 467 | 234 | 1170 |
| Mean (SD) | 49.3 (9.8) | 49.6 (8.8) | 49.7 (9.1) | 49.5 (9.3) |
| Median | 50.0 | 50.0 | 50.0 | 50.0 |
| Min:Max | 14:75 | 17:76 | 22:74 | 14:76 |
| *History of gestational diabetes [n (%)]* | | | | |
| Number (Female) | 247 | 230 | 101 | 578 |
| Yes (Female) | 20 (8.1%) | 12 (5.2%) | 6 (5.9%) | 38 (6.6%) |
| No (Female) | 227 (91.9%) | 218 (94.8%) | 95 (94.1%) | 540 (93.4%) |
| *Duration of metformin treatment (years)* | | | | |
| Number | 466 | 466 | 232 | 1164 |
| Mean (SD) | 6.42 (4.85) | 6.46 (4.70) | 6.12 (4.45) | 6.38 (4.71) |
| Median | 5.25 | 5.45 | 5.45 | 5.37 |
| Min:Max | 0.3:34.2 | 0.3:26.4 | 0.2:24.7 | 0.2:34.2 |
| *Daily dose of metformin at baseline (mg)* | | | | |
| Number | 469 | 467 | 234 | 1170 |
| Mean (SD) | 2246.1 (456.8) | 2244.7 (444.7) | 2267.3 (427.4) | 2249.8 (445.9) |
| Median | 2000.0 | 2000.0 | 2000.0 | 2000.0 |
| Min:Max | 1000:3000 | 1000:3000 | 1000:3000 | 1000:3000 |
| *Categorized daily dose of metformin at baseline (mg) [n (%)]* | | | | |
| Number | 469 | 467 | 234 | 1170 |
| <1500 | 3 (0.6%) | 4 (0.9%) | 1 (0.4%) | 8 (0.7%) |
| ≥1500-<2500 | 283 (60.3%) | 285 (61.0%) | 139 (59.4%) | 707 (60.4%) |
| ≥2500-<3000 | 98 (20.9%) | 98 (21.0%) | 55 (23.5%) | 251 (21.5%) |
| ≥3000 | 85 (18.1%) | 80 (17.1%) | 39 (16.7%) | 204 (17.4%) |
| *Second OAD use at screening by class [n (%)]* | | | | |
| Number (Yes) | 274 (58.4%) | 270 (57.8%) | 133 (56.8%) | 677 (57.9%) |
| Sulfonylurea | 259 (55.2%) | 249 (53.3%) | 123 (52.6%) | 631 (53.9%) |
| Glinide | 3 (0.6%) | 10 (2.1%) | 5 (2.1%) | 18 (1.5%) |
| SGLT-2 inhibitor | 2 (0.4%) | 2 (0.4%) | 0 | 4 (0.3%) |
| DPP-4 inhibitor | 12 (2.6%) | 11 (2.4%) | 5 (2.1%) | 28 (2.4%) |
| *Duration of second OAD treatment (years)* | | | | |
| Number | 274 | 269 | 133 | 676 |
| Mean (SD) | 3.98 (4.07) | 4.61 (4.67) | 3.94 (3.54) | 4.22 (4.23) |
| Median | 2.59 | 3.26 | 2.49 | 2.82 |
| Min:Max | 0.3:21.3 | 0.3:25.4 | 0.3:16.0 | 0.3:25.4 |
| *Prior use of GLP-1 receptor agonist [n (%)]* | | | | |
| Number | 469 | 467 | 234 | 1170 |
| Yes | 15 (3.2%) | 21 (4.5%) | 10 (4.3%) | 46 (3.9%) |
| No | 454 (96.8%) | 446 (95.5%) | 224 (95.7%) | 1124 (96.1%) |
| *Prior use of insulin [n (%)]* | | | | |
| Number | 469 | 467 | 234 | 1170 |
| Yes | 11 (2.3%) | 14 (3.0%) | 4 (1.7%) | 29 (2.5%) |
| No | 458 (97.7%) | 453 (97.0%) | 230 (98.3%) | 1141 (97.5%) |
| *Diabetic retinopathy [n (%)]* | | | | |
| Number | 469 | 467 | 234 | 1170 |
| Yes | 44 (9.4%) | 27 (5.8%) | 26 (11.1%) | 97 (8.3%) |
| Photocoagulation performed: Yes | 4 (0.9%) | 2 (0.4%) | 0 | 6 (0.5%) |

TABLE 4-continued

Disease characteristics at screening or baseline - Randomized population

|  | Fixed Ratio Combination (N = 469) | Insulin Glargine (N = 467) | Lixisenatide (N = 234) | All (N = 1170) |
|---|---|---|---|---|
| Photocoagulation performed: No | 39 (8.3%) | 25 (5.4%) | 23 (9.8%) | 87 (7.4%) |
| Photocoagulation performed: Unknown | 1 (0.2%) | 0 | 3 (1.3%) | 4 (0.3%) |
| Vitrectomy performed because of diabetic retinopathy: Yes | 0 | 0 | 0 | 0 |
| Vitrectomy performed because of diabetic retinopathy: No | 42 (9.0%) | 27 (5.8%) | 22 (9.4%) | 91 (7.8%) |
| Vitrectomy performed because of diabetic retinopathy: Unknown | 2 (0.4%) | 0 | 4 (1.7%) | 6 (0.5%) |
| No | 416 (88.7%) | 429 (91.9%) | 199 (85.0%) | 1044 (89.2%) |
| Unknown | 9 (1.9%) | 11 (2.4%) | 9 (3.8%) | 29 (2.5%) |
| Diabetic sensory or motor neuropathy [n (%)] | | | | |
| Number | 469 | 467 | 234 | 1170 |
| Yes | 111 (23.7%) | 98 (21.0%) | 51 (21.8%) | 260 (22.2%) |
| No | 347 (74.0%) | 360 (77.1%) | 180 (76.9%) | 887 (75.8%) |
| Unknown | 11 (2.3%) | 9 (1.9%) | 3 (1.3%) | 23 (2.0%) |
| Diabetic autonomic neuropathy [n (%)] | | | | |
| Number | 469 | 467 | 234 | 1170 |
| Yes | 5 (1.1%) | 5 (1.1%) | 3 (1.3%) | 13 (1.1%) |
| No | 450 (95.9%) | 453 (97.0%) | 224 (95.7%) | 1127 (96.3%) |
| Unknown | 14 (3.0%) | 9 (1.9%) | 7 (3.0%) | 30 (2.6%) |
| Diabetic nephropathy [n (%)] | | | | |
| Number | 469 | 467 | 234 | 1170 |
| Yes | 33 (7.0%) | 13 (2.8%) | 8 (3.4%) | 54 (4.6%) |
| Impaired renal function (estimated GFR by MDRD below 60 ml/min) | 2 (0.4%) | 0 | 1 (0.4%) | 3 (0.3%) |
| Microalbuminuria (30 to 299 mcg per mg creatinine) | 23 (4.9%) | 8 (1.7%) | 7 (3.0%) | 38 (3.2%) |
| Overt proteinuria (equal to or above 300 mcg per mg creatinine) | 7 (1.5%) | 5 (1.1%) | 0 | 12 (1.0%) |
| No | 424 (90.4%) | 445 (95.3%) | 218 (93.2%) | 1087 (92.9%) |
| Unknown | 12 (2.6%) | 9 (1.9%) | 8 (3.4%) | 29 (2.5%) |
| Baseline urinary albumin/creatinine ratio (µg/mg) [n (%)] | | | | |
| Number | 466 | 466 | 234 | 1166 |
| <30 (normal) | 365 (78.3%) | 380 (81.5%) | 187 (79.9%) | 932 (79.9%) |
| ≥30-<300 (microalbuminuria) | 89 (19.1%) | 74 (15.9%) | 41 (17.5%) | 204 (17.5%) |
| ≥300 (macroalbuminuria) | 12 (2.6%) | 12 (2.6%) | 6 (2.6%) | 30 (2.6%) |
| Creatinine clearance at screening (mL/min) | | | | |
| Number | 465 | 464 | 232 | 1161 |
| Mean (SD) | 116.02 (34.99) | 115.10 (36.25) | 116.50 (33.12) | 115.75 (35.12) |
| Median | 109.93 | 107.86 | 114.02 | 110.42 |
| Min:Max | 51.8:263.9 | 49.3:255.0 | 46.6:239.0 | 46.6:263.9 |
| Creatinine clearance (mL/min) categories at screening [n (%)] | | | | |
| Number | 465 | 464 | 232 | 1161 |
| <15 (end stage renal disease) | 0 | 0 | 0 | 0 |
| ≥15-<30 (severe decrease in GFR) | 0 | 0 | 0 | 0 |

TABLE 4-continued

Disease characteristics at screening or baseline - Randomized population

|  | Fixed Ratio Combination (N = 469) | Insulin Glargine (N = 467) | Lixisenatide (N = 234) | All (N = 1170) |
|---|---|---|---|---|
| ≥30-<60 (moderate decrease in GFR) | 4 (0.9%) | 3 (0.6%) | 3 (1.3%) | 10 (0.9%) |
| ≥60-<90 (mild decrease in GFR) | 117 (25.2%) | 128 (27.6%) | 44 (19.0%) | 289 (24.9%) |
| ≥90 (normal) | 344 (74.0%) | 333 (71.8%) | 185 (79.7%) | 862 (74.2%) |

OAD = Oral anti-diabetic drug,
SGLT-2 = Sodium glucose co-transporter 2,
DPP-4 = Dipeptidyl-peptidase 4,
GLP-1 = Glucagon like peptide-1,
GFR = glomerular filtration rate.
Creatinine clearance value is derived using the equation of Cockroft and Gault.
Albumin/creatinine ratio is presented in μg/mg, equivalent to mg/g, and the conversion factor to the standard international unit mg/mmol is 0.1130.

3.1.4 Dosage and Duration of Investigational Medicinal Product

TABLE 5

Exposure to IMP—Safety population

|  | Fixed Ratio Combination (N = 469) | Insulin Glargine (N = 467) | Lixisenatide (N = 233) |
|---|---|---|---|
| Cumulative duration of treatment exposure (patient years) | 261.5 | 261.2 | 124.6 |
| Duration of study treatment (days) | | | |
| Number | 468 | 467 | 232 |
| Mean (SD) | 204.1 (33.9) | 204.3 (32.5) | 196.1 (48.2) |
| Median | 211.0 | 211.0 | 211.0 |
| Min:Max | 2:252 | 1:249 | 6:224 |
| Duration of study treatment by category [n (%)] | | | |
| Missing duration | 1 (0.2%) | 0 | 1 (0.4%) |
| 1-14 days | 3 (0.6%) | 4 (0.9%) | 4 (1.7%) |
| 15-28 days | 3 (0.6%) | 5 (1.1%) | 3 (1.3%) |
| 29-56 days | 6 (1.3%) | 2 (0.4%) | 7 (3.0%) |
| 57-84 days | 3 (0.6%) | 2 (0.4%) | 3 (1.3%) |
| 85-126 days | 6 (1.3%) | 5 (1.1%) | 4 (1.7%) |
| 127-168 days | 6 (1.3%) | 4 (0.9%) | 2 (0.9%) |
| 169-210 days | 113 (24.1%) | 200 (42.8%) | 66 (28.3%) |
| >210 days | 328 (69.9%) | 245 (52.5%) | 143 (61.4%) |
| Cumulative duration of study treatment by category [n (%)] | | | |
| Missing duration | 1 (0.2%) | 0 | 1 (0.4%) |
| ≥1 day | 468 (99.8%) | 467 (100%) | 232 (99.6%) |
| ≥15 days | 465 (99.1%) | 463 (99.1%) | 228 (97.9%) |
| ≥29 days | 462 (98.5%) | 458 (98.1%) | 225 (96.6%) |
| ≥57 days | 456 (97.2%) | 456 (97.6%) | 218 (93.6%) |
| ≥85 days | 453 (96.6%) | 454 (97.2%) | 215 (92.3%) |
| ≥127 days | 447 (95.3%) | 449 (96.1%) | 211 (90.6%) |
| ≥169 days | 441 (94.0%) | 445 (95.3%) | 209 (89.7%) |
| ≥211 days | 328 (69.9%) | 245 (52.5%) | 143 (61.4%) |

IMP: Investigational Medicinal Product
Duration of exposure = (date of the last open-label IMP injection − date of the first open-label IMP injection) + 1.
Note:
Patients are considered in the treatment group they actually received at randomization.

TABLE 6

Number (%) of patients by final insulin dose at the end of the open-label treatment—Safety population

| Final Insulin Dose | Fixed Ratio Combination (N = 469) | Insulin Glargine (N = 467) |
|---|---|---|
| <20 U | 59 (12.6%) | 43 (9.2%) |
| ≥20 U to <30 U | 76 (16.2%) | 96 (20.6%) |
| ≥30 U to ≤40 U | 126 (26.9%) | 117 (25.1%) |
| >40 U to ≤60 U | 208 (44.3%) | 209 (44.8%) |
| >60 U | 0 | 2 (0.4%) |
| =60 U | 73 (15.6%) | 94 (20.1%) |
| <20 U | 59 (12.6%) | 43 (9.2%) |
| Pen A [a] | | |
| <20 U | 59 (12.6%) | |
| ≥20 U to <30 U | 75 (16.0%) | |
| ≥30 U to ≤40 U | 104 (22.2%) | |
| >40 U to ≤60 U | 2 (0.4%) | |
| >60 U | 0 | |
| Pen B [b] | | |
| <20 U | 0 | |
| ≥20 U to <30 U | 0 | |
| ≥30 U to ≤40 U | 21 (4.5%) | |
| >40 U to ≤60 U | 206 (43.9%) | |
| >60 U | 0 | |

[a] 2 U/1 μg fixed ratio for insulin glargine/lixisenatide intended to administer daily doses between 10 and 40 U (10 U/5 μg and 40 U/20 μg)
[b] 3 U/1 μg fixed ratio for insulin glargine/lixisenatide intended to administer daily doses between 41 and 60 U (≈41 U/14 μg and 60 U/20 μg)
Note:
Percentages are calculated using the number of safety patients as the denominator.

TABLE 7

Number (%) of fixed ratio combination patients by final lixisenatide dose at the end of open-label treatment—Safety population

| Final Lixisenatide Dose | Fixed Ratio Combination (N = 469) |
|---|---|
| <10 μg | 59 (12.6%) |
| ≥10 μg to <15 μg | 131 (27.9%) |
| ≥15 μg to ≤20 μg | 275 (58.6%) |
| <10 μg | 59 (12.6%) |
| >20 μg | 2 (0.4%) |
| Pen A [a] | |
| <10 μg | 59 (12.6%) |
| ≥10 μg to <15 μg | 75 (16.0%) |
| ≥15 μg to ≤20 μg | 104 (22.2%) |
| >20 μg | 2 (0.4%) |

TABLE 7-continued

Number (%) of fixed ratio combination patients by final lixisenatide dose at the end of open-label treatment—Safety population

| Final Lixisenatide Dose | Fixed Ratio Combination (N = 469) |
|---|---|
| Pen B [b] | |
| ≥10 μg to <15 μg | 56 (11.9%) |
| ≥15 μg to ≤20 μg | 171 (36.5%) |

[a] 2 U/1 μg fixed ratio for insulin glargine/lixisenatide intended to administer daily doses between 10 and 40 U (10 U/5 μg and 40 U/20 μg)
[b] 3 U/1 μg fixed ratio for insulin glargine/lixisenatide intended to administer daily doses between 41 and 60 U (≈41 U/14 μg and 60 U/20 μg)
Note:
Percentages are calculated using the number of safety patients as the denominator.

TABLE 8

Number (%) of patients by final lixisenatide dose at the end of open-label treatment—Safety population

| Final Lixisenatide Dose | Lixisenatide (N = 233) |
|---|---|
| 10 μg | 26 (11.2%) |
| 20 μg | 207 (88.8%) |

Note:
Percentages are calculated using the number of safety patients as the denominator.

3.2 Efficacy

3.2.1 Primary Efficacy Endpoint

TABLE 9

Figure 2:
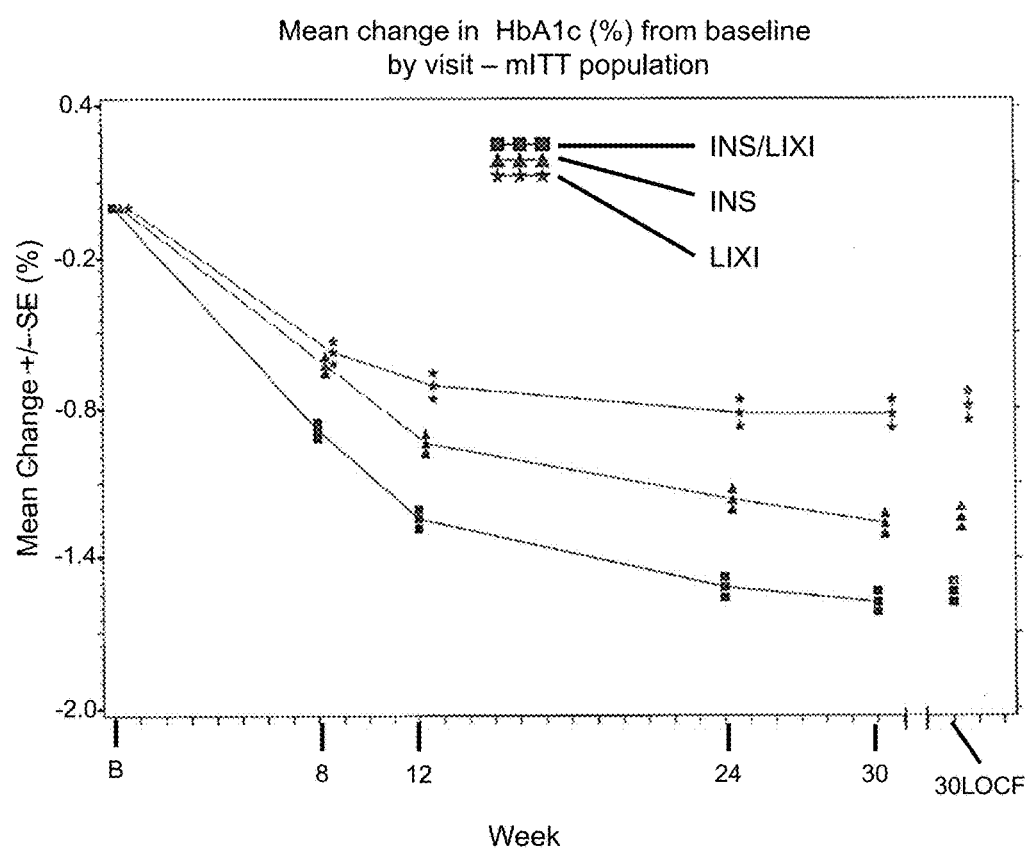
FIG. 2—Mean change in HbA1c (%) from baseline by visit—mITT population. B=Baseline, LOCF=Last observation carried forward. INS/LIXI=fixed ratio combination, INS=Insulin Glargine, LIXI=Lixisenatide. Note: The plot included all scheduled measurements obtained during the study, including those obtained after IMP discontinuation or introduction of rescue medication.

Mean change in HbA1c (%) from baseline to Week 30 using MMRM—mITT population (FIGS. 1 and 2)

| HbA1c(%) | Fixed Ratio Combination (N = 468) | Insulin Glargine (N = 466) | Lixisenatide (N = 233) |
|---|---|---|---|
| Baseline | | | |
| Number | 467 | 464 | 233 |
| Mean (SD) | 8.08 (0.71) | 8.08 (0.69) | 8.13 (0.72) |
| Median | 8.00 | 8.00 | 8.00 |
| Min:Max | 4.5:10.2 | 5.9:10.4 | 6.7:10.3 |
| Week 30 | | | |
| Number | 443 | 446 | 221 |
| Mean (SD) | 6.50 (0.75) | 6.81 (0.76) | 7.31 (0.87) |
| Median | 6.30 | 6.70 | 7.20 |
| Min:Max | 4.9:9.6 | 4.6:10.7 | 5.2:11.0 |
| Change from baseline to Week 30 | | | |
| Number | 467 | 464 | 233 |
| LS Mean (SE)[a] | −1.63 (0.038) | −1.34 (0.039) | −0.85 (0.052) |
| LS mean difference (SE) vs insulin glargine[a] | −0.29 (0.048) | — | — |
| 95% CI | (−0.384 to −0.194) | — | — |
| p-value | <0.0001 | — | — |
| LS mean difference (SE) vs lixisenatide[a] | −0.78 (0.059) | — | — |
| 95% CI | (−0.898 to −0.665) | — | — |
| p-value | <0.0001 | — | — |

[a] Mixed-effect model with repeated measures (MMRM) with treatment groups (fixed ratio combination, insulin glargine alone, lixisenatide alone), randomization strata of HbA1c (<8.0%, ≥8.0%) at Visit 4 (Week −1), randomization strata of second OAD use at screening (Yes, No), visit (Week 8, 12, 24, and 30), treatment-by-visit interaction, and country as fixed effects, and baseline HbA1c value-by-visit interaction as a covariate.

Countries with fewer than 5 patients were grouped with the country with the lowest number of patients that is 5 or more.

The analysis included all scheduled measurements obtained during the study, including those obtained after IMP discontinuation or introduction of rescue therapy.

Included are patients who have measurements at baseline and post-baseline.

3.2.2 Other Key Efficacy Endpoints

TABLE 10

Number (%) of patients with HbA1c value ≤6.5% or <7.0% at Week 30—mITT population

| HbA1c (%) | Fixed Ratio Combination (N = 468) | Insulin Glargine (N = 466) | Lixisenatide (N = 233) |
|---|---|---|---|
| Number | 468 | 466 | 233 |
| ≤6.5% | 261 (55.8%) | 184 (39.5%) | 45 (19.3%) |
| Proportion difference (95% CI) vs. insulin glargine[a] | 16.35% (10.13% to 22.58%) | — | — |
| Proportion difference (95% ) vs. lixisenatide[a] | 36.38% (29.81% to 42.95%) | — | — |
| <7% | 345 (73.7%) | 277 (59.4%) | 77 (33.0%) |
| Proportion difference (95% ) vs. insulin glargine[a] | 14.31% (8.37% to 20.25%) | — | — |
| Proportion difference (95% CI) vs. lixisenatide[a] | 40.61% (33.63% to 47.59%) | — | — |

[a] Weighted average of proportion difference between treatment groups (fixed ratio combination, insulin glargine, lixisenatide) from each strata (randomization strata of HbA1c [<8.0, ≥8.0%] at Visit 4 (Week −1), randomization strata of second OAD use at screening [Yes, No]) using Cochran-Mantel-Haenszel (CMH) weights.
Proportion difference = difference of the proportions of patients achieving HbA1c value ≤6.5% or <7%.

All measurements at Week 30 were used, including those obtained after IMP discontinuation or introduction of rescue therapy. If no assessment was available at Week 30 at all, patients were treated as non-responders.

TABLE 11

Mean change in 2-hour plasma glucose excursion (mmol/L) during a standardized meal test from baseline to Week 30 using ANCOVA—mITT population

| 2-hour plasma glucose excursion (mmol/L) | Fixed Ratio Combination (N = 468) | Insulin Glargine (N = 466) | Lixisenatide (N = 233) |
| --- | --- | --- | --- |
| Baseline | | | |
| Number | 428 | 425 | 192 |
| Mean (SD) | 5.31 (2.86) | 5.02 (2.96) | 5.07 (2.54) |
| Median | 5.20 | 4.90 | 5.00 |
| Min:Max | −4.3:14.2 | −4.7:14.5 | −3.2:12.2 |
| Week 30 (LOCF) | | | |
| Number | 428 | 425 | 192 |
| Mean (SD) | 2.81 (2.84) | 4.80 (2.90) | 1.70 (3.23) |
| Median | 2.80 | 4.70 | 1.05 |
| Min:Max | −4.3:12.3 | −5.5:14.4 | −5.0:10.2 |
| Change from baseline to Week 30 (LOCF) | | | |
| Number | 428 | 425 | 192 |
| Mean (SD) | −2.49 (3.37) | −0.22 (2.86) | −3.37 (3.41) |
| Median | −2.40 | −0.10 | −3.45 |
| Min:Max | −12.2:10.1 | −13.1:7.9 | −12.4:4.8 |
| LS Mean (SE)[a] | −2.31 (0.154) | −0.18 (0.157) | −3.23 (0.216) |
| LS mean difference (SE) vs insulin glargine[a] | −2.13 (0.185) | — | — |
| 95% CI | (−2.498 to −1.770) | — | — |
| p-value | <0.0001 | — | — |
| LS mean difference (SE) vs lixisenatide[a] | 0.91 (0.237) | — | — |
| 95% CI | (0.448 to 1.377) | — | — |

LOCF = Last observation carried forward.

[a] Analysis of covariance (ANCOVA) model with treatment groups (fixed ratio combination, insulin glargine, lixisenatide), randomization strata of HbA1c (<8.0%, ≥8.0%) at Visit 4 (Week −1), randomization strata of second OAD use at screening (Yes, No), and country as fixed effects and baseline 2-hour plasma glucose excursion value as a covariate.

Countries with fewer than 5 patients were grouped with the country with the lowest number of patients that is 5 or more.

The analysis included measurements collected during the study, including those obtained after IMP discontinuation or introduction of rescue therapy.

Patients injecting IMP in the morning in the lixisenatide group and all patients in fixed ratio combination or insulin glargine group with both baseline and Week 30 (LOCF) measurements were included.

TABLE 12

Mean change in 2-hour postprandial plasma glucose (mmol/L) during a standardized meal test from baseline to Week 30 using ANCOVA—mITT population

| 2-hour postprandial plasma glucose (mmol/L) | Fixed Ratio Combination (N = 468) | Insulin Glargine (N = 466) | Lixisenatide (N = 233) |
| --- | --- | --- | --- |
| Baseline | | | |
| Number | 430 | 430 | 196 |
| Mean (SD) | 15.19 (3.63) | 14.61 (3.64) | 14.72 (3.32) |
| Median | 15.20 | 14.50 | 14.70 |
| Min:Max | 3.1:24.6 | 4.4:26.6 | 4.9:24.1 |
| Week 30 (LOCF) | | | |
| Number | 430 | 430 | 196 |
| Mean (SD) | 9.15 (3.20) | 11.35 (3.12) | 9.99 (3.91) |
| Median | 8.90 | 11.20 | 9.45 |
| Min:Max | 2.8:24.0 | 3.3:19.9 | 4.0:25.8 |
| Change from baseline to Week 30 (LOCF) | | | |
| Number | 430 | 430 | 196 |

TABLE 12-continued

Mean change in 2-hour postprandial plasma glucose (mmol/L) during a standardized meal test from baseline to Week 30 using ANCOVA—mITT population

| 2-hour postprandial plasma glucose (mmol/L) | Fixed Ratio Combination (N = 468) | Insulin Glargine (N = 466) | Lixisenatide (N = 233) |
|---|---|---|---|
| Mean (SD) | −6.04 (4.27) | −3.26 (3.54) | −4.73 (4.11) |
| Median | −6.00 | −3.35 | −5.05 |
| Min:Max | −18.1:6.7 | −17.2:6.3 | −13.8:8.4 |
| LS Mean (SE)[a] | −5.68 (0.176) | −3.31 (0.178) | −4.58 (0.245) |
| LS mean difference (SE) vs insulin glargine[a] | −2.38 (0.212) | — | — |
| 95% CI | (−2.794 to −1.963) | — | — |
| LS mean difference (SE) vs lixisenatide[a] | −1.10 (0.269) | — | — |
| 95% CI | (−1.627 to −0.573) | — | — |

LOCF = Last observation carried forward.
[a]Analysis of covariance (ANCOVA) model with treatment groups (fixed ratio combination, insulin glargine, lixisenatide), randomization strata of HbA1c (<8.0%, ≥8.0%) at Visit 4 (Week −1), randomization strata of second OAD use at screening (Yes, No), and country as fixed effects and baseline 2-hour postprandial plasma glucose value as a covariate.

Countries with fewer than 5 patients were grouped with the country with the lowest number of patients that is 5 or more.

The analysis included measurements collected during the study, including those obtained after IMP discontinuation or introduction of rescue therapy.

Patients injecting IMP in the morning in the lixisenatide group and all patients in fixed ratio combination or insulin glargine group with both baseline and Week 30 (LOCF) measurements were included.

TABLE 13

Figure 3:
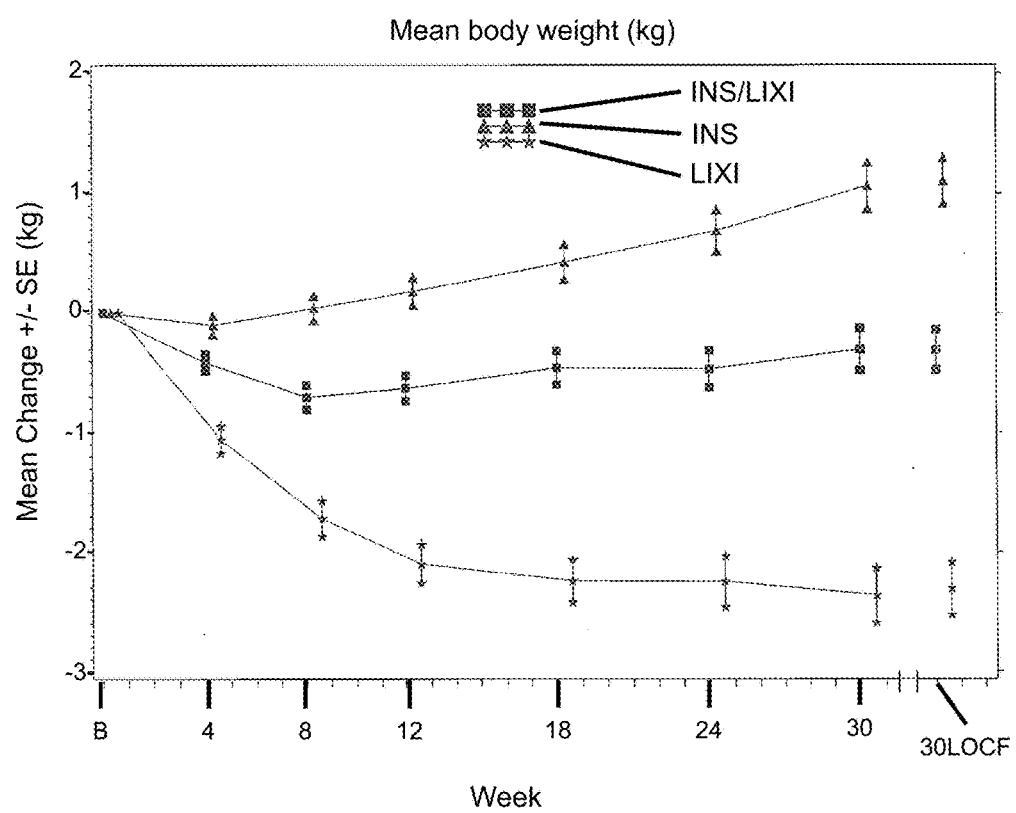
FIG. 3—Mean body weight (kg). B=Baseline, LOCF=Last observation carried forward. INS/LIXI=fixed ratio combination, INS=Insulin Glargine, LIXI=Lixisenatide. The analysis included all scheduled measurements obtained during the study, including those obtained after IMP discontinuation or introduction of rescue therapy.

Mean change in body weight (kg) from baseline to Week 30 using MMRM—mITT population (FIG. 3)

| Body Weight (kg) | Fixed Ratio Combination (N = 468) | Insulin Glargine (N = 466) | Lixisenatide (N = 233) |
|---|---|---|---|
| Baseline | | | |
| Number | 467 | 465 | 233 |
| Mean (SD) | 89.44 (17.16) | 89.75 (16.34) | 90.79 (16.25) |
| Median | 88.90 | 88.50 | 91.00 |
| Min:Max | 46.7:147.0 | 47.4:137.3 | 54.3:144.0 |
| Week 30 | | | |
| Number | 448 | 446 | 222 |
| Mean (SD) | 89.16 (17.34) | 90.68 (16.03) | 88.57 (16.20) |
| Median | 88.00 | 89.00 | 88.90 |
| Min:Max | 45.2:145.5 | 51.2:143.6 | 53.5:152.3 |
| Change from baseline to Week 30 | | | |
| Number | 467 | 465 | 233 |
| LS Mean (SE)[a] | −0.29 (0.182) | 1.11 (0.183) | −2.30 (0.256) |
| LS mean difference (SE) vs insulin glargine[a] | −1.40 (0.250) | — | — |
| 95% CI | (−1.891 to −0.910) | — | — |
| p-value | <0.0001 | — | — |
| LS mean difference (SE) vs lixisenatide[a] | 2.01 (0.307) | — | — |
| 95% CI | (1.404 to 2.609) | — | — |

[a]Mixed-effect model with repeated measures (MMRM) with treatment groups (fixed ratio combination, insulin glargine alone, lixisenatide alone), randomization strata of HbA1c (<8.0%, ≥8.0%) at Visit 4 (Week −1), randomization strata of second OAD use at screening (Yes, No), scheduled visit, treatment-by-visit interaction and country as fixed effects, and baseline body weight value-by-visit interaction as a covariate.

Countries with fewer than 5 patients were grouped with the country with the lowest number of patients that is 5 or more.

The analysis included all scheduled measurements obtained during the study, including those obtained after IMP discontinuation or introduction of rescue therapy.

Included are patients who have measurements at baseline and post-baseline.

TABLE 14

Figure 4:
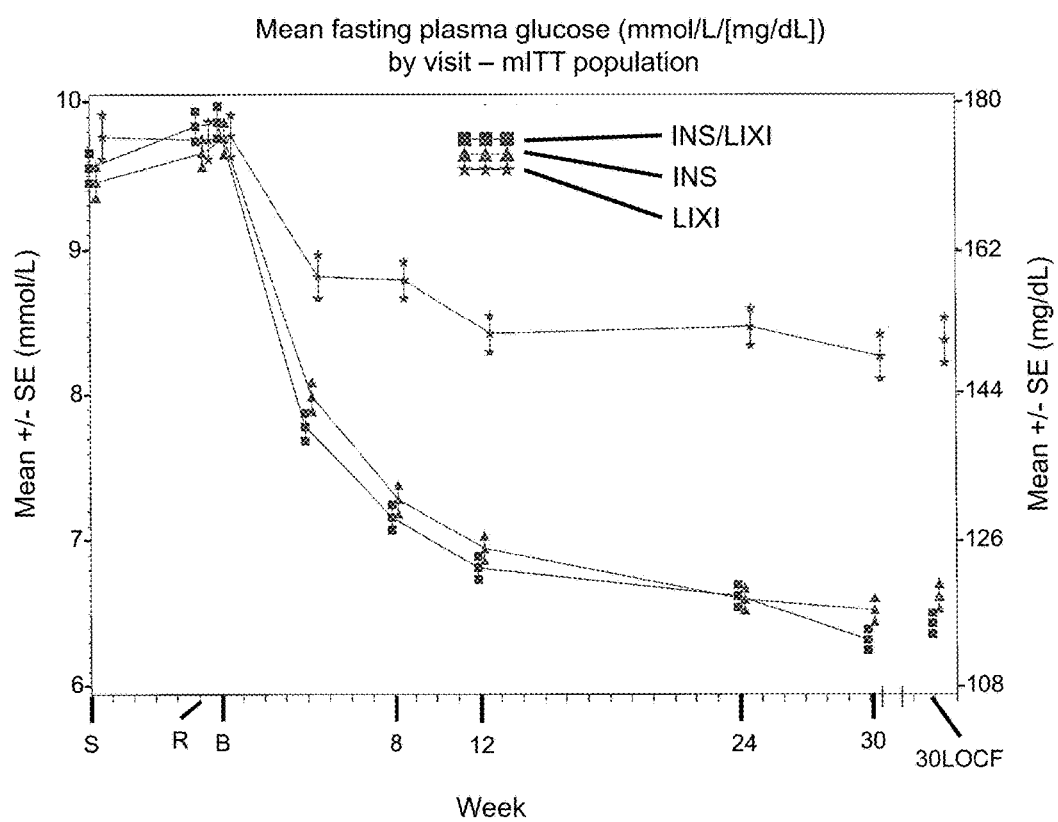
FIG. 4—Mean fasting plasma glucose (mmol/L/[mg/dL]) by visit—mITT population. S=Screening (Week −6), R=Run-in (Week −1), B=Baseline, LOCF=Last observation carried forward. INS/LIXI=fixed ratio combination, INS=Insulin Glargine, LIXI=Lixisenatide. The analysis included all scheduled measurements obtained during the study, including those obtained after IMP discontinuation or introduction of rescue therapy.
Figure 5:
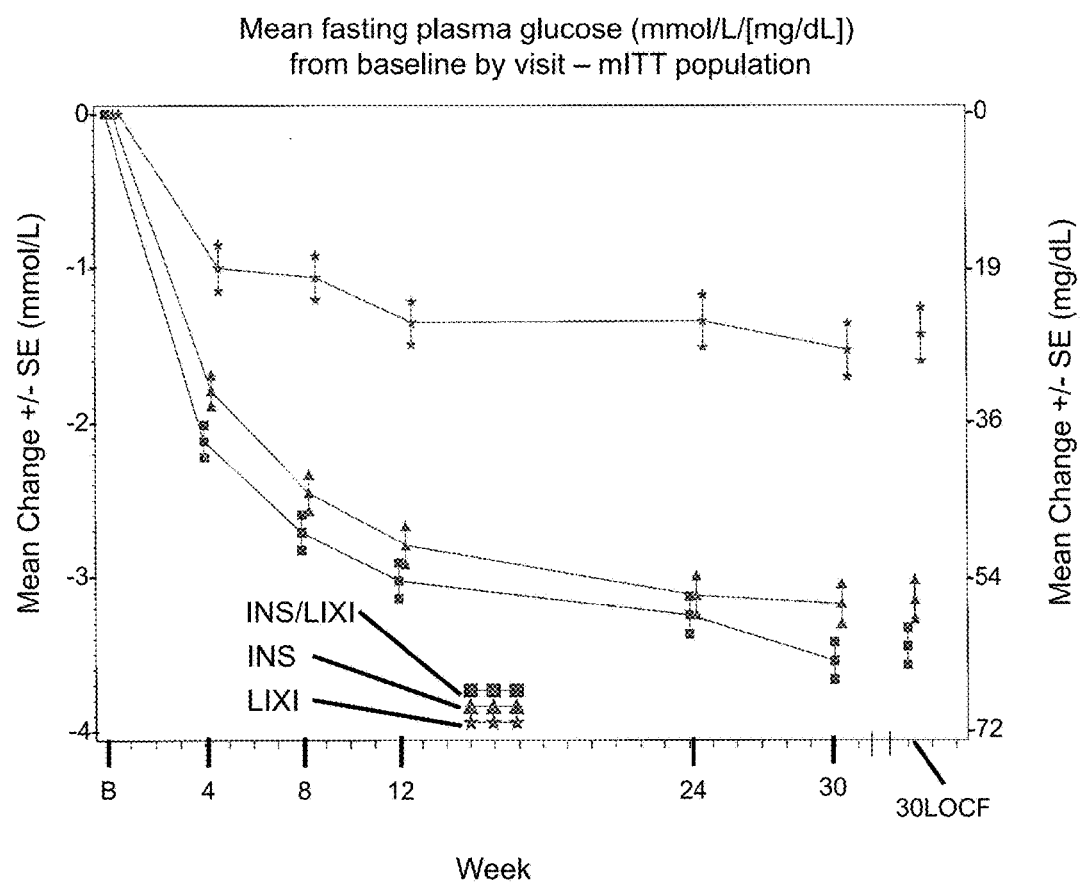
FIG. 5—Mean fasting plasma glucose (mmol/L/[mg/dL]) from baseline by visit—mITT population. B=Baseline, LOCF=Last observation carried forward. INS/LIXI=fixed ratio combination, INS=Insulin Glargine, LIXI=Lixisenatide. The analysis included all scheduled measurements obtained during the study, including those obtained after IMP discontinuation or introduction of rescue therapy.

Mean change in fasting plasma glucose (mmol/L) from baseline to Week 30 using MMRM—mITT population (FIGS. 4 and 5)

| Fasting plasma glucose (mmol/L) | Fixed Ratio Combination (N = 468) | Insulin Glargine (N = 466) | Lixisenatide (N = 233) |
|---|---|---|---|
| Baseline | | | |
| Number | 465 | 465 | 232 |
| Mean (SD) | 9.88 (2.34) | 9.75 (2.33) | 9.79 (2.16) |
| Median | 9.70 | 9.30 | 9.70 |
| Min:Max | 4.3:17.8 | 4.7:21.5 | 5.5:19.4 |
| Week 30 | | | |
| Number | 436 | 438 | 216 |
| Mean (SD) | 6.32 (1.47) | 6.53 (1.76) | 8.27 (2.24) |
| Median | 6.00 | 6.20 | 8.00 |
| Min:Max | 3.1:14.3 | 3.3:15.9 | 3.2:24.4 |
| Change from baseline to Week 30 | | | |
| Number | 465 | 465 | 232 |
| LS Mean (SE)[a] | −3.46 (0.090) | −3.27 (0.091) | −1.50 (0.124) |
| LS mean difference (SE) vs insulin glargine[a] | −0.19 (0.117) | — | — |
| 95% CI | (−0.420 to 0.038) | — | — |
| p-value | 0.1017 | — | — |
| LS mean difference (SE) vs lixisenatide[a] | −1.96 (0.144) | — | — |
| 95% CI | (−2.246 to −1.682) | — | — |
| p-value | <0.0001 | — | — |

[a]Mixed-effect model with repeated measures (MMRM) with treatment groups (fixed ratio combination, insulin glargine alone, lixisenatide alone), randomization strata of HbA1c (<8.0%, ≥8.0%) at Visit 4 (Week −1), randomization strata of second OAD use at screening (Yes, No), scheduled visit, treatment-by-visit interaction and country as fixed effects, and baseline fasting plasma glucose value-by-visit interaction as a covariate.

Countries with fewer than 5 patients were grouped with the country with the lowest number of patients that is 5 or more.

The analysis included all scheduled measurements obtained during the study, including those obtained after IMP discontinuation or introduction of rescue therapy.

Included are patients who have measurements at baseline and post-baseline.

TABLE 15

Mean change in average 7-point SMPG (mmol/L) from baseline to Week 30 using MMRM—mITT population (FIG. 6)

| Average of 7-point SMPG (mmol/L) | Fixed Ratio Combination (N = 468) | Insulin Glargine (N = 466) | Lixisenatide (N = 233) |
|---|---|---|---|
| Baseline | | | |
| Number | 421 | 411 | 204 |
| Mean (SD) | 10.47 (2.15) | 10.31 (2.15) | 10.41 (2.01) |
| Median | 10.03 | 10.07 | 10.33 |
| Min:Max | 5.2:16.8 | 5.8:18.3 | 6.0:17.2 |
| Week 30 | | | |
| Number | 382 | 368 | 184 |
| Mean (SD) | 7.09 (1.25) | 7.75 (1.49) | 8.54 (1.79) |
| Median | 6.90 | 7.49 | 8.42 |
| Min:Max | 4.9:13.6 | 5.0:15.5 | 5.4:18.1 |
| Change from baseline to Week 30 | | | |
| Number | 421 | 411 | 204 |
| LS Mean (SE)[a] | −3.35 (0.081) | −2.66 (0.084) | −1.95 (0.111) |
| LS mean difference (SE) vs insulin glargine[a] | −0.69 (0.101) | — | — |
| 95% CI | (−0.892 to −0.495) | — | — |
| p-value | <0.0001 | — | — |
| LS mean difference (SE) vs lixisenatide[a] | −1.40 (0.124) | — | — |
| 95% CI | (−1.645 to −1.158) | — | — |
| p-value | <0.0001 | — | — |

SMPG = Self-monitored plasma glucose.
[a]Mixed-effect model with repeated measures (MMRM) with treatment groups (fixed ratio combination, insulin glargine alone, lixisenatide alone), randomization strata of HbA1c (<8.0%, ≥8.0%) at Visit 4 (Week −1), randomization strata of second OAD use at screening (Yes, No), scheduled visit, treatment-by-visit interaction and country as fixed effects, and baseline average SMPG value-by-visit interaction as a covariate.

Countries with fewer than 5 patients were grouped with the country with the lowest number of patients that is 5 or more.

The analysis included all scheduled measurements obtained during the study, including those obtained after IMP discontinuation or introduction of rescue therapy.

Included are patients who have measurements at baseline and post-baseline.

TABLE 16

Number (%) of patients reaching HbA1c <7.0% with no body weight gain at Week 30—mITT population

| HbA1c <7% with no body weight gain | Fixed Ratio Combination (N = 468) | Insulin Glargine (N = 466) | Lixisenatide (N = 233) |
|---|---|---|---|
| Number | 468 | 466 | 233 |
| Yes | 202 (43.2%) | 117 (25.1%) | 65 (27.9%) |
| Proportion difference (95% CI) vs. insulin glargine[a] | 18.08% (12.15% to 24.01%) | — | — |
| p-value | <.0001 | — | — |

TABLE 16-continued

Number (%) of patients reaching HbA1c <7.0% with no body weight gain at Week 30—mITT population

| HbA1c <7% with no body weight gain | Fixed Ratio Combination (N = 468) | Insulin Glargine (N = 466) | Lixisenatide (N = 233) |
|---|---|---|---|
| Proportion difference (95% CI) vs. lixisenatide[a] | 15.22% (8.05% to 22.39%) | — | — |

[a]Weighted average of proportion difference between treatment groups (fixed ratio combination, insulin glargine, lixisenatide) from each strata (randomization strata of HbA1c [<8.0, ≥8.0%] at Visit 4 (Week −1), randomization strata of second OAD use at screening [Yes, No]) using Cochran-Mantel-Haenszel (CMH) weights.

The analysis included HbA1c and body weight measurements at week 30, including those obtained after the IMP discontinuation or the introduction of rescue medication.

Patients were treated as non-responders if they have no HbA1c and/or body weight assessments at week 30.

TABLE 17

Number (%) of patients reaching HbA1c <7.0% with no body weight gain at Week 30 and with no documented symptomatic hypoglycemia (plasma glucose concentration ≤70 mg/dL [3.9 mmol/L]) during the study—mITT population

| HbA1c <7% with no weight gain and with no documented symptomatic hypoglycemia | Fixed Ratio Combination (N = 468) | Insulin Glargine (N = 466) | Lixisenatide (N = 233) |
|---|---|---|---|
| Number | 468 | 466 | 233 |
| Yes | 149 (31.8%) | 88 (18.9%) | 61 (26.2%) |
| Proportion difference (95% CI) vs. insulin glargine[a] | 12.98% (7.50% to 18.45%) | — | — |
| p-value | <.0001 | — | — |
| Proportion difference (95% CI) vs. lixisenatide[a] | 5.61% (−1.33% to 12.55%) | — | — |

[a]Weighted average of proportion difference between treatment groups (fixed ratio combination, insulin glargine, lixisenatide) from each strata (randomization strata of HbA1c [<8.0, ≥8.0%] at Visit 4 (Week −1), randomization strata of second OAD use at screening [Yes, No]) using Cochran-Mantel-Haenszel (CMH) weights.

Documented symptomatic hypoglycemia is an event during which typical symptoms of hypoglycemia are accompanied by a measured plasma glucose of 70 mg/dL (3.9 mmol/L).

The analysis included all HbA1c and body weight measurements at week 30, including those obtained after the IMP discontinuation or the introduction of rescue medication. Patients were treated as non-responders if they have no HbA1c and/or body weight assessments at week 30.

All documented symptomatic hypoglycemia occurred during the 30-week open-label treatment period was considered, including those occurred after the IMP discontinuation or the introduction of rescue medication.

TABLE 18

Average daily insulin glargine dose (U) at Week 30 using MMRM—mITT population (FIG. 7)

| Average daily insulin glargine dose (U) | Fixed Ratio Combination (N = 468) | Insulin Glargine (N = 466) |
|---|---|---|
| Week 30 | | |
| Number | 438 | 440 |
| Mean (SD) | 39.75 (14.87) | 40.34 (14.85) |
| Median | 40.00 | 40.00 |
| Min:Max | 10.0:60.0 | 4.0:62.0 |

TABLE 18-continued

Average daily insulin glargine dose (U) at Week 30 using MMRM—mITT population (FIG. 7)

| Average daily insulin glargine dose (U) | Fixed Ratio Combination (N = 468) | Insulin Glargine (N = 466) |
|---|---|---|
| Week 30 | | |
| Number | 467 | 463 |
| LS Mean (SE)[a] | 39.77 (0.699) | 40.46 (0.701) |
| LS mean difference (SE) vs insulin glargine[a] | −0.69 (0.990) | — |
| 95% CI | (−2.632 to 1.252) | — |
| p-value | 0.4857 | — |

[a]Mixed-effect model with repeated measures (MMRM) with treatment groups (fixed ratio combination, insulin glargine), randomization strata of HbA1c (<8.0%, ≥8.0%) at Visit 4 (Week −1), randomization strata of second OAD use at screening (Yes, No), scheduled visit, treatment-by-visit interaction, and country as fixed effects.

Countries with fewer than 5 patients were grouped with the country with the lowest number of patients that is 5 or more.

The analysis included scheduled measurements obtained up to the date of last injection of the IMP, including those obtained after introduction of rescue therapy.

3.3 Safety

Symptomatic hypoglycemia events were documented on a specific hypoglycemia event form, and not an AE CRF page, and thus were not included in the TEAE summaries. They are summarized separately from TEAEs.

TABLE 19

Overview of adverse event profile: treatment emergent adverse events-Safety population

| n (%) | Fixed Ratio Combination (N = 469) | Insulin Glargine (N = 467) | Lixisenatide (N = 233) |
|---|---|---|---|
| Patients with any TEAE | 267 (56.9%) | 227 (48.6%) | 157 (67.4%) |
| Patients with any serious TEAE | 18 (3.8%) | 19 (4.1%) | 9 (3.9%) |
| Patients with any TEAE leading to permanent treatment discontinuation | 12 (2.6%) | 9 (1.9%) | 21 (9.0%) |
| Patients with any TEAE leading to death | 2 (0.4%) | 3 (0.6%) | 1 (0.4%) |

TEAE: Treatment Emergent Adverse Event.
n (%) = number and percentage of patients with at least one TEAE.

TABLE 20

Number (%) of patients experiencing TEAE(s) (PT ≥ 3% in any treatment group) by primary SOC and PT-Safety population

| Primary System Organ Class Preferred Term n (%) | Fixed Ratio Combination (N = 469) | Insulin Glargine (N = 467) | Lixisenatide (N = 233) |
|---|---|---|---|
| Any TEAE | 267 (56.9%) | 227 (48.6%) | 157 (67.4%) |
| Infections and infestations | 130 (27.7%) | 126 (27.0%) | 60 (25.8%) |
| Influenza | 15 (3.2%) | 11 (2.4%) | 4 (1.7%) |
| Nasopharyngitis | 26 (5.5%) | 25 (5.4%) | 15 (6.4%) |
| Upper respiratory tract infection | 33 (7.0%) | 23 (4.9%) | 12 (5.2%) |
| Nervous system disorders | 50 (10.7%) | 30 (6.4%) | 31 (13.3%) |
| Dizziness | 16 (3.4%) | 7 (1.5%) | 7 (3.0%) |
| Headache | 24 (5.1%) | 15 (3.2%) | 18 (7.7%) |
| Gastrointestinal disorders | 102 (21.7%) | 59 (12.6%) | 86 (36.9%) |
| Diarrhoea | 42 (9.0%) | 20 (4.3%) | 21 (9.0%) |
| Nausea | 45 (9.6%) | 17 (3.6%) | 56 (24.0%) |
| Vomiting | 15 (3.2%) | 7 (1.5%) | 15 (6.4%) |
| Any TEAE | 267 (56.9%) | 227 (48.6%) | 157 (67.4%) |
| Musculoskeletal and connective tissue disorders | 51 (10.9%) | 41 (8.8%) | 29 (12.4%) |
| Back pain | 16 (3.4%) | 10 (2.1%) | 8 (3.4%) |

TEAE: Treatment emergent adverse event, SOC: System Organ Class, PT: Preferred Term.
MedDRA 18.0
n (%) = number and percentage of patients with at least one TEAE.
Note:
Table sorted by SOC internationally agreed order and PT alphabetic order.
Only SOC with at least one PT ≥ 3% in at least one group are presented.

3.3.1 Deaths, Serious Treatment-Emergent Adverse Events

Six patients experienced at least 1 TEAE leading to death: 2 from the fixed ratio combination group, 3 from the insulin glargine group and 1 from the lixisenatide group (Table 21). None of the fatal events were considered related to the IMP by the Investigator.

Fixed ratio combination group:
  A 64 year-old male patient died of lung cancer metastatic.
  A 72 year-old male patient died of cardiac failure congestive.
Insulin glargine group:
  A 55 year-old male patient died from acute myocardial infarction and acute pulmonary edema.
  A 62 year-old male patient died of cardiac failure acute.
  A 60 year-old male died about 3 months after the treatment period due to the worsening of undifferentiated keratinized squamous cell carcinoma in mouth (diagnosed during the on-treatment period).
Lixisenatide group:
  A 63 year-old female, was reported to be found dead on her bed due to unknown reasons 208 days after the first dose of the study drug. Autopsy was not performed. No other information was provided. This case was adjudicated by the CAC as CV Death.

TABLE 21

Number (%) of patients experiencing TEAE(s) leading to death by primary SOC and PT-Safety population

| Primary System Organ Class Preferred Term [n (%)] | Fixed Ratio Combination (N = 469) | Insulin Glargine (N = 467) | Lixisenatide (N = 233) |
|---|---|---|---|
| Any TEAE leading to death | 2 (0.4%) | 3 (0.6%) | 1 (0.4%) |
| Neoplasms benign, malignant and unspecified (incl cysts and polyps) | 1 (0.2%) | 1 (0.2%) | 0 |
| Lung cancer metastatic | 1 (0.2%) | 0 | 0 |
| Squamous cell carcinoma of the oral cavity | 0 | 1 (0.2%) | 0 |
| Cardiac disorders | 1 (0.2%) | 2 (0.4%) | 0 |
| Acute myocardial infarction | 0 | 1 (0.2%) | 0 |
| Cardiac failure acute | 0 | 1 (0.2%) | 0 |
| Cardiac failure congestive | 1 (0.2%) | 0 | 0 |

TABLE 21-continued

Number (%) of patients experiencing TEAE(s) leading to
death by primary SOC and PT-Safety population

| Primary System Organ Class<br>Preferred Term [n (%)] | Fixed Ratio<br>Combination<br>(N = 469) | Insulin<br>Glargine<br>(N = 467) | Lixisenatide<br>(N = 233) |
|---|---|---|---|
| Respiratory, thoracic and mediastinal disorders | 0 | 1 (0.2%) | 0 |
| Acute pulmonary oedema | 0 | 1 (0.2%) | 0 |
| General disorders and administration site conditions | 0 | 0 | 1 (0.4%) |
| Death | 0 | 0 | 1 (0.4%) |

TEAE: Treatment Emergent Adverse Event, SOC: System Organ Class, PT: Preferred Term.
MedDRA 18.0
n (%) = number and percentage of patients with at least one TEAE leading to death.
Note:
Table sorted by SOC internationally agreed order and PT alphabetic order.

TABLE 22

Number (%) of patients experiencing serious TEAE(s)
presented by primary SOC and PT-Safety population

| Primary System Organ Class<br>Preferred Term [n (%)] | Fixed Ratio<br>Combination<br>(N = 469) | Insulin<br>Glargine<br>(N = 467) | Lixisenatide<br>(N = 233) |
|---|---|---|---|
| Any serious TEAE | 18 (3.8%) | 19 (4.1%) | 9 (3.9%) |
| Infections and infestations | 4 (0.9%) | 2 (0.4%) | 2 (0.9%) |
| Bronchitis | 0 | 1 (0.2%) | 0 |
| Erysipelas | 1 (0.2%) | 0 | 1 (0.4%) |
| Febrile infection | 1 (0.2%) | 0 | 0 |
| Meningitis staphylococcal | 0 | 0 | 1 (0.4%) |
| Pneumonia | 0 | 1 (0.2%) | 0 |
| Pyelonephritis acute | 0 | 1 (0.2%) | 0 |
| Urinary tract infection | 2 (0.4%) | 0 | 0 |
| Urosepsis | 0 | 1 (0.2%) | 0 |
| Neoplasms benign, malignant and unspecified (incl cysts and polyps) | 2 (0.4%) | 4 (0.9%) | 1 (0.4%) |
| Lung cancer metastatic | 1 (0.2%) | 0 | 0 |
| Lung neoplasm malignant | 0 | 0 | 1 (0.4%) |
| Metastases to liver | 0 | 0 | 1 (0.4%) |
| Pancreatic carcinoma | 0 | 1 (0.2%) | 0 |
| Prostate cancer recurrent | 0 | 1 (0.2%) | 0 |
| Squamous cell carcinoma of skin | 1 (0.2%) | 0 | 0 |
| Squamous cell carcinoma of the oral cavity | 0 | 1 (0.2%) | 0 |
| Thyroid adenoma | 0 | 1 (0.2%) | 0 |
| Blood and lymphatic system disorders | 0 | 1 (0.2%) | 0 |
| Pancytopenia | 0 | 1 (0.2%) | 0 |
| Any serious TEAE | 18 (3.8%) | 19 (4.1%) | 9 (3.9%) |
| Immune system disorders | 0 | 0 | 1 (0.4%) |
| Anaphylactic reaction | 0 | 0 | 1 (0.4%) |
| Metabolism and nutrition disorders | 0 | 0 | 2 (0.9%) |
| Diabetes mellitus inadequate control | 0 | 0 | 1 (0.4%) |
| Metabolic acidosis | 0 | 0 | 1 (0.4%) |
| Nervous system disorders | 1 (0.2%) | 1 (0.2%) | 2 (0.9%) |
| Lacunar infarction | 0 | 1 (0.2%) | 0 |
| Radiculopathy | 0 | 0 | 1 (0.4%) |
| Transient ischaemic attack | 1 (0.2%) | 0 | 1 (0.4%) |
| Cardiac disorders | 2 (0.4%) | 6 (1.3%) | 0 |
| Acute myocardial infarction | 0 | 1 (0.2%) | 0 |
| Cardiac failure acute | 0 | 1 (0.2%) | 0 |
| Cardiac failure chronic | 0 | 1 (0.2%) | 0 |
| Cardiac failure congestive | 1 (0.2%) | 1 (0.2%) | 0 |
| Coronary artery disease | 0 | 1 (0.2%) | 0 |
| Myocardial infarction | 0 | 1 (0.2%) | 0 |
| Palpitations | 1 (0.2%) | 0 | 0 |
| Vascular disorders | 1 (0.2%) | 1 (0.2%) | 0 |
| Hypertension | 1 (0.2%) | 1 (0.2%) | 0 |
| Respiratory, thoracic and mediastinal disorders | 0 | 3 (0.6%) | 1 (0.4%) |
| Acute pulmonary oedema | 0 | 1 (0.2%) | 0 |
| Chronic obstructive pulmonary disease | 0 | 1 (0.2%) | 0 |
| Any serious TEAE | 18 (3.8%) | 19 (4.1%) | 9 (3.9%) |
| Dyspnoea | 0 | 1 (0.2%) | 0 |
| Respiratory failure | 0 | 0 | 1 (0.4%) |
| Gastrointestinal disorders | 1 (0.2%) | 0 | 0 |
| Oesophagitis | 1 (0.2%) | 0 | 0 |
| Hepatobiliary disorders | 1 (0.2%) | 0 | 0 |
| Cholecystitis chronic | 1 (0.2%) | 0 | 0 |
| Skin and subcutaneous tissue disorders | 2 (0.4%) | 0 | 0 |
| Angioedema | 1 (0.2%) | 0 | 0 |
| Urticaria | 1 (0.2%) | 0 | 0 |
| Musculoskeletal and connective tissue disorders | 0 | 1 (0.2%) | 1 (0.4%) |
| Costochondritis | 0 | 1 (0.2%) | 0 |
| Spinal osteoarthritis | 0 | 0 | 1 (0.4%) |
| Renal and urinary disorders | 1 (0.2%) | 2 (0.4%) | 1 (0.4%) |
| Acute kidney injury | 0 | 0 | 1 (0.4%) |
| Bladder prolapse | 0 | 1 (0.2%) | 0 |
| Calculus urinary | 0 | 1 (0.2%) | 0 |
| Hydronephrosis | 0 | 1 (0.2%) | 0 |
| Renal colic | 1 (0.2%) | 0 | 0 |
| Reproductive system and breast disorders | 3 (0.6%) | 0 | 0 |
| Acquired phimosis | 1 (0.2%) | 0 | 0 |
| Any serious TEAE | 18 (3.8%) | 19 (4.1%) | 9 (3.9%) |
| Cervical dysplasia | 1 (0.2%) | 0 | 0 |
| Metrorrhagia | 1 (0.2%) | 0 | 0 |
| General disorders and administration site conditions | 0 | 1 (0.2%) | 1 (0.4%) |
| Death | 0 | 0 | 1 (0.4%) |
| Non-cardiac chest pain | 0 | 1 (0.2%) | 0 |
| Investigations | 1 (0.2%) | 1 (0.2%) | 0 |
| Electrocardiogram ST-T segment abnormal | 1 (0.2%) | 0 | 0 |
| Lipase increased | 0 | 1 (0.2%) | 0 |
| Injury, poisoning and procedural complications | 1 (0.2%) | 1 (0.2%) | 1 (0.4%) |
| Comminuted fracture | 0 | 1 (0.2%) | 0 |
| Tendon rupture | 1 (0.2%) | 0 | 0 |
| Toxicity to various agents | 0 | 0 | 1 (0.4%) |

TEAE: Treatment Emergent Adverse Event, SOC: System Organ Class, PT: Preferred Term.
MedDRA 18.0
n (%) = number and percentage of patients with at least one serious TEAE.
Note:
Table sorted by SOC internationally agreed order and PT alphabetic order.

3.3.2 Adverse Events Leading to Withdrawal

TABLE 23

Number (%) of patients experiencing TEAE(s) leading to permanent treatment discontinuation by primary SOC and PT-Safety population

| Primary System Organ Class Preferred Term [n (%)] | Fixed Ratio Combination (N = 469) | Insulin Glargine (N = 467) | Lixisenatide (N = 233) |
|---|---|---|---|
| Any TEAE leading to permanent treatment discontinuation | 12 (2.6%) | 9 (1.9%) | 21 (9.0%) |
| Infections and infestations | 1 (0.2%) | 1 (0.2%) | 1 (0.4%) |
| Bacteraemia | 0 | 0 | 1 (0.4%) |
| Bronchitis | 0 | 1 (0.2%) | 0 |
| Extradural abscess | 0 | 0 | 1 (0.4%) |
| Meningitis staphylococcal | 0 | 0 | 1 (0.4%) |
| Urinary tract infection | 1 (0.2%) | 0 | 0 |
| Neoplasms benign, malignant and unspecified (incl cysts and polyps) | 1 (0.2%) | 1 (0.2%) | 1 (0.4%) |
| Lung cancer metastatic | 1 (0.2%) | 0 | 0 |
| Lung neoplasm malignant | 0 | 0 | 1 (0.4%) |
| Pancreatic carcinoma | 0 | 1 (0.2%) | 0 |
| Immune system disorders | 0 | 1 (0.2%) | 1 (0.4%) |
| Anaphylactic reaction | 0 | 0 | 1 (0.4%) |
| Drug hypersensitivity | 0 | 1 (0.2%) | 0 |
| Metabolism and nutrition disorders | 0 | 0 | 1 (0.4%) |
| Decreased appetite | 0 | 0 | 1 (0.4%) |
| Any TEAE leading to permanent treatment discontinuation | 12 (2.6%) | 9 (1.9%) | 21 (9.0%) |
| Psychiatric disorders | 1 (0.2%) | 1 (0.2%) | 0 |
| Depression | 0 | 1 (0.2%) | 0 |
| Insomnia | 1 (0.2%) | 0 | 0 |
| Nervous system disorders | 0 | 1 (0.2%) | 1 (0.4%) |
| Diabetic mononeuropathy | 0 | 0 | 1 (0.4%) |
| Headache | 0 | 1 (0.2%) | 1 (0.4%) |
| Cardiac disorders | 1 (0.2%) | 3 (0.6%) | 1 (0.4%) |
| Acute myocardial infarction | 0 | 1 (0.2%) | 0 |
| Atrial fibrillation | 0 | 0 | 1 (0.4%) |
| Cardiac failure acute | 0 | 1 (0.2%) | 0 |
| Cardiac failure congestive | 1 (0.2%) | 0 | 0 |
| Myocardial infarction | 0 | 1 (0.2%) | 0 |
| Respiratory, thoracic and mediastinal disorders | 0 | 2 (0.4%) | 0 |
| Acute pulmonary oedema | 0 | 1 (0.2%) | 0 |
| Cough | 0 | 1 (0.2%) | 0 |
| Gastrointestinal disorders | 4 (0.9%) | 1 (0.2%) | 12 (5.2%) |
| Abdominal distension | 0 | 0 | 1 (0.4%) |
| Abdominal pain | 0 | 0 | 1 (0.4%) |
| Colitis | 0 | 0 | 1 (0.4%) |
| Diarrhoea | 1 (0.2%) | 0 | 2 (0.9%) |
| Dyspepsia | 0 | 1 (0.2%) | 0 |
| Gastritis erosive | 0 | 0 | 1 (0.4%) |
| Any TEAE leading to permanent treatment discontinuation | 12 (2.6%) | 9 (1.9%) | 21 (9.0%) |
| Nausea | 2 (0.4%) | 0 | 6 (2.6%) |
| Vomiting | 2 (0.4%) | 0 | 4 (1.7%) |
| Skin and subcutaneous tissue disorders | 4 (0.9%) | 1 (0.2%) | 1 (0.4%) |
| Rash | 0 | 1 (0.2%) | 0 |
| Skin burning sensation | 1 (0.2%) | 0 | 0 |
| Urticaria | 3 (0.6%) | 0 | 1 (0.4%) |
| Musculoskeletal and connective tissue disorders | 1 (0.2%) | 0 | 0 |
| Back pain | 1 (0.2%) | 0 | 0 |
| General disorders and administration site conditions | 0 | 1 (0.2%) | 2 (0.9%) |
| Death | 0 | 0 | 1 (0.4%) |
| Fatigue | 0 | 1 (0.2%) | 0 |
| Injection site erythema | 0 | 0 | 1 (0.4%) |
| Investigations | 0 | 1 (0.2%) | 2 (0.9%) |
| Alanine aminotransferase increased | 0 | 0 | 1 (0.4%) |
| Blood creatinine increased | 0 | 0 | 1 (0.4%) |
| Lipase increased | 0 | 1 (0.2%) | 0 |
| Any TEAE leading to permanent treatment discontinuation | 12 (2.6%) | 9 (1.9%) | 21 (9.0%) |
| Injury, poisoning and procedural complications | 0 | 1 (0.2%) | 0 |
| Comminuted fracture | 0 | 1 (0.2%) | 0 |

TEAE: Treatment Emergent Adverse Event, SOC: System Organ Class, PT: Preferred Term.
MedDRA 18.0
n (%) = number and percentage of patients with at least one TEAE leading to permanent treatment discontinuation.
Note:
Table sorted by SOC internationally agreed order and PT alphabetic order.

TABLE 24

Number (%) of patients experiencing injection site reactions during the on-treatment period-Safety population

| Event source Preferred Term | Fixed Ratio Combination (N = 469) | Insulin Glargine (N = 467) | Lixisenatide (N = 233) |
|---|---|---|---|
| Any injection site reactions | 12 (2.6%) | 8 (1.7%) | 7 (3.0%) |
| PTs coded from the investigator reported terms | 12 (2.6%) | 8 (1.7%) | 7 (3.0%) |
| Injection site bruising | 4 (0.9%) | 4 (0.9%) | 0 |
| Injection site pain | 2 (0.4%) | 2 (0.4%) | 3 (1.3%) |
| Injection site reaction | 2 (0.4%) | 1 (0.2%) | 2 (0.9%) |
| Injection site discomfort | 1 (0.2%) | 0 | 0 |
| Injection site irritation | 1 (0.2%) | 0 | 0 |
| Injection site nodule | 1 (0.2%) | 0 | 0 |
| Injection site papule | 1 (0.2%) | 0 | 0 |
| Injection site rash | 1 (0.2%) | 0 | 0 |
| Injection site erythema | 0 | 0 | 2 (0.9%) |
| Injection site haemorrhage | 0 | 2 (0.4%) | 0 |
| Injection site swelling | 0 | 1 (0.2%) | 0 |
| Injection site warmth | 0 | 1 (0.2%) | 0 |
| PTs coded from the ARAC diagnosis terms | 2 (0.4%) | 0 | 2 (0.9%) |
| Injection site reaction | 2 (0.4%) | 0 | 2 (0.9%) |

ARAC = Allergic Reaction Assessment Committee, PT = Preferred term.

One case of injection site erythema reported in the lixisenatide group led to treatment discontinuation. A 56-year old female patient developed erythema at the site of the lixisenatide injection (abdomen and anterior regions of the thighs), accompanied by local swelling and itching. Injection site erythema of mild intensity was diagnosed, and subsequently the patient permanently discontinued IMP. No corrective treatment was given and the patient recovered without sequelae. The Investigator considered the event to be related to IMP.

TABLE 25

Number (%) of patients with events adjudicated as allergic reaction by ARAC during the on-treatment period-Safety population

| Relationship to Study Treatment (by ARAC) | ARAC Diagnosis Categories | MedDRA Coded Term (PT) for ARAC Diagnosis | Fixed Ratio Combination (N = 469) | Insulin Glargine (N = 467) | Lixisenatide (N = 233) |
|---|---|---|---|---|---|
| All | Any category | Any event | 6 (1.3%) | 3 (0.6%) | 2 (0.9%) |
|  | Urticaria (hives) | Urticaria | 3 (0.6%) | 1 (0.2%) | 1 (0.4%) |
|  | Angioedema | Angioedema | 3 (0.6%) | 0 | 0 |
|  | Anaphylactic reaction | Anaphylactic reaction | 0 | 0 | 1 (0.4%) |
|  | Other allergic reaction | Conjunctivitis allergic | 0 | 1 (0.2%) | 0 |
| All | Any category | Any event | 6 (1.3%) | 3 (0.6%) | 2 (0.9%) |
|  |  | Rhinitis allergic | 0 | 2 (0.4%) | 0 |
| Possibly related to IMP | Any category | Any event | 3 (0.6%) | 0 | 2 (0.9%) |
|  | Urticaria (hives) | Urticaria | 3 (0.6%) | 0 | 1 (0.4%) |
|  | Anaphylactic reaction | Anaphylactic reaction | 0 | 0 | 1 (0.4%) |
| Not related to IMP | Any category | Any event | 3 (0.6%) | 3 (0.6%) | 0 |
|  | Urticaria (hives) | Urticaria | 0 | 1 (0.2%) | 0 |
|  | Angioedema | Angioedema | 3 (0.6%) | 0 | 0 |
|  | Other allergic reaction | Conjunctivitis allergic | 0 | 1 (0.2%) | 0 |
|  |  | Rhinitis allergic | 0 | 2 (0.4%) | 0 |

ARAC = Allergic Reaction Assessment Committee, IMP = Investigational medicinal product.

One allergic event adjudicated as anaphylactic reaction by the ARAC was reported in the lixisenatide group and occurred in a 60 year-old female patient 1 hour after IMP administration. The patient developed generalized itching, skin eruption, hand and face edema, and wheezing. She was taken to the emergency room and recovered following intramuscular dexamethasone.

TABLE 26

Number (%) of patients with pancreatic events positively adjudicated by PSAC during the on-treatment period-Safety population

|  | Fixed Ratio Combination (N = 469) | Insulin Glargine (N = 467) | Lixisenatide (N = 233) |
|---|---|---|---|
| Any with "Yes" for pancreatitis by PSAC | 0 | 0 | 0 |
| Acute pancreatitis | 0 | 0 | 0 |
| Acute on chronic pancreatitis | 0 | 0 | 0 |
| Chronic pancreatitis | 0 | 0 | 0 |
| Unknown pancreatitis | 0 | 0 | 0 |

PSAC = Pancreatic Safety Assessment Committee.

Note:
The on-treatment period is defined as the time from the first injection of IMP up to 3 days after the last injection of IMP, regardless of the introduction of rescue therapy.

One case of pancreatic cancer was reported in the insulin glargine group. A 75 year-old male patient was diagnosed with pancreatic carcinoma and permanently discontinued insulin glargine. Two months afterwards the patient died of gastrointestinal hemorrhage. The patient had a history of peptic ulcer disease. This fatal event was considered not to be possibly related to IMP by the Investigator. The case was adjudicated by PSAC as pancreatic carcinoma not related to IMP.

TABLE 27

Number (%) of patients with events adjudicated as major cardiovascular events by CAC during the on-treatment period-Safety population

| n (%) | Fixed Ratio Combination (N = 469) | Insulin Glargine (N = 467) | Lixisenatide (N = 233) |
|---|---|---|---|
| Any | 2 (0.4%) | 7 (1.5%) | 2 (0.9%) |
| Cardiovascular death | 1 (0.2%) | 2 (0.4%) | 1 (0.4%) |
| Non-fatal myocardial infarction | 0 | 0 | 0 |
| Non-fatal stroke | 0 | 1 (0.2%) | 1 (0.4%) |
| Hospitalization for unstable angina | 1 (0.2%) | 1 (0.2%) | 0 |
| Hospitalization for heart failure | 0 | 2 (0.4%) | 0 |
| Coronary revascularization procedure | 0 | 1 (0.2%) | 0 |

CAC = Cardiovascular Events Adjudication Committee n (%) = number and percentage of patients with events adjudicated as major cardiovascular events by CAC.

TABLE 28

Number (%) of patients with events reported on the AE form for increased calcitonin (≥20 ng/L) during the on-treatment period-Safety population

| Preferred Term | Fixed Ratio Combination (N = 469) | Insulin Glargine (N = 467) | Lixisenatide (N = 233) |
|---|---|---|---|
| Any | 0 | 1 (0.2%) | 0 |
| Blood calcitonin increased | 0 | 1 (0.2%) | 0 | n (%) = number and percentage of patients with any cases reported on the AE form for increased calcitonin ≥20 pg/mL along with complementary form.

TABLE 29

Number (%) of patients with events reported on the AE form for ALT increase during the on-treatment period-Safety population

| Preferred Term | Fixed Ratio Combination (N = 469) | Insulin Glargine (N = 467) | Lixisenatide (N = 233) |
|---|---|---|---|
| Any | 1 (0.2%) | 2 (0.4%) | 1 (0.4%) |
| Alanine aminotransferase increased | 1 (0.2%) | 2 (0.4%) | 1 (0.4%) | n (%) = number and percentage of patients with any cases reported on the AE form for ALT increase along with complementary form.

TABLE 30

Number (%) of patients with events reported in pen-related event questionnaire during the on-treatment period-Safety population

| | Fixed Ratio Combination (N = 469) | Insulin Glargine (N = 467) | Lixisenatide (N = 233) |
|---|---|---|---|
| Any pen-related events | 25 (5.3%) | 10 (2.1%) | 9 (3.9%) |
| Associated with a clinical event | 0 | 0 | 0 |
| Not associated with a clinical event | 25 (5.3%) | 10 (2.1%) | 9 (3.9%) |

Clinical event = symptomatic hypoglycemic event, hyperglycemic adverse event or other adverse event collected in pen-related questionnaire.

3.3.3 Other Safety Observation—Symptomatic Hypoglycemia

TABLE 31

Summary of symptomatic hypoglycemia recorded on the dedicated eCRF page and meeting protocol definition during the on-treatment period-Safety population

| | Fixed Ratio Combination (N = 469) | Insulin Glargine (N = 467) | Lixisenatide (N = 233) |
|---|---|---|---|
| Total patient years of exposure | 263.1 | 262.5 | 125.2 |
| Symptomatic hypoglycemia | | | |
| Number of patients with events, n (%) | 128 (27.3%) | 119 (25.5%) | 15 (6.4%) |
| Number of patients with events per patient year$^a$ | 0.49 | 0.45 | 0.12 |
| Number of events | 409 | 338 | 46 |
| Number of events per patient year$^b$ | 1.55 | 1.29 | 0.37 |
| Documented symptomatic hypoglycemia (plasma glucose ≤70 mg/dL [3.9 mmol/L]) | | | |
| Total patient years of exposure | 263.1 | 262.5 | 125.2 |
| Number of patients with events, n (%) | 120 (25.6%) | 110 (23.6%) | 15 (6.4%) |
| Number of patients with events per patient year$^a$ | 0.46 | 0.42 | 0.12 |
| Number of events | 378 | 321 | 43 |
| Number of events per patient year$^b$ | 1.44 | 1.22 | 0.34 |
| Documented symptomatic hypoglycemia (plasma glucose <60 mg/dL [3.3 mmol/L]) | | | |
| Number of patients with events, n (%) | 66 (14.1%) | 50 (10.7%) | 6 (2.6%) |
| Number of patients with events per patient year$^a$ | 0.25 | 0.19 | 0.05 |
| Number of events | 128 | 75 | 13 |
| Number of events per patient year$^b$ | 0.49 | 0.29 | 0.10 |
| Probable symptomatic hypoglycemia | | | |
| Number of patients with events, n (%) | 17 (3.6%) | 12 (2.6%) | 2 (0.9%) |
| Number of patients with events per patient year$^a$ | 0.06 | 0.05 | 0.02 |
| Number of events | 31 | 16 | 3 |
| Number of events per patient year$^b$ | 0.12 | 0.06 | 0.02 |
| Severe symptomatic hypoglycemia | | | |
| Number of patients with events, n (%) | 0 | 1 (0.2%) | 0 |
| Number of patients with events per patient year$^a$ | 0 | <0.01 | 0 |
| Number of events | 0 | 1 | 0 |

TABLE 31-continued

Summary of symptomatic hypoglycemia recorded on the dedicated eCRF page and meeting protocol definition during the on-treatment period-Safety population

|  | Fixed Ratio Combination (N = 469) | Insulin Glargine (N = 467) | Lixisenatide (N = 233) |
| --- | --- | --- | --- |
| Total patient years of exposure | 263.1 | 262.5 | 125.2 |
| Number of events per patient year[b] | 0 | <0.01 | 0 |

IMP: Investigational Medicinal Product, eCRF: electronic Case Report Form.
Patient years of exposure: calculated as time from the first to the last injection of IMP plus 1 day.
[a]:Calculated as number of patients with events divided by total patient years of exposure..
[b]:Calculated as number of events divided by total patient years of exposure.
Symptomatic hypoglycemia = symptomatic hypoglycemia recorded on the dedicated eCRF and meeting protocol definition for severe, or documented, or probable symptomatic hypoglycemia.

On-treatment period is defined as the time from the first injection of IMP up to 1 day for symptomatic hypoglycemia after the last injection of IMP, regardless of the introduction of rescue therapy.

EXAMPLE 3

A randomized, 30-week, active-controlled, open label, 2-treatment arm, parallel-group, multicenter study comparing the efficacy and safety of the insulin glargine/lixisenatide fixed ratio combination to insulin glargine with or without metformin in patients with T2DM
AE: Adverse event
ALT: Alanine aminotransferase
ARAC: Allergic Reaction Assessment Committee
ANCOVA: Analysis of covariance
BMI: Body mass index
CAC: Cardiovascular Events Adjudication Committee
CI: Confidence interval
CMH: Cochran-Mantel-Haenszel
ECG: Electrocardiogram
FPG: Fasting plasma glucose
GFR: Glomerular filtration rate
GLP-1: Glucagon-like peptide-1
HbA1 Glycosylated hemoglobin
cIMP: Investigational medicinal product
LOCF: Last observation carried forward
LS: Least squares
mITT: Modified Intent-To-Treat
OAD: Oral anti-diabetic drug
PG: Plasma glucose
PPG: Post-prandial plasma glucose
PSAC: Pancreas Safety Assessment Committee
PT: Preferred term
SAE: Serious adverse event
SD: Standard deviation
SMPG: Self-monitored plasma glucose
SOC: System orgn class
TEAE: Treatment-emergent adverse event
ULN Upper limit of normal

2 SYNOPSIS

Title of the Study:
A randomized, 30-week, active-controlled, open label, 2-treatment arm, parallel-group, multicenter study comparing the efficacy and safety of the insulin glargine/lixisenatide fixed ratio combination to insulin glargine with or without metformin in patients with T2DM Study Center(s):
Multicenter (236 centers in 18 countries)
Phase of Development:
Phase 3
Objectives:
Primary Objective
To demonstrate the superiority of the insulin glargine/lixisenatide fixed ratio combination to insulin glargine in HbA1c change from baseline to Week 30.
Secondary Objective(s)
To assess the effects of the insulin glargine/lixisenatide fixed ratio combination in comparison with insulin glargine over 30 weeks on:
  Percentage of patients reaching HbA1c targets,
  Glycemic control in relation to a meal as evaluated by 2-hour post-prandial plasma glucose (PPG) and glucose excursion during a standardized meal test,
  Body weight,
  7-point self-monitored plasma glucose (SMPG) profile,
  Percentage of patients reaching HbA1c targets with no body weight gain and/or documented symptomatic hypoglycemia,
  Insulin glargine dose,
  Fasting plasma glucose (FPG).
To assess the safety and tolerability in each treatment group.
Methodology:
This was an open-label, 1:1 randomized, active-controlled, 2-arm, 30-week treatment duration, parallel-group multinational and multicenter study. The randomization was stratified by value of HbA1cat Visit 5 (Week −1) (<8%, 8%) and metformin use at screening (Y, N).
The study comprised 3 periods:
  An up-to 8-week screening period, which included an up to 2-week screening phase and a 6-week run-in phase with switching to (if appropriate) and/or titration/stabilization of insulin glargine dose, continuation of metformin (if appropriate) and discontinuation of sulfonylurea (SU), glinide, sodium-glucose co-transporter 2 inhibitor (SGLT-2i) or dipeptidyl-peptidase-4 inhibitor (DPP-4i) if previously taken at Visit 2
  A 30-week open-label randomized treatment period
  A 3-day post-treatment safety follow-up period

| Number of patients: | Planned: 700; Randomized: 736; Treated: 730 |
| --- | --- |
| Evaluated: | Efficacy: 731 Safety: 730 |

Diagnosis and criteria for inclusion: Inclusion criteria: Patients with type 2 diabetes mellitus diagnosed for at least 1 year and inadequately controlled on their current antidiabetic treatment. Patients had to be treated with basal insulin for at least 6 months at a stable daily dose of 15 to 40 U, alone or combined with 1 or 2 oral anti-diabetic drugs ((metformin, an SU, a glinide, a DPP-4 inhibitor, or a SGLT-2 inhibitor) at a stable dose for at least 3 months. Key exclusion criteria for randomization (at the end of the run-in phase): HbA1c<7% or >10% at Visit 5 (week-1); mean fasting SMPG>140 mg/dL (7.8 mmol/L) for the 7 days before the randomization Visit (Visit 6); average insulin glargine daily dose <20 U or >50 U calculated for the last 3 days before Visit 6.

Study Treatments

Investigational Medicinal Product(s) (IMPs):

Insulin glargine/lixisenatide fixed ratio combination and insulin glargine (Lantus)

Formulation:

Test Drug: Insulin Glargine/Lixisenatide Fixed Ratio Combination

Insulin glargine/lixisenatide fixed ratio combination (hereafter referred to as fixed ratio combination) was supplied as a sterile aqueous solution in a pre-filled disposable SoloStar® pen-injector.

Two pens (A and B) with different fixed ratios were available to allow insulin glargine titration over a range of 10 to 60 U/day while limiting the lixisenatide dose to a maximum of 20 g/day:

Pen A contained 100 U/mL of insulin glargine and 50 μg of lixisenatide in a ratio of 2:1 (2 units of insulin glargine per 1 μg lixisenatide). Doses could be set from 10 to 40 units in steps of 1 unit, allowing administration of daily combination doses between 10 U/5 μg and 40 U/20 μg Pen B contained 100 U/mL insulin glargine and 33 μg/mL lixisenatide in a ratio of 3:1. Doses could be set from 30 to 60 units in steps of 1 unit, allowing administration of daily combination doses between 30 U/10 μg and 60 U/20 μg.

The maximum daily dose was 60 units (60 U insulin glargine and 20 μg lixisenatide).

Control Drug: Insulin Glargine (Lantus)

Insulin glargine was supplied as a sterile aqueous solution in a pre-filled disposable SoloStar® pen-injector (100 U/mL glargine). Doses could be set from 1 to 80 units in steps of 1 unit. However, in this study the maximum insulin glargine daily dose allowed was 60 U.

Route of administration: subcutaneous injection self-administered

Dose Regimen:

During Run-in Phase

Starting from Visit 2, insulin glargine was the only basal insulin allowed. Patients receiving any basal insulin other than insulin glargine before screening switched to once daily insulin glargine at Visit 2.1 nsulin glargine was administered at any time of the day and at around the same time every day. The injection time was selected at the discretion of the patient and the investigator at Visit 2 and was to remain the same throughout the study (during the run-in phase for all patients and during the randomized treatment period for patients randomized to insulin glargine).

During the Open-Label Randomized Treatment Period

The combination treatment was injected once daily within the house before breakfast. The starting dose was 20 U/10 μg given with Pen A if the insulin glargine dose on the day before randomization was <30 U, and 30 U/10 μg given with Pen B if the insulin glargine dose on the day before randomization was ≥30 U. The dose was kept stable for 2 weeks, then titrated once a week based on the insulin glargine dose, to reach and maintain a target fasting SMPG of 80 to 100 mg/dL [4.4 to 5.6 mmol/L] while avoiding hypoglycemia episodes.

Patients randomized to insulin glargine started the randomized treatment period with the same daily dose as that received the day before randomization, with subsequent insulin dose titration as necessary.

The same dose adjustment algorithm was recommended for insulin glargine/lixisenatide fixed ratio combination and insulin glargine.

Noninvestigational Medicinal Product(s):

Background treatment metformin (if taken) and rescue therapy were considered as NIMP(s)

Metformin: tablets, administered orally. Dose regimen was in accordance with locally approved label. If previously taken, was to be continued at a stable dose throughout the study unless prevented by a specific safety issue related to this treatment.

Other Oral anti-diabetic treatment: SUs, glinides, SGLT-2 inhibitors and DPP-4 inhibitors, if previously taken, were stopped at the start of run-in (Visit 2).

Rescue Therapy:

Routine fasting SMPG and central lab alerts on FPG (and HbA1c after Week 12) were set up to ensure that glycemic parameters remained under predefined threshold values. If values were above predefined thresholds, and no explanations were found, or appropriate actions failed, or a dose >60 U was necessary to decrease FPG and/or HbA1c below the threshold values, rescue therapy was to be introduced along with IMP and metformin (if taken). Newly initiated anti-diabetic medications, or an increase from baseline in background metformin dose were considered as a rescue therapy.

Duration of Treatment:

Up to 30 weeks

Duration of Observation:

Up to 39 weeks (up to 8-week screening period+30-week randomized treatment period+3-day post treatment safety follow-up)

Criteria for Evaluation:

Efficacy:

Primary efficacy endpoint: Change in HbA1c from baseline to Week 30.

Secondary efficacy endpoints: percent of patients with HbA1c<7% or 6.5% at Week 30, change from baseline to Week 30 in 2-hour postprandial plasma glucose and plasma glucose excursion, body weight, average 7-point SMPG; percentage of patients reaching HbA1c<7% with no body weight gain at Week 30 and/or with no documented (PG 70 mg/dL [3.9 mmol/L]) symptomatic hypoglycemia during the 30-week randomized treatment period; change in daily dose of insulin glargine; change in fasting plasma glucose; percentage of patients requiring rescue therapy during the 30-week randomized treatment period.

Safety:

Symptomatic hypoglycemia

Documented: typical symptoms of hypoglycemia with a plasma glucose concentration 70 mg/dL (3.9 mmol/L)

Probably: symptoms of hypoglycemia without plasma glucose determination, but was presumably caused by a plasma glucose concentration 70 mg/dL (3.9 mmol/L)

Severe: event requiring assistance of another person to actively administer carbohydrate, glucagon, or other resuscitative actions Treatment-emergent adverse events (TEAEs), serious TEAEs, TEAEs leading to death, TEAEs leading to treatment discontinuation, adverse events of special interest (EASIs) (i.e., increase in alanine aminotransferase (ALT), pregnancy, symptomatic overdose with IMP/NIMP), major cardiovascular events, potential allergic reactions, pancreatic events (confirmed increased amylase/lipase >2× upper limit of normal (ULN), pancreatitis, pancreatic neoplasm, events of confirmed increased calcitonin 20 pg/mL (5.9 pmol/L), pen-related events Safety laboratory data (hematology, clinical chemistry, lipase/amylase and calcitonin)

Statistical Methods:

Efficacy analysis was based on modified intent-to-treat (mITT) population using efficacy assessment collected during the study, including those obtained after IMP discontinuation or introduction of rescue therapy. The mITT population consisted of all randomized patients who had both a baseline assessment and at least one post-baseline assessment of any primary or secondary efficacy variables.

The primary efficacy endpoint was analyzed using a mixed-effect model with repeated measures (MMRM). The MMRM model included the treatment groups, randomization strata, visit, treatment-by-visit interaction, and country as fixed-effect factors, and the baseline HbA1c-by-visit interaction as covariate. The adjusted mean change in HbA1c from baseline to Week 30 for each treatment group was estimated in the framework of this model, as well as the between-group difference and the 95% CI for the adjusted mean.

Similar MMRM method or analysis of covariance (ANCOVA) was applied on continuous secondary efficacy endpoints and the Cochran-Mantel-Haenszel method stratified by randomization strata was applied for categorical efficacy endpoints.

A step-down testing procedure was applied in order to control the type 1 error. Once the primary endpoint was statistically significant at the 5% 2-sided level, testing was performed on selected secondary endpoints in the following order: 2-hour plasma glucose excursion, body weight, average 7-point SMPG, percent of patients reaching HbA1c<7% with no body weight gain at Week 30, daily dose of insulin glargine, percentage of patients reaching HbA1c<7% with no body weight gain at Week 30 and with no documented symptomatic hypoglycemia, and FPG. When an endpoint was not statistically significant at the 5% level, subsequent tests were not performed.

SUMMARY

Population Characteristics:

A total of 736 patients were randomized to one of the two treatment groups (367 in the insulin glargine/lixisenatide fixed ratio combination group, 369 in the insulin glargine group).

A total of 731 randomized patients were included in the mITT population for efficacy analyses and 730 randomized patients were exposed to open-label treatment and included in the safety population (Table 1). Demographics and baseline characteristics were generally similar between the two treatment groups. The median age was 60.0 years, the mean diabetes duration was about 12 years and the mean BMI was about 31 kg/m$^2$ at screening. The study population was primarily Caucasian (91.7%), and 53.3% of the population were female (Table 3).

Efficacy Results:

Primary Efficacy Endpoint:

The primary objective of the study was met as statistical superiority of the fixed ratio combination over insulin glargine was demonstrated in change in HbA1c from baseline to Week 30.

The least squared (LS) mean changes in HbA1c from baseline to Week 30 were −1.13% for the fixed ratio combination group and −0.62% for the insulin glargine group, reaching mean HbA1c levels of 6.9% and 7.5% at Week 30, respectively.

Statistical superiority of the fixed ratio combination over insulin glargine was demonstrated (LS mean difference=−0.52%, 95% CI: −0.633% to −0.397%, p<0.0001) (Table 8).

Secondary Efficacy Endpoints:

At Week 30, significantly more patients treated with the combination (54.9%) reached an HbA1c<7.0% compared to those receiving insulin glargine (29.6%) with a difference of 25.5% and p<0.0001. In addition, the percentage of patients reaching HbA1c≤6.5% was significantly higher in the combination group (33.9%) than in the insulin glargine group (14.2%) (difference=19.76%, p<0.0001) (Table 9).

Treatment with the combination significantly improved postprandial glycemic control during a standardized liquid breakfast meal in comparison to insulin glargine as shown by the results for the mean change in 2-hour glucose excursion from baseline to Week 30 (LS mean was −3.90 and −0.47 mmol/L, respectively; difference=−3.43 mmol/L, p<0.0001) (Table 10). For the 2-hour PPG assessment the LS mean change was −4.72 in the combination group and −1.39 mmol/L in the insulin glargine group with a difference of −3.33 mmol/L and 95% CI: −3.889 mmol/L to −2.774 mmol/L (Table 11).

Body weight decreased in the combination group and increased in the insulin glargine group with LS mean changes from baseline to Week 30 of −0.67 kg and +0.70 kg, respectively. The difference (−1.37 kg) between the two groups was statistically significant (p<0.0001) (Table 12).

Figure 12:
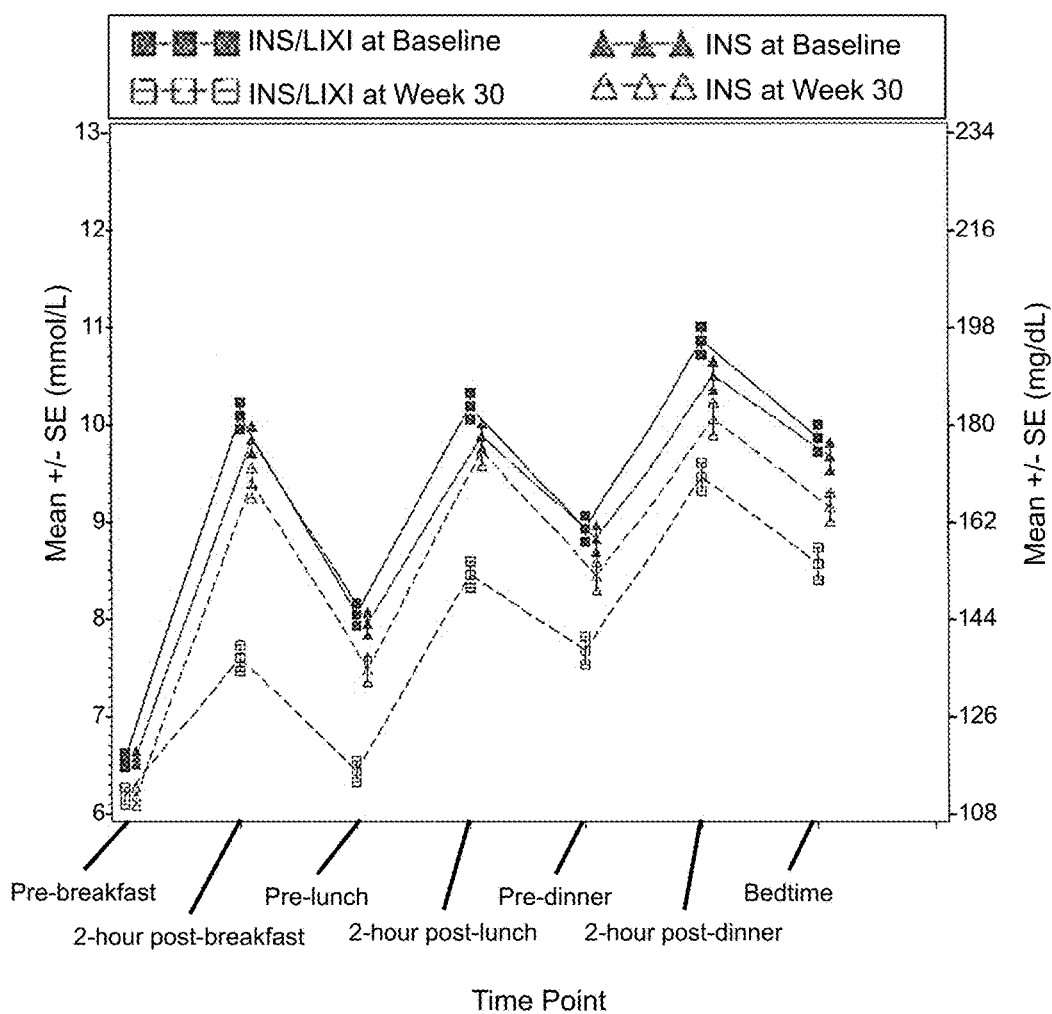
FIG. 12—Plot of mean 7-point SMPG at baseline and Week 30—mITT population. SMPG=Self-monitored plasma glucose. INS/LIXI=Fixed Ratio Combination, INS=Insulin Glargine. The analysis included all scheduled measurements obtained during the study, including those obtained after IMP discontinuation or introduction of rescue therapy.

Patients treated with the combination had a statistically significant greater decrease in average 7-point SMPG profiles compared to patients treated with insulin glargine (difference=−0.90 mmol/L, p<0.0001) (Table 13). Graphical presentation of the 7-point SMPG profiles showed that values at all time-points at Week 30 decreased from baseline in both treatment groups. After 30 weeks of treatment, the 7-point SMPG profiles showed that the values at all time-points were lower in the combination group compared to the insulin glargine group (except for the similar pre-breakfast values) (FIG. 12).

A significantly higher percentage of patients reached HbA1c<7.0% with no body weight gain at Week 30 in the fixed ratio combination group (34.2%) compared to the insulin glargine group (13.4%) with a difference of 20.82% and p<0.0001 (Table 14). The percentage of patients reaching HbA1c<7.0% at Week 30 with no documented symptomatic hypoglycemia during the 30-week treatment period was higher in the combination group (31.7%) compared to the insulin glargine group (18.6%) (difference=13.22%, 95% CI: 7.12% to 19.32%) (Table 18). Moreover, more patients reached HbA1c<7.0% with no body weight gain at Week 30 and with no documented symptomatic hypoglycemia during the 30-week treatment period in the combination group (19.9%) compared to the insulin glargine group (9.0%) (difference=10.94%, 95% CI: 5.93% to 15.96%) (Table 16).

A similar increase in the daily dose of insulin glargine from baseline was observed in both treatment groups (10.64 U in the combination group and 10.89 U in the insulin glargine group, difference=−0.26 U, p=0.7362) with a similar mean daily dose at Week 30 of about 47 U. (Table 15).

The LS mean reductions in FPG from baseline to Week 30 were similar in the combination group (−0.35 mmol/L) and the insulin glargine group (−0.46 mmol/L) (difference=0.11 mmol/L, 95% CI: −0.207 to 0.428) (Table 17).

A total of 10 (2.7%) patients in the combination group and 22 (6.0%) patients in the insulin glargine group received rescue therapy (difference=−3.35%, 95% CI: −6.33% to −0.36%) (Table 19).

Safety Results:

The fixed dose combination was overall well tolerated during the 30-week on-treatment period; the safety profile of the combination arm reflected those of its component parts.

A total of 195 (53.4%) patients in the combination group and 191 (52.3%) in the insulin glargine group reported treatment-emergent adverse events (Table 20).

The most frequently reported TEAEs in the combination group were nausea (10.4% versus 0.5% in the insulin glargine group), and nasopharyngitis in the insulin glargine group (8.8% versus 8.8% in the combination group). The incidence of gastrointestinal disorder (System organ class) events was 17.0% in the combination group and 7.9% in the insulin glargine group, in which nausea: 10.4% versus 0.5%, vomiting: 3.6% versus 0.5% and diarrhoea: 4.4% versus 2.7% were mainly reported in the corresponding groups. (Table 21).

Three patients experienced at least 1 TEAE leading to death: 1 from the combination group (PT: Pneumonia) and 2 from the insulin glargine group (PTs: Gallbladder cancer and Cardiopulmonary failure).

Serious TEAEs were reported by a similar proportion of patients in each treatment group: 20 (5.5%) patients in the combination group and 18 (4.9%) in the insulin glargine group (Table 22). There were no Suspected Unexpected Serious Adverse Reactions (SUSARs) reported in either group.

A higher number of patients withdrew from treatment due to TEAEs in the combination group (10 [2.7%]) than from the insulin glargine group (3 [0.8%]). The difference is mainly attributable to the number of patients discontinuing due to nausea (4 [1.1%] patients in the combination group versus none in the insulin glargine group) (Table 23).

A total of 2 patients (none in the combination group and 2 patients the insulin glargine group) experienced injection site reactions (Table 24). None of those reactions were considered serious or severe or led to treatment discontinuation.

One event of allergic rhinitis reported in the insulin glargine group was adjudicated by the Allergic Reaction Assessment Committee (ARAC) as allergic reaction not related to the IMP. No events in the combination group were adjudicated as an allergic reaction by the ARAC. (Table 25).

There were no cases of pancreatitis positively adjudicated by the Pancreatic Safety Assessment Committee (PSAC). In addition, no pancreatic neoplasms were reported in the study.

Five patients (1.4%) in the combination group and 4 patients (1.1%) in the insulin glargine group reported events adjudicated as major cardiovascular events by the Cardiovascular Events Adjudication Committee (CAC) (Table 26).

Two patients in the insulin glargine group reported a TEAE of increased calcitonin (≥20 pg/mL) versus none in the combination group (Table 27).

One patient in the combination group and 2 patients in the insulin glargine group experienced an AE of ALT increase during the on-treatment period (Table 28). No event met the definition for Hy's Law.

No symptomatic overdose with IMP was reported in either treatment group during the on-treatment period.

There was one pregnancy (in the insulin glargine group) reported during the treatment period with outcome of the pregnancy not available yet.

A total of 26 patients (the combination: 11 [3.0%] and insulin glargine: 15 [4.1%]) reported pen-related events in the pen-related event questionnaire during the on-treatment period. None was associated with a clinical event (i.e. symptomatic hypoglycemic event, hyperglycemic adverse event or any other adverse event) (Table 29).

Forty percent of the patients in the combination group and 42.5% of patients in the insulin glargine group reported at least one event of documented (PG 70 mg/dL) symptomatic hypoglycemia. The corresponding event rates per patient-year were 3.03 and 4.22, respectively.

Four patients (1.1%) in the combination group and 1 patient (0.3%) in the insulin glargine group reported 5 and 1 events of severe symptomatic hypoglycemia, respectively (Table 30). All events of severe symptomatic hypoglycemia were also reported as SAEs. Preliminary Conclusions:

The primary objective of the study was met as the statistical superiority of the fixed ratio combination over insulin glargine in HbA1c change from baseline to Week 30 was demonstrated. The fixed ratio combination with or without metformin for patients not adequately controlled with basal insulin with or without OADs significantly improved HbA1c, allowed more patients to reach HbA1c treatment target, reduced 2-hour glucose excursions and 2-hour PPG, average 7-point SMPG and body weight in comparison to insulin glargine.

The fixed ratio combination was well tolerated with a safety profile reflecting those of its component parts. Nausea was the most frequently reported adverse event in the combination group. The incidence of gastrointestinal TEAEs (nausea and vomiting) was reported less frequently in this study compared to what is usually reported with GLP-1 receptor agonists including lixisenatide. The incidence of symptomatic hypoglycemia was similar in the combination and insulin glargine treatment groups.

3 RESULTS 3.1 Study Patients 3.1.1 Patient Accountability

Of the 1930 patients screened, 1018 (52.7%) entered the 6-week run-in period and 736 were randomized to one of the two treatment groups (367 in the combination group and 369 in the insulin glargine group) in 187 centers across 18 countries (Australia, Canada, Chile, Czech Republic, Denmark, Estonia, Hungary, Lithuania, Mexico, Netherlands, Poland, Romania, Russian Federation, Slovakia, Spain, Sweden, Ukraine, and United States of America). The main reason for screening failure was an HbA1c value at the screening visit out of the protocol-defined range (458 [23.7%]).

A total of 731 randomized patients were included in the mITT population for efficacy analyses, and 730 randomized patients were exposed to open-label treatment and included in the safety population (Table 1). Five randomized patients (1 in the combination group and 4 in the insulin glargine) were not included in the mITT population because they did not have any post baseline efficacy data. Six patients were randomized but not treated: 5 of 6 patients were randomized by mistake as the patients were not eligible for randomization and one patient withdrew informed consent.

TABLE 1

Analysis populations-Randomized Population

|  | Fixed Ratio Combination | Insulin Glargine | All |
|---|---|---|---|
| Randomized population | 367 (100%) | 369 (100%) | 736 (100%) |
| Efficacy population | 366 (99.7%) | 365 (98.9%) | 731 (99.3%) |
| Modified Intent-to-Treat (MITT) |  |  |  |
| Safety population | 365 | 365 | 730 |

Note:
The safety population patients are tabulated according to treatment actually received (as treated).
For the efficacy population, patients are tabulated according to their randomized treatment.
There is no patient randomized in a group and taking another study treatment.
There is no patient having switched their treatment during the study.

3.1.2 Study Disposition

TABLE 2

Patient disposition-Randomized population

|  | Fixed Ratio Combination (N = 367) | Insulin Glargine (N = 369) |
|---|---|---|
| Randomized and treated | 365 (99.5%) | 365 (98.9%) |
| Completed the open-label study treatment period | 336 (91.6%) | 355 (96.2%) |
| Did not complete the open-label study treatment period | 29 (7.9%) | 10 (2.7%) |
| Subject's request for treatment discontinuation | 19 (5.2%) | 7 (1.9%) |
| Reason for study treatment discontinuation |  |  |
| Adverse event | 12 (3.3%) | 3 (0.8%) |
| Lack of efficacy | 0 | 0 |
| Poor compliance to protocol | 4 (1.1%) | 1 (0.3%) |
| Lost to follow-up | 1 (0.3%) | 0 |
| Other reasons | 12 (3.3%) | 6 (1.6%) |
| Status at last study contact |  |  |
| Alive | 366 (99.7%) | 367 (99.5%) |
| Dead | 1 (0.3%) | 2 (0.5%) |
| Lost to follow-up | 0 | 0 |

Note:
Percentages are calculated using the number of patients randomized as denominator.

3.1.3 Demographics and Baseline Characteristics

TABLE 3

Demographics and patient characteristics at screening or baseline-Randomized population

|  | Fixed Ratio Combination (N = 367) | Insulin Glargine (N = 369) | All (N = 736) |
|---|---|---|---|
| Age (years) |  |  |  |
| Number | 367 | 369 | 736 |
| Mean (SD) | 59.6 (9.4) | 60.3 (8.7) | 60.0 (9.1) |
| Median | 60.0 | 61.0 | 60.0 |
| Min:Max | 36:85 | 32:80 | 32:85 |

TABLE 3-continued

Demographics and patient characteristics at screening or baseline-Randomized population

|  | Fixed Ratio Combination (N = 367) | Insulin Glargine (N = 369) | All (N = 736) |
|---|---|---|---|
| Age group (years) [n (%)] |  |  |  |
| Number | 367 | 369 | 736 |
| <50 | 50 (13.6%) | 42 (11.4%) | 92 (12.5%) |
| ≥50 to <65 | 207 (56.4%) | 207 (56.1%) | 414 (56.3%) |
| ≥65 to <75 | 89 (24.3%) | 102 (27.6%) | 191 (26.0%) |
| ≥75 | 21 (5.7%) | 13 (4.9%) | 39 (5.3%) |
| Gender [n (%)] |  |  |  |
| Number | 367 | 369 | 736 |
| Male | 165 (45.0%) | 179 (48.5%) | 344 (46.7%) |
| Female | 202 (55.0%) | 190 (51.5%) | 392 (513%) |
| Race [n (%)] |  |  |  |
| Number | 367 | 369 | 736 |
| Caucasian/White | 337 (91.8%) | 338 (91.6%) | 675 (91.7%) |
| Black | 17 (4.6%) | 21 (5.7%) | 38 (5.2%) |
| Asian/Oriental | 12 (3.3%) | 8 (2.2%) | 20 (2.7%) |
| Other | 1 (0.3%) | 2 (0.5%) | 3 (0.4%) |
| Ethnicity [n (%)] |  |  |  |
| Number | 367 | 369 | 736 |
| Hispanic | 66 (18.0%) | 66 (17.9%) | 132 (17.9%) |
| Not Hispanic | 301 (82.0%) | 303 (82.1%) | 604 (82.1%) |
| HbA1c (%) at visit 1 (Week −8) |  |  |  |
| Number | 367 | 369 | 736 |
| Mean (SD) | 8.51 (0.65) | 8.54 (0.67) | 8.53 (0.66) |
| Median | 8.40 | 8.50 | 8.40 |
| Min:Max | 7.5:10.0 | 7.5:10.0 | 7.5:10.0 |
| HbA1c (%) at visit 5 (Week −1) |  |  |  |
| Number | 367 | 369 | 736 |
| Mean (SD) | 8.19 (0.64) | 8.24 (0.71) | 8.21 (0.68) |
| Median | 8.20 | 8.20 | 8.20 |
| Min:Max | 7.0:10.0 | 7.0:10.0 | 7.0:10.0 |
| Randomization strata of HbA1c (%) at visit 5 (Week −1) [n (%)] |  |  |  |
| Number | 367 | 369 | 736 |
| <8 | 140 (38.1%) | 142 (38.5%) | 282 (38.3%) |
| ≥8 | 227 (61.9%) | 227 (615%) | 454 (61.7%) |
| Randomization strata of Metformin use at screening [n (%)] |  |  |  |
| Number | 367 | 369 | 736 |
| Yes | 332 (90.5%) | 331 (89.7%) | 663 (90.1%) |
| No | 35 (9.5%) | 38 (10.3%) | 73 (9.9%) |
| Screening BMI (kg/m²) |  |  |  |
| Number | 367 | 369 | 736 |
| Mean (SD) | 31.46 (4.27) | 31.08 (4.17) | 31.27 (4.22) |
| Median | 31.31 | 30.76 | 30.99 |
| Min:Max | 20.4:40.0 | 20.3:40.0 | 20.3:40.0 |
| Screening BMI categories (kg/m²) [n (%)] |  |  |  |
| Number | 367 | 369 | 736 |
| <30 | 148 (40.3%) | 157 (42.5%) | 305 (41.4%) |
| ≥30 | 219 (59.7%) | 212 (57.5%) | 431 (58.6%) |

TABLE 3-continued

Demographics and patient characteristics at screening or baseline-Randomized population

| | Fixed Ratio Combination (N = 367) | Insulin Glargine (N = 369) | All (N = 736) |
|---|---|---|---|
| Baseline BMI (kg/m²) | | | |
| Number | 367 | 369 | 736 |
| Mean (SD) | 31.33 (4.25) | 30.96 (4.15) | 31.14 (4.20) |
| Median | 31.18 | 30.62 | 30.86 |
| Min:Max | 21.2:40.8 | 20.5:41.5 | 20.5:41.5 |
| Baseline BMI categories (kg/m²) [n (%)] | | | |
| Number | 367 | 369 | 736 |
| <30 | 156 (42.5%) | 158 (42.8%) | 314 (42.7%) |
| ≥30 | 211 (57.5%) | 211 (57.2%) | 422 (57.3%) |

BMI = Body Mass Index

TABLE 4

| Disease characteristics at screening or baseline-Randomized population | | | |
|---|---|---|---|
| | Fixed Ratio Combination (N = 367) | Insulin Glargine (N = 369) | All (N = 736) |
| Duration of diabetes (years) | | | |
| Number | 367 | 368 | 735 |
| Mean (SD) | 12.02 (6.64) | 12.13 (6.85) | 12.08 (6.74) |
| Median | 10.49 | 11.32 | 10.75 |
| Min:Max | 1.1:36.7 | 1.0:42.7 | 1.0:42.7 |
| Age at onset of Type 2 diabetes (years) | | | |
| Number | 367 | 368 | 735 |
| Mean (SD) | 47.5 (9.6) | 48.1 (9.0) | 47.8 (9.3) |
| Median | 47.0 | 48.0 | 48.0 |
| Min:Max | 22:79 | 20:72 | 20:79 |
| Duration of prior basal insulin treatment (years) | | | |
| Number | 367 | 369 | 736 |
| Mean (SD) | 3.12 (3.06) | 3.31 (3.08) | 3.22 (3.07) |
| Median | 2.15 | 2.29 | 2.20 |
| Min:Max | 0.4:20.6 | 0.2:24.8 | 0.2:24.8 |
| Prior basal insulin use by type/regimen (Visit 2) | | | |
| Number | 367 | 369 | 736 |
| Insulin glargine | 233 (63.5%) | 241 (65.3%) | 474 (64.4%) |
| Insulin detemir | 48 (13.1%) | 56 (15.2%) | 104 (14.1%) |
| NPH | 86 (23.4%) | 72 (19.5%) | 158 (21.5%) |
| Daily dose of prior basal insulin (U) at run-in (Visit 2) | | | |
| Number | 367 | 369 | 736 |
| Mean (SD) | 28.36 (8.22) | 29.00 (8.14) | 28.68 (8.18) |
| Median | 30.00 | 28.00 | 28.00 |
| Min:Max | 10.0:44.0 | 12.0:50.0 | 10.0:50.0 |
| Average daily dose of insulin glargine (U) at randomization (Visit 6)[a] | | | |
| Number | 366 | 369 | 735 |
| Mean (SD) | 35.04 (9.22) | 35.23 (8.63) | 35.13 (8.92) |
| Median | 35.00 | 36.00 | 36.00 |
| Min:Max | 15.0:58.0 | 12.0:52.0 | 12.0:58.0 |
| Metformin use at screening recorded in eCRF [n (%)] | | | |
| Number | 367 | 369 | 736 |
| Yes | 329 (89.6%) | 329 (89.2%) | 658 (89.4%) |
| No | 38 (10.4%) | 40 (10.8%) | 78 (10.6%) |
| Duration of metformin treatment (years)[b] | | | |
| Number | 329 | 329 | 658 |
| Mean (SD) | 8.45 (5.48) | 832 (5.62) | 8.39 (5.55) |
| Median | 7.76 | 7.54 | 7.69 |
| Min:Max | 0.3:28.3 | 0.4:30.8 | 0.3:30.8 |
| Daily dose of metformin at baseline (mg)[b] | | | |
| Number | 329 | 329 | 658 |
| Mean (SD) | 2082.8 (499.2) | 2042.0 (455.9) | 2062.4 (478.1) |
| Median | 2000.0 | 2000.0 | 2000.0 |
| Min:Max | 850:3500 | 500:4000 | 500:4000 |

TABLE 4-continued

Disease characteristics at screening or baseline-Randomized population

| | Fixed Ratio Combination (N = 367) | Insulin Glargine (N = 369) | All (N = 736) |
|---|---|---|---|
| Categorized daily dose of metformin at baseline (mg) [n (%)][b] | | | |
| Number | 329 | 329 | 658 |
| <1500 | 19 (5.8%) | 10 (3.0%) | 29 (4.4%) |
| ≥1500-<2500 | 217 (66.0%) | 244 (74.2%) | 461 (70.1%) |
| ≥2500-<3000 | 57 (17.3%) | 48 (14.6%) | 105 (16.0%) |
| ≥3000 | 36 (10.9%) | 27 (8.2%) | 63 (9.6%) |
| Number of OAD use at screening [n (%)] | | | |
| Number | 367 | 369 | 736 |
| No OAD | 18 (4.9%) | 19 (5.1%) | 37 (5.0%) |
| 1 OAD | 189 (51.5%) | 210 (56.9%) | 399 (54.2%) |
| 2 OADs | 160 (43.6%) | 140 (37.9%) | 300 (40.8%) |
| OAD use by drug class at screening [n (%)] | | | |
| Number | 349 | 350 | 699 |
| 1 OAD | 189 (51.5%) | 210 (56.9%) | 399 (54.2%) |
| Metformin only | 170 (48.7%) | 190 (54.3%) | 360 (51.5%) |
| Sulfonylurea only | 16 (4.6%) | 14 (4.0%) | 30 (4.3%) |
| DPP-4 inhibitor only | 2 (0.6%) | 4 (1.1%) | 6 (0.9%) |
| SCLT-2 inhibitor only | 0 | 1 (0.3%) | 1 (0.1%) |
| Glinide only | 1 (0.3%) | 1 (0.3%) | 2 (0.3%) |
| Combination of 2 OADs | 160 (43.6%) | 140 (37.9%) | 300 (40.8%) |
| Metformin plus Sulfonylurea | 137 39.3%) | 118 (33.7%) | 255 (36.5%) |
| Metformin plus DPP-4 inhibitor | 20 (5.7%) | 18 (5.1%) | 38 (5.4%) |
| Metformin plus Glinide | 2 (0.6%) | 3 (0.9%) | 5 (0.7%) |
| Sulfonylurea plus DPP-4 inhibitor | 1 (0.3%) | 1 (0.3%) | 2 (0.3%) |
| Duration of first OAD use (years)[c] | | | |
| Number | 349 | 350 | 699 |
| Mean (SD) | 8.40 (5.51) | 8.24 (5.64) | 8.32 (5.57) |
| Median | 7.75 | 7.41 | 7.54 |
| Min:Max | 0.3:28.3 | 0.3:30.8 | 0.3:30.8 |
| Duration of second OAD use (years)[d] | | | |
| Number | 161 | 141 | 302 |
| Mean (SD) | 4.35 (3.53) | 4.75 (4.95) | 4.53 (4.25) |
| Median | 3.55 | 3.05 | 3.32 |
| Min:Max | 0.3:23.6 | 0.2:29.7 | 0.2:29.7 |
| History of gestational diabetes [n (%)] | | | |
| Number | 202 | 190 | 392 |
| Yes (Female) | 10 (5.0%) | 10 (5.3%) | 20 (5.1%) |
| No (Female) | 192 (95.0%) | 180 (94.7%) | 372 (94.9%) |
| Prior use of GLP-1 receptor agonist [n (%)] | | | |
| Number | 367 | 369 | 736 |
| Yes | 29 (7.9%) | 17 (4.6%) | 46 (6.3%) |
| No | 338 (92.1%) | 352 (95.4%) | 690 (93.8%) |
| Creatinine clearance at screening (mL/min) | | | |
| Number | 366 | 367 | 733 |
| Mean (SD) | 106.75 (32.32) | 106.06 (31.08) | 106.40 (31.69) |
| Median | 103.85 | 101.31 | 102.24 |
| Min:Max | 34.3:223.7 | 43.8:222.1 | 34.3:223.7 |
| Creatinine clearance categories at screening (mL/min) [n (%)] Number | 366 | 367 | 733 |
| <15 (end stage renal disease) | 0 | 0 | 0 |
| ≥15-<30 (severe decrease in GFR) | 0 | 0 | 0 |
| ≥30-<60 (moderate decrease in GFR) | 18 (4.9%) | 9 (2.5%) | 27 (3.7%) |
| ≥60-<90 (mild decrease in GFR) | 104 (28.4%) | 117 (31.9%) | 221 (30.2%) |
| ≥90 (normal) | 244 (66.7%) | 241 (65.7%) | 485 (66.2%) |

[a]Averaged daily dose of insulin glargine recorded in eCRF for the 3 days before randomization.
[b]for patients who took metformin at screening;
[c]for patients who took OAD at screening;
[d]for patients who took 2$^{nd}$ OAD at screening.
OAD = Oral anti-diabetic drug,
SGLT-2 = Sodium glucose co-transporter 2,
DPP-4 = Dipeptidyl-peptidase 4,
GLP-1 = Glucagon like peptide-1,
GFR = glomerular filtration rate.

Duration of first OAD is calculated based on eCFR History of Diabetics page and derived as: (Date of informed consent−earliest start date of OADs including metformin, sulfonylurea, glinide, DPP-4, or SGLT-2+1)/365.25.

Similarly, duration of second OAD is based on the $2^{nd}$ earliest start date of OADs recorded.

Creatinine clearance value is derived using the equation of Cockcroft and Gault.

3.1.4 Dosage and Duration

TABLE 5

Exposure to investigational medicinal product-Safety population

|  | Fixed Ratio Combination (N = 365) | Insulin Glargine (N = 365) |
|---|---|---|
| Cumulative duration of treatment exposure (patient years) | 200.3 | 207.1 |
| Duration of study treatment (days) | | |
| Number | 363 | 363 |
| Mean (SD) | 201.5 (38.0) | 208.4 (18.4) |
| Median | 211.0 | 210.0 |
| Min:Max | 1:242 | 12:224 |
| Duration of study treatment by category [n (%)] | | |
| Missing duration | 2 (0.5%) | 2 (0.5%) |
| 1-14 days | 5 (1.4%) | 1 (0.3%) |
| 15-28 days | 2 (0.5%) | 1 (0.3%) |
| 29-56 days | 2 (0.5%) | 0 |
| 57-84 days | 6 (1.6%) | 0 |
| 55-126 days | 8 (2.2%) | 3 (0.8%) |
| 127-168 days | 0 | 1 (0.3%) |
| 169-210 days | 153 (41.9%) | 202 (55.3%) |
| >210 days | 187 (51.2%) | 155 (42.5%) |
| Cumulative duration of study treatment by category [n (%)] | | |
| Missing duration | 2 (0.5%) | 2 (0.5%) |
| ≥1 day | 363 (99.5%) | 363 (99.5%) |
| ≥15 days | 358 (98.1%) | 362 (99.2%) |
| ≥29 days | 356 (97.5%) | 361 (98.9%) |
| ≥57 days | 354 (97.0%) | 361 (93.9%) |
| ≥85 days | 348 (95.3%) | 361 (98.9%) |
| ≥127 days | 340 (93.2%) | 358 (98.1%) |
| ≥169 days | 340 (93.2%) | 357 (97.8%) |
| ≥211 days | 187 (51.2%) | 155 (42.5%) |

IMP: Investigational Medicinal Product
Duration of exposure = (date of the last open-label IMP injection-date of the first open-label IMP injection) + 1.
Note:
Patients are considered in the treatment group they actually received at randomization.

In the combination group, 1 patient (840539002) reported the final insulin dose (in category of >40 U to 60 U) without kit number and pen used. Therefore, pen information (pen A or pen B) used at the end of treatment period was treated as missing (Table 6). For the same reason the final lixisenatide dose could not be derived for this patient (Table 7).

TABLE 6

Number (%) of patients by final insulin dose at the end of open-label treatment-Safety population

| Final Insulin Dose | Fixed Ratio Combination (N = 365) | Insulin Glargine (N = 365) |
|---|---|---|
| <20 U | 2 (0.5%) | 3 (0.8%) |
| ≥20 U to <30 U | 44 (12.1%) | 39 (10.7%) |
| ≥30 U to ≤40 U | 97 (26.6%) | 87 (23.8%) |

TABLE 6-continued

Number (%) of patients by final insulin dose at the end of open-label treatment-Safety population

| Final Insulin Dose | Fixed Ratio Combination (N = 365) | Insulin Glargine (N = 365) |
|---|---|---|
| >40 U to ≤60 U | 222 (60.8%) | 236 (64.7%) |
| >60 U | 0 | 0 |
| =60 U | 99 (27.1%) | 112 (30.7%) |
| Pen A [a] | | |
| <20 U | 2 (0.5%) | |
| ≥20 U to <30 U | 43 (11.8%) | |
| ≥30 U to ≤40 U | 53 (14.5%) | |
| >40 U to ≤60 U | 2 (0.5%) | |
| >60 U | 0 | |
| Pen B [b] | | |
| <20 U | | |
| ≥20 U to <30 U | 1 (0.3%) | |
| ≥30 U to ≤40 U | 44 (12.1%) | |
| >40 U to ≤60 U | 219 (60.0%) | |
| >60 U | 0 | |

[a] 2U/1 μg fixed ratio for insulin glargine/lixisenatide.
[b] 3U/1 μg fixed ratio for insulin glargine/lixisenatide.
Note:
Percentages are calculated using the number of safety patients as the denominator.

TABLE 7

Number (%) of patients by final lixisenatide dose at the end of open-label treatment Safety population

| Final Lixisenatide Dose | Fixed Ratio Combination (N = 365) |
|---|---|
| <10 μg | 3 (0.8%) |
| ≥10 μg to <15 μg | 108 (29.6%) |
| ≥15 μg to ≤20 μg | 251 (68.8%) |
| >20 μg | 2 (0.5%) |
| Pen A [a] | |
| <10 μg | 2 (0.5%) |
| ≥10 μg to <15 μg | 43 (11.8%) |
| ≥15 μg to ≤20 μg | 53 (14.5%) |
| >20 μg | 2 (0.5%) |
| Pen B [b] | |
| <10 μg | 1 (0.3%) |
| ≥10 μg to <15 μg | 65 (17.8%) |
| ≥15 μg to ≤20 μg | 198 (54.2%) |
| >20 μg | 0 |

[a] 2U/1 μg fixed ratio for insulin glargine/lixisenatide.
[b] 3U/1 μg fixed ratio for insulin glargine/lixisenatide.
Note:
Percentages are calculated using the number of safety patients as the denominator.

3.2 Efficacy

3.2.1 Primary Efficacy Endpoint

TABLE 8

Mean change in HbA1c (%) from baseline to Week 30 using MMRM-mITT population

| HbA1c(%) | Fixed Ratio Combination (N = 366) | Insulin Glargine (N = 365) |
|---|---|---|
| Baseline | | |
| Number | 364 | 364 |
| Mean (SD) | 8.07 (0.68) | 8.08 (0.73) |

TABLE 8-continued

Mean change in HbA1c (%) from baseline to Week 30 using MMRM-mITT population

| HbA1c(%) | Fixed Ratio Combination (N = 366) | Insulin Glargine (N = 365) |
|---|---|---|
| Median | 8.00 | 8.00 |
| Min:Max | 6.6:10.2 | 3.9:10.0 |
| Week 30 | | |
| Number | 346 | 355 |
| Mean (SD) | 6.94 (0.87) | 7.48 (0.91) |
| Median | 6.80 | 7.40 |
| Min:Max | 5.0:9.8 | 5.6:11.2 |
| Change from baseline to Week 30 | | |
| Number | 364 | 364 |
| LS Mean (SE)[a] | −1.13 (0.037) | −0.62 (0.055) |
| LS mean difference (SE) vs insulin glargine[a] | −0.52 (0.060) | — |
| 95% CI | (−0.633 to −0.397) | — |
| p-value | <0.0001 | — |

[a]Mixed-effect model with repeated measures (MMRM) with treatment groups (fixed ratio combination and insulin glargine), randomization strata of HbA1c (<8.0%, ≥8.0%) at Visit 5 (Week −1), randomization strata of metformin use at screening (Yes, No), visit (Week 8, 12, 24, and 30), treatment-by-visit interaction, and country as fixed effects, and baseline HbA1c value-by-visit interaction as covariates.

Countries with fewer than 5 patients were grouped with the country with the lowest number of patients that is 5 or more.

The analysis included all scheduled measurements obtained during the study, including those obtained after IMP discontinuation or introduction of rescue therapy. Included are patients who have measurements at baseline and post-baseline.

Figure 9:
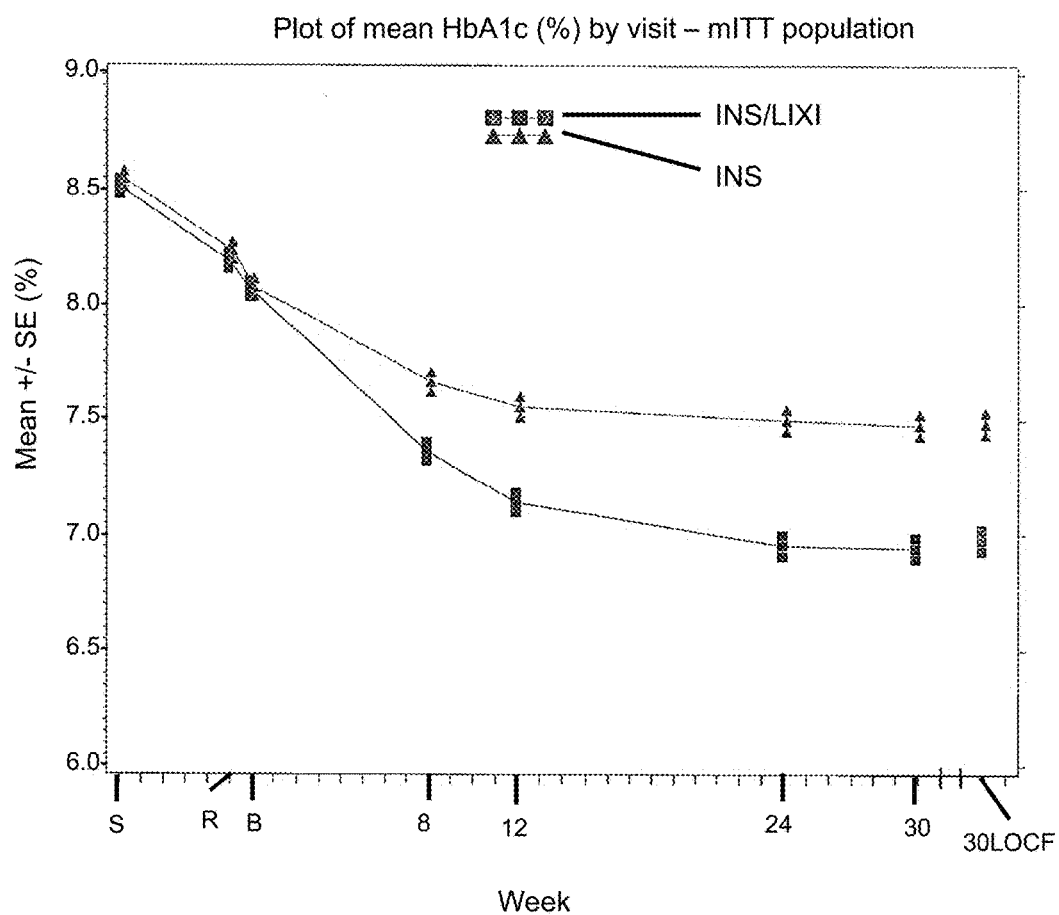
FIG. 9—Plot of mean HbA1c (%) by visit—mITT population. S=Screening (Week −8), R=Run-in (Week −1), B=Baseline, LOCF=Last observation carried forward. INS/LIXI=Fixed Ratio Combination, INS=Insulin Glargine. Note: The plot included all scheduled measurements obtained during the study, including those obtained after IMP discontinuation or introduction of rescue medication.
Figure 10:
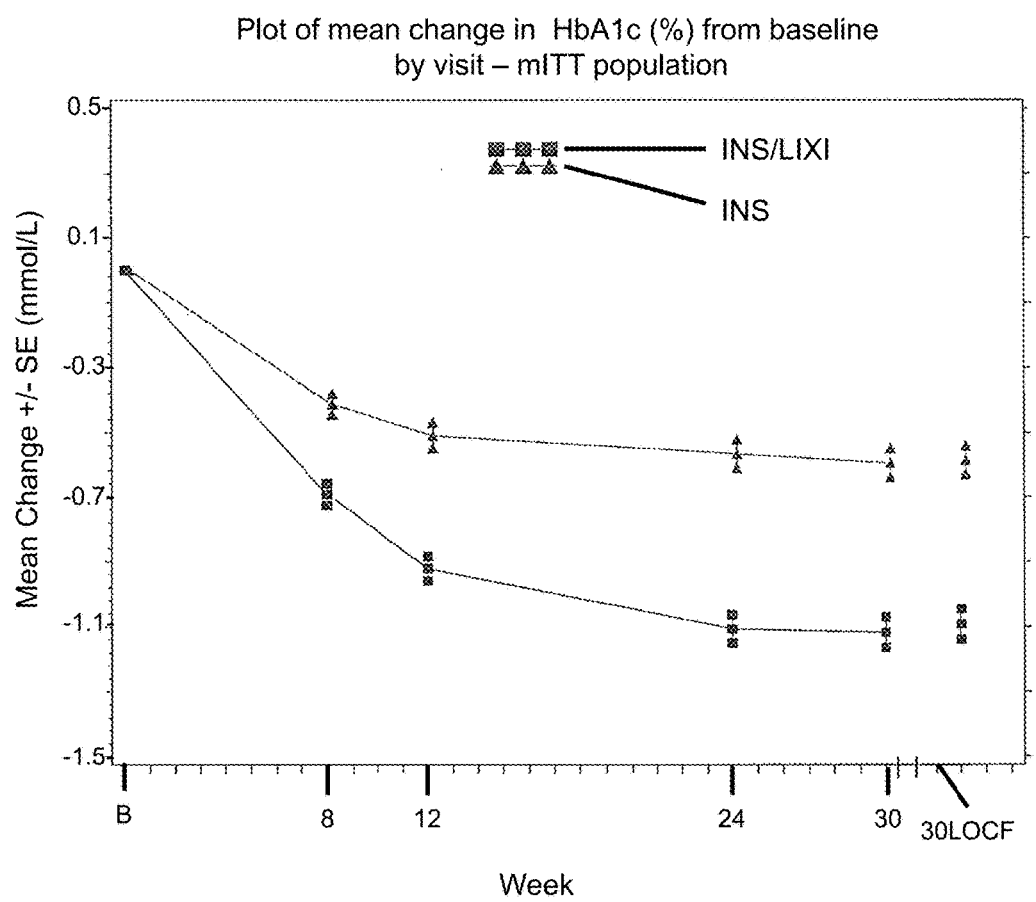
FIG. 10—Plot of mean change in HbA1c (%) from baseline by visit—mITT population. B=Baseline, LOCF=Last observation carried forward. INS/LIXI=Fixed Ratio Combination, INS=Insulin Glargine. Note: The plot included all scheduled measurements obtained during the study, including those obtained after IMP discontinuation or introduction of rescue medication.

Mean HbA1c values (%) by visit and mean change of HbA1c (%) from baseline by visit are shown in FIGS. 9 and 10

3.2.2 Other Key Efficacy Endpoints

TABLE 9

Number (%) of patients with HbA1c value <= 6.5% or <7% at Week 30-mITT population

| HbA1c (%) | Fixed Ratio Combination (N = 366) | Insulin Glargine (N = 365) |
|---|---|---|
| Number | 366 | 365 |
| ≤6.5% | 124 (33.9%) | 52 (14.2%) |
| Proportion difference (95% CI) vs. insulin glargine[a] | 19.76% (13.90% to 25.62%) | — |
| p-value | <.0001 | — |
| <7% | 201 (54.9%) | 108 (29.6%) |
| Proportion difference (95% CI) vs. insulin glargine[a] | 25.52% (18.94% to 32.10%) | — |
| p-value | <.0001 | — |

[a]Weighted average of proportion difference between treatment groups (fixed ratio combination and insulin glargine) from each strata (randomization strata of HbA1c [<8.0%, ≥8.0%] at Visit 5 (Week −1), randomization strata of metformin use at screening [Yes,No]) using Cochran-Mantel-Haenszel (CHM) weights.
Proportion difference = difference of the proportions of patients achieving HbA1c value ≤6.5% or <7%.

All measurements at week 30 were used, including those obtained after IMP discontinuation or introduction of rescue therapy. If no assessment was available at week 30 at all, patients were treated as non-responders.

TABLE 10

Mean change in 2-hour plasma glucose excursion (mmol/L) during a standardized mean test from baseline to Week 30 using ANCOVA-mITT population

| 2-hour plasma glucose excursion (mmol/L) | Fixed Ratio Combination (N = 366) | Insulin Glargine (N = 365) |
|---|---|---|
| Baseline | | |
| Number | 329 | 336 |
| Mean (SD) | 7.01 (3.47) | 7.14 (3.11) |
| Median | 7.10 | 7.05 |
| Min:Max | −5.1:17.4 | −1.1:17.7 |
| Week 30 (LOCF) | | |
| Number | 329 | 336 |
| Mean (SD) | 3.11 (3.55) | 6.71 (3.34) |
| Median | 2.90 | 6.40 |
| Min:Max | −9.5:15.9 | −5.7:16.7 |
| Change from baseline to Week 30 (LOCF) | | |
| Number | 329 | 336 |
| Mean (SD) | −3.90 (4.17) | −0.44 (3.34) |
| Median | −3.70 | −0.30 |
| Min:Max | −18.2:9.8 | −13.1:11.2 |
| LS Mean (SE)[a] | −3.90 (0.285) | −0.47 (0.274) |
| LS mean difference (SE) vs insulin glargine[a] | −3.43 (0.251) | — |
| 95% CI | (−3.925 to −2.939) | — |
| p-value | <0.0001 | — |

LOCF = Last observation carried forward.
[a]Analysis of covariance (ANCOVA) model with treatment groups (fixed ratio combination and insulin glargine), randomization strata of HbA1c (<8.0%, ≥8.0%) at Visit 5 (Week −1), randomization strata of metformin use at screening (Yes, No), and country as fixed effects and baseline 2-hour plasma glucose excursion value as a covariate.

Countries with fewer than 5 patients were grouped with the country with the lowest number of patients that is 5 or more.

The analysis included measurements collected during the study, including those obtained after IMP discontinuation or introduction of rescue therapy.

Patients with both baseline and Week 30 (LOCF) measurements are included.

TABLE 11

Mean change in 2-hour postprandial plasma glucose (mmol/L) during a standardized meal test from baseline to Week 30 using ANCOVA-mITT population

| 2-hour postprandial plasma glucose (mmol/L) | Fixed Ratio Combination (N = 366) | Insulin Glargine (N = 365) |
|---|---|---|
| Baseline | | |
| Number | 332 | 340 |
| Mean (SD) | 14.85 (3.82) | 14.97 (3.67) |
| Median | 14.75 | 14.80 |
| Min:Max | 3.5:25.9 | 4.9:27.5 |
| Week 30 (LOCF) | | |
| Number | 332 | 340 |
| Mean (SD) | 9.91 (3.90) | 13.41 (3.83) |
| Median | 9.20 | 13.10 |
| Min:Max | 2.9:25.7 | 3.9:33.1 |
| Change from baseline to Week 30 (LOCF) | | |
| Number | 332 | 340 |
| Mean (SD) | −4.94 (4.49) | −1.56 (4.20) |
| Median | −5.10 | −1.50 |
| Min:Max | −17.7: 11.5 | −16.1:23.8 |
| LS Mean (SE)[a] | −4.72 (0.322) | −1.39 (0.310) |
| LS mean difference (SE) vs insulin glargine[a] | −3.33 (0.284) | — |
| 95% CI | (−3.889 to −2.774) | — |

LOCF = Last observation carried forward.
[a]Analysis of covariance (ANCOVA) model with treatment groups (fixed ratio combination and insulin glargine), randomization strata of HbA1c (<8.0%, ≥8.0%) at Visit 5 (Week −1), randomization strata of metformin use at screening (Yes, No), and country as fixed effects and baseline 2-hour postprandial plasma glucose value as a covariate.

Countries with fewer than 5 patients were grouped with the country with the lowest number of patients that is 5 or more.

The analysis included measurements collected during the study, including those obtained after IMP discontinuation or introduction of rescue therapy.

Patients with both baseline and Week 30 (LOCF) measurements are included.

TABLE 12

Mean change in body weight (kg) from baseline to Week 30 using MMRM-mITT population

| Body Weight (kg) | Fixed Ratio Combination (N = 366) | Insulin Glargine (N = 365) |
|---|---|---|
| Baseline | | |
| Number | 365 | 365 |
| Mean (SD) | 87.81 (14.42) | 87.09 (14.75) |
| Median | 88.00 | 84.90 |
| Min:Max | 44.3:127.5 | 44.8:135.6 |
| Week 30 | | |
| Number | 348 | 357 |
| Mean (SD) | 87.48 (14.35) | 87.96 (15.08) |
| Median | 87.00 | 85.90 |
| Min:Max | 43.5:127.9 | 45.7:137.0 |

TABLE 12-continued

Mean change in body weight (kg) from baseline to Week 30 using MMRM-mITT population

| Body Weight (kg) | Fixed Ratio Combination (N = 366) | Insulin Glargine (N = 365) |
|---|---|---|
| Change from baseline to Week 30 | | |
| Number | 365 | 365 |
| LS Mean (SE)[a] | −0.67 (0.181) | 0.70 (0.178) |
| LS mean difference (SE) vs insulin glargine[a] | −1.37 (0.224) | — |
| 95% CI | (−1.808 to −0.930) | — |
| p-value | <0.0001 | — |

[a]Mixed-effect model with repeated measures (MMRM) with treatment groups (fixed ratio combination and insulin glargine), randomization strata of HbA1c <8.0%, ≥8.0%) (Week −1), randomization strata of metformin use at screening (Yes, No), scheduled visit, treatment-by-visit interaction and country as fixed effects, and baseline body weight value-by-visit interaction as a covariate.

Countries with fewer than 5 patients were grouped with the country with the lowest number of patients that is 5 or more.

The analysis included all scheduled measurements obtained during the study, including those obtained after IMP discontinuation or introduction of rescue therapy.

Included are patients who have measurements at baseline and post-baseline.

Figure 11:
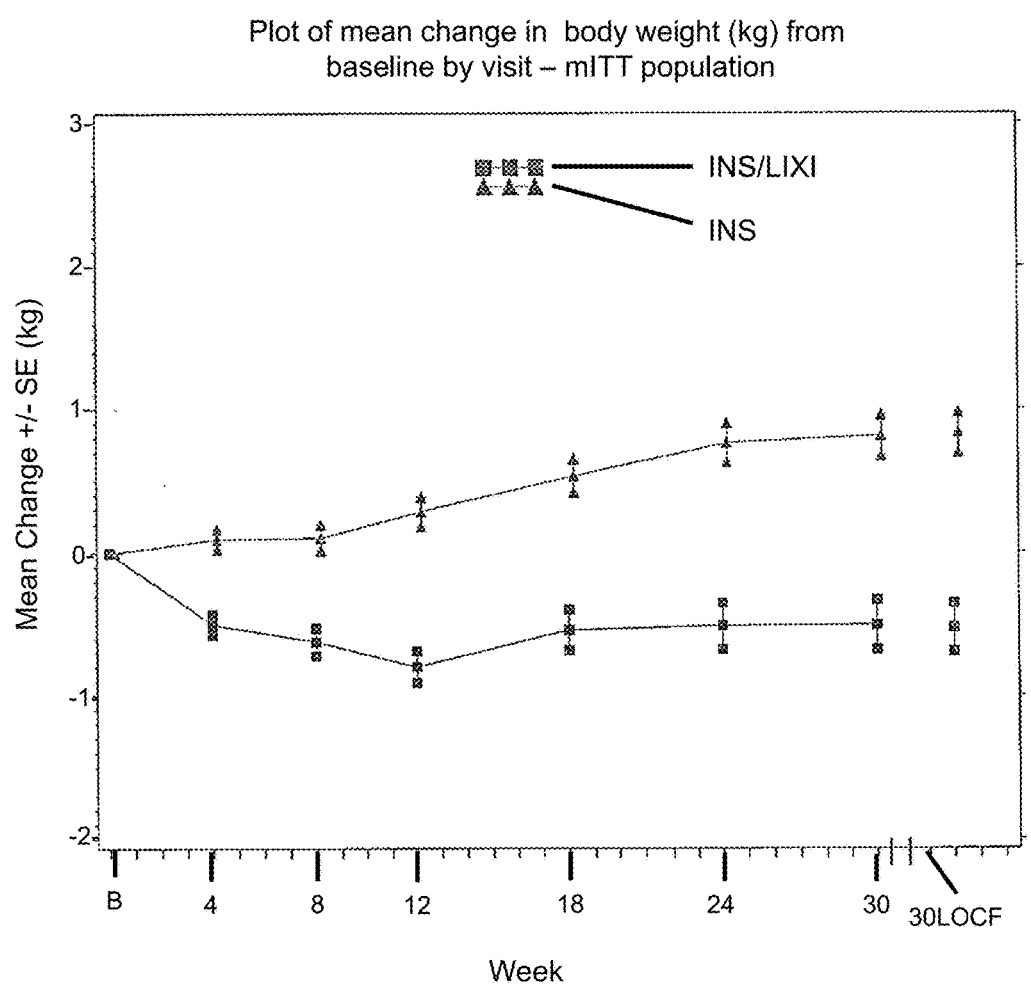
FIG. 11—Plot of mean change in body weight (kg) from baseline by visit—mITT population. B=Baseline, LOCF=Last observation carried forward. INS/LIXI=Fixed Ratio Combination, INS=Insulin Glargine. The analysis included all scheduled measurements obtained during the study, including those obtained after IMP discontinuation or introduction of rescue therapy.

Mean change in body weight from baseline by visit is shown in FIG. 11.

TABLE 13

Mean change in average 7-point SMPG (mmol/L) from baseline to Week 30 using MMRM mITT population

| Average of 7-point SMPG (mmol/L) | Fixed Ratio Combination (N = 366) | Insulin Glargine (N = 365) |
|---|---|---|
| Baseline | | |
| Number | 323 | 320 |
| Mean (SD) | 9.22 (1.56) | 9.05 (1.59) |
| Median | 9.14 | 8.96 |
| Min:Max | 5.3:13.8 | 4.9:15.7 |
| Week 30 | | |
| Number | 301 | 305 |
| Mean (SD) | 7.75 (1.71) | 8.62 (1.74) |
| Median | 7.40 | 8.26 |
| Min:Max | 4.7:14.3 | 5.1:16.3 |

TABLE 13-continued

Mean change in average 7-point SMPG (mmol/L) from baseline to Week 30 using MMRM mITT population

| Average of 7-point SMPG (mmol/L) | Fixed Ratio Combination (N = 366) | Insulin Glargine (N = 365) |
|---|---|---|
| Change from baseline to Week 30 | | |
| Number | 323 | 320 |
| LS Mean (SE)[a] | −1.50 (0.137) | −0.60 (0.130) |
| LS mean difference (SE) vs insulin glargine[a] | −0.90 (0.131) | — |
| 95% CI | (−1.154 to −0.640) | — |
| p-value | <0.0001 | — |

SMPG = Self-monitored plasma glucose.
[a]Mixed-effect model with repeated measures (MMRM) with treatment groups (fixed ratio combination and insulin glargine), randomization strata oh HbA1c <8.0%, ≥8.0%) (Week −1), randomization strata of metformin use at screening (Yes, No), scheduled visit, treatment-by-visit interaction and country as fixed effects, and baseline average SMPG value-by-visit interaction as a covariate.

Countries with fewer than 5 patients were grouped with the country with the lowest number of patients that is 5 or more.

The analysis included all scheduled measurements obtained during the study, including those obtained after IMP discontinuation or introduction of rescue therapy.

Included are patients who have measurements at baseline and post-baseline.

FIG. 12 shows a plot of mean 7-point SMPG at baseline and week 30.

TABLE 14

Number (%) of patients reaching HbA1c <7% with no body weight gain at Week 30-mITT population

| HbA1c <7% with no body weight gain | Fixed Ratio Combination (N = 366) | Insulin Glargine (N = 365) |
|---|---|---|
| Number | 366 | 365 |
| Yes | 125 (34.2%) | 49 (13.4%) |
| Proportion difference (95% CI) vs insulin glargine[a] | 20.82% (14.98% to 26.66%) | — |
| p-value | <0.0001 | — |

[a]Weighted average of proportion difference between treatment groups (fixed ratio combination and insulin glargine) from each strata (randomization strata oh HbA1c <8.0%, ≥8.0%) 8.0%] at Visit 5 (Week −1), randomization strata of metformin use at screening [Yes, No]) using Cocharn-Mantel-Haenszel (CMH) weights.

The analysis included HbA1c and body weight measurements at week 30, including those obtained after the UMP discontinuation or the introduction of rescue medication. Patients were treated as on-responders if they have no HbA1c and/or body weight assessments at week 30.

TABLE 15

Mean change in daily insulin glargine dose (U) from baseline to Week 30 using MMRM mITT population

| Average daily insulin glargine dose (U) | Fixed Ratio Combination (N = 366) | Insulin Glargine (N = 365) |
|---|---|---|
| Baseline | | |
| Number | 364 | 365 |
| Mean (SD) | 34.98 (9.20) | 35.23 (8.64) |
| Median | 34.50 | 36.00 |
| Min:Max | 15.0:58.0 | 12.0:52.0 |
| Week 30 | | |
| Number | 336 | 353 |
| Mean (SD) | 46.67 (12.64) | 46.71 (12.49) |
| Median | 50.00 | 48.00 |
| Min:Max | 12.0:60.0 | 14.0:60.0 |
| Change from baseline to Week 30 | | |
| Number | 364 | 365 |
| LS Mean (SE)$^a$ | 10.64 (0.601) | 10.89 (0.587) |
| LS mean difference (SE) vs insulin glargine$^a$ | −0.26 (0.766) | — |
| 95% CI | (−1.762 to 1.246) | — |
| p-value | 0.7362 | — |

$^a$Mixed-effect model with repeated measures (MMRM) with treatment groups (fixed ratio combination and insulin glargine), randomization strata of HbA1c (<8.0%, ≥8.0%) at Visit 5 (Week −1), randomization strata of metformin use at screening (Yes, No), scheduled visit, treatment-by-visit interaction, and country as fixed effects, and baseline daily insulin glargine dose-by-visit interaction as a covariate.

Countries with fewer than 5 patients were grouped with the country with the lowest number of patients that is 5 or more.

The analysis included scheduled measurements obtained up to the date of last injection of the IMP, including those obtained after introduction of rescue therapy.

Figure 13:
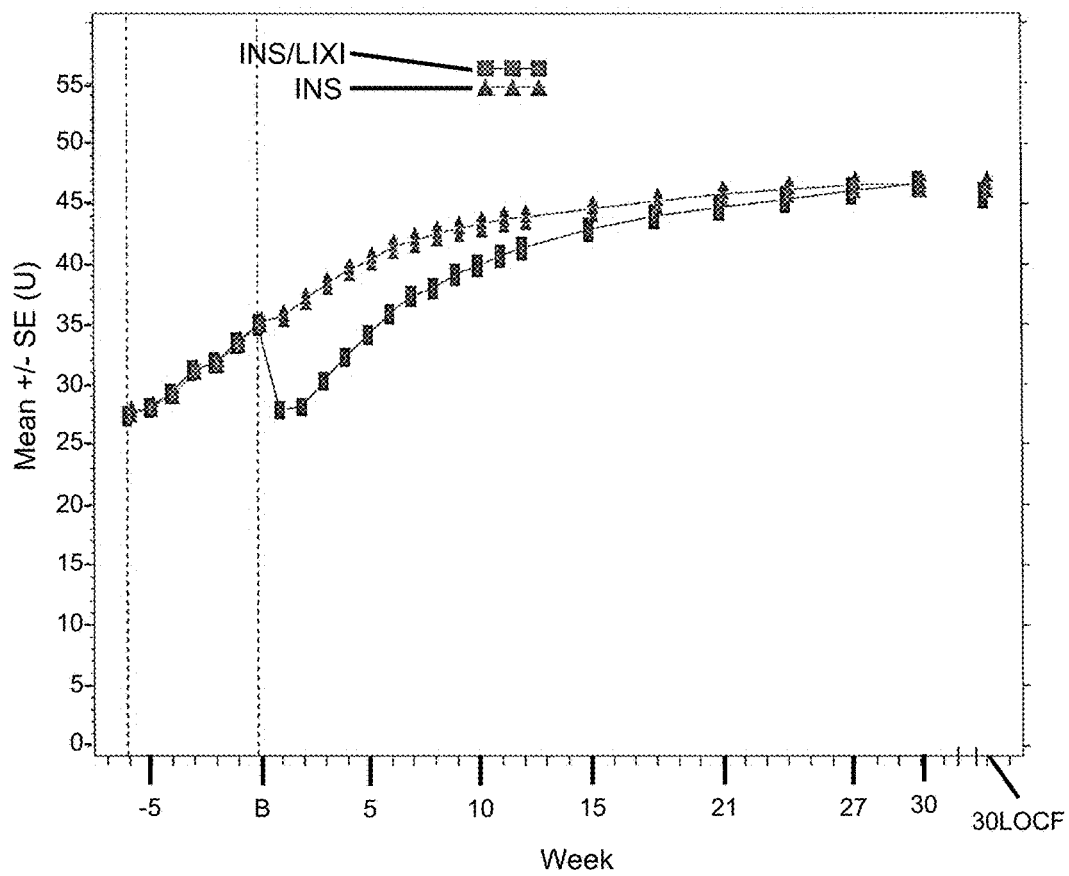
FIG. 13—Plot of mean daily insulin glargine dose (U) by visit—mITT population. Week-6=First week of run-in, B=Baseline, LOCF=Last observation carried forward. INS/LIXI=Fixed Ratio Combination, INS=Insulin Glargine. The analysis included scheduled measurements obtained up to the date of last injection of the IMP, including those obtained after introduction of rescue therapy.

FIG. 13 shows a plot of mean daily insulin glargine dose by visit.

Per the testing strategy for multiplicity adjustment which is described in the protocol, the inferential testing for the two following variables (the percentage of patients reaching HbA1c<7.0% with no body weight gain at Week 30 and with no documented symptomatic hypoglycemia, and FPG) was exploratory since the analysis on daily dose of insulin glargine failed to show a statistically significant difference.

TABLE 16

Number (%) of patients reaching HbA1c <7% with no body weight gain at Week 30 and with no documented (plasma glucose ≤70 mg/dL [3.9 mmol/L] symptomatic hypoglycemia during the study-mITT population

| HbA1 <7% with no weight gain and with no documented symptomatic hypoglycemia | Fixed Ratio Combination (N = 366) | Insulin Glargine (N = 365) |
|---|---|---|
| Number | 366 | 365 |
| Yes | 73 (19.9%) | 33 (9.0%) |
| Proportion difference (95% CI) vs. insulin glargine$^a$ | 10.94% (5.93% to 15.96%) | — |
| p-value | <.0001 | — |

$^a$Weighted average of proportion difference between treatment groups (fixed ratio combination and insulin glargine) from each strata (randomization strata of HbA1c [<8.0, ≥8.0%] at Visit 5 (Week −1), randomization strata of metformin use at screening [Yes, No]) using Cochran-Mantel-Haenszel (CMH) weights.

Documented symptomatic hypoglycemia is an event during which typical symptoms of hypoglycemia are accompanied by a measured plasma glucose of 70 mg/dL (3.9 mmol/L). The analysis included all HbA1c and body weight measurements at week 30, including those obtained after the IMP discontinuation or the introduction of rescue medication. Patients were treated as non-responders if they have no HbA1c and/or body weight assessments at week 30.

All documented symptomatic hypoglycemia occurred during the 30-week open-label treatment period was considered, including those occurred after the UMP discontinuation or the introduction of rescue medication.

TABLE 17

Mean change in fasting plasma glucose (mmol/L) from baseline to Week 30 using MMR-mITT population

| Fasting plasma glucose (mmol/L) | Fixed Ratio Combination (N = 366) | Insulin Glargine (N = 365) |
|---|---|---|
| Baseline | | |
| Number | 364 | 364 |
| Mean (SD) | 7.33 (1.94) | 7.32 (2.07) |
| Median | 7.10 | 7.00 |
| Min:Max | 3.2:15.7 | 3.3:17.2 |
| Week 30 | | |
| Number | 341 | 349 |
| Mean (SD) | 678 (2.26) | 6.69 (2.05) |
| Median | 6.30 | 6.30 |
| Min:Max | 2.8:20.6 | 2.8:18.0 |
| Change from baseline to Week 30 | | |
| Number | 364 | 364 |
| LS Mean (SE)[a] | −0.35 (0.142) | −0.46 (0.138) |
| LS mean difference (SE) vs insulin glargine[a] | 0.11 (0.162) | — |
| 95% CI | (−0.207 to 0.428) | — |
| p-value | 0.4951 | — |

[a]Mixed-effect model with repeated measures (MMRM) with treatment groups (fixed ratio combination and insulin glargine), randomization strata of HbA1c (<8.0%, ≥8.0%) at Visit 5 (Week −1), randomization strata of metformin use at screening (Yes, No), scheduled visit, treatment-by-visit interaction and country as fixed effects, and baseline fasting plasma glucose value-y-visit interaction as a covariate.

Countries with fewer than 5 patients were grouped with the country with the lowest number of patients that is 5 or more.

The analysis included all scheduled measurements obtained during the study, including those obtained and after IMP discontinuation or introduction of rescue therapy. Included are patients who have measurements at baseline and post-baseline.

Figure 14:
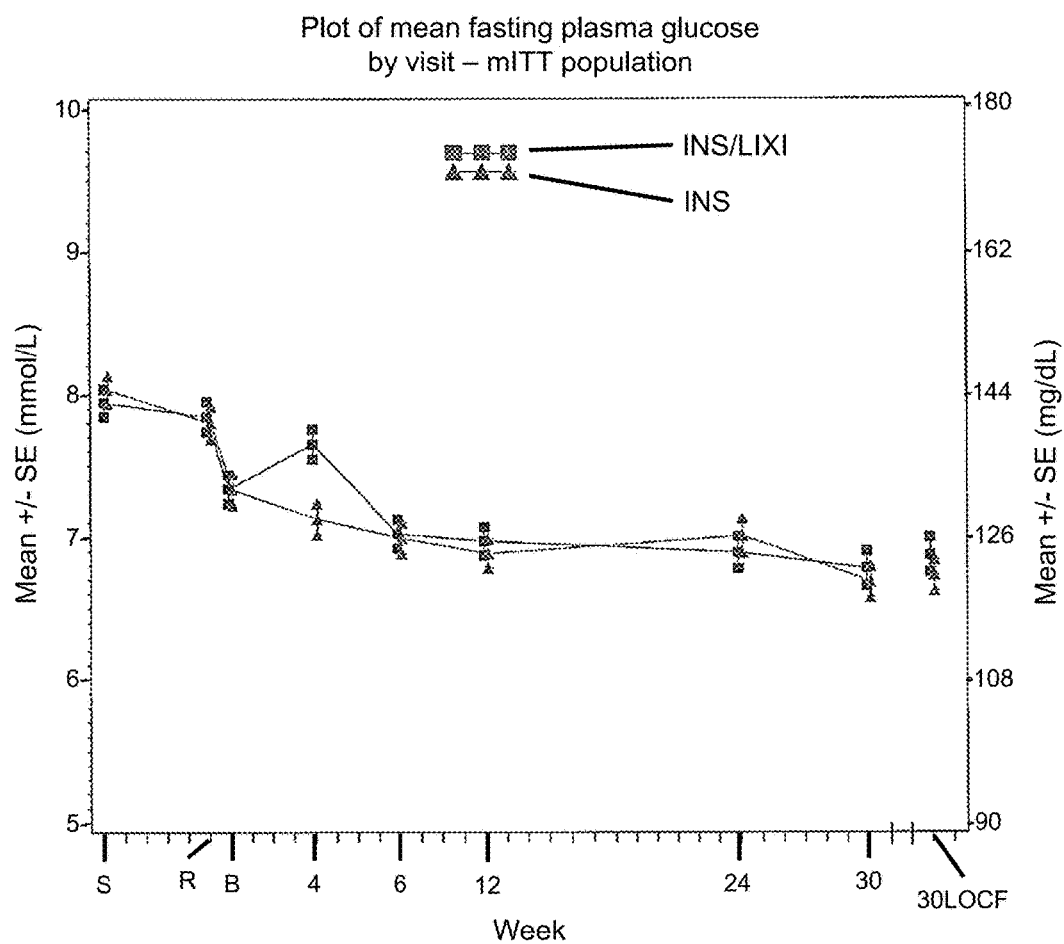
FIG. 14—Plot of mean fasting plasma glucose by visit—mITT population. S=Screening (Week −8), R=Run-in (Week −1), B=Baseline, LOCF=Last observation carried forward. INS/LIXI=Fixed Ratio Combination, INS=Insulin Glargine. The analysis included all scheduled measurements obtained during the study, including those obtained after IMP discontinuation or introduction of rescue therapy.

FIG. 14 shows a plot of mean fasting plasma glucose by visit

TABLE 18

Number (%) of patients reaching HbA1c <7% at Week 30 with no documented (plasma glucose ≤70 mg/dL [3.9 mmol/L] symptomatic hypoglycemia during the study-mITT population

| HbA1 <7% with no documented symptomatic hypoglycemia | Fixed Ratio Combination (N = 366) | Insulin Glargine (N = 365) |
|---|---|---|
| Number | 366 | 365 |
| Yes | 116 (31.7%) | 68 (18.6%) |
| Proportion difference (95% CI) vs. insulin glargine[a] | 13.22% (7.12% to 19.32%) | — |

[a]Weighted average of proportion difference between treatment groups (fixed ratio combination and insulin glargine) from each strata (randomization strata oh HbA1c <8.0, ≥8.0%) at Visit 5 (Week −1), randomization strata of metformin use at screening [Yes,No]) using Cochran-Mantel-Haenszel (CMH) weights.

Documented symptomatic hypoglycemia is an event during which typical symptoms of hypoglycemia are accompanied by a measured plasma glucose of 70 mg/dL (3.9 mmol/L).

The analysis included all HJbA1c measurements at week 30, including those obtained after the UMP discontinuation or the introduction of rescue mediation. Patients were treated as non-responders if they have no HbA1c assessments at week 30. All documented symptomatic hypoglycemia occurred during the 30-week open-label treatment period was considered, including those occurred after the IMP discontinuation or the introduction of rescue medication.

TABLE 19

Number (%) of patients requiring rescue therapy during the 30 week open-label treatment period-mITT population

| Requiring rescue therapy | Fixed Ratio Combination (N = 366) | Insulin Glargine (N = 365) |
|---|---|---|
| Number | 366 | 365 |
| Yes | 10 (2.7%) | 22 (6.0%) |
| Proportion difference (95% CI) vs. insulin glargine[a] | −3.35% (−6.33% to −0.36%) | — |

[a]Weighted average of risk difference between treatment groups (fixed ratio combination and insulin glargine) from each strata (randomization strata of HbA1c <8.0, ≥8.0%] at Visit 5 (Week −1), randomization strata of metformin use at screening [Yes, No]) using Cochran-Mantel-Haenszel (CMH) weights.
[b]Based on CMH method stratified by randomization strata of HbA1c <8.0, ≥8.0%] at Visit 5 (Week −1_ and randomization strata of metformin use at screening [Yes,No].

3.3 Safety

Symptomatic hypoglycemia events were documented on a specific hypoglycemia event form, and not an AE CRF page, and thus were not included in the TEAE summaries. They are summarized separately (see Section 3.3.5).

3.3.1 Treatment-Emergent Adverse Events

TABLE 20

Overview of adverse event profile: treatment emergent adverse events-Safety population

| n (%) | Fixed Ratio Combination (N = 365) | Insulin Giargine (N = 365) |
|---|---|---|
| Patients with any TEAS | 195 (53.4%) | 191 (52.3%) |
| Patients with any serious TEAE | 20 (5.5%) | 18 (4.9%) |
| Patients with any TEAS leading to death | 1 (0.3%) | 2 (0.5%) |
| Patients with any TEAE leading to permanent treatment discontinuation | 10 (2.7%) | 3 (0.8%) |

TEAE: Treatment Emergent Adverse Event
n (%) = number and percentage of patients with at least one TEAE

TABLE 21

Number (%) of patients experiencing common TEAE(s) (PT ≥3% in any treatment group by primary SOC and PT-Safety population

| Primary System Organ Class Preferred Term n(%) | Fixed Ratio Combination (N = 365) | Insulin Glargine (N = 365) |
|---|---|---|
| Any TAE | 195 (53.4%) | 191 (52.3%) |
| Infections and infestations | 98 (26.8%) | 112 (30.7%) |
| Influenza | 15 (4.1%) | 11 (3.0%) |
| Nasopharyngitis | 32 (8.8%) | 32 (8.8%) |

TABLE 21-continued

Number (%) of patients experiencing common TEAE(s) (PT ≥3% in any treatment group by primary SOC and PT-Safety population

| Primary System Organ Class Preferred Term n(%) | Fixed Ratio Combination (N = 365) | Insulin Glargine (N = 365) |
|---|---|---|
| Upper respiratory tract infection | 13 (3.6%) | 11 (3.0%) |
| Nervous system disorders | 39 (10.7%) | 19 (5.2%) |
| Headache | 21 (5.8%) | 10 (2.7%) |
| Gastrointestinal disorders | 62 (17.0%) | 29 (7.9%) |
| Diarrhoea | 16 (4.4%) | 10 (2.7%) |
| Nausea | 38 (10.4%) | 2 (0.5%) |
| Vomiting | 13 (3.6%) | 2 (0.5%) |

TEAE: Treatment emergent adverse event,
SOC: System Organ Class,
PT: Preferred Term.
MedDRA version: 18.0
n (%) = number and percentage of patients with at least one TEAE.
Note:
Table sorted by SOC internationally agreed order and PT alphabetic order.
Only SOC with at least one PT ≥3% in at least one group are presented.

3.3.2 Deaths, Serious Treatment-Emergent Adverse Events

Three patients experienced at least 1 TEAE leading to death: 1 from the combination group, 2 from the insulin glargine group:
Combination group:
  A 74 year-old male patient (ID 840519010) died of pneumonia. The event was not considered as possibly related to the IMP by the Investigator.
Insulin glargine group:
  A 63 year-old female patient (ID 840550018) died of gallbladder cancer.
  A 54 year-old male patient (ID 703504004) died of cardiopulmonary failure. Patient's medical history included hypertension. 171 days after the first dose of IMP, the patient experienced cardiorespiratory failure (intensity-severe) and died on the same day at 09:32 hours at home. Autopsy was performed and the cause of death was reported as cardiorespiratory failure, heart hypertrophy, and coronary atherosclerosis grade III. No any other AEs or hypoglycemia were reported during the study.
These 2 fatal events for 2 patients were not considered as possibly related to the IMP by the Investigator.

TABLE 22

Number (%) of patients experiencing serious TEAE(s) presented by primary SOC, and P-Safety population

| Primary System Organ Class Preferred Term [n (%)] | Fixed Ratio Combination (N = 365) | Insulin Glargine (N = 365) |
|---|---|---|
| Any serious TEAE | 20 (5.5%) | 18 (4.9%) |
| Infections and infestations | 1 (0.3%) | 3 (0.8%) |
| Osteomyelitis | 0 | 1 (0.3%) |
| Pneumonia | 1 (0.3%) | 1 (0.3%) |
| Wound infection | 0 | 1 (0.3%) |
| Neoplasms benign, malignant and unspecified (incl cysts and polyps) | 4 (1.1%) | 2 (0.5%) |
| Benign breast neoplasm | 1 (0.3%) | 0 |
| Benign gastric neoplasm | 1 (0.3%) | 0 |
| Breast cancer | 1 (0.3%) | 0 |
| Gallbladder cancer | 0 | 1 (0.3%) |
| Kaposi's sarcoma | 0 | 1 (0.3%) |
| Squamous cell carcinoma of the tongue | 1 (0.3%) | 0 |
| Metabotistn and nutrition disorders | 2 (0.5%) | 1 (0.3%) |
| Hypoglycaemia | 2 (0.5%) | 1 (0.3%) |
| Nervous system disorders | 3 (0.8%) | 0 |
| Hypoglycaemic seizure | 1 (0.3%) | 0 |
| Hypoglycaemic unconsciousness | 2 (0.5%) | 0 |
| Eye disorders | 0 | 1 (0 3%) |
| Glaucoma | 0 | 1 (0.3%) |
| Cardiac disorders | 7 (1.9%) | 2 (0.5%) |
| Acute myocardial infarction | 2 (0.5%) | 0 |
| Angina unstable | 2 (0.5%) | 0 |
| Arteriosclerosis coronary artery | 1 (0.3%) | 0 |
| Cardiac failure congestive | 0 | 1 (0.3%) |
| Cardiopulmonary failure | 0 | 1 (0.3%) |
| Myocardial infarction | 1 (0.3%) | 0 |
| Supraventricular tachycardia | 1 (0.3%) | 0 |
| Vascular disorders | 0 | 1 (0.3%) |
| Hypertension | 0 | 1 (0.3%) |
| Hepatobiliary disorders | 1 (0.3%) | 1 (0.3%) |
| Cholecystitis acute | 0 | 1 (0.3%) |
| Cholecystitis chronic | 1 (0.3%) | 0 |
| Musculoskeletal and connective tissue disorders | 2 (0.5%) | 1 (0.3%) |
| Intervertebral disc protrusion | 0 | 1 (0.3%) |
| Osteoarthritis | 1 (0.3%) | 0 |
| Tendonitis | 1 (0.3%) | 0 |
| Renal and urinary disorders | 0 | 1 (0.3%) |
| Renal impairment | 0 | 1 (0.3%) |
| Reproductive system and breast disorders | 0 | 1 (0.3%) |
| Benign prostatic hyperplasia | 0 | 1 (0.3%) |
| General disorders and administration site conditions | 0 | 3 (0.8%) |
| Chest discomfort | 0 | 1 (0.3%) |
| Non-cardiac chest pain | 0 | 2 (0.5%) |
| Injury, poisoning and procedural complications | 2 (0.5%) | 1 (0.3%) |
| Meniscus injury | 0 | 1 (0.3%) |
| Scar | 1 (0.3%) | 0 |
| Subdural haematoma | 1 (0.3%) | 0 |

TEAE: Treatment Emergent Adverse Event,
SOC: System Organ Class,
PT: Preferred Term.
MedDRA version: 18.0
n (%) = number and percentage of patients with at least one serious TEAE.
Note:
Table sorted by SOC internationally agreed order and PT alphabetic order.

3.3.3 Adverse Events Leading to Withdrawal

TABLE 23

Number (%) of patients experiencing TEAE(s) leading to permanent treatment discontinuation by primary SOC and PT-Safety population

| Primary System Organ Class Preferred Term [n (%)] | Fixed Ratio Combination (N = 365) | Insulin Glargine (N = 365) |
|---|---|---|
| Any TEAE leading to permanent treatment discontinuation | 10 (2.7%) | 3 (0.8%) |
| Infections and infestations | 1 (0.3%) | 0 |
| Pneumonia | 1 (0.3%) | 0 |
| Neoplasms benign, malignant and unspecified (incl cysts and polyps) | 1 (0.3%) | 1 (0.3%) |
| Benign gastric neoplasm | 1 (0.3%) | 0 |
| Gallbladder cancer | 0 | 1 (0.3%) |
| Nervous system disorders | 2 (0.5%) | 0 |
| Dizziness | 1 (0.3%) | 0 |
| Hypoglycaemic unconsciousness | 1 (0.3%) | 0 |
| Cardiac disorders | 1 (0.3%) | 1 (0.3%) |
| Angina unstable | 1 (0.3%) | 0 |
| Cardiopulmonary failure | 0 | 1 (0.3%) |
| Gastrointestinal disorders | 4 (1.1%) | 0 |
| Nausea | 4 (1.1%) | 0 |
| Pregnancy, puerperium and perinatal conditions | 0 | 1 (0.3%) |
| Pregnancy | 0 | 1 (0.3%) |
| Investigations | 1 (0.3%) | 0 |
| Weight increased | 1 (0.3%) | 0 |

TEAE: Treatment Emergent Adverse Event,
SOC: System Organ Class,
PT: Preferred Term.
MedDRA version: 18.0
n (%) = number and percentage of patients with at least one TEAE leading to permanent treatment discontinuation.
Note:
Table sorted by SOC internationally agreed order and PT alphabetic order.

3.3.4 Other Significant Adverse Events

Local Tolerability

TABLE 24

Number (%) of patients experiencing injection site reactions during the on-treatment period-Safety population

| Event source Preferred Term | Fixed Ratio Combination (N = 365) | Insulin Glargine (N = 365) |
|---|---|---|
| Any injection site reactions | 0 | 2 (0.5%) |
| PTs coded from the investigator reported terms | 0 | 2 (0.5%) |
| Injection site hypertrophy | 0 | 1 (0.3%) |
| Injection site reaction | 0 | 1 (0.3%) |

ARAC = Allergic Reaction Assessment Committee,
PT = Preferred term.
Note:
The on-treatment period is defined as the time from the first injection of IMP up to 3 days after the last injection of IMP, regardless of the introduction or rescue therapy.

Allergic Reactions

TABLE 25

Number (%) of patients with events adjudicated as allergic reaction by ARAC during the on-treatment period-Safety population

| Relationship to study treatment (by ARAC) | ARAC diagnosis categories | MedDRA coded term (PT) for ARAC diagnosis | Fixed Ratio Combination (N = 365) | Insulin Glargine (N = 365) |
|---|---|---|---|---|
| All | Any category | Any event | 0 | 1 (0.3%) |
|  | Other |  | 0 | 1 (0.3%) |
|  |  | Rhinitis allergic | 0 | 1 (0.3%) |
| Not Related to IMP |  |  | 0 | 1 (0.3%) |
|  | Other |  | 0 | 1 (0.3%) |
|  |  | Rhinitis allergic | 0 | 1 (0.3%) |

ARAC = Allergic Reaction Assessment Committee,
IMP = Investigational medicinal product.
Note:
The on-treatment period is defined as the time from the first injection of IMP up to 3 days after the last injection of IM, regardless of the introduction of rescue therapy.

Pancreatic Events

No events were adjudicated as pancreatitis by the PSAC. In addition, no pancreatic neoplasms were reported in the study.

Major Cardiovascular Events

TABLE 26

Number (%) of patients with events adjudicated as major cardiovascular events by CAC during the on-treatment period-Safety population

| n(%) | Fixed Ratio Combination (N = 365) | Insulin Glargine (N = 365) |
|---|---|---|
| Any | 5 (1.4%) | 4 (1.1%) |
| Cardiovascular death | 0 | 1 (0.3%) |
| Non-fatal myocardial infarction | 2 (0.5%) | 0 |
| Non-fatal stroke | 0 | 0 |
| Hospitalization for unstable angina | 0 | 0 |
| Hospitalization for heart failure | 0 | 1 (0.3%) |
| Coronary revascularization procedure | 5 (1.4%) | 3 (0.8%) |

CAC = Cardiovascular Events Adjudication Committee
n (%) = number and percentage of patients with events adjudicated as major cardiovascular evens by CAC.
Note:
The on-treatment period is defined as the time from the first injection of IMP up to 3 days after the last injection of IMP, regardless of the introduction of rescue therapy.

Increased Calcitonin

TABLE 27

Number (%) of patients with events reported on the AE form for increased calcitonin (≥20 ng/L) during the on-treatment period-Safety population

| Preferred Term | Fixed Ratio Combination (N = 365) | Insulin Glargine (N = 365) |
|---|---|---|
| Any | 0 | 2 (0.5%) |
| Blood calcitonin increased | 0 | 2 (0.5%) | n (%) = number and percentage of patients with any cases reported on the AE form for increased calcitonin ≥20 pg/mL along with complementary form.
Note:
The on-treatment period is defined as the time from the first injection of IMP up to 3 days after the last injection of IMP, regardless of the introduction of rescue therapy.

Increased ALT

TABLE 28

Number (%) of patients with events reported on the AE form for ALT increase during the on-treatment period-Safety population

| Preferred Term | Fixed Ratio Combination (N = 365) | Insulin Glargine (N = 365) |
|---|---|---|
| Any | 1 (0.3%) | 2 (0.5%) |
| Alanine aminotransferase increased | 0 | 2 (0.5%) |
| Hepatic enzyme increased | 1 (0.3%) | 0 | n (%) = number and percentage of patients with an cases reported on the AE form for ALT increase along with complementary form.
Note:
The on-treatment period is defined as the time from the first injection of IMP up to 3 days after the last injection of IMP, regardless of the introduction of rescue therapy.

Pen-Related Events

TABLE 29

Number (%) of patients with events reported in pen-related event questionnaire during the on-treatment period-Safety population

| | Fixed Ratio Combination (N = 365) | Insulin Glargine (N = 365) |
|---|---|---|
| Any pen-related events | 11 (3.0%) | 15 (4.1%) |
| Associated with a clinical event | 0 | 0 |
| Not associated with a clinical event | 11 (3.0%) | 15 (4.1%) |

Clinical event = symptomatic hypoglycemic even, hyperglycemic adverse event or other adverse event collected in pen-related questionnaire.
Note:
The on-treatment period is defined as the time from the first injection of IMP up to 3 days after the last injection of IMP, regardless of the introduction of rescue therapy.

3.3.5 Other Safety Observation—Symptomatic Hypoglycemia

TABLE 30

Summary of symptomatic hypoglycemia recorded on the dedicated eCRF and meeting protocol definition during the on-treatment period-Safety population

| | Fixed Ratio Combination (N = 365) | Insulin Glargine (N = 365) |
|---|---|---|
| Total patient years of exposure | 201.9 | 208.6 |
| Symptomatic hypoglycemia | | |
| Number of patients with events, n (%) | 152 (41.6%) | 161 (44.1%) |
| Number of patients with events per patient year [a] | 0.75 | 0.77 |
| Number of events | 639 | 910 |
| Number of events per patient year [b] | 3.17 | 4.36 |
| Documented symptomatic hypoglycaemia (plasma glucose ≤70 mg/dL [3.9 mmol/L]) | | |
| Number of patients with events, n (%) | 146 (40.0%) | 155 (42.5%) |
| Number of patients with events per patient year [a] | 0.72 | 0.74 |
| Number of events | 612 | 880 |
| Number of events per patient year [b] | 3.03 | 4.22 |
| Documented symptomatic hypoglycaemia (plasma glucose <60 mg/dL [3.3 mmol/L]) | | |
| Number of patients with events, n (%) | 89 (24.4%) | 83 (22.7%) |
| Number of patients with events per patient year [a] | 0.44 | 0.40 |
| Number of events | 229 | 235 |
| Number of events per patient year [b] | 1.13 | 1.13 |
| Probable symptomatic hypoglycaemia | | |
| Number of patients with events, n (%) | 13 (3.6%) | 20 (5.5%) |
| Number of patients with events per patient year [a] | 0.06 | 0.10 |
| Number of events | 22 | 29 |
| Number of events per patient year [b] | 0.11 | 0.14 |
| Severe symptomatic hypoglycaemia | | |
| Number of patients with events, a (%) | 4 (1.1%) | 1 (0.3%) |
| Number of patients with events per patient year [a] | 0.02 | <0.01 |
| Number of events | 5 | 1 |
| Number of events per patient year [b] | 0.02 | <0.01 |

IMP: Investigational Medicinal Product,
eCRF: electronic Case Report Form.
Patient years of exposure: calculated as time from the first to the alst injection of IMP plus 1 day.
[a] Calculated as number of patients with events divided by total patient years of exposure.
[b] Calculated as number of events divided by total patient years of exposure.
Symptomatic hypoglycemia = symptomatic hypoglycemia recorded on the dedicated eCRF and meeting protocol definition for severe, or documented, or probable symptomatic hypoglycemia.

On-treatment period is defined as the time from the first injection of IMP up to 1 day for symptomatic hypoglycemia after the last injection of IMP, regardless of the introduction of rescue therapy.

The invention claimed is:

1. A method of improving glycemic control in a patient with type 2 diabetes mellitus in need thereof, the method comprising administering to the patient a pharmaceutical composition comprising:
    (a) lixisenatide or a pharmaceutically acceptable salt thereof at a concentration of 33 μg/mL, and
    (b) insulin glargine or a pharmaceutically acceptable salt thereof at a concentration of 100 U/mL
    wherein the patient's type 2 diabetes mellitus is inadequately controlled by treatment with lixisenatide.

2. The method of claim 1, wherein the pharmaceutical composition is administered to the patient parenterally.

3. The method of claim 1, wherein the patient has a glycated hemoglobin (HbA1c) value between about 7% and about 10% when treated with lixisenatide.

4. The method of claim 1, wherein the patient's type 2 diabetes mellitus is inadequately controlled when treated with lixisenatide at the onset of treatment with the pharmaceutical composition.

5. The method of claim 1, wherein the patient's type 2 diabetes mellitus is inadequately controlled when treated with lixisenatide and metformin.

6. The method of claim 1, wherein the patient's type 2 diabetes mellitus is inadequately controlled when treated with lixisenatide, metformin, and a second oral antidiabetic drug (OAD).

7. The method of claim 6, wherein the second OAD is a sulfonylurea, a dipeptidyl-peptidase 4 (DPP-4) inhibitor, a sodium glucose co-transporter 2 (SGLT-2) inhibitor, a glinide, or a combination thereof.

* * * * *

SEQUENCE LISTING

```
<160> NUMBER OF SEQ ID NOS: 2

<210> SEQ ID NO 1
<211> LENGTH: 44
<212> TYPE: PRT
<213> ORGANISM: Artificial
<220> FEATURE:
<223> OTHER INFORMATION: desPro36-Exendin-4(1-39)-Lys6-NH2

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Lys
            35                  40
```

```
<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```